US012655178B2

(12) United States Patent
Tartaglia et al.

(10) Patent No.: US 12,655,178 B2
(45) Date of Patent: *Jun. 16, 2026

(54) METHOD OF TREATING MELANOCORTIN-4 RECEPTOR-ASSOCIATED DISORDERS IN HETEROZYGOUS CARRIERS

(71) Applicant: RHYTHM PHARMACEUTICALS, INC., Boston, MA (US)

(72) Inventors: Louis Anthony Tartaglia, Newton, MA (US); Bart Henderson, Belmont, MA (US); Leonardus H.T. Van Der Ploeg, Newton, MA (US)

(73) Assignee: RHYTHM PHARMACEUTICALS, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/204,672

(22) Filed: Jun. 1, 2023

(65) Prior Publication Data

US 2024/0190914 A1 Jun. 13, 2024

Related U.S. Application Data

(63) Continuation of application No. 17/097,122, filed on Nov. 13, 2020, now Pat. No. 11,702,448, which is a continuation of application No. 16/383,889, filed on Apr. 15, 2019, now Pat. No. 10,954,268, which is a continuation of application No. 16/117,767, filed on Aug. 30, 2018, now abandoned, which is a continuation of application No. 15/789,118, filed on Oct. 20, 2017, now Pat. No. 10,167,312, which is a continuation of application No. 14/369,116, filed as application No. PCT/US2012/072026 on Dec. 28, 2012, now Pat. No. 9,845,339.

(60) Provisional application No. 61/581,391, filed on Dec. 29, 2011.

(51) Int. Cl.

| | |
|---|---|
| ***C07K 5/00*** | (2006.01) |
| ***A61K 38/08*** | (2019.01) |
| ***C07K 5/08*** | (2006.01) |
| ***C07K 7/06*** | (2006.01) |
| ***C07K 14/68*** | (2006.01) |
| ***C07K 14/72*** | (2006.01) |

(52) U.S. Cl.

CPC ............ *C07K 5/0802* (2013.01); *A61K 38/08* (2013.01); *C07K 7/06* (2013.01); *C07K 14/68* (2013.01); *C07K 14/723* (2013.01)

(58) Field of Classification Search

CPC ........ C07K 5/0802; C07K 7/06; C07K 14/68; C07K 14/723; A61K 38/08; A61P 3/00; A61P 3/04

See application file for complete search history.

(56) References Cited

U.S. PATENT DOCUMENTS

| | | | |
|---|---|---|---|
| 7,968,548 | B2 | 6/2011 | Sharma et al. |
| 8,039,435 | B2 | 10/2011 | Dong et al. |
| 8,114,844 | B2 | 2/2012 | Sharma et al. |
| 8,247,530 | B2 | 8/2012 | Sharma et al. |
| 8,263,608 | B2 | 9/2012 | Shi et al. |
| 8,349,797 | B2 | 1/2013 | Dong et al. |
| 8,563,000 | B2 | 10/2013 | Dong et al. |
| 9,155,777 | B2 | 10/2015 | Halem et al. |
| 9,845,339 | B2 | 12/2017 | Tartaglia et al. |
| 10,167,312 | B2 | 1/2019 | Tartaglia et al. |
| 2005/0267147 | A1 | 12/2005 | Poitout et al. |
| 2006/0173036 | A1 | 8/2006 | Poitout et al. |
| 2006/0281784 | A1 | 12/2006 | Poitout et al. |
| 2007/0021433 | A1 | 1/2007 | Fan et al. |
| 2009/0176712 | A1 | 7/2009 | Haskell-Luevano |
| 2009/0209531 | A1 | 8/2009 | Poitout et al. |
| 2010/0120783 | A1 | 5/2010 | Lee et al. |
| 2010/0173834 | A1 | 7/2010 | Dong |
| 2010/0184646 | A1 | 7/2010 | Dong et al. |
| 2010/0190793 | A1 | 7/2010 | Weber et al. |
| 2010/0279922 | A1 | 11/2010 | Dong et al. |
| 2010/0280079 | A1 | 11/2010 | Eisinger et al. |
| 2010/0311647 | A1 | 12/2010 | Halem et al. |
| 2010/0311648 | A1 | 12/2010 | Dodd et al. |
| 2011/0065652 | A1 | 3/2011 | Shi et al. |
| 2011/0183886 | A1 | 7/2011 | Dong et al. |
| 2011/0263490 | A1 | 10/2011 | Kaplan et al. |
| 2012/0135923 | A1 | 5/2012 | Halem et al. |
| 2012/0225816 | A1 | 9/2012 | Dong et al. |
| 2012/0226018 | A1 | 9/2012 | Dong |
| 2014/0127303 | A1 | 5/2014 | Richard et al. |
| 2015/0157719 | A1 | 6/2015 | Baronnet et al. |
| 2016/0022764 | A1 | 1/2016 | Sharma et al. |
| 2018/0311309 | A1 | 11/2018 | Ploeg et al. |

FOREIGN PATENT DOCUMENTS

| | | | |
|---|---|---|---|
| WO | 2005/000339 | A2 | 1/2005 |
| WO | 2007/008684 | A2 | 1/2007 |

(Continued)

OTHER PUBLICATIONS

Baker et al. "Childhood Body-Mass Index and the Risk of Coronary Heart Disease in Adulthood," The New England Journal of Medicine (2007) vol. 357. No 23, pp. 2329-2337.
Farooqi et al. "Dominant and recessive inheritance of morbid obesity associated with melanocortin 4 receptor deficiency", The Journal of Clinical Investigation (2000) vol. 106, No. 2, pp. 271-279.
International Search Report for PCT/US2012/072026 filing date Dec. 28, 2012.

(Continued)

*Primary Examiner* — Jeanette M Lieb
(74) *Attorney, Agent, or Firm* — Lando & Anastasi, LLP

(57) ABSTRACT

A method of treating a disorder in a subject. The method comprises administering to said subject an effective amount of an agonist of the melanocortin-4 receptor (MC4R). The subject is a heterozygous carrier of an MC4R mutation, and the disorder results from an attenuated response of MC4R to α-melanocortin stimulating hormone (α-MSH).

8 Claims, 4 Drawing Sheets

Specification includes a Sequence Listing.

(56) References Cited

FOREIGN PATENT DOCUMENTS

| | | | |
|---|---|---|---|
| WO | 2007/008704 | A2 | 1/2007 |
| WO | 2008/087186 | A2 | 7/2008 |
| WO | 2008/087187 | A1 | 7/2008 |
| WO | 2008/087188 | A2 | 7/2008 |
| WO | 2008/087189 | A2 | 7/2008 |
| WO | 2008/116665 | A1 | 10/2008 |
| WO | 2008/147556 | A2 | 12/2008 |
| WO | 2008/156677 | A2 | 12/2008 |
| WO | 2009/010299 | A1 | 1/2009 |
| WO | 2009/061411 | A2 | 5/2009 |
| WO | 2009/151383 | A1 | 12/2009 |
| WO | 2009/152079 | A1 | 12/2009 |
| WO | 2010/015972 | A1 | 2/2010 |
| WO | 2010/025142 | A1 | 3/2010 |
| WO | 2010/034500 | A1 | 4/2010 |
| WO | 2010/037081 | A1 | 4/2010 |
| WO | 2010/052255 | A1 | 5/2010 |
| WO | 2010/052256 | A1 | 5/2010 |
| WO | 2010/060901 | A1 | 6/2010 |
| WO | 2010/065799 | A2 | 6/2010 |
| WO | 2010/065800 | A1 | 6/2010 |
| WO | 2010/065801 | A1 | 6/2010 |
| WO | 2010/065802 | A2 | 6/2010 |
| WO | 2010/081666 | A1 | 7/2010 |
| WO | 2010/096854 | A1 | 9/2010 |
| WO | 2010/144341 | A2 | 12/2010 |
| WO | 2010/144344 | A2 | 12/2010 |
| WO | 2011017209 | A1 | 2/2011 |
| WO | 2011/026015 | A2 | 3/2011 |
| WO | 2011/060352 | A1 | 5/2011 |
| WO | 2011/104378 | A1 | 9/2011 |
| WO | 2011/104379 | A1 | 9/2011 |
| WO | 2012/172433 | A2 | 12/2012 |
| WO | 2013/182653 | A1 | 12/2013 |
| WO | 2014/144260 | A1 | 9/2014 |
| WO | 2014/144842 | A2 | 9/2014 |
| WO | 2019/099735 | A1 | 5/2019 |

OTHER PUBLICATIONS

Online Mendelian Inheritance in Man (OMIM), a database of human genes and genetic disorders, under the accession No. 155541 (MC4R) (more precisely, accession Nos. 155541.0001-155541.0023) at the URL <http://omim.org/entry/155541>; created on Oct. 1, 1993; last edited on Jun. 23, 2015.

Reinehr et al. "Lifestyle Intervention in Obese Children With Variations in the Melanocortin 4 Receptor Gene," Obesity Journal (2009), vol. 17 No 2.

Vaisse et al. "Melanocortin-4 receptor mutations are a frequent and heterogeneous cause of morbid obesity", The Journal of Clinical Investigation (2000) vol. 106, No. 2, pp. 253-262.

Xiang et al. "Pharmacological characterization of 30 human melanocortin-4 receptor polymorphisms with the endogenous proopiomelanocortin-derived agonists, synthetic agonists, and the endogenous agouti-related protein antagonist." Biochemistry (2010), No. 49(22), pp. 4583-4600.

Partial European Search Report from 12863862.4 dated Sep. 21, 2015.

Govaerts et al., "Obesity-associated mutations in the melanocortin 4 receptor provide novel insights into its function" Peptides (2005) vol. 26 pp. 1909-1919.

Extended European Search Report for PCT/U.S. Pat. No. 2012072026 dated Apr. 18, 2016.

Extended European Search Report from Application No. 19158126.3 dated Jun. 18, 2019.

Table 1

Sequence variants of *MC4R* detected in 243 subjects with severe early-onset obesity

| Sequence Variant | Number of obese subjects with mutation[A] | Number of controls with mutation[B] | Number of subjects previously described |
|---|---|---|---|
| GT insertion at codon 279 | 2 | 0 | None |
| C deletion 28-bp downstream of stop codon | 1 | 0 | None |
| N62S | 1 (hom) | 0 | None |
| T112M | 1 | 0 | 2 (11, 12) |
| R165Q | 1 | 0 | None |
| V253I | 1 | 0 | None |
| C271Y | 1 | 0 | None |
| I251L | 7 | 3 | 1 (12) |
| V103I | 3 | 1 | 2 (11, 12) |

FIG. 2A

Table 2

MC4-R mutation screening in morbidly obese patients and nonobese controls

| Base change | Effect on amino acid sequence | Morbidly obese ($n$ – 209) | Control 1 ($n$ – 254) | Control 2 ($n$ – 112) |
|---|---|---|---|---|
| A-307-G | Val103 Ile | 8 | 8 | 3 |
| A-751-C | Ile251Leu | 3 | 3 | 0 |
| C-593-T | Silent | 1 | ND | 1 |
| 47-48insG | 16 + 12 amino-acids | 1 | 0 | 0 |
| A-31-G | Thr11Ser | 1 | 0 | 0 |
| C-52-T | Arg18Cys | 1 | 0 | 0 |
| C-449-T | Thr150Ile | 1 | 0 | 0 |
| A-508-G | Ile170Val | 1 | 0 | 0 |
| C-493-T | Arg165Trp | 1 | 0 | 0 |
| T-749-A | Leu250Gln | 1 | 0 | 0 |
| T-902-C | Ile301Thr | 1 | 0 | 0 |

The morbidly obese and the control 2 populations were screened by PCR-SSCP. The control 1 population was screened by PCT-RFLP for every functionally relevant mutation detected in the morbidly obese population. ND, not determined.

FIG. 2B

METHOD OF TREATING MELANOCORTIN-4 RECEPTOR-ASSOCIATED DISORDERS IN HETEROZYGOUS CARRIERS

RELATED APPLICATIONS

The present application is a continuation of U.S. application Ser. No. 17/007,122, now U.S. Pat. No. 11,702,448, filed Nov. 13, 2020, which is a continuation of U.S. application Ser. No. 16/383,889, now U.S. Pat. No. 10,954,268, filed Apr. 15, 2019, which is a continuation of U.S. application Ser. No. 16/117,767, filed Aug. 30, 2018, which is a continuation of U.S. application Ser. No. 15/789,118, now U.S. Pat. No. 10,167,312, filed Oct. 20, 2017, which is a continuation of U.S. application Ser. No. 14/369,116, now U.S. Pat. No. 9,845,339, filed Jun. 26, 2014, which is a U.S. national stage application under 35 U.S.C. § 371 of International Application No. PCT/US2012/072026, filed Dec. 28, 2012, which claims the benefit of U.S. Provisional Application No. 61/581,391, filed Dec. 29, 2011. The entire teachings of the above applications are incorporated herein by reference.

SEQUENCE LISTING

A Sequence Listing conforming to the rules of WIPO Standard ST.26 is hereby incorporated by reference. Said Sequence Listing has been filed as an electronic document via Patent Center encoded as XML in UTF-8 text. The electronic document, created on Jul. 29, 2023, is entitled "R2054-700024_ST26.xml", and is 19,356 bytes in size.

BACKGROUND OF THE INVENTION

Melanocortin 4 receptor (MC4R) mutations can result in genetically derived cause of human obesity or metabolic syndrome. MC4R receptor is a heterotrimeric G-protein-coupled receptor, which transduces signals by activating adenylate cyclase. Expressed in hypothalamic nuclei and other neuronal and non-neuronal tissues, controlling feeding behavior and energy homeostasis, MC4R integrates an agonist (anorexigenic) signal provided by the α-melanocyte stimulating hormone (α-MSH), and an antagonist (orexigenic) signal provided by the agouti-related peptide (AGPR).

As shown in FIG. 1, MC4R is a part of the leptin-melanocortin pathway. Leptin is released from adipose tissue and binds to leptin receptors (LEPR) on AGPR- and pro-opiomelanocortin (POMC)-releasing neurons in the arcuate nucleus (ARC) of the hypothalamus. Leptin binding inhibits AGPR release and stimulates the release of POMC, which undergoes post-translational modification by the prohormone convertase PC1/3 to generate a range of peptides, including α-MSH. AGPR binding to MC4R suppresses MC4R activity, while α-MSH binding stimulates the MC4R. Suppressed receptor activity generates orexigenic signal, whereas stimulated receptor activity generates anorexigenic signal. Signals from MC4R modulate feeding behavior through secondary effector neurons.

Humans affected by a monogenic MC4R-caused disorders, e.g., obesity, are mostly heterozygous carriers of mutant human MC4R (hMC4R) gene with an autosomal dominant inheritance and penetrance and expressivity that varies with age and generational influences. The functional consequences of hMC4R mutations can be schematically divided into the following categories: nonfunctional receptor (e.g. due to missense or frameshift mutations), intracellular retention of the expressed receptor, altered basal activity of the receptor, and altered α-MSH stimulation of the receptor.

SUMMARY OF THE INVENTION

The need exists for a method of treating disorders associated with MC4R mutations. It has now been discovered that certain individuals that carry an MC4R mutations can respond to pharmacological agents that activate MC4R-mediated signaling pathway. These individuals are heterozygous carriers of an MC4R mutation. Based on this discovery, it is now possible to treat MC4R-mediated disorders in a class of patients that was previously considered unresponsive to MC4R agonists.

Accordingly, an example embodiment of the present invention is a method of treating a disorder in a subject in need thereof. The method comprises administering to said subject an effective amount of an agonist of the melanocortin-4 receptor (MC4R). The subject is a heterozygous carrier of an MC4R mutation, and the disorder results from an attenuated response of MC4R to α-melanocortin stimulating hormone (α-MSH).

In a particular embodiment, the disorder is obesity (for example, obesity caused by an MC4R mutation, such as loss of function) and the subject is heterozygous with respect to the MC4R gene. In this embodiment, treatment of such a subject with a pharmacological agent that activates MC4R-mediated signaling pathway, such as described herein, may confer a number of unexpected advantages and benefits. For instance, most subjects heterozygous for MC4R may respond to treatment with sustained weight loss. A proportion of subjects may have MC4R functionality restored to wild type levels, resulting in body weight and body composition normalization. Additional benefits may include overcoming hyperinsulinemia, and improving glucose control and hyperphagia. A further benefit may be that weight loss is sustained throughout the treatment period as well as for prolonged periods of time on treatment cessation.

Additional unexpected benefits of treating an MC4R-mediated obesity in an MC4R-heterozygous subject by a pharmacological agent that activates MC4R-mediated signaling pathway, when compared to an obese subject that is wild-type with respect to MC4R, may include one or more of: an unexpectedly long ability to sustain a drug holiday, without gaining weight; a more profound improvement in insulin and glucose management; a longer lasting and sustained reduction in meal size and food intake; a more profound effect on reducing sleep apnea and increasing quality of sleep; an unexpected and more profound improvement effect on parameters of male or female sexual dysfunction; a more profound reduction in the incidence of obesity-associated cancers; a more profoundly reduced incidence in obesity-associated inflammatory disease including rheumatoid arthritis and endothelial and micro-vascular dysfunction; a more profoundly reduced incidence of heart attack and stroke; more profound improvements in cardiovascular parameters including heart rate and blood pressure.

There are additional benefits to treatment of an MC4R-mediated obesity in an MC4R-heterozygous subject (MC4R+/−) by a pharmacological agent that activates MC4R-mediated signaling pathway, when compared to an obese subject that is wild-type with respect to MC4R. MC4R+/− obese individuals are more at risk than wild type obese individuals of the consequences of obesity because of the intractability of their obesity, and the duration of the MC4R-mediated obesity, that often has a high rate of childhood onset. For example, MC4+/− obese individuals are resistant to weight management by diet/exercise regimens. (Reinhhr et. al, "Lifestyle Intervention in Obese Children With Variations in the Melanocortin 4 Receptor Gene," Obesity Journal, Vol. 17 No. 2, 2009). It is well-established, however, that higher childhood body-mass index (BMI) values elevate the risk of having a Coronary Heart Disease event in adulthood. (Baker et al., "Childhood Body-Mass Index and the Risk of Coronary Heart Disease in Adulthood," N. Engl. J. Med 2007; 357:2329-2337 (2007).) Treatment of this higher risk patient group may provide a treatment option not previously available (e.g., a treatment that achieves long term weight management).

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 2A and 2B show Tables 1 and 2 which list examples of the MC4R mutations that cause obesity in humans.

DETAILED DESCRIPTION OF THE INVENTION

Figure 1:
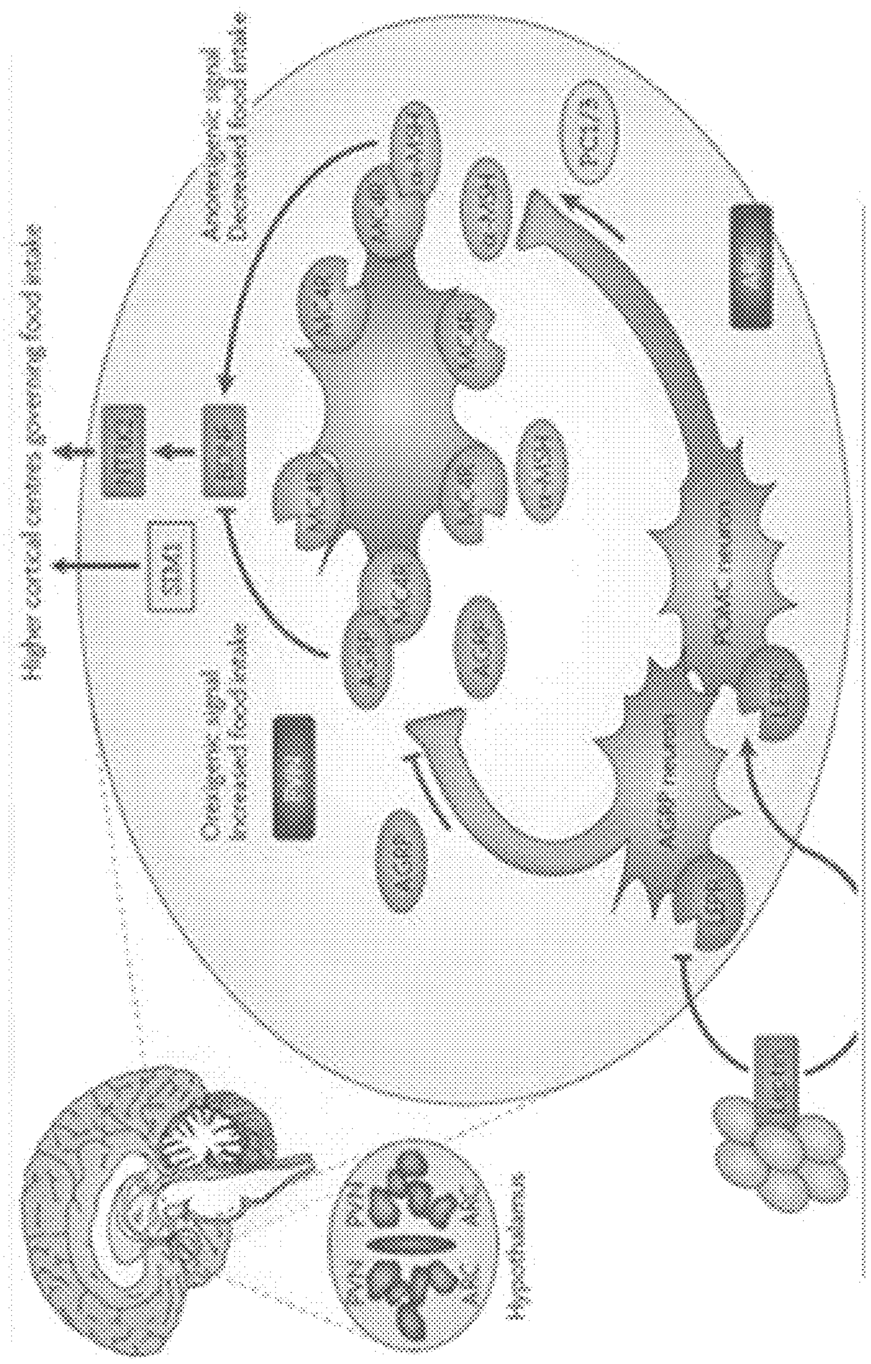
FIG. 1 is a schematic diagram of the leptin-melanocortin pathway.

A description of example embodiments of the invention follows.

The present invention relates to a method of treating a disorder in a subject suffering from an attenuated response of MC4R to α-melanocortin stimulating hormone (α-MSH). The method comprises administering an effective amount of an agonist of the melanocortin-4 receptor (MC4R). In an example embodiment, the subject is a heterozygous carrier of an MC4R mutation resulting in the attenuated response of MC4R to α-melanocortin stimulating hormone (α-MSH). Because heterozygous carriers retain an ability to respond to the natural ligand of MC4R, treating MC4R-associated disorders in heterozygous carriers by administration of an MC4R agonist does not rely on the knowledge of the type of the MC4R mutation.

In one example embodiment, the disorder is obesity, for example, MC4R-associated obesity. In another example embodiment, the disorder is metabolic syndrome.

As used herein, the term "obese" refers to a subject having a body mass index (BMI) within the ranges defined as "obese" by the Center for Disease Control. See, URL http://www.cdc.gov/obesity/defining.html, last accessed on Oct. 28, 2011. For example, an adult who has a BMI of 30 or higher is considered obese, As used herein, the term "metabolic syndrome" refers to a group of symptoms that occur together and increase the risk for coronary artery disease, stroke, and type 2 diabetes. According to the American Heart Association and the National Heart, Lung, and Blood Institute, metabolic syndrome also referred to as Syndrome X) is present if a subject has three or more of the following signs:

1) Blood pressure equal to or higher than 130/85 mmHg;
2) Fasting blood sugar (glucose) equal to or higher than 100 mg/dL;
3) Large waist circumference (length around the waist):
   Men-40 inches or more;
   Women-35 inches or more;
4) Low HDL cholesterol:
   Men-under 40 mg/dL;
   Women-under 50 mg/dL;
5) Triglycerides equal to or higher than 150 mg/dL.

Metabolic syndrome can be diagnosed by testing subject's blood pressure, blood glucose level, HDL cholesterol level, LDL cholesterol level, total cholesterol level, and triglyceride level.

As used herein, the phrase "attenuated response" refers to reduction, but not complete abrogation, of a signaling activity of a receptor in response to its cognate naturally occurring or synthetic ligand.

As used herein, the term "agonist" refers to any chemical compound, either naturally occurring or synthetic, that, upon interacting with (e.g., binding to) its target, here, MC4R, raises the signaling activity of MC4R above its basal level. An agonist can be a superagonist (i.e. a compound that is capable of producing a greater maximal response than the endogenous agonist for the target receptor, and thus has an efficacy of more than 100%), a full agonist (i.e. a compound that elicits a maximal response following receptor occupation and activation) or a partial agonist (i.e. a compounds that can activate receptors but are unable to elicit the maximal response of the receptor system).

Examples of naturally occurring MC4R agonists include α-MSH, β-MSH, γ-MSH and adrenocorticotropic hormone (ACTH) or a functional fragment thereof. Examples of synthetic MC4R agonists will be described in detail below.

As used herein, an "effective amount" is a therapeutically or prophylactically sufficient amount of the MC4R agonist to treat the target disorder. Examples of effective amounts typically range from about from 0.005 mg/kg of body weight to 500 mg/kg of body weight. In other examples, effective amounts range from about from 0.01 mg/kg of body weight to 50 mg/kg of body weight, or from 0.01 mg/kg of body weight to 20 mg/kg of body weight.

As used herein "treating" includes achieving, partially or substantially, one or more of the following results: partially or totally reducing the body weight (as measured, for example, by a body mass index, BMI); ameliorating or improving a clinical symptom or indicators associated with obesity, such as type-II diabetes, pre-diabetic condition, blood level of haemoglobin A1C (Hb1Ac) above 6%, hyperinsulinemia, hyperlipidemia, insulin insensitivity, glucose intolerance etc; delaying, inhibiting or preventing the progression of obesity and obesity related indication; or partially or totally delaying, inhibiting or preventing the onset or development of obesity or obesity related indication. Delaying, inhibiting or preventing the progression of the obesity includes for example, delaying, inhibiting or preventing the progression of a subject having normal weight to obesity.

The term "treating" further includes partially or totally reducing the risk for coronary artery disease, stroke, and type 2 diabetes associated with the metabolic syndrome as well as ameliorating or improving a clinical symptom or signs of metabolic syndrome associated with metabolic syndrome, such as any one or more of the five indicators listed above. For example, the term "treating" includes delaying, inhibiting or preventing the progression of parameters associated with the metabolic syndrome, including insulin resistance, glucose clearance and parameters of cardiovascular disease including heart rate and blood pressure.

"Prophylactic treatment" refers to treatment before onset of obesity to prevent, inhibit or reduce its occurrence.

As used herein, the term "subject" refers to a mammal, preferably a human, but can also mean an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

hMC4R is a well-characterized protein encoded by a genomic sequence having GenBank accession number CH471077.

Mutations in the MC4R receptor are an associated cause of severe childhood obesity. The carrier prevalence for MC4R mutations in a juvenile-onset obese population has been noted to be around 2.5% with a highest prevalence of 6% among severe obese children. Humans with MC4R mutations show a more or less similar phenotype as has been described for mice with mutations in the MC4 receptor gene. Those people show clear hyperphagia, hyperinsulinemia, increased fat mass, accompanied by lean body mass, bone mineral density and linear growth rate, with no changes in cortisol levels, gonadotropin, thyroid and sex steroid levels. In contrast to MC4 receptor deletion, hyperphagia and hyperinsulinemia tends to subside with age in human subjects. Similar to the MC4R knockout mice, the phenotype in heterozygote carriers is intermediate in comparison to homozygote carriers. The exhibited hyperphagia observed upon a test meal is less severe than that observed in people with a leptin deficiency. The severity of MC4 receptor dysfunction seen in assays in vitro can predict the amount of food ingested at a test meal by the subject harboring that particular mutation and correlates with the onset and severity of the obese phenotype. At east 90 different MC4 receptor mutations have been associated with obesity and additional mutations in the MC4 receptor are likely to be discovered, leading to a similar obesity phenotype.

Examples of the MC4R mutations that cause obesity in humans are shown in FIGS. 2A and 2B as Table 1 and Table 2 (adopted from Farooqi et al., *The Journal of Clinical Investigation*, July 2000, vol. 106 (2), pp. 271-279 and Vaisse et al., *The Journal of Clinical Investigation*, July 2000, vol. 106 (2), pp. 253-262, the relevant portions of which are incorporated herein by reference).

Additional mutations that potentially cause obesity in humans include, R18H, R18L, S36Y, P48S, V50M, F51L, E61K, 169T, D90N, S94R, G98R, 1121T, A154D, Y157S, W174C, G181D, F202L, A219 V, I226T, G231S, G238D, N240S, C271R, S295P, P299L, E308K, 1317V, L325F, and 750DelGA, as described in Xiang et al., "Pharmacological characterization of 30 human melanocortin-4 receptor polymorphisms with the endogenous proopiomelanocortin-derived agonists, synthetic agonists, and the endogenous agouti-related protein antagonist." Biochemistry, 2010 Jun. 8; 49 (22): 4583-600, the relevant portions of which are incorporated herein by reference.

Further examples of mutations that potentially cause obesity in humans are those listed in Online Mendelian Inheritance in Man (OMIM), a database of human genes and genetic disorders, under the accession number 155541 (MC4R) (more precisely, accession nos. 155541.0001-155541.0023) at the URL http://omim.org/entry/155541. Representative examples include 4-BP DEL, NT631; 4-BP INS, NT732; TYR35TER; ASP37VAL; SER58CYS; ILE102SER; ASN274SER; 1-BP INS, 112A; 4-BP DEL, 211CTCT; ILE125LYS; ALA175THR; ILE316SER; TYR287TER; ASN97ASP; 15-BP DEL (delta88-92 codons); and SER127LEU. The relevant portions of the OMIM database are incorporated herein by reference.

In example embodiments, the MC4R mutation results in retention of the MC4R signaling activity.

Mutations in the genomic sequence encoding MC4R can be detected by the methods that are well known to a person of ordinary skill in the art. For example, the genomic sequence can be cloned using nucleotide primers, such as e.g., the primers described in Farooqi et al., The Journal of Clinical Investigation, July 2000, vol. 106 (2), pp. 271-279 and Vaisse et al., The Journal of Clinical Investigation, July 2000, vol. 106 (2), pp. 253-262, and the cloned sequence analyzed using commercially available sequencers and software.

Activity of MC4R can be measured by the methods well known to a person of ordinary skill in the art. For example, cells can be transiently transfected with the cloned MC4R DNA, the transfected cells contacted by an agonist of MC4R (e.g. α-MSH), and the intracellular level of CAMP, the secondary messenger of MC4R, measured by an electrochemiluminescence assay described, e.g., in Roubert et al., Journal of Endocrinology (2010) 207, pp. 177-183. A reduction in MC4R signaling can be ascertained by comparing the intracellular level of cAMP produced in response to a given agonist by a wild type MC4R to that produced by a mutant MC4R.

In an example embodiment, an agonist employed by the methods of the present invention can be any known agonist of MC4R. In some example embodiment, the MC4R agonist is not an adrenocorticotropic hormone (ACTH) or a fragment thereof.

In an example embodiment, an MC4R agonist is any of the peptides disclosed in International Application published as WO/2005/000339. Specifically, examples include peptides of the following structural formula:

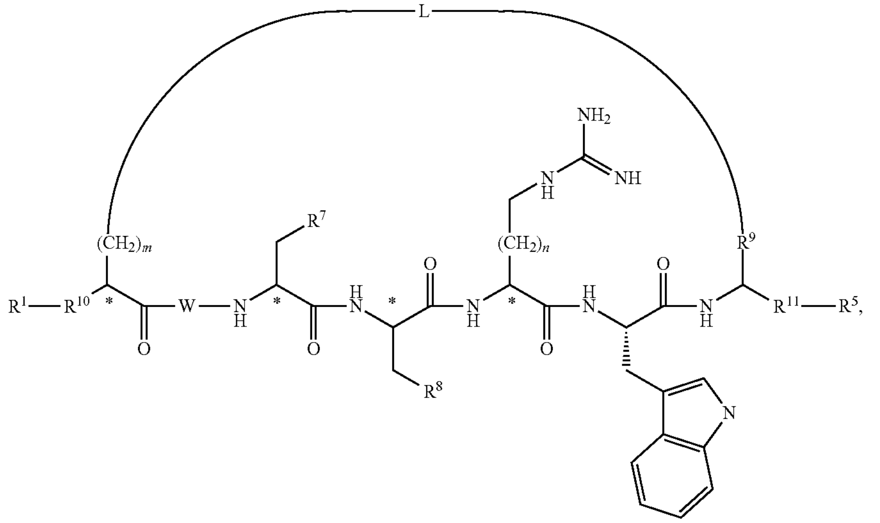

wherein

W is Glu, Gln, Asp, Asn, Ala, Gly, Thr, Ser, Pro, Met, Ile, Val, Arg, His, Tyr, Trp,

Phe, Lys, Leu, Cya, or is absent;

$R^1$ is —H, —C(O)$CH_3$, —C(O)$(CH_2)_{1-4}CH_3$, —C(O)$(CH_2)_{1-4}$NHC(NH)$NH_2$, Tyr-βArg-, Ac-Tyr-β-hArg-, gluconoyl-Tyr-Arg-, Ac-diaminobutyryl-, Ac-diaminopropionyl-, N-propionyl-, N-butyryl-, N-valeryl-, N-methyl-Tyr-Arg-, N-glutaryl-Tyr-Arg-, N-succinyl-Tyr-Arg-, $R^6$—$SO_2$NHC(O)$CH_2CH_2$C(O)—, $R^6$—$SO_2$NHC(O)$CH_2CH_2$C(O)Arg-, $R^6$—$SO_2NHCH_2CH_2CH_2$C(O)—, $C_3$-$C_7$ cycloalkylcarbonyl, pheylsulfonyl, $C_8$-$C_{14}$ bicyclic arylsulfonyl, phenyl-$(CH_2)_q$C(O)—, $C_8$-$C_{14}$ bicyclic aryl-$(CH_2)_q$C(O)—,

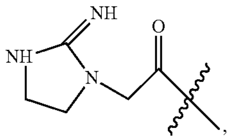

,

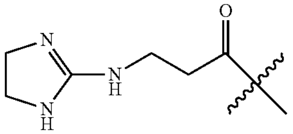

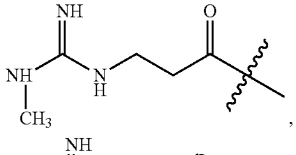

,

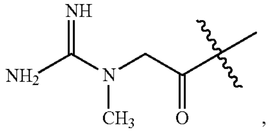

, or

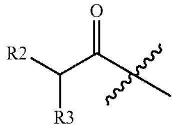

, wherein $R^2$ is —H, —$NH_2$, —NHC(O)$CH_3$, —NHC(O)$(CH_2)_{1-4}CH_3$, —NH-TyrC(O)$CH_3$, $R^6SO_2$NH—, Ac-Cya-NH—, Tyr-NH—, HO—$(C_6H_5)$—$CH_2CH_2$C(O)NH—, or $CH_3$—$(C_6H_5)$—C(O)$CH_2CH_2$C(O)NH—;

$R^3$ is $C_1$-$C_4$ straight or branched alkyl, $NH_2$—$CH_2$—$(CH_2)_q$—, HO—$CH_2$—, $(CH_3)_2CHNH(CH_2)_4$—, $R^6(CH_2)_q$—, $R^6SO_2$NH—, Ser, Ile,

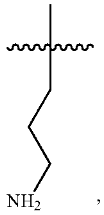

,

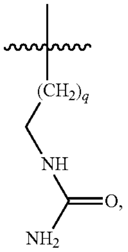

or

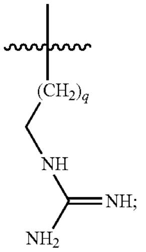

q is 0, 1, 2, or 3;

$R^6$ is a phenyl or $C_8$-$C_{14}$ bicyclic aryl;

mis 1 or 2;

n is 1, 2, 3, or 4;

$R^9$ is $(CH_2)_p$ or $(CH_3)_2$C—;

p is 1 or 2;

$R^{10}$ is NH— or is absent;

$R^7$ is a 5- or 6-membered heteroaryl or a 5- or 6-membered heteroaryl ring optionally substituted with $R^4$;

$R^4$ is H, $C_1$-$C_4$ straight or branched alkyl, phenyl, benzyl, or $(C_6H_5)$—$CH_2$—O—$CH_2$—;

$R^8$ is phenyl, a phenyl ring optionally substituted with X, or cyclohexyl;

X is H, Cl, F, Br, methyl, or methoxy;

$R^{11}$ is —C(O) or —$CH_2$;

$R^5$ is —$NH_2$, —OH, glycinol, $NH_2$-Pro-Ser-, $NH_2$-Pro-Lys-, HO-Ser-,

HO-Pro-Ser-, HO-Lys-, Ser alcohol, -Ser-Pro alcohol, -Lys-Pro alcohol, $HOCH_2CH_2$—O—$CH_2CH_2$NH—, $NH_2$-Phe-Arg-, $NH_2$-Glu-, $NH_2CH_2RCH_2$NH—, RHN—, RO— where R is a $C_1$-$C_4$ straight or branched alkyl; and L is —S—S— or —S—$CH_2$—S—.

Other examples of MC4R agonists include peptides of the following structural formula:

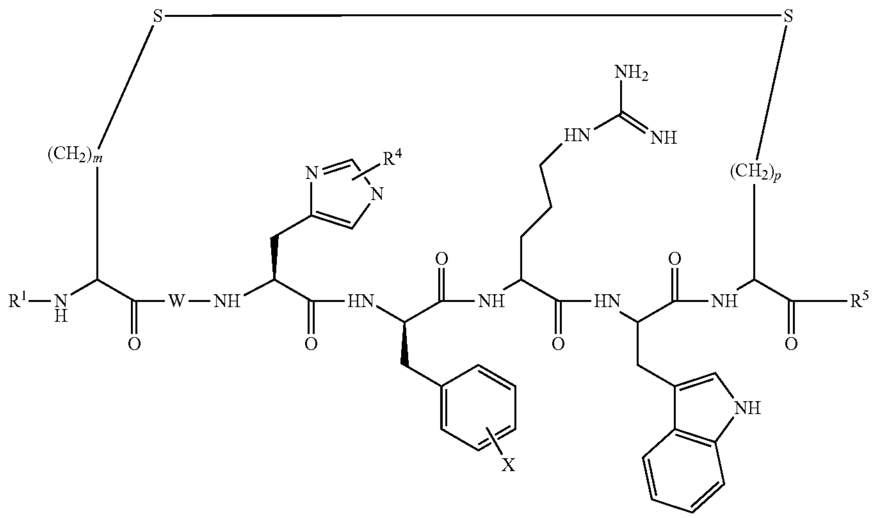

wherein:

W is a single bond, Glu, Gln, Asp, Asn, Ala, Gly, Thr, Ser, Pro, Met, Ile, Val, Arg, His, Tyr, Trp, or Phe;

$R^1$ is —H, —$C(O)CH_3$, —$C(O)(CH_2)_{1-4}CH_3$, —$C(O)(CH_2)_{1-4}$—$NHC(NH)NH_2$, Tyr-βArg, gluconoyl-Tyr-Arg, Ac-Dab, Ac-Dap, N-succinyl-Tyr-Arg, N-propionyl, N-valeryl, N-glutaryl-Tyr-Arg, N-butyryl,

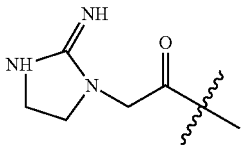,

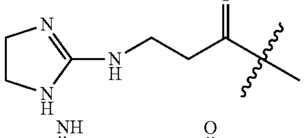

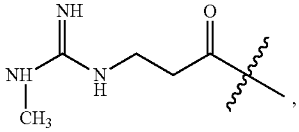,

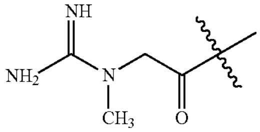, or 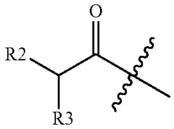, wherein $R^2$ is —H, —$NH_2$, —$NHC(O)CH_3$, —$NHC(O)(CH_2)_{1-4}CH_3$, or —NH-Tyr$C(O)CH_3$;

$R^3$ is $C_1$-$C_4$ straight or branched alkyl, Ser, Ile,

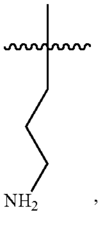, 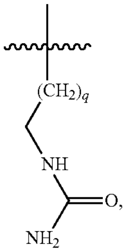, or 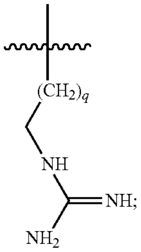;

q is 0, 1, 2, or 3;

m is 1 or 2;

p is 1 or 2;

$R^4$ is H or $C_1$-$C_4$ straight or branched alkyl;

X is H, Cl, F, Br, methyl, or methoxy; and $R^5$ is —$NH_2$, —OH, glycinol, -Ser-Pro-$NH_2$, -Lys-Pro-$NH_2$, -Ser-OH, -Ser-Pro-OH, -Lys-Pro-OH-Arg-Phe-$NH_2$, -Glu-$NH_2$, —NHR, or —OR, where R is a $C_1$-$C_4$ straight or branched alkyl.

In yet another example embodiment, the MC4R agonist can be represented by the following structural formula:

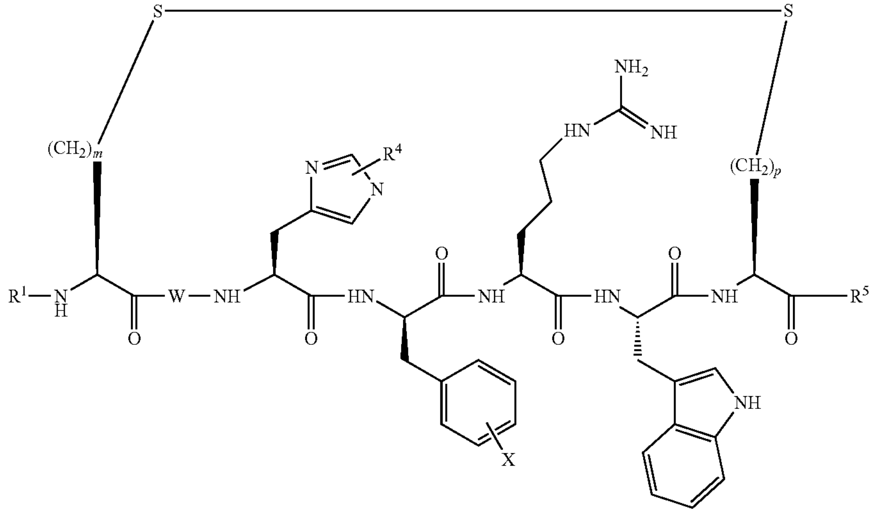

wherein

W is Glu, Gln, Asp, Ala, Gly, Thr, Ser, Pro, Met, Ile, Val, Arg, His, Tyr, Trp, Phe,

Lys, Leu, Cya, or is absent;

$R^1$ is —H, —C(O)$CH_3$, —C(O)$(CH_2)_{1-4}CH_3$, —C(O)$(CH_2)_{1-4}$NHC(NH)$NH_2$, Tyr-βArg-, Ac-Tyr-β-hArg-, gluconoyl-Tyr-Arg-, Ac-diaminobutyryl-, Ac-diaminopropionyl-, N-propionyl-, N-butyryl-, N-valeryl-, N-methyl-Tyr-Arg-, N-glutaryl-Tyr-Arg-, N-succinyl-Tyr-Arg-, $R^6$—$SO_2$NHC(O)$CH_2CH_2$C(O)—, $R^6$—$SO_2$NHC(O)$CH_2CH_2$C(O)Arg-, $R^6$—$SO_2NHCH_2CH_2CH_2$C(O)—, $C_3$-$C_7$ cycloalkylcarbonyl, phenylsulfonyl, $C_8$-$C_{14}$ bicyclic arylsulfonyl, phenyl-$(CH_2)_q$C(O)—, $C_8$-$C_{14}$ bicyclic aryl-$(CH_2)_q$C(O)—,

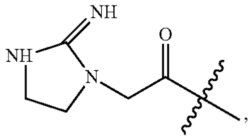,

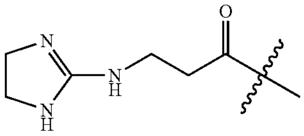

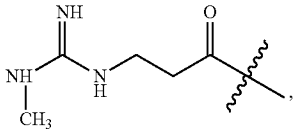,

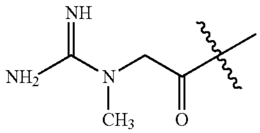, or 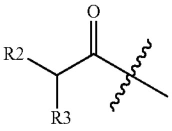, wherein $R^2$ is —H, —$NH_2$, —NHC(O)$CH_3$, —NHC(O)$(CH_2)_{1-4}CH_3$, —NH-TyrC(O)$CH_3$, $R^6SO_2$NH—, Ac-Cya-NH—, Tyr-NH—, HO—$(C_6H_5)$—$CH_2CH_2$C(O)NH—, or $CH_3$—$(C_6H_5)$—C(O)$CH_2CH_2$C(O)NH—;

$R^3$ is $C_1$-$C_4$ straight or branched alkyl, $NH_2$—$CH_2$—$(CH_2)_q$—, HO—$CH_2$—, $(CH_3)_2CHNH(CH_2)_4$—, $R^6(CH_2)_q$—, $R^6SO_2$NH—, Ser, Ile,

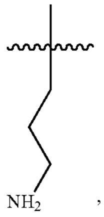, 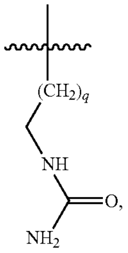 or 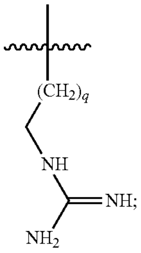;

q is 0, 1, 2, or 3;

$R^6$ is a phenyl or $C_8$-$C_{14}$ bicyclic aryl;

m is 1 or 2;

p is 1 or 2;

$R^4$ is H, $C_1$-$C_4$ straight or branched alkyl, phenyl, benzyl, or $(C_6H_5)$—$CH_2$—O—$CH_2$—;

X is H, Cl, F, Br, methyl, or methoxy; and $R^5$ is —$NH_2$, —OH, glycinol, $NH_2$-Pro-Ser-, $NH_2$-Pro-Lys-, HO-Ser-, HO-Pro-Ser-, HO-Lys-, -Ser alcohol, -Ser-Pro alcohol, -Lys-Pro alcohol, $HOCH_2CH_2$—O—$CH_2CH_2$NH—, $NH_2$-Phe-Arg-, $NH_2$-Glu-, $NH_2CH_2RCH_2$NH—, or RO— where R is a $C_1$-$C_4$ straight or branched alkyl.

Additional examples of MC4R agonists useful to practice the present invention are found in WO2011104378; WO2011104379; WO201060901; WO200887189, WO200887188, WO200887187, WO200887186; US20110065652; WO2010144341; WO2010144344; WO201065799; WO201065800; WO201065801; WO201065802; WO201037081; WO2009152079; WO2009151383; US20100311648; US20100280079; WO201081666; WO201034500; WO200910299; WO2008116665; WO201052256; WO201052255; WO201126015; US20100120783; WO201096854; US20100190793; WO201025142; and WO201015972. Further examples of MC4R agonists useful to practice the present invention are found in U.S. Pat. Nos. 8,263,608; 8,247,530; 8,114,844; and 7,968,548. The entire teachings of these publications are incorporated herein by reference.

In one example embodiment, the agonist of MC4R is a tripeptide D-Phe-Arg-Trp (SEQ ID NO: 560) or a pharmaceutical salt thereof. In another example, the agonist is any peptide that includes SEQ ID NO: 560 or a pharmaceutical salt thereof. In yet another example, the MC4R agonist is an acetylated tripeptide Ac-D-Phe-Arg-Trp-$NH_2$ (SEQ ID NO: 561) or a pharmaceutical salt thereof.

In an example embodiment, the agonists of MC4R are those of Formula (I) or a pharmaceutically acceptable salt, hydrate, solvate or a prodrug thereof (see International Patent Application Publication Number WO 2007/008704, incorporated herein by reference in its entirety):

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \quad \text{(I).}$$

In Formula (I):

$A^1$ is Acc, HN—$(CH_2)_m$—C(O), L- or D-amino acid, or deleted;

$A^2$ is Cys, D-Cys, hCys, D-hCys, Pen, D-Pen, Asp, or Glu;

$A^3$ is Gly, Ala, β-Ala, Gaba, Aib, D-amino acid, or deleted;

$A^4$ is His, 2-Pal, 3-Pal, 4-Pal, Taz, 2-Thi, 3-Thi, or ($X^1$, $X^2$, $X^3$, $X^4$, $X^5$) Phe;

$A^5$ is D-Phe, D-1-Nal, D-2-Nal, D-Trp, D-Bal, D-($X^1$, $X^2$, $X^3$, $X^4$, $X^5$) Phe, L-Phe or D-(Et) Tyr;

$A^6$ is Arg, hArg, Dab, Dap, Lys, Or, or HN—CH($(CH_2)_n$—N($R^4R^5$))—C(O);

$A^7$ is Trp, 1-Nal, 2-Nal, Bal, Bip, D-Trp, D-2-Nal, D-Bal or D-Bip;

$A^8$ is Gly, D-Ala, Acc, Ala, 13-Ala, Gaba, Apn, Ahx, Aha, HN—$(CH_2)_s$—C(O), or deleted;

$A^9$ is Cys, D-Cys, hCys, D-hCys, Pen, D-Pen, Dab, Dap, Orn, or Lys;

$A^{10}$ is Acc, HN—$(CH_2)$, —C(O), L- or D-amino acid, or deleted;

$R^1$ is OH or $NH_2$;

each of $R^2$ and $R^3$ is, independently for each occurrence, selected from the group consisting of H, ($C_1$-$C_{30}$)alkyl, ($C_1$-$C_{30}$) heteroalkyl, ($C_1$-$C_{30}$) acyl, ($C_2$-$C_{30}$)alkenyl, ($C_2$-$C_{30}$)alkynyl, aryl($C_1$-$C_{30}$)alkyl, aryl($C_1$-$C_{30}$) acyl, substituted ($C_1$-$C_{30}$)alkyl, substituted ($C_1$-$C_{30}$) heteroalkyl, substituted ($C_1$-$C_{30}$) acyl, substituted ($C_2$-$C_{30}$)alkenyl, substituted ($C_2$-$C_{30}$)alkynyl, substituted aryl($C_1$-$C_{30}$)alkyl, and substituted aryl($C_1$-$C_{30}$) acyl;

each of $R^4$ and $R^5$ is, independently for each occurrence, H, ($C_1$-$C_{40}$)alkyl, ($C_1$-$C_{40}$) heteroalkyl, ($C_1$-$C_{40}$) acyl, ($C_2$-$C_{40}$)alkenyl, ($C_2$-$C_{40}$)alkynyl, aryl($C_1$-$C_{40}$)alkyl, aryl($C_1$-$C_{40}$) acyl, substituted ($C_1$-$C_{40}$)alkyl, substituted ($C_1$-$C_{40}$) heteroalkyl, substituted ($C_1$-$C_{40}$) acyl, substituted ($C_2$-$C_{40}$)alkenyl, substituted ($C_2$-$C_{40}$)alkynyl, substituted aryl($C_1$-$C_{40}$)alkyl, substituted aryl($C_1$-$C_{40}$) acyl, ($C_1$-$C_{40}$)alkylsulfonyl, or —C(NH)—$NH_2$;

m is, independently for each occurrence, 1, 2, 3, 4, 5, 6 or 7;

n is, independently for each occurrence, 1, 2, 3, 4 or 5;

s is, independently for each occurrence, 1, 2, 3, 4, 5, 6, or 7;

tis, independently for each occurrence, 1, 2, 3, 4, 5, 6, or 7;

X', $X^2$, $X^3$, $X^4$, and $X^8$ each is, independently for each occurrence, H, F, Cl, Br, I, ($C_{1-10}$)alkyl, substituted ($C_{1-10}$)alkyl, ($C_{2-10}$)alkenyl, substituted ($C_{2-10}$)alkenyl, ($C_{2-10}$)alkynyl, substituted ($C_{2-10}$)alkynyl, aryl, substituted aryl, OH, $NH_2$, $NO_2$, or CN.

In exemplary embodiments of the agonists of Formula (I):

(I) when $R^4$ is ($C_1$-$C_{40}$) acyl, aryl($C_1$-$C_{40}$) acyl, substituted ($C_1$-$C_{40}$) acyl, substituted aryl($C_1$-$C_{40}$) acyl, ($C_1$-$C_{40}$)alkylsulfonyl, or —C(NH)—$NH_2$, then $R^5$ is H or ($C_1$-$C_{40}$)alkyl, ($C_1$-$C_{40}$) heteroalkyl, ($C_2$-$C_{40}$)alkenyl, ($C_2$-$C_{40}$)alkynyl, aryl($C_1$-$C_{40}$)alkyl, substituted ($C_1$-$C_{40}$)alkyl, substituted ($C_1$-$C_{40}$) heteroalkyl, substituted ($C_2$-$C_{40}$)alkenyl, substituted ($C_2$-$C_{40}$)alkynyl, or substituted aryl($C_1$-$C_{40}$)alkyl;

(II) when $R^2$ is ($C_1$-$C_{30}$) acyl, aryl($C_1$-$C_{30}$) acyl, substituted ($C_1$-$C_{30}$) acyl, or substituted aryl($C_1$-$C_{30}$) acyl, then $R^3$ is H, ($C_1$-$C_{30}$)alkyl, ($C_1$-$C_{30}$) heteroalkyl, ($C_2$-$C_{30}$)alkenyl, ($C_2$-$C_{30}$)alkynyl, aryl($C_1$-$C_{30}$)alkyl, substituted ($C_1$-$C_{30}$)alkyl, substituted ($C_1$-$C_{30}$) heteroalkyl, substituted ($C_2$-$C_{30}$)alkenyl, substituted ($C_2$-$C_{30}$) alkynyl, or substituted aryl($C_1$-$C_{30}$)alkyl;

(III) either $A^3$ or $A^8$ or both must be present in said compound;

(IV) when $A^2$ is Cys, D-Cys, hCys, D-hCys, Pen, or D-Pen, then $A^9$ is Cys, D-Cys, hCys, D-hCys, Pen, or D-Pcn;

(V) when $A^2$ is Asp or Glu, then $A^9$ is Dab, Dap, Orn, or Lys;

(VI) when $A^8$ is Ala or Gly, then $A^1$ is not NIe; and (VII) when $A^1$ is deleted, then $R^2$ and $R^3$ cannot both be H.

In an example embodiment, the agonists employed by the methods described herein are the compounds of Formula I, wherein:

$A^1$ is $A^6$c, Arg, D-Arg, Cha, D-Cha, hCha, Chg, D-Chg, Gaba, Ile, Leu, hLeu, Met, β-hMet, 2-Nal, D-2-Nal, Nip, Nle, Oic, Phe, D-Phe, hPhe, hPro, Val, or deleted;

$A^2$ is Asp, Cys, D-Cys, hCys, D-hCys, Glu, Pen, or D-Pen;

$A^3$ is D-Abu, Aib, Ala, β-Ala, D-Ala, D-Cha, Gaba, D-Glu, Gly, D-Ile, D-Leu, D-Tle, D-Val, or deleted;

$A^4$ is His or 3-Pal;

$A^5$ is D-Bal, D-1-Nal, D-2-Nal, D-Phe, D-Trp, or D-(Et) Tyr;

$A^6$ is Arg, or hArg;

$A^7$ is Bal, Bip, 1-Nal, 2-Nal, Trp, D-Trp;

$A^8$ is $A^6$c, D-Ala, Aha, Ahx, Ala, β-Ala, Apn, Gaba, Gly or deleted;

$A^9$ is Cys, D-Cys, hCys, D-hCys, Lys, Pen, or D-Pen;

$A^{10}$ is Thr, or deleted, wherein at least one of $A^3$ or $A^8$ is deleted, but not both, or pharmaceutically acceptable salts thereof.

In an example embodiments, agonists of Formula (I) useful in practicing the invention described herein are compounds of the following formula or a pharmaceutically acceptable salt thereof:

SEQ ID NO: 1

Ac-Nle-c(Asp-His-D-Phe-Arg-Trp-β-Ala-Lys)-$NH_2$;

SEQ ID NO: 2

Ac-Nle-c(Asp-His-D-Phe-Arg-Trp-A6c-Lys)-$NH_2$;

-continued

SEQ ID NO: 3
Ac-Nle-c(Cys-His-D-Phe-Arg-Trp-Ahx-Cys)-$NH_2$;

SEQ ID NO: 4
D-Phe-c(Cys-His-D-Phe-Arg-Trp-Ala-D-Cys)-Thr-$NH_2$;

SEQ ID NO: 5
D-Phe-c(Cys-His-D-Phe-Arg-Trp-β-Ala-D-Cys)-Thr-$NH_2$;

SEQ ID NO: 6
D-Phe-c(Cys-His-D-Phe-Arg-Trp-Gaba-D-Cys)-Thr-$NH_2$;

SEQ ID NO: 7
Ac-Nle-c(Cys-His-D-Phe-Arg-Trp-Apn-Cys)-$NH_2$;

SEQ ID NO: 8
Ac-Nle-c(Asp-His-D-Phe-Arg-Trp-Apn-Lys)-$NH_2$;

SEQ ID NO: 9
Ac-A6c-c(Asp-His-D-Phe-Arg-Trp-Gaba-Lys)-$NH_2$;

SEQ ID NO: 10
Ac-D-2-Nal-c(Asp-His-D-Phe-Arg-Trp-Gaba-Lys)-$NH_2$;

SEQ ID NO: 11
Ac-Cha-c(Asp-His-D-Phe-Arg-Trp-Gaba-Lys)-$NH_2$;

SEQ ID NO: 12
Ac-Nle-c(Asp-His-D-Phe-Arg-Trp-Gaba-Lys)-$NH_2$;

SEQ ID NO: 13
Ac-Nle-c(Cys-D-Ala-His-D-Phe-Arg-Trp-Cys)-$NH_2$;

SEQ ID NO: 14
Ac-Nle-c(Cys-β-Ala-His-D-Phe-Arg-Trp-Cys)-$NH_2$;

SEQ ID NO: 15
Ac-Nle-c(Cys-Gaba-His-D-Phe-Arg-Trp-Cys)-$NH_2$;

SEQ ID NO: 16
Ac-Nle-c(Cys-Aib-His-D-Phe-Arg-Trp-Cys)-$NH_2$;

SEQ ID NO: 17
Ac-Nle-c(Cys-Gly-His-D-Phe-Arg-Trp-Cys)-$NH_2$;

SEQ ID NO: 18
Ac-Nle-c(D-Cys-Ala-His-D-Phe-Arg-Trp-Cys)-$NH_2$;

SEQ ID NO: 19
Ac-Nle-c(D-Cys-D-Ala-His-D-Phe-Arg-Trp-Cys)-$NH_2$;

SEQ ID NO: 20
Ac-Nle-c(D-Cys-β-Ala-His-D-Phe-Arg-Trp-Cys)-$NH_2$;

SEQ ID NO: 21
Ac-Nle-c(D-Cys-Gaba-His-D-Phe-Arg-Trp-Cys)-$NH_2$;

SEQ ID NO: 22
Ac-Nle-c(D-Cys-Aib-His-D-Phe-Arg-Trp-Cys)-$NH_2$;

SEQ ID NO: 23
Ac-Nle-c(D-Cys-Gly-His-D-Phe-Arg-Trp-Cys)-$NH_2$;

SEQ ID NO: 24
Ac-Nle-c(Cys-D-Ala-His-D-Phe-Arg-Trp-D-Cys)-$NH_2$;

SEQ ID NO: 25
Ac-Nle-c(Cys-β-Ala-His-D-Phe-Arg-Trp-D-Cys)-$NH_2$;

SEQ ID NO: 26
Ac-Nle-c(Cys-Gaba-His-D-Phe-Arg-Trp-D-Cys)-$NH_2$;

SEQ ID NO: 27
Ac-Nle-c(Cys-Aib-His-D-Phe-Arg-Trp-D-Cys)-$NH_2$;

SEQ ID NO: 28
Ac-Nle-c(Cys-Gly-His-D-Phe-Arg-Trp-D-Cys)-$NH_2$;

SEQ ID NO: 29
Ac-Nle-c(D-Cys-Ala-His-D-Phe-Arg-Trp-D-Cys)-$NH_2$;

-continued

SEQ ID NO: 30
Ac-Nle-c(D-Cys-D-Ala-His-D-Phe-Arg-Trp-D-Cys)-$NH_2$;

SEQ ID NO: 31
Ac-Nle-c(D-Cys-β-Ala-His-D-Phe-Arg-Trp-D-Cys)-$NH_2$;

SEQ ID NO: 32
Ac-Nle-c(D-Cys-Gaba-His-D-Phe-Arg-Trp-D-Cys)-$NH_2$;

SEQ ID NO: 33
Ac-Nle-c(D-Cys-Aib-His-D-Phe-Arg-Trp-D-Cys)-$NH_2$;

SEQ ID NO: 34
Ac-Oic-c(Asp-His-D-Phe-Arg-Trp-Gaba-Lys)-$NH_2$;

SEQ ID NO: 35
Ac-Chg-c(Asp-His-D-Phe-Arg-Trp-Gaba-Lys)-$NH_2$;

SEQ ID NO: 36
Ac-hCha-c(Asp-His-D-Phe-Arg-Trp-Gaba-Lys)-$NH_2$;

SEQ ID NO: 37
Ac-D-Cha-c(Asp-His-D-Phe-Arg-Trp-Gaba-Lys)-$NH_2$;

SEQ ID NO: 38
Ac-D-hCha-c(Asp-His-D-Phe-Arg-Trp-Gaba-Lys)-$NH_2$;

SEQ ID NO: 39
Ac-Nip-c(Asp-His-D-Phe-Arg-Trp-Gaba-Lys)-$NH_2$;

SEQ ID NO: 40
Ac-hPro-c(Asp-His-D-Phe-Arg-Trp-Gaba-Lys)-$NH_2$;

SEQ ID NO: 41
Ac-hLeu-c(Asp-His-D-Phe-Arg-Trp-Gaba-Lys)-$NH_2$;

SEQ ID NO: 42
Ac-Phe-c(Asp-His-D-Phe-Arg-Trp-Gaba-Lys)-$NH_2$;

SEQ ID NO: 43
Ac-D-Phe-c(Asp-His-D-Phe-Arg-Trp-Gaba-Lys)-$NH_2$;

SEQ ID NO: 44
Ac-D-Chg-c(Asp-His-D-Phe-Arg-Trp-Gaba-Lys)-$NH_2$;

SEQ ID NO: 45
n-butanoyl-Cha-c(Asp-His-D-Phe-Arg-Trp-Gaba-Lys)-$NH_2$;

SEQ ID NO: 46
n-butyryl-Cha-c(Asp-His-D-Phe-Arg-Trp-Gaba-Lys)-$NH_2$;

SEQ ID NO: 47
Ac-hPhe-c(Asp-His-D-Phe-Arg-Trp-Gaba-Lys)-$NH_2$;

SEQ ID NO: 48
Ac-β-hMet-c(Asp-His-D-Phe-Arg-Trp-Gaba-Lys)-$NH_2$;

SEQ ID NO: 49
Ac-Gaba-c(Asp-His-D-Phe-Arg-Trp-Gaba-Lys)-$NH_2$;

SEQ ID NO: 50
Ac-Cha-c(Asp-His-D-Phe-Arg-D-Trp-Ala-Lys)-$NH_2$;

SEQ ID NO: 51
Ac-hCha-c(Asp-His-D-Phe-Arg-D-Trp-Ala-Lys)-$NH_2$;

SEQ ID NO: 52
Ac-Leu-c(Asp-His-D-Phe-Arg-D-Trp-Ala-Lys)-$NH_2$;

SEQ ID NO: 53
Ac-hLeu-c(Asp-His-D-Phe-Arg-D-Trp-Ala-Lys)-$NH_2$;

SEQ ID NO: 54
Ac-Phe-c(Asp-His-D-Phe-Arg-D-Trp-Ala-Lys)-$NH_2$;

SEQ ID NO: 55
Ac-Nle-c(Asp-His-D-Phe-Arg-D-Trp-D-Ala-Lys)-$NH_2$;

SEQ ID NO: 56
Ac-Nle-c(Asp-His-D-Phe-Arg-D-Trp-β-Ala-Lys)-$NH_2$;

-continued

SEQ ID NO: 57
Ac-Nle-c(Asp-His-D-Phe-Arg-D-Trp-Gaba-Lys)-$NH_2$;

SEQ ID NO: 58
Ac-Nle-c(Asp-His-D-Phe-Arg-D-Trp-Aha-Lys)-$NH_2$;

SEQ ID NO: 59
Ac-Nle-c(Asp-His-D-Phe-Arg-D-Trp-Apn-Lys)-$NH_2$;

SEQ ID NO: 60
Ac-Nle-c(Cys-His-D-Phe-Arg-D-Trp-Apn-Cys)-$NH_2$;

SEQ ID NO: 61
Ac-Nle-c(Cys-His-D-Phe-Arg-D-Trp-Gaba-Cys)-$NH_2$;

SEQ ID NO: 62
Ac-Nle-c(Cys-His-D-Phe-Arg-D-Trp-Ahx-Cys)-$NH_2$;

SEQ ID NO: 63
Ac-Nle-c(Cys-His-D-Phe-Arg-D-Trp-β-Ala-Cys)-$NH_2$;

SEQ ID NO: 64
Ac-Nle-c(Cys-His-D-Phe-Arg-D-Trp-D-Ala-Cys)-$NH_2$;

SEQ ID NO: 65
Ac-Nle-c(Cys-D-Ala-His-D-2-Nal-Arg-Trp-Cys)-$NH_2$;

SEQ ID NO: 66
Ac-Nle-c(Cys-D-Ala-His-D-2-Nal-Arg-2-Nal-Cys)-$NH_2$;

SEQ ID NO: 67
Ac-Nle-c(Cys-D-Ala-His-D-2-Nal-Arg-1-Nal-Cys)-$NH_2$;

SEQ ID NO: 68
n-butanoyl-Nle-c(Cys-D-Ala-His-D-Phe-Arg-2-Nal-Cys)-$NH_2$;

SEQ ID NO: 69
n-butanoyl-Nle-c(Cys-D-Ala-His-D-Phe-Arg-Trp-Cys)-$NH_2$;

SEQ ID NO: 70
Ac-Nle-c(Cys-D-Ala-His-D-Phe-Arg-2-Nal-Cys)-$NH_2$;

SEQ ID NO: 71
Ac-Nle-c(Cys-D-Ala-His-D-Phe-Arg-1-Nal-Cys)-$NH_2$;

SEQ ID NO: 72
Ac-Nle-c(Cys-D-Ala-His-D-Phe-Arg-Bal-Cys)-$NH_2$;

SEQ ID NO: 73
Ac-Nle-c(Cys-D-Glu-His-D-Phe-Arg-Trp-Cys)-$NH_2$;

SEQ ID NO: 74
Ac-Nle-c(Asp-His-D-Phe-Arg-Trp-D-Ala-Lys)-$NH_2$;

SEQ ID NO: 75
Ac-Nle-c(Cys-D-Ala-His-D-2-Nal-Arg-Bal-Cys)-$NH_2$;

SEQ ID NO: 76
Ac-Nle-c(Pen-D-Ala-His-D-Phe-Arg-Trp-Cys)-$NH_2$;

SEQ ID NO: 77
Ac-Nle-c(Cys-D-Ala-His-D-Phe-Arg-Trp-Pen)-$NH_2$;

SEQ ID NO: 78
Ac-Nle-c(Pen-D-Ala-His-D-Phe-Arg-Trp-Pen)-$NH_2$;

SEQ ID NO: 79
D-Phe-c(Cys-His-D-Phe-hArg-Trp-β-Ala-D-Cys)-Thr-$NH_2$;

SEQ ID NO: 80
D-Phe-c(Cys-His-D-(Et)Tyr-Arg-Trp-β-Ala-D-Cys)-Thr-$NH_2$;

SEQ ID NO: 81
D-Phe-c(Cys-His-D-Phe-Arg-Bip-β-Ala-D-Cys)-Thr-$NH_2$;

SEQ ID NO: 82
D-Phe-c(Cys-His-D-(Et)Tyr-hArg-Trp-β-Ala-D-Cys)-Thr-$NH_2$;

SEQ ID NO: 83
D-Phe-c(Cys-His-D-Phe-hArg-Bip-β-Ala-D-Cys)-Thr-$NH_2$;

-continued

SEQ ID NO: 84
D-Phe-c(Cys-His-D-(Et)Tyr-hArg-Bip-β-Ala-D-Cys)-Thr-$NH_2$;

SEQ ID NO: 85
Nle-c(Cys-His-D-Phe-Arg-Trp-Apn-Cys)-$NH_2$;

SEQ ID NO: 86
Ac-Nle-c(Asp-D-Ala-His-D-Phe-Arg-Trp-Lys)-$NH_2$;

SEQ ID NO: 87
Ac-Nle-c(Asp-D-Ala-His-D-Phe-Arg-Bal-Lys)-$NH_2$;

SEQ ID NO: 88
Ac-Nle-c(Cys-D-Ala-His-D-Phe-Arg-Trp-Pen)-OH;

SEQ ID NO: 89
Ac-Nle-c(Cys-D-Abu-His-D-Phe-Arg-Trp-Cys)-$NH_2$;

SEQ ID NO: 90
Ac-Nle-c(Cys-D-Val-His-D-Phe-Arg-Trp-Cys)-$NH_2$;

SEQ ID NO: 91
Ac-Nle-c(Cys-D-Ile-His-D-Phe-Arg-Trp-Cys)-$NH_2$;

SEQ ID NO: 92
Ac-Nle-c(Cys-D-Leu-His-D-Phe-Arg-Trp-Cys)-$NH_2$;

SEQ ID NO: 93
Ac-Nle-c(Cys-D-Tle-His-D-Phe-Arg-Trp-Cys)-$NH_2$;

SEQ ID NO: 94
Ac-Nle-c(Cys-D-Cha-His-D-Phe-Arg-Trp-Cys)-$NH_2$;

SEQ ID NO: 95
Ac-Nle-c(Pen-His-D-Phe-Arg-Trp-Gaba-Cys)-$NH_2$;

SEQ ID NO: 96
Ac-Nle-c(Cys-His-D-Phe-Arg-Trp-Gaba-Pen)-$NH_2$;

SEQ ID NO: 97
Ac-Nle-c(Pen-His-D-Phe-Arg-Trp-Gaba-Pen)-$NH_2$;

SEQ ID NO: 98
Ac-Leu-c(Cys-His-D-Phe-Arg-Trp-Gaba-Cys)-$NH_2$;

SEQ ID NO: 99
Ac-Cha-c(Cys-His-D-Phe-Arg-Trp-Gaba-Cys)-$NH_2$;

SEQ ID NO: 100
Ac-Ile-c(Cys-His-D-Phe-Arg-Trp-Gaba-Cys)-$NH_2$;

SEQ ID NO: 101
Ac-Phe-c(Cys-His-D-Phe-Arg-Trp-Gaba-Cys)-$NH_2$;

SEQ ID NO: 102
Ac-Val-c(Cys-His-D-Phe-Arg-Trp-Gaba-Cys)-$NH_2$;

SEQ ID NO: 103
Ac-2-Nal-c(Cys-His-D-Phe-Arg-Trp-Gaba-Cys)-$NH_2$;

SEQ ID NO: 104
Nle-c(Cys-His-D-Phe-Arg-Trp-Gaba-Cys)-$NH_2$;

SEQ ID NO: 105
Phe-c(Cys-His-D-Phe-Arg-Trp-Gaba-Cys)-$NH_2$;

SEQ ID NO: 106
Ac-Nle-c(Cys-β-Pal-D-Phe-Arg-Trp-Gaba-Cys)-$NH_2$;

SEQ ID NO: 107
Ac-Nle-c(Cys-D-Ala-His-D-Phe-Arg-Trp-Cys)-OH;

SEQ ID NO: 108
Ac-Nle-c(Cys-His-Phe-Arg-D-Trp-Gaba-Cys)-$NH_2$;

SEQ ID NO: 109
Ac-Nle-c(Asp-His-D-2-Nal-Arg-Trp-Ala-Lys)-$NH_2$;

SEQ ID NO: 110
Ac-Nle-c(Asp-His-D-2-Nal-Arg-Trp-β-Ala-Lys)-$NH_2$;

-continued

SEQ ID NO: 111
Ac-Nle-c(Cys-His-D-2-Nal-Arg-Trp-Gaba-Cys)-$NH_2$;

SEQ ID NO: 112
Ac-Nle-c(Cys-His-D-2-Nal-Arg-Trp-Ahx-Cys)-$NH_2$;

SEQ ID NO: 113
Ac-hPhe-c(Asp-His-D-2-Nal-Arg-Trp-Gaba-Lys)-$NH_2$;

SEQ ID NO: 114
Ac-Cha-c(Asp-His-D-2-Nal-Arg-Trp-Gaba-Lys)-$NH_2$;

SEQ ID NO: 115
Ac-Nle-c(Asp-His-D-Phe-Arg-Trp-β-Ala-Lys)-OH;

SEQ ID NO: 116
Ac-Nle-c(Cys-His-D-Phe-Arg-Trp-Ahx-Cys)-OH;

SEQ ID NO: 117
D-Phe-c(Cys-His-D-Phe-Arg-Trp-Ala-D-Cys)-Thr-OH;

SEQ ID NO: 118
D-Phe-c(Cys-His-D-Phe-Arg-Trp-β-Ala-D-Cys)-Thr-OH;

SEQ ID NO: 119
D-Phe-c(Cys-His-D-Phe-Arg-Trp-Gaba-D-Cys)-Thr-OH;

SEQ ID NO: 120
Ac-Nle-c(Cys-His-D-Phe-Arg-Trp-Apn-Cys)-OH;

SEQ ID NO: 121
Ac-Nle-c(Asp-His-D-Phe-Arg-Trp-Apn-Lys)-OH;

SEQ ID NO: 122
Ac-Cha-c(Asp-His-D-Phe-Arg-Trp-Gaba-Lys)-OH;

SEQ ID NO: 123
Ac-Nle-c(Asp-His-D-Phe-Arg-Trp-Gaba-Lys)-OH;

SEQ ID NO: 124
Ac-Chg-c(Asp-His-D-Phe-Arg-Trp-Gaba-Lys)-OH;

SEQ ID NO: 125
Ac-D-Cha-c(Asp-His-D-Phe-Arg-Trp-Gaba-Lys)-OH;

SEQ ID NO: 126
Ac-hCha-c(Asp-His-D-Phe-Arg-Trp-Gaba-Lys)-OH;

SEQ ID NO: 127
Ac-D-Chg-c(Asp-His-D-Phe-Arg-Trp-Gaba-Lys)-OH;

SEQ ID NO: 128
Ac-hPhe-c(Asp-His-D-Phe-Arg-Trp-Gaba-Lys)-OH;

SEQ ID NO: 129
Ac-Nle-c(Cys-His-D-Phe-Arg-D-Trp-Gaba-Cys)-OH;

SEQ ID NO: 130
Ac-Nle-c(Cys-His-D-Phe-Arg-D-Trp-Ahx-Cys)-OH;

SEQ ID NO: 131
Ac-Nle-c(Cys-His-D-Phe-Arg-D-Trp-β-Ala-Cys)-OH;

SEQ ID NO: 132
Ac-Nle-c(Cys-His-D-Phe-Arg-D-Trp-D-Ala-Cys)-OH;

SEQ ID NO: 133
Ac-Nle-c(Cys-D-Ala-His-D-2-Nal-Arg-Trp-Cys)-OH;

SEQ ID NO: 134
Ac-Nle-c(Cys-D-Ala-His-D-2-Nal-Arg-2-Nal-Cys)-OH;

SEQ ID NO: 135
Ac-Nle-c(Cys-D-Ala-His-D-2-Nal-Arg-1-Nal-Cys)-OH;

SEQ ID NO: 136
Ac-Nle-c(Cys-D-Ala-His-D-2-Nal-Arg-Bal-Cys)-OH;

SEQ ID NO: 137
Ac-Nle-c(Pen-D-Ala-His-D-Phe-Arg-Trp-Cys)-OH;

-continued

SEQ ID NO: 138
Ac-Nle-c(Cys-His-D-Phe-Arg-Trp-Gaba-Pen)-OH;

SEQ ID NO: 139
Ac-Arg-c(Cys-D-Ala-His-D-2-Nal-Arg-Trp-Cys)-$NH_2$;

SEQ ID NO: 140
Ac-Arg-c(Cys-D-Ala-His-D-Phe-Arg-Trp-Cys)-$NH_2$;

SEQ ID NO: 141
Ac-D-Arg-c(Cys-D-Ala-His-D-Phe-Arg-Trp-Cys)-$NH_2$;

SEQ ID NO: 142
Ac-D-Arg-c(Cys-D-Ala-His-D-Phe-Arg-Trp-Pen)-$NH_2$;

SEQ ID NO: 143
Ac-D-Arg-c(Cys-His-D-Phe-Arg-Trp-Gaba-Pen)-$NH_2$;

SEQ ID NO: 144
Ac-Arg-c(Cys-His-D-Phe-Arg-Trp-Gaba-Pen)-$NH_2$;

SEQ ID NO: 145
Ac-Arg-c(Cys-D-Ala-His-D-Phe-Arg-Trp-Pen)-$NH_2$;

SEQ ID NO: 146
Ac-D-Arg-c(Asp-His-D-Phe-Arg-Trp-Ala-Lys)-$NH_2$;
or

SEQ ID NO: 147
Ac-Arg-c(Asp-His-D-Phe-Arg-Trp-Ala-Lys)-$NH_2$;

or pharmaceutically acceptable salts thereof.

In an example embodiment, an agonist of MC4R receptor useful for practicing methods described herein is any of the compounds described by Formula (II) or a pharmaceutically acceptable salt, hydrate, solvate or a prodrug thereof (see International Patent Application Publication Number WO 2007/008704 incorporated herein by reference in its entirety):

$$(R^2R^3)\text{-}A^1\text{-}c(A^2\text{-}A^3\text{-}A^4\text{-}A^5\text{-}A^6\text{-}A^7\text{-}A^8\text{-}A^9)\text{—}NH_2 \quad \text{(II)}$$

In formula (11):

$A^1$ is Nle or deleted;

$A^2$ is Cys or Asp;

$A^3$ is Glu or D-Ala;

$A^4$ is His;

$A^5$ is D-Phe;

$A^6$ is Arg;

$A^7$ is Trp, 2-Nal or Bal;

$A^8$ is Gly, Ala, D-Ala, (3-Ala, Gaba or Apn;

$A^9$ is Cys or Lys;

each of $R^2$ and $R^3$ is independently selected from the group consisting of H or ($C_1$-$C_6$) acyl.

In exemplary embodiments of Formula (II):

(I) when $R^2$ is ($C_1$-$C_6$) acyl, then $R^3$ is H; and (II) when $A^2$ is Cys, then $A^9$ is Cys.

In alternative example embodiments of the present invention, the compounds useful for practicing the methods disclosed herein are:

SEQ ID NO:148
Ac-Nle-c(Cys-D-Ala-His-D-Phe-Arg-Trp-Gly-Cys)-$NH_2$;

SEQ ID NO: 149
Ac-Nle-c(Cys-D-Ala-His-D-Phe-Arg-Trp-D-Ala-Cys)$NH_2$;

SEQ ID NO: 150
Ac-Nle-c(Cys-D-Ala-His-D-Phe-Arg-Trp-β-Ala-Cys)-$NH_2$;

-continued

SEQ ID NO: 151
Ac-Nle-c(Cys-D-Ala-His-D-Phe-Arg-Trp-Gaba-Cys)-$NH_2$;

SEQ ID NO: 152
Ac-Nle-c(Cys-D-Ala-His-D-Phe-Arg-Trp-Apn-Cys)-$NH_2$;

SEQ ID NO: 153
Ac-c(Cys-Glu-His-D-Phe-Arg-Trp-Ala-Cys)-$NH_2$;

SEQ ID NO: 154
Ac-c(Cys-Glu-His-D-Phe-Arg-2-Nal-Ala-Cys)-$NH_2$;

SEQ ID NO: 155
Ac-c(Cys-D-Ala-His-D-Phe-Arg-Trp-Ala-Cys)-$NH_2$;

SEQ ID NO: 156
Ac-c(Cys-D-Ala-His-D-Phe-Arg-2-Nal-Ala-Cys)-$NH_2$;

SEQ ID NO: 157
Ac-Nle-c(Cys-D-Ala-His-D-Phe-Arg-Trp-Ala-Cys)-$NH_2$;
or

SEQ ID NO: 158
Ac-Nle-c(Asp-D-Ala-His-D-Phe-Arg-Bal-Ala-Lys)-$NH_2$;

or a pharmaceutically acceptable salt thereof.

In an exemplary embodiment, the agonists of MC4R useful for practicing the methods described herein is any of the compounds of Formula (III), or a pharmaceutically acceptable salt, hydrate, solvate or a prodrug thereof (see International Application Publication Number WO 2007/008684, incorporated herein by reference in its entirety):

$$(R^2R^3)\text{—}B^1\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}A^{11}\text{-}A^{12}\text{-}A^{13}\text{-}B^2\text{—}B^3\text{—}R^1 \quad \text{(III).}$$

In Formula (III):

$B^1$ is a peptide moiety which contains 5, 6, 7, 8, 9, 10, 11, 12, 13, 14, or 15 amino acids, wherein at least 5 amino acids are independently selected from the group consisting of L-Arg, D-Arg, L-hArg and D-hArg, or $B^1$ is optionally deleted;

$A^1$ is Acc, HN—$(CH_2)_m$—C(O), L- or D-amino acid or deleted;

$A^2$ is Cys, D-Cys, hCys, D-hCys, Pen, D-Pen, Asp or Glu;

$A^3$ is Gly, Glu, Ala, β-Ala, Gaba, Aib, D-amino acid or deleted;

$A^4$ is His, 2-Pal, 3-Pal, 4-Pal, Taz, 2-Thi, 3-Thi or (X', $X^2$, $X^3$, $X^4$, $X^5$) Phe;

$A^5$ is D-Phe, D-1-Nal, D-2-Nal, D-Trp, D-Bal, D-($X^1$, $X^2$, $X^3$, $X^4$, $X^5$) Phe, D-(Et) Tyr, D-Dip, D-Bip or D-Bpa, $A^6$ is Arg, hArg, Dab, Dap, Lys, Orn or HN—CH($(CH_2)_n$—N($R^4R^5$))—C(O);

$A^7$ is Trp, 1-Nal, 2-Nal, Bal, Bip, Dip, Bpa, D-Trp, D-1-Nal, D-2-Nal, D-Bal, D-Bip, D-Dip or D-Bpa;

$A^8$ is Gly, D-Ala, Acc, Ala, β-Ala, Gaba, Apn, Ahx, Aha, HN—$(CH_2)_s$—C(O) or deleted;

$A^9$ is Cys, D-Cys, hCys, D-hCys, Pen, D-Pen, Dab, Dap, Orn or Lys;

$A^{10}$ is Acc, HN—$(CH_2)_t$—C(O), Pro, hPro, 3-Hyp, 4-Hyp, Thr, an L- or D-amino acid or deleted;

$A^{11}$ is Pro, hPro, 3-Hyp, 4-Hyp or deleted;

$A^{12}$ is Lys, Dab, Dap, Arg, hArg or deleted;

$A^{13}$ is Asp, Glu or deleted;

$B^2$ is a peptide moiety containing 1, 2, 3, 4, or 5 amino acids or deleted, $B^3$ is a peptide moiety which contains 5, 6, 7, 8, 9, 10, 11, 12, 13, 14 or 15 amino acids wherein at least 5 amino acids are independently selected from the group consisting of L-Arg, D-Arg, L-hArg and D-hArg, or is deleted;

$R^1$ is OH or $NH_2$;

$R^2$ and $R^3$ each is, independently for each occurrence, selected from the group consisting of H, ($C_1$-$C_{30}$)alkyl, ($C_1$-$C_{30}$) heteroalkyl, ($C_1$-$C_{30}$) acyl, ($C_2$-$C_{30}$)alkenyl, ($C_2$-$C_{30}$)alkynyl, aryl($C_1$-$C_{30}$)alkyl, aryl($C_1$-$C_{30}$) acyl, substituted ($C_1$-$C_{30}$)alkyl, substituted ($C_1$-$C_{30}$) heteroalkyl, substituted ($C_1$-$C_{30}$) acyl, substituted ($C_2$-$C_{30}$)alkenyl, substituted ($C_2$-$C_{30}$)alkynyl, substituted aryl($C_1$-$C_{30}$)alkyl and substituted aryl($C_1$-$C_{30}$) acyl;

$R^4$ and $R^5$ each is, independently for each occurrence, H, ($C_1$-$C_{40}$)alkyl, ($C_1$-$C_{40}$) heteroalkyl, ($C_1$-$C_{40}$) acyl, ($C_2$-$C_{40}$)alkenyl, ($C_2$-$C_{40}$)alkynyl, aryl($C_1$-$C_{40}$)alkyl, aryl($C_1$-$C_{40}$) acyl, substituted ($C_1$-$C_{40}$)alkyl, substituted ($C_1$-$C_{40}$) heteroalkyl, substituted ($C_1$-$C_{40}$) acyl, substituted ($C_2$-$C_{40}$)alkenyl, substituted ($C_2$-$C_{40}$)alkynyl, substituted aryl($C_1$-$C_{40}$)alkyl, substituted aryl($C_1$-$C_{40}$) acyl, ($C_1$-$C_{40}$)alkylsulfonyl or C(NH)—$NH_2$;

n is, independently for each occurrence, 1, 2, 3, 4 or 5;

m is, independently for each occurrence, 1, 2, 3, 4, 5, 6 or 7;

s is, independently for each occurrence, 1, 2, 3, 4, 5, 6 or 7;

t is, independently for each occurrence, 1, 2, 3, 4, 5, 6 or 7;

$X^1$, $X^2$, $X^3$, $X^4$ and $X^5$ each is, independently for each occurrence, H, F, Cl, Br, I, ($C_{1-10}$)alkyl, substituted ($C_{1-10}$)alkyl, ($C_{2-10}$)alkenyl, substituted ($C_{2-10}$)alkenyl, ($C_{2-10}$)alkynyl, substituted ($C_{2-10}$)alkynyl, aryl, substituted aryl, OH, $NH_2$, $NO_2$ or CN.

In an example embodiments of Formula (III):

(I) when $R^4$ is ($C_1$-$C_{40}$) acyl, aryl($C_1$-$C_{40}$) acyl, substituted ($C_1$-$C_{40}$) acyl, substituted aryl($C_1$-$C_{40}$) acyl, ($C_1$-$C_{40}$)alkylsulfonyl or C(NH) $NH_2$, then $R^5$ is H, ($C_1$-$C_{40}$)alkyl, ($C_1$-$C_{40}$) heteroalkyl, ($C_2$-$C_{40}$)alkenyl, ($C_2$-$C_{40}$)alkynyl, aryl($C_1$—$C_{40}$)alkyl, substituted ($C_1$-$C_{40}$) alkyl, substituted ($C_1$-$C_{40}$) heteroalkyl, substituted ($C_2$-$C_{40}$)alkenyl, substituted ($C_2$-$C_{40}$)alkynyl or substituted aryl($C_1$-$C_{40}$)alkyl;

(II) when $R^2$ is ($C_1$-$C_{30}$) acyl, aryl($C_1$-$C_{30}$) acyl, substituted ($C_1$-$C_{30}$) acyl or substituted aryl($C_1$-$C_{30}$) acyl, then $R^3$ is H, ($C_1$-$C_{30}$)alkyl, ($C_1$-$C_{30}$) heteroalkyl, ($C_2$-$C_{30}$)alkenyl, ($C_2$-$C_{30}$)alkynyl, aryl($C_1$-$C_{30}$)alkyl, substituted ($C_1$-$C_{30}$)alkyl, substituted ($C_1$-$C_{30}$) heteroalkyl, substituted ($C_2$-$C_{30}$)alkenyl, substituted ($C_2$-$C_{30}$) alkynyl or substituted aryl($C_1$-$C_{30}$)alkyl;

(III) neither $B^1$ nor $B^2$ contains one or more of the following amino acid sequences: Arg-$(Lys)_2$-$(Arg)_2$-Gln-$(Arg)_3$, Tyr-Ala-Arg-Lys-Ala-$(Arg)_2$-Gln-Ala-$(Arg)_2$, Tyr-Ala-Arg-$(Ala)_2$-$(Arg)_2$-$(Ala)_2$-$(Arg)_2$, Tyr-Ala-$(Arg)_9$, Tyr-$(Ala)_3$-$(Arg)_7$, Tyr-Ala-Arg-Ala-Pro-$(Arg)_2$-Ala-$(Arg)_3$ or Tyr-Ala-Arg-Ala-Pro-$(Arg)_2$-Pro-$(Arg)_2$;

(IV) either $B^1$ or $B^2$ or both must be present in said compound;

(V) when $A^2$ is Cys, D-Cys, hCys, D-hCys, Pen or D-Pen, then $A^9$ is Cys,

D-Cys, hCys, D-hCys, Pen or D-Pen; and (VI) when $A^2$ is Asp or Glu, then $A^9$ is Dab, Dap, Orn or Lys.

In exemplary embodiments, in Formula (III);

$B^1$ is Arg-Lys-Gln-Lys-$(Arg)_5$, Arg-$(Lys)_2$-Arg-Gln-$(Arg)_4$, Arg-$(Lys)_2$-$(Arg)_3$-Gln-$(Arg)_2$, Arg-$(Lys)_2$-$(Arg)_4$-Gln-Arg, Arg-$(Lys)_2$-$(Arg)_5$-Gln, Arg-$(Lys)_2$-Gln-$(Arg)_5$, Arg-Gln-$(Lys)_2$-$(Arg)_5$, Arg-Gln-$(Arg)_7$, Arg-Gln-$(Arg)_8$, $(Arg)_2$-Gln-$(Arg)_6$, $(Arg)_2$-Gln-$(Arg)_7$, $(Arg)_3$-Gln-$(Arg)_5$, $(Arg)_3$-Gln-$(Arg)_6$, $(Arg)_4$-Gln-$(Arg)_4$, $(Arg)_4$-Gln-$(Arg)_5$, $(Arg)_5$, $(Arg)_5$-Gln-$(Arg)_3$, $(Arg)_5$-Gln-$(Arg)_4$, $(Arg)_6$, $(Arg)_6$-Gln-$(Arg)_3$, $(Arg)_7$, $(Arg)_7$-Gln-$(Arg)_2$, $(Arg)_8$, (Arg)s-Gln-Arg, $(Arg)_9$, $(Arg)_9$-Gln, (D-$Arg)_5$, (D-$Arg)_6$, (D-$Arg)_7$, (D-$Arg)_8$, (D-$Arg)_9$, Gln-Arg-$(Lys)_2$-$(Arg)_5$, Gln-$(Arg)_8$, Gln-$(Arg)_9$, Tyr-Gly-Arg-$(Lys)_2$-$(Arg)_2$-Gln-$(Arg)_3$, Tyr-Gly-Arg-$(Lys)_2$-$(Arg)_2$-Gln-$(Arg)_3$-Doc; or deleted;

$B^2$ is β-Ala, β-Ala-Gly, β-Ala-Tyr, β-Ala-Tyr-Gly, $(β\text{-}Ala)_2$, $(β\text{-}Ala)_2$-Gly, $(β\text{-}Ala)_2$-Tyr, $(β\text{-}Ala)_2$-Tyr-Gly, Doc, Doc-Gly, Doc-Tyr, Doc-Tyr-Gly, $(Doc)_2$, $(Doc)_2$-Gly, $(Doc)_2$-Tyr, $Doc)_2$-Tyr-Gly, or deleted;

$B^3$ is Arg-Lys-Gln-Lys-$(Arg)_5$, Arg-Lys-$(Arg)_3$-Gln-$(Arg)_3$, Arg-$(Lys)_2$-Arg-Gln-$(Arg)_4$, Arg-$(Lys)_2$-Gln-$(Arg)_5$, Arg-$(Lys)_2$-$(Arg)_2$-Gln-$(Arg)_3$, Arg-$(Lys)_2$-$(Arg)_3$-Gln-$(Arg)_2$, Arg-$(Lys)_2$-$(Arg)_4$-Gln-Arg, Arg-$(Lys)_2$-$(Arg)_5$-Gln, Arg-Gln-$(Lys)_2$-$(Arg)_5$, Arg-Gln-$(Arg)_7$, Arg-Gln-$(Arg)_s$, $(Arg)_2$-Lys-$(Arg)_2$-Gln-$(Arg)_3$, $(Arg)_2$-Gln-$(Arg)_6$, $(Arg)_2$-Gln-$(Arg)_7$, $(Arg)_3$-Gln-$(Arg)_5$, $(Arg)_3$-Gln-$(Arg)_6$, $(Arg)_4$-Gln-$(Arg)_4$, $(Arg)_4$-Gln-$(Arg)_5$, $(Arg)_5$, $(Arg)_s$-Gln-$(Arg)_3$, $(Arg)_5$-Gln-$(Arg)_4$, $(Arg)_6$, $(Arg)_6$-Gln-$(Arg)_3$, $(Arg)_7$, $(Arg)_7$-Gln-$(Arg)_2$, $(Arg)_8$, $(Arg)_s$-Gln-Arg, $(Arg)_9$, $(Arg)_9$-Gln, (D-$Arg)_5$, (D-$Arg)_6$, (D-$Arg)_7$, (D-$Arg)_8$, (D-$Arg)_9$, Gln-Arg-$(Lys)_2$-$(Arg)_5$, Gln-$(Arg)_8$, Gln-$(Arg)_9$, or deleted;

$A^1$ is A6c, Cha, hCha, Chg, D-Chg, hChg, Gaba, hLeu, Met, β-hMet, D-2-Nal, Nip, Nle, Oic, Phe, D-Phe, hPhe, hPro, or deleted;

$A^2$ is Cys;

$A^3$ is D-Abu, Aib, Ala, β-Ala, D-Ala, D-Cha, Gaba, Glu, Gly, D-Ile, D-Leu, D-Met, D-Nle, D-Phe, D-Tle, D-Trp, D-Tyr, D-Val, or deleted;

$A^4$ is H;

$A^5$ is D-Bal, D-1-Nal, D-2-Nal, D-Phe, D-($X^1$, $X^2$, $X^3$, $X^4$, $X^5$) Phe, D-Trp, or D-(Et) Tyr;

$A^6$ is Arg or hArg;

$A^7$ is Bal, Bip, 1-Nal, 2-Nal, Trp, or D-Trp;

$A^8$ is A5c, $A^6$c, Aha, Ahx, Ala, β-Ala, Apn, Gaba, Gly, or deleted;

$A^9$ is Cys, D-Cys, hCys, D-hCys, Lys, Pen, or D-Pen;

$A^{10}$ is Pro, Thr or deleted;

$A^{11}$ is Pro or deleted;

$A^{12}$ is arg, Lys, or deleted;

$A^{13}$ is Asp or deleted;

each of $R^2$ and $R^3$ is, independently, H or acyl;

or pharmaceutically acceptable salts thereof.

In exemplary embodiments, the MC4R agonists useful for practicing the methods of the present invention are at least one of the following compounds:

(SEQ ID NO: 159)
Tyr-Gly-Arg-(Lys)$_2$-(Arg)$_2$-Gln-(Arg)$_3$-Nle-c(Asp-His-D-2-Nal-Arg-Trp-Lys)-$NH_2$;

(SEQ ID NO: 160)
Tyr-Gly-Arg-(Lys)$_2$-(Arg)$_2$-Gln-(Arg)$_3$-Doc-Nle-c(Asp-His-D-2-Nal-Arg-Trp-Lys)-$NH_2$;

(SEQ ID NO: 161)
Nle-c(Asp-His-D-2-Nal-Arg-Trp-Lys)-β-Ala-Tyr-Gly-Arg-(Lys)$_2$-(Arg)$_2$-Gln-(Arg)$_3$-$NH_2$;

(SEQ ID NO: 162)
Ac-Nle-c(Asp-His-D-2-Nal-Arg-Trp-Lys)-β-Ala-Tyr-Gly-Arg-(Lys)$_2$-(Arg)$_2$-Gln-(Arg)$_3$-$NH_2$;

(SEQ ID NO: 163)
Nle-c(Asp-His-D-2-Nal-Arg-Trp-Lys)-(Doc)$_2$-Tyr-Gly-Arg-(Lys)$_2$-(Arg)$_2$-Gln-(Arg)$_3$-$NH_2$;

(SEQ ID NO: 164)
Ac-Nle-c(Asp-His-D-2-Nal-Arg-Trp-Lys)-(Pro)$_2$-Lys-Asp-Tyr-Gly-Arg-(Lys)$_2$-(Arg)$_2$-Gln-(Arg)$_3$-$NH_2$;

(SEQ ID NO: 165)
Ac-c(Cys-Glu-His-D-2-Nal-Arg-Trp-Gly-Cys)-(Pro)$_2$-Lys-Asp-Tyr-Gly-Arg-(Lys)$_2$-(Arg)$_2$-Gln-(Arg)$_3$-$NH_2$;

(SEQ ID NO: 166)
Ac-Nle-c(Asp-His-D-2-Nal-Arg-Trp-Lys)-(β-Ala)$_2$-Tyr-Gly-Arg-(Lys)$_2$-(Arg)$_2$-Gln-(Arg)$_3$-$NH_2$;

(SEQ ID NO: 167)
Ac-Nle-c(Asp-His-D-2-Nal-Arg-Trp-Lys)-(Pro)$_2$-Lys-Asp-Doc-Tyr-Gly-Arg-(Lys)$_2$-(Arg)$_2$-Gln-(Arg)$_3$-$NH_2$;

(SEQ ID NO: 168)
Ac-c(Cys-Glu-His-D-2-Nal-Arg-Trp-Gly-Cys)-(Pro)$_2$-Lys-Asp-Doc-Tyr-Gly-Arg-(Lys)$_2$-(Arg)$_2$-Gln-(Arg)$_3$-$NH_2$;

(SEQ ID NO: 169)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_2$-Gln-(Arg)$_3$-$NH_2$;

(SEQ ID NO: 170)
Ac-c(Cys-Glu-His-D-2-Nal-Arg-Trp-Ala-Cys)-(Pro)$_2$-Lys-Asp-Doc-Tyr-Gly-Arg-(Lys)$_2$-(Arg)$_2$-Gln-(Arg)$_3$-$NH_2$;

(SEQ ID NO: 171)
Ac-Nle-c(Asp-His-D-2-Nal-Arg-Trp-Lys)-(Doc)$_2$-Tyr-Gly-Arg-(Lys)$_2$-(Arg)$_2$-Gln-(Arg)$_3$-$NH_2$;

(SEQ ID NO: 172)
Ac-c(Cys-Glu-His-D-2-Nal-Arg-2-Nal-Ala-Cys)-(Pro)$_2$-Lys-Asp-β-Ala-Tyr-Gly-Arg-(Lys)$_2$-(Arg)$_2$-Gln-(Arg)$_3$-$NH_2$;

(SEQ ID NO: 173)
Ac-c(Cys-Glu-His-D-2-Nal-Arg-Bal-Ala-Cys)-(Pro)$_2$-Lys-Asp-β-Ala-(Arg)$_5$-Gln-(Arg)$_3$-$NH_2$;

(SEQ ID NO: 174)
Ac-c(Cys-Glu-His-D-2-Nal-Arg-Bal-Ala-Cys)-(Pro)$_2$-Lys-Asp-β-Ala-Gly-(Arg)$_5$-Gln-(Arg)$_3$-$NH_2$;

(SEQ ID NO: 175)
Ac-c(Cys-Glu-His-D-2-Nal-Arg-Bal-Ala-Cys)-(Pro)$_2$-Lys-Asp-β-Ala-Tyr-Gly-(Arg)$_5$-Gln-(Arg)$_3$-$NH_2$;

(SEQ ID NO: 176)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-Arg-Gln-(Arg)$_4$-$NH_2$;

(SEQ ID NO: 177)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-Gln-(Arg)$_5$-$NH_2$;

(SEQ ID NO: 178)
Ac-c(Cys-Glu-His-D-2-Nal-Arg-Trp-Ala-Cys)-(Pro)$_2$-Lys-Asp-β-Ala-Tyr-Gly-Arg-Lys-Gln-Lys-(Arg)$_5$-$NH_2$;

-continued (SEQ ID NO: 179)
Ac-c(Cys-Glu-His-D-2-Nal-Arg-Trp-Ala-Cys)-$(Pro)_2$-Lys-Asp-β-Ala-Tyr-Gly-Arg-$(Lys)_2$-$(Arg)_4$-Gln-Arg-$NH_2$;

(SEQ ID NO: 180)
Ac-c(Cys-Glu-His-D-2-Nal-Arg-Bal-Ala-Cys)-$(Pro)_2$-Lys-Asp-β-Ala-Tyr-Aib-Arg-$(Lys)_2$-$(Arg)_2$-Gln-$(Arg)_3$-$NH_2$;

(SEQ ID NO: 181)
Ac-c(Cys-Glu-His-D-2-Nal-Arg-1-Nal-Ala-Cys)-$(Pro)_2$-Arg-Asp-β-Ala-$(Arg)_5$-Gln-$(Arg)_3$-$NH_2$;

(SEQ ID NO: 182)
Ac-c(Cys-Glu-His-D-2-Nal-Arg-1-Nal-Ala-Cys)-$(Pro)_2$-Lys-Asp-β-Ala-$(Arg)_5$-Gln-$(Arg)_3$-$NH_2$;

(SEQ ID NO: 183)
Ac-c(Cys-Glu-His-D-2-Nal-Arg-1-Nal-Ala-Cys)-$(Pro)_2$-Lys-Asp-β-Ala-$(Arg)_6$-Gln-$(Arg)_3$-$NH_2$;

(SEQ ID NO: 184)
Ac-c(Cys-Glu-His-D-2-Nal-Arg-2-Nal-Ala-Cys)-$(Pro)_2$-Arg-Asp-β-Ala-$(Arg)_5$-Gln-$(Arg)_3$-$NH_2$;

(SEQ ID NO: 185)
Ac-c(Cys-Glu-His-D-2-Nal-Arg-2-Nal-Ala-Cys)-$(Pro)_2$-Lys-Asp-β-Ala-$(Arg)_5$-Gln-$(Arg)_3$-$NH_2$;

(SEQ ID NO: 186)
Ac-c(Cys-Glu-His-D-2-Nal-Arg-2-Nal-Ala-Cys)-$(Pro)_2$-Lys-Asp-β-Ala-$(Arg)_6$-Gln-$(Arg)_3$-$NH_2$;

(SEQ ID NO: 187)
Ac-c(Cys-Glu-His-D-2-Nal-Arg-Bal-Ala-Cys)-$(Pro)_2$-Arg-Asp-β-Ala-$(Arg)_6$-Gln-$(Arg)_3$-$NH_2$;

(SEQ ID NO: 188)
Ac-c(Cys-Glu-His-D-2-Nal-Arg-Bal-Ala-Cys)-$(Pro)_2$-Arg-Asp-β-Ala-$(Arg)_5$-Gln-$(Arg)_3$-$NH_2$;

(SEQ ID NO: 189)
Ac-c(Cys-Glu-His-D-2-Nal-Arg-Bal-Ala-Cys)-$(Pro)_2$-Lys-Asp-β-Ala-$(Arg)_6$-Gln-$(Arg)_3$-$NH_2$;

(SEQ ID NO: 190)
Ac-c(Cys-Glu-His-D-2-Nal-Arg-Trp-Ala-Cys)-$(Pro)_2$-Lys-Asp-β-Ala-Tyr-Gly-Arg-$(Lys)_2$-$(Arg)_3$-Gln-$(Arg)_2$-$NH_2$;

(SEQ ID NO: 191)
Ac-c(Cys-Glu-His-D-2-Nal-Arg-Trp-Ala-Cys)-$(Pro)_2$-Lys-Asp-β-Ala-Tyr-Gly-Arg-Gln-$(Lys)_2$-$(Arg)_5$-$NH_2$;

(SEQ ID NO: 192)
Ac-c(Cys-Glu-His-D-2-Nal-Arg-Trp-Ala-Cys)-$(Pro)_2$-Lys-Asp-β-Ala-Tyr-Gly-Arg-$(Lys)_2$-$(Arg)_5$-Gln-$NH_2$;

(SEQ ID NO: 193)
Ac-c(Cys-Glu-His-D-2-Nal-Arg-1-Nal-Ala-Cys)-$(Pro)_2$-Lys-Asp-β-Ala-Tyr-Gly-Arg-$(Lys)_2$-$(Arg)_2$-Gln-$(Arg)_3$-$NH_2$;

(SEQ ID NO: 194)
Ac-c(Cys-Glu-His-D-2-Nal-Arg-Bal-Ala-Cys)-$(Pro)_2$-Lys-Asp-β-Ala-Tyr-Gly-Arg-$(Lys)_2$-$(Arg)_2$-Gln-$(Arg)_3$-$NH_2$;

(SEQ ID NO: 195)
Ac-c(Cys-Glu-His-D-2-Nal-Arg-1-Nal-Ala-Cys)-$(Pro)_2$-Lys-Asp-β-Ala-$(Arg)_2$-Lys-$(Arg)_2$-Gln-$(Arg)_3$-$NH_2$;

(SEQ ID NO: 196)
Ac-c(Cys-Glu-His-D-2-Nal-Arg-1-Nal-Ala-Cys)-$(Pro)_2$-Lys-Asp-β-Ala-Arg-Lys-$(Arg)_3$-Gln-$(Arg)_3$-$NH_2$;

(SEQ ID NO: 197)
Ac-c(Cys-Glu-His-D-2-Nal-Arg-2-Nal-Ala-Cys)-$(Pro)_2$-Lys-Asp-β-Ala-$(Arg)_2$-Lys-$(Arg)_2$-Gln-$(Arg)_3$-$NH_2$;

(SEQ ID NO: 198)
Ac-c(Cys-Glu-His-D-2-Nal-Arg-2-Nal-Ala-Cys)-$(Pro)_2$-Lys-Asp-β-Ala-Tyr-Gly-$(Arg)_2$-Lys-$(Arg)_2$-Gln-$(Arg)_3$-$NH_2$;

(SEQ ID NO: 199)
Ac-c(Cys-Glu-His-D-2-Nal-Arg-2-Nal-Ala-Cys)-$(Pro)_2$-Lys-Asp-β-Ala-Gly-$(Arg)_2$-Lys-$(Arg)_2$-Gln-$(Arg)_3$-$NH_2$;

-continued (SEQ ID NO: 200)
Ac-c(Cys-Glu-His-D-2-Nal-Arg-2-Nal-Ala-Cys)-$(Pro)_2$-Lys-Asp-β-Ala-Gly-Arg-Lys-$(Arg)_3$-Gln-$(Arg)_3$-$NH_2$;

(SEQ ID NO: 201)
Ac-c(Cys-Glu-His-D-2-Nal-Arg-1-Nal-Ala-Cys)-$(Pro)_2$-Lys-Asp-β-Ala-Tyr-Gly-$(Arg)_2$-Lys-$(Arg)_2$-Gln-$(Arg)_3$-$NH_2$;

(SEQ ID NO: 202)
Ac-c(Cys-Glu-His-D-2-Nal-Arg-1-Nal-Ala-Cys)-$(Pro)_2$-Lys-Asp-β-Ala-Tyr-Gly-Arg-Lys-$(Arg)_3$-Gln-$(Arg)_3$-$NH_2$;

(SEQ ID NO: 203)
Ac-c(Cys-Glu-His-D-2-Nal-Arg-1-Nal-Ala-Cys)-$(Pro)_2$-Lys-Asp-β-Ala-Gly-$(Arg)_2$-Lys-$(Arg)_2$-Gln-$(Arg)_3$-$NH_2$;

(SEQ ID NO: 204)
Ac-c(Cys-Glu-His-D-2-Nal-Arg-1-Nal-Ala-Cys)-$(Pro)_2$-Lys-Asp-β-Ala-Gly-Arg-Lys-$(Arg)_3$-Gln-$(Arg)_3$-$NH_2$;

(SEQ ID NO: 205)
Ac-c(Cys-Glu-His-D-2-Nal-Arg-2-Nal-Ala-Cys)-$(Pro)_2$-Lys-Asp-β-Ala-$(Arg)_2$-Lys-$(Arg)_2$-Gln-$(Arg)_3$-$NH_2$;

(SEQ ID NO: 206)
Ac-c(Cys-Glu-His-D-2-Nal-Arg-2-Nal-Ala-Cys)-$(Pro)_2$-Lys-Asp-β-Ala-Arg-Lys-$(Arg)_3$-Gln-$(Arg)_3$-$NH_2$;

(SEQ ID NO: 207)
Ac-c(Cys-Glu-His-D-2-Nal-Arg-2-Nal-Ala-Cys)-$(Pro)_2$-Lys-Asp-β-Ala-Tyr-Gly-Arg-Lys-$(Arg)_3$-Gln-$(Arg)_3$-$NH_2$;

(SEQ ID NO: 208)
Ac-c(Cys-Glu-His-D-2-Nal-Arg-Bal-Ala-Cys)-$(Pro)_2$-Lys-Asp-β-Ala-$(Arg)_2$-Lys-$(Arg)_2$-Gln-$(Arg)_3$-$NH_2$;

(SEQ ID NO: 209)
Ac-c(Cys-Glu-His-D-2-Nal-Arg-Bal-Ala-Cys)-$(Pro)_2$-Lys-Asp-β-Ala-Arg-Lys-$(Arg)_3$-Gln-$(Arg)_3$-$NH_2$;

(SEQ ID NO: 210)
Ac-c(Cys-Glu-His-D-2-Nal-Arg-Bal-Ala-Cys)-$(Pro)_2$-Lys-Asp-β-Ala-Tyr-Gly-$(Arg)_2$-Lys-$(Arg)_2$-Gln-$(Arg)_3$-$NH_2$;

(SEQ ID NO: 211)
Ac-c(Cys-Glu-His-D-2-Nal-Arg-Bal-Ala-Cys)-$(Pro)_2$-Lys-Asp-β-Ala-Tyr-Gly-Arg-Lys-$(Arg)_3$-Gln-$(Arg)_3$-$NH_2$;

(SEQ ID NO: 212)
Ac-c(Cys-Glu-His-D-2-Nal-Arg-Bal-Ala-Cys)-$(Pro)_2$-Lys-Asp-β-Ala-Gly-$(Arg)_2$-Lys-$(Arg)_2$-Gln-$(Arg)_3$-$NH_2$;

(SEQ ID NO: 213)
Ac-c(Cys-Glu-His-D-2-Nal-Arg-Bal-Ala-Cys)-$(Pro)_2$-Lys-Asp-β-Ala-Gly-Arg-Lys-$(Arg)_3$-Gln-$(Arg)_3$-$NH_2$;

(SEQ ID NO: 214)
Ac-c(Cys-Glu-His-D-2-Nal-Arg-Trp-Ala-Cys)-$(Pro)_2$-Lys-Asp-β-Ala-$(Arg)_5$-Gln-$(Arg)_3$-$NH_2$;

(SEQ ID NO: 215)
Ac-c(Cys-Glu-His-D-2-Nal-Arg-Trp-Ala-Cys)-$(Pro)_2$-Arg-Asp-β-Ala-$(Arg)_5$-Gln-$(Arg)_3$-$NH_2$;

(SEQ ID NO: 216)
Ac-c(Cys-Glu-His-D-2-Nal-Arg-Trp-Ala-Cys)-$(Pro)_2$-Lys-Asp-β-Ala-Tyr-Gly-$(Arg)_5$-Gln-$(Arg)_3$-$NH_2$;

(SEQ ID NO: 217)
Ac-c(Cys-Glu-His-D-2-Nal-Arg-Trp-Ala-Cys)-$(Pro)_2$-Arg-Asp-β-Ala-Tyr-Gly-$(Arg)_5$-Gln-$(Arg)_3$-$NH_2$;

(SEQ ID NO: 218)
Ac-c(Cys-Glu-His-D-2-Nal-Arg-Trp-Ala-Cys)-$(Pro)_2$-Lys-Asp-β-Ala-$(Arg)_5$-Gln-$(Arg)_4$-$NH_2$;

(SEQ ID NO: 219)
Ac-c(Cys-Glu-His-D-2-Nal-Arg-Trp-Ala-Cys)-$(Pro)_2$-Arg-Asp-β-Ala-$(Arg)_5$-Gln-$(Arg)_4$-$NH_2$;

(SEQ ID NO: 220)
Ac-c(Cys-Glu-His-D-2-Nal-Arg-Trp-Ala-Cys)-$(Pro)_2$-Lys-Asp-β-Ala-Tyr-Gly-$(Arg)_5$-Gln-$(Arg)_4$-$NH_2$;

-continued (SEQ ID NO: 221)
Ac-c(Cys-Glu-His-D-2-Nal-Arg-Trp-Ala-Cys)-$(Pro)_2$-Arg-Asp-β-Ala-Tyr-Gly-$(Arg)_5$-Gln-$(Arg)_4$-$NH_2$;

(SEQ ID NO: 222)
Ac-c(Cys-Glu-His-D-2-Nal-Arg-1-Nal-Ala-Cys)-$(Pro)_2$-Lys-Asp-β-Ala-$(Arg)_5$-Gln-$(Arg)_4$-$NH_2$;

(SEQ ID NO: 223)
Ac-c(Cys-Glu-His-D-2-Nal-Arg-1-Nal-Ala-Cys)-$(Pro)_2$-Arg-Asp-β-Ala-$(Arg)_5$-Gln-$(Arg)_4$-$NH_2$;

(SEQ ID NO: 224)
Ac-c(Cys-Glu-His-D-2-Nal-Arg-1-Nal-Ala-Cys)-$(Pro)_2$-Arg-Asp-β-Ala-$(Arg)_6$-Gln-$(Arg)_3$-$NH_2$;

(SEQ ID NO: 225)
Ac-c(Cys-Glu-His-D-2-Nal-Arg-1-Nal-Ala-Cys)-$(Pro)_2$-Lys-Asp-β-Ala-Tyr-Gly-$(Arg)_5$-Gln-$(Arg)_3$-$NH_2$;

(SEQ ID NO: 226)
Ac-c(Cys-Glu-His-D-2-Nal-Arg-1-Nal-Ala-Cys)-$(Pro)_2$-Arg-Asp-β-Ala-Tyr-Gly-$(Arg)_5$-Gln-$(Arg)_3$-$NH_2$;

(SEQ ID NO: 227)
Ac-c(Cys-Glu-His-D-2-Nal-Arg-1-Nal-Ala-Cys)-$(Pro)_2$-Lys-Asp-β-Ala-Tyr-Gly-$(Arg)_5$-Gln-$(Arg)_4$-$NH_2$;

(SEQ ID NO: 228)
Ac-c(Cys-Glu-His-D-2-Nal-Arg-1-Nal-Ala-Cys)-$(Pro)_2$-Arg-Asp-β-Ala-Tyr-Gly-$(Arg)_5$-Gln-$(Arg)_4$-$NH_2$;

(SEQ ID NO: 229)
Ac-c(Cys-Glu-His-D-2-Nal-Arg-1-Nal-Ala-Cys)-$(Pro)_2$-Lys-Asp-β-Ala-Tyr-Gly-$(Arg)_6$-Gln-$(Arg)_3$-$NH_2$;

(SEQ ID NO: 230)
Ac-c(Cys-Glu-His-D-2-Nal-Arg-1-Nal-Ala-Cys)-$(Pro)_2$-Arg-Asp-β-Ala-Tyr-Gly-$(Arg)_6$-Gln-$(Arg)_3$-$NH_2$;

(SEQ ID NO: 231)
Ac-c(Cys-Glu-His-D-2-Nal-Arg-2-Nal-Ala-Cys)-$(Pro)_2$-Arg-Asp-β-Ala-$(Arg)_6$-Gln-$(Arg)_3$-$NH_2$;

(SEQ ID NO: 232)
Ac-c(Cys-Glu-His-D-2-Nal-Arg-2-Nal-Ala-Cys)-$(Pro)_2$-Lys-Asp-β-Ala-$(Arg)_5$-Gln-$(Arg)_4$-$NH_2$;

(SEQ ID NO: 233)
Ac-c(Cys-Glu-His-D-2-Nal-Arg-2-Nal-Ala-Cys)-$(Pro)_2$-Arg-Asp-β-Ala-$(Arg)_5$-Gln-$(Arg)_4$-$NH_2$;

(SEQ ID NO: 234)
Ac-c(Cys-Glu-His-D-2-Nal-Arg-2-Nal-Ala-Cys)-$(Pro)_2$-Lys-Asp-β-Ala-Tyr-Gly-$(Arg)_5$-Gln-$(Arg)_3$-$NH_2$;

(SEQ ID NO: 235)
Ac-c(Cys-Glu-His-D-2-Nal-Arg-2-Nal-Ala-Cys)-$(Pro)_2$-Arg-Asp-β-Ala-Tyr-Gly-$(Arg)_5$-Gln-$(Arg)_3$-$NH_2$;

(SEQ ID NO: 236)
Ac-c(Cys-Glu-His-D-2-Nal-Arg-2-Nal-Ala-Cys)-$(Pro)_2$-Lys-Asp-β-Ala-Tyr-Gly-$(Arg)_6$-Gln-$(Arg)_3$-$NH_2$;

(SEQ ID NO: 237)
Ac-c(Cys-Glu-His-D-2-Nal-Arg-2-Nal-Ala-Cys)-$(Pro)_2$-Arg-Asp-β-Ala-Tyr-Gly-$(Arg)_6$-Gln-$(Arg)_3$-$NH_2$;

(SEQ ID NO: 238)
Ac-c(Cys-Glu-His-D-2-Nal-Arg-2-Nal-Ala-Cys)-$(Pro)_2$-Lys-Asp-β-Ala-Tyr-Gly-$(Arg)_5$-Gln-$(Arg)_4$-$NH_2$;

(SEQ ID NO: 239)
Ac-c(Cys-Glu-His-D-2-Nal-Arg-2-Nal-Ala-Cys)-$(Pro)_2$-Arg-Asp-β-Ala-Tyr-Gly-$(Arg)_5$-Gln-$(Arg)_4$-$NH_2$;

(SEQ ID NO: 240)
Ac-c(Cys-Glu-His-D-2-Nal-Arg-Bal-Ala-Cys)-$(Pro)_2$-Lys-Asp-β-Ala-$(Arg)_5$-Gln-$(Arg)_4$-$NH_2$;

-continued (SEQ ID NO: 241)
Ac-c(Cys-Glu-His-D-2-Nal-Arg-Bal-Ala-Cys)-$(Pro)_2$-Arg-Asp-β-Ala-$(Arg)_5$-Gln-$(Arg)_4$-$NH_2$;

(SEQ ID NO: 242)
Ac-c(Cys-Glu-His-D-2-Nal-Arg-Bal-Ala-Cys)-$(Pro)_2$-Arg-Asp-β-Ala-Tyr-Gly-$(Arg)_5$-Gln-$(Arg)_3$-$NH_2$;

(SEQ ID NO: 243)
Ac-c(Cys-Glu-His-D-2-Nal-Arg-Bal-Ala-Cys)-$(Pro)_2$-Lys-Asp-β-Ala-Tyr-Gly-$(Arg)_5$-Gln-$(Arg)_4$-$NH_2$;

(SEQ ID NO: 244)
Ac-c(Cys-Glu-His-D-2-Nal-Arg-Bal-Ala-Cys)-$(Pro)_2$-Arg-Asp-β-Ala-Tyr-Gly-$(Arg)_5$-Gln-$(Arg)_4$-$NH_2$;

(SEQ ID NO: 245)
Ac-c(Cys-Glu-His-D-2-Nal-Arg-Bal-Ala-Cys)-$(Pro)_2$-Lys-Asp-β-Ala-Tyr-Gly-$(Arg)_6$-Gln-$(Arg)_3$-$NH_2$;

(SEQ ID NO: 246)
Ac-c(Cys-Glu-His-D-2-Nal-Arg-Bal-Ala-Cys)-$(Pro)_2$-Arg-Asp-β-Ala-Tyr-Gly-$(Arg)_6$-Gln-$(Arg)_3$-$NH_2$;

(SEQ ID NO: 247)
Ac-Nle-c(Cys-D-Ala-His-D-Phe-Arg-Trp-Cys)-$(Doc)_2$-Tyr-Gly-Arg-$(Lys)_2$-$(Arg)_2$-Gln-$(Arg)_3$-$NH_2$;

(SEQ ID NO: 248)
Ac-Nle-c(Cys-D-Ala-His-D-Phe-Arg-Trp-Cys)-β-Ala-Tyr-Gly-Arg-$(Lys)_2$-Arg-Gln-$(Arg)_4$-$NH_2$;

(SEQ ID NO: 249)
Ac-Nle-c(Cys-D-Ala-His-D-Phe-Arg-Trp-Cys)-Doc-Tyr-Gly-Arg-$(Lys)_2$-$(Arg)_2$-Gln-$(Arg)_3$-$NH_2$;

(SEQ ID NO: 250)
Ac-Nle-c(Cys-D-Ala-His-D-Phe-Arg-Trp-Cys)-β-Ala-$(Arg)_5$-Gln-$(Arg)_3$-$NH_2$;

(SEQ ID NO: 251)
Ac-Nle-c(Cys-D-Ala-His-D-Phe-Arg-Trp-Cys)-β-Ala-Gly-$(Arg)_5$-Gln-$(Arg)_3$-$NH_2$;

(SEQ ID NO: 252)
Ac-Nle-c(Cys-D-Ala-His-D-Phe-Arg-Trp-Cys)-β-Ala-Tyr-Gly-$(Arg)_5$-Gln-$(Arg)_3$-$NH_2$;

(SEQ ID NO: 253)
Ac-Nle-c(Cys-D-Ala-His-D-Phe-Arg-Trp-Cys)-β-Ala-Gly-$(Arg)_5$-Gln-$(Arg)_4$-$NH_2$;

(SEQ ID NO: 254)
Ac-Nle-c(Cys-D-Ala-His-D-Phe-Arg-Trp-Cys)-β-Ala-Tyr-Gly-$(Arg)_2$-Lys-$(Arg)_2$-Gln-$(Arg)_3$-$NH_2$;

(SEQ ID NO: 255)
Ac-Nle-c(Cys-D-Ala-His-D-Phe-Arg-Trp-Cys)-β-Ala-Tyr-Gly-Arg-Lys-$(Arg)_3$-Gln-$(Arg)_3$-$NH_2$;

(SEQ ID NO: 256)
Ac-Nle-c(Cys-D-Ala-His-D-Phe-Arg-Trp-Cys)-β-Ala-Gly-$(Arg)_2$-Lys-$(Arg)_2$-Gln-$(Arg)_3$-$NH_2$;

(SEQ ID NO: 257)
Ac-Nle-c(Cys-D-Ala-His-D-Phe-Arg-Trp-Cys)-β-Ala-Gly-Arg-Lys-$(Arg)_3$-Gln-$(Arg)_3$-$NH_2$;

(SEQ ID NO: 258)
Ac-Nle-c(Cys-D-Ala-His-D-Phe-Arg-Trp-Cys)-β-Ala-$(Arg)_2$-Lys-$(Arg)_2$-Gln-$(Arg)_3$-$NH_2$;

(SEQ ID NO: 259)
Ac-Nle-c(Cys-D-Ala-His-D-Phe-Arg-Trp-Cys)-β-Ala-Arg-Lys-$(Arg)_3$-Gln-$(Arg)_3$-$NH_2$;

(SEQ ID NO: 260)
Ac-Nle-c(Cys-D-Ala-His-D-Phe-Arg-Trp-Cys)-$(β\text{-}Ala)_2$-$(Arg)_5$-Gln-$(Arg)_3$-$NH_2$;

(SEQ ID NO: 261)
Ac-Nle-c(Cys-D-Ala-His-D-Phe-Arg-Trp-Cys)-$(β\text{-}Ala)_2$-Gly-$(Arg)_5$-Gln-$(Arg)_3$-$NH_2$;

(SEQ ID NO: 262)
Ac-Nle-c(Cys-D-Ala-His-D-Phe-Arg-Trp-Cys)-$(β\text{-}Ala)_2$-Tyr-Gly-$(Arg)_5$-Gln-$(Arg)_3$-$NH_2$;

(SEQ ID NO: 263)
Ac-Nle-c(Cys-D-Ala-His-D-Phe-Arg-Trp-Cys)-Doc-$(Arg)_5$-Gln-$(Arg)_3$-$NH_2$;

-continued (SEQ ID NO: 264)
Ac-Nle-c(Cys-D-Ala-His-D-Phe-Arg-Trp-Cys)-Doc-Gly-$(Arg)_5$-Gln-$(Arg)_3$-$NH_2$;

(SEQ ID NO: 265)
Ac-Nle-c(Cys-D-Ala-His-D-Phe-Arg-Trp-Cys)-Doc-Tyr-Gly-$(Arg)_5$-Gln-$(Arg)_3$-$NH_2$;

(SEQ ID NO: 266)
Ac-Nle-c(Cys-D-Ala-His-D-Phe-Arg-Trp-Cys)-$(Doc)_2$-$(Arg)_5$-Gln-$(Arg)_3$-$NH_2$;

(SEQ ID NO: 267)
Ac-Nle-c(Cys-D-Ala-His-D-Phe-Arg-Trp-Cys)-$(Doc)_2$-Gly-$(Arg)_5$-Gln-$(Arg)_3$-$NH_2$;

(SEQ ID NO: 268)
Ac-Nle-c(Cys-D-Ala-His-D-Phe-Arg-Trp-Cys)-$(Doc)_2$-Tyr-Gly-$(Arg)_5$-Gln-$(Arg)_3$-$NH_2$;

(SEQ ID NO: 269)
Ac-Nle-c(Cys-D-Ala-His-D-Phe-Arg-Trp-Cys)-β-Ala-$(Arg)_5$-Gln-$(Arg)_4$-$NH_2$;

(SEQ ID NO: 270)
Ac-Nle-c(Cys-D-Ala-His-D-Phe-Arg-Trp-Cys)-β-Ala-Tyr-Gly-$(Arg)_5$-Gln-$(Arg)_4$-$NH_2$;

(SEQ ID NO: 271)
Ac-Nle-c(Cys-D-Ala-His-D-Phe-Arg-Trp-Cys)-$(β\text{-}Ala)_2$-$(Arg)_5$-Gln-$(Arg)_4$-$NH_2$;

(SEQ ID NO: 272)
Ac-Nle-c(Cys-D-Ala-His-D-Phe-Arg-Trp-Cys)-$(β\text{-}Ala)_2$-Gly-$(Arg)_5$-Gln-$(Arg)_4$-$NH_2$;

(SEQ ID NO: 273)
Ac-Nle-c(Cys-D-Ala-His-D-Phe-Arg-Trp-Cys)-$(β\text{-}Ala)_2$-Tyr-Gly-$(Arg)_5$-Gln-$(Arg)_4$-$NH_2$;

(SEQ ID NO: 274)
Ac-Nle-c(Cys-D-Ala-His-D-Phe-Arg-Trp-Cys)-Doc-$(Arg)_5$-Gln-$(Arg)_4$-$NH_2$;

(SEQ ID NO: 275)
Ac-Nle-c(Cys-D-Ala-His-D-Phe-Arg-Trp-Cys)-Doc-Gly-$(Arg)_5$-Gln-$(Arg)_4$-$NH_2$;

(SEQ ID NO: 276)
Ac-Nle-c(Cys-D-Ala-His-D-Phe-Arg-Trp-Cys)-Doc-Tyr-Gly-$(Arg)_5$-Gln-$(Arg)_4$-$NH_2$;

(SEQ ID NO: 277)
Ac-Nle-c(Cys-D-Ala-His-D-Phe-Arg-Trp-Cys)-$(Doc)_2$-$(Arg)_5$-Gln-$(Arg)_4$-$NH_2$;

(SEQ ID NO: 278)
Ac-Nle-c(Cys-D-Ala-His-D-Phe-Arg-Trp-Cys)-$(Doc)_2$-Gly-$(Arg)_5$-Gln-$(Arg)_4$-$NH_2$;

(SEQ ID NO: 279)
Ac-Nle-c(Cys-D-Ala-His-D-Phe-Arg-Trp-Cys)-$(Doc)_2$-Tyr-Gly-$(Arg)_5$-Gln-$(Arg)_4$-$NH_2$;

(SEQ ID NO: 280)
Ac-Nle-c(Cys-His-D-Phe-Arg-Trp-Gaba-Cys)-β-Ala-Tyr-Gly-$(Arg)_5$-Gln-$(Arg)_3$-$NH_2$;

(SEQ ID NO: 281)
Ac-Nle-c(Cys-His-D-Phe-Arg-Trp-Gaba-Cys)-β-Ala-$(Arg)_5$-Gln-$(Arg)_3$-$NH_2$;

(SEQ ID NO: 282)
Ac-Nle-c(Asp-His-D-Phe-Arg-Trp-Ala-Lys)-β-Ala-Tyr-Gly-$(Arg)_5$-Gln-$(Arg)_3$-$NH_2$;

(SEQ ID NO: 283)
Ac-Nle-c(Asp-His-D-Phe-Arg-Trp-Ala-Lys)-β-Ala-$(Arg)_5$-Gln-$(Arg)_3$-$NH_2$;

(SEQ ID NO: 284)
Ac-Nle-c(Asp-His-D-Phe-Arg-Trp-Lys)-β-Ala-Tyr-Gly-$(Arg)_5$-Gln-$(Arg)_3$-$NH_2$;

(SEQ ID NO: 285)
Ac-Nle-c(Asp-His-D-Phe-Arg-Trp-Lys)-β-Ala-Gly-$(Arg)_5$-Gln-$(Arg)_3$-$NH_2$;

(SEQ ID NO: 286)
Ac-Nle-c(Asp-His-D-Phe-Arg-Trp-Lys)-β-Ala-$(Arg)_5$-Gln-$(Arg)_3$-$NH_2$;

(SEQ ID NO: 287)
Ac-Nle-c(Asp-His-D-Phe-Arg-Trp-Lys)-$(β\text{-}Ala)_2$-Tyr-Gly-$(Arg)_5$-Gln-$(Arg)_3$-$NH_2$;

(SEQ ID NO: 288)
Ac-Nle-c(Asp-His-D-Phe-Arg-Trp-Lys)-$(β\text{-}Ala)_2$-Gly-$(Arg)_5$-Gln-$(Arg)_3$-$NH_2$;

(SEQ ID NO: 289)
Ac-Nle-c(Asp-His-D-Phe-Arg-Trp-Lys)-$(β\text{-}Ala)_2$-$(Arg)_5$-Gln-$(Arg)_3$-$NH_2$;

(SEQ ID NO: 290)
Ac-Nle-c(Asp-His-D-Phe-Arg-Trp-Lys)-Doc-Tyr-Gly-$(Arg)_5$-Gln-$(Arg)_3$-$NH_2$;

-continued (SEQ ID NO: 291)
Ac-Nle-c(Asp-His-D-Phe-Arg-Trp-Lys)-Doc-Gly-$(Arg)_5$-Gln-$(Arg)_3$-$NH_2$;

(SEQ ID NO: 292)
Ac-Nle-c(Asp-His-D-Phe-Arg-Trp-Lys)-Doc-$(Arg)_5$-Gln-$(Arg)_3$-$NH_2$;

(SEQ ID NO: 293)
Ac-Nle-c(Asp-His-D-Phe-Arg-Trp-Lys)-$(Doc)_2$-Tyr-Gly-$(Arg)_5$-Gln-$(Arg)_3$-$NH_2$;

(SEQ ID NO: 294)
Ac-Nle-c(Asp-His-D-Phe-Arg-Trp-Lys)-$(Doc)_2$-Gly-$(Arg)_5$-Gln-$(Arg)_3$-$NH_2$;

(SEQ ID NO: 295)
Ac-Nle-c(Asp-His-D-Phe-Arg-Trp-Lys)-$(Doc)_2$-$(Arg)_5$-Gln-(Arg)3-$NH_2$;

(SEQ ID NO: 296)
Ac-Nle-c(Asp-His-D-Phe-Arg-Trp-Lys)-β-Ala-Tyr-Gly-$(Arg)_5$-Gln-$(Arg)_4$-$NH_2$;

(SEQ ID NO: 297)
Ac-Nle-c(Asp-His-D-Phe-Arg-Trp-Lys)-β-Ala-Gly-$(Arg)_5$-Gln-$(Arg)_4$-$NH_2$;

(SEQ ID NO: 298)
Ac-Nle-c(Asp-His-D-Phe-Arg-Trp-Lys)-β-Ala-$(Arg)_5$-Gln-$(Arg)_4$-$NH_2$;

(SEQ ID NO: 299)
Ac-Nle-c(Asp-His-D-Phe-Arg-Trp-Lys)-$(\beta\text{-Ala})_2$-Tyr-Gly-$(Arg)_5$-Gln-$(Arg)_4$-$NH_2$;

(SEQ ID NO: 300)
Ac-Nle-c(Asp-His-D-Phe-Arg-Trp-Lys)-$(\beta\text{-Ala})_2$-Gly-$(Arg)_5$-Gln-$(Arg)_4$-$NH_2$;

(SEQ ID NO: 301)
Ac-Nle-c(Asp-His-D-Phe-Arg-Trp-Lys)-$(\beta\text{-Ala})_2$-$(Arg)_5$-Gln-$(Arg)_4$-$NH_2$;

(SEQ ID NO: 302)
Ac-Nle-c(Asp-His-D-Phe-Arg-Trp-Lys)-Doc-Tyr-Gly-$(Arg)_5$-Gln-$(Arg)_4$-$NH_2$;

(SEQ ID NO: 303)
Ac-Nle-c(Asp-His-D-Phe-Arg-Trp-Lys)-Doc-Gly-$(Arg)_5$-Gln-$(Arg)_4$-$NH_2$;

(SEQ ID NO: 304)
Ac-Nle-c(Asp-His-D-Phe-Arg-Trp-Lys)-Doc-$(Arg)_5$-Gln-$(Arg)_4$-$NH_2$;

(SEQ ID NO: 305)
Ac-Nle-c(Asp-His-D-Phe-Arg-Trp-Lys)-$(Doc)_2$-Tyr-Gly-$(Arg)_5$-Gln-$(Arg)_4$-$NH_2$;

(SEQ ID NO: 306)
Ac-Nle-c(Asp-His-D-Phe-Arg-Trp-Lys)-$(Doc)_2$-Gly-$(Arg)_5$-Gln-$(Arg)_4$-$NH_2$;

(SEQ ID NO: 307)
Ac-Nle-c(Asp-His-D-Phe-Arg-Trp-Lys)-$(Doc)_2$-$(Arg)_5$-Gln-$(Arg)_4$-$NH_2$;

(SEQ ID NO: 308)
Ac-Nle-c(Asp-His-D-Phe-Arg-Trp-β-Ala-Lys)-β-Ala-Tyr-Gly-$(Arg)_5$-Gln-$(Arg)_3$-$NH_2$;

(SEQ ID NO: 309)
Ac-Nle-c(Asp-His-D-Phe-Arg-Trp-β-Ala-Lys)-β-Ala-$(Arg)_5$-Gln-$(Arg)_3$-$NH_2$;

(SEQ ID NO: 310)
Ac-Nle-c(Cys-His-D-Phe-Arg-Trp-Ahx-Cys)-β-Ala-Tyr-Gly-$(Arg)_5$-Gln-$(Arg)_3$-$NH_2$;

(SEQ ID NO: 311)
Ac-Nle-c(Cys-His-D-Phe-Arg-Trp-Ahx-Cys)-β-Ala-$(Arg)_5$-Gln-$(Arg)_3$-$NH_2$;

(SEQ ID NO: 312)
D-Phe-c(Cys-His-D-Phe-Arg-Trp-β-Ala-D-Cys)-Thr-β-Ala-Tyr-Gly-$(Arg)_5$-Gln-$(Arg)_3$-$NH_2$;

(SEQ ID NO: 313)
D-Phe-c(Cys-His-D-Phe-Arg-Trp-β-Ala-D-Cys)-Thr-β-Ala-$(Arg)_5$-Gln-$(Arg)_3$-$NH_2$;

(SEQ ID NO: 314)
Ac-Nle-c(Cys-His-D-Phe-Arg-Trp-Apn-Cys)-β-Ala-Tyr-Gly-$(Arg)_5$-Gln-$(Arg)_3$-$NH_2$;

(SEQ ID NO: 315)
Ac-Nle-c(Cys-His-D-Phe-Arg-Trp-Apn-Cys)-β-Ala-$(Arg)_5$-Gln-$(Arg)_3$-$NH_2$;

(SEQ ID NO: 316)
Ac-Cha-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 317)
Ac-Cha-c(Asp-His-D-Phe-Arg-Trp-Gaba-Lys)-β-Ala-$(Arg)_5$-Gln-$(Arg)_3$-$NH_2$;

-continued (SEQ ID NO: 318)
Ac-Nle-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 319)
Ac-Nle-c(Asp-His-D-Phe-Arg-Trp-Gaba-Lys)-β-Ala-$(Arg)_5$-Gln-$(Arg)_3$-$NH_2$;

(SEQ ID NO: 320)
Ac-Chg-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 321)
Ac-Chg-c(Asp-His-D-Phe-Arg-Trp-Gaba-Lys)-β-Ala-$(Arg)_5$-Gln-$(Arg)_3$-$NH_2$;

(SEQ ID NO: 322)
Ac-hCha-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 323)
Ac-hCha-c(Asp-His-D-Phe-Arg-Trp-Gaba-Lys)-β-Ala-$(Arg)_5$-Gln-$(Arg)_3$-$NH_2$;

(SEQ ID NO: 324)
Ac-hCha-c(Asp-His-D-Phe-Arg-Trp-Gaba-Lys)-$(β\text{-Ala})_2$-Tyr-Gly-$(Arg)_5$-Gln-$(Arg)_3$-$NH_2$;

(SEQ ID NO: 325)
Ac-hCha-c(Asp-His-D-Phe-Arg-Trp-Gaba-Lys)-$(β\text{-Ala})_2$-$(Arg)_5$-Gln-$(Arg)_3$-$NH_2$;

(SEQ ID NO: 326)
Ac-hCha-c(Asp-His-D-Phe-Arg-Trp-Gaba-Lys)-Doc-Tyr-Gly-$(Arg)_5$-Gln-$(Arg)_3$-$NH_2$;

(SEQ ID NO: 327)
Ac-hCha-c(Asp-His-D-Phe-Arg-Trp-Gaba-Lys)-Doc-$(Arg)_5$-Gln-$(Arg)_3$-$NH_2$;

(SEQ ID NO: 328)
Ac-hCha-c(Asp-His-D-Phe-Arg-Trp-Gaba-Lys)-$(Doc)_2$-Tyr-Gly-$(Arg)_5$-Gln-$(Arg)_3$-$NH_2$;

(SEQ ID NO: 329)
Ac-hCha-c(Asp-His-D-Phe-Arg-Trp-Gaba-Lys)-$(Doc)_2$-$(Arg)_5$-Gln-$(Arg)_3$-$NH_2$;

(SEQ ID NO: 330)
Ac-hCha-c(Asp-His-D-Phe-Arg-Trp-Gaba-Lys)-β-Ala-Tyr-Gly-$(Arg)_5$-Gln-$(Arg)_4$-$NH_2$;

(SEQ ID NO: 331)
Ac-hCha-c(Asp-His-D-Phe-Arg-Trp-Gaba-Lys)-β-Ala-$(Arg)_5$-Gln-$(Arg)_4$-$NH_2$;

(SEQ ID NO: 332)
Ac-hCha-c(Asp-His-D-Phe-Arg-Trp-Gaba-Lys)-$(β\text{-Ala})_2$-Tyr-Gly-$(Arg)_5$-Gln-$(Arg)_4$-$NH_2$;

(SEQ ID NO: 333)
Ac-hCha-c(Asp-His-D-Phe-Arg-Trp-Gaba-Lys)-$(β\text{-Ala})_2$-$(Arg)_5$-Gln-$(Arg)_4$-$NH_2$;

(SEQ ID NO: 334)
Ac-hCha-c(Asp-His-D-Phe-Arg-Trp-Gaba-Lys)-Doc-Tyr-Gly-$(Arg)_5$-Gln-$(Arg)_4$-$NH_2$;

(SEQ ID NO: 335)
Ac-hCha-c(Asp-His-D-Phe-Arg-Trp-Gaba-Lys)-Doc-$(Arg)_5$-Gln-$(Arg)_4$-$NH_2$;

(SEQ ID NO: 336)
Ac-hCha-c(Asp-His-D-Phe-Arg-Trp-Gaba-Lys)-$(Doc)_2$-Tyr-Gly-$(Arg)_5$-Gln-$(Arg)_4$-$NH_2$;

(SEQ ID NO: 337)
Ac-hCha-c(Asp-His-D-Phe-Arg-Trp-Gaba-Lys)-$(Doc)_2$-$(Arg)_5$-Gln-$(Arg)_4$-$NH_2$;

(SEQ ID NO: 338)
Ac-D-Chg-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 339)
Ac-D-Chg-c(Asp-His-D-Phe-Arg-Trp-Gaba-Lys)-β-Ala-$(Arg)_5$-Gln-$(Arg)_3$-$NH_2$;

(SEQ ID NO: 340)
Ac-hPhe-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 341)
Ac-hPhe-c(Asp-His-D-Phe-Arg-Trp-Gaba-Lys)-β-Ala-$(Arg)_5$-Gln-$(Arg)_3$-$NH_2$;

(SEQ ID NO: 342)
Ac-Nle-c(Cys-His-D-Phe-Arg-D-Trp-Apn-Cys)-β-Ala-Tyr-Gly-$(Arg)_5$-Gln-$(Arg)_3$-$NH_2$;

(SEQ ID NO: 343)
Ac-Nle-c(Cys-His-D-Phe-Arg-D-Trp-Apn-Cys)-β-Ala-$(Arg)_5$-Gln-$(Arg)_3$-$NH_2$;

(SEQ ID NO: 344)
Ac-Nle-c(Cys-His-D-Phe-Arg-D-Trp-Ahx-Cys)-β-Ala-Tyr-Gly-$(Arg)_5$-Gln-$(Arg)_3$-$NH_2$;

-continued (SEQ ID NO: 345)
Ac-Nle-c(Cys-His-D-Phe-Arg-D-Trp-Ahx-Cys)-β-Ala-$(Arg)_5$-Gln-$(Arg)_3$-$NH_2$;

(SEQ ID NO: 346)
Ac-Nle-c(Cys-His-D-Phe-Arg-D-Trp-3-Ala-Cys)-β-Ala-Tyr-Gly-$(Arg)_5$-Gln-$(Arg)_3$-$NH_2$;

(SEQ ID NO: 347)
Ac-Nle-c(Cys-His-D-Phe-Arg-D-Trp-P-Ala-Cys)-β-Ala-$(Arg)_5$-Gln-$(Arg)_3$-$NH_2$;

(SEQ ID NO: 348)
Ac-Nle-c(Cys-D-Ala-His-D-Phe-Arg-Trp-Pen)-β-Ala-Tyr-Gly-$(Arg)_5$-Gln-$(Arg)_3$-$NH_2$;

(SEQ ID NO: 349)
Ac-Nle-c(Cys-D-Ala-His-D-Phe-Arg-Trp-Pen)-β-Ala-Gly-$(Arg)_5$-Gln-$(Arg)_3$-$NH_2$;

(SEQ ID NO: 350)
Ac-Nle-c(Cys-D-Ala-His-D-Phe-Arg-Trp-Pen)-β-Ala-$(Arg)_5$-Gln-$(Arg)_3$-$NH_2$;

(SEQ ID NO: 351)
Ac-Nle-c(Cys-D-Ala-His-D-Phe-Arg-Trp-Pen)-$(β-Ala)_2$-Tyr-Gly-$(Arg)_5$-Gln-$(Arg)_3$-$NH_2$;

(SEQ ID NO: 352)
Ac-Nle-c(Cys-D-Ala-His-D-Phe-Arg-Trp-Pen)-$(β-Ala)_2$-Gly-$(Arg)_5$-Gln-$(Arg)_3$-$NH_2$;

(SEQ ID NO: 353)
Ac-Nle-c(Cys-D-Ala-His-D-Phe-Arg-Trp-Pen)-$(β-Ala)_2$-$(Arg)_5$-Gln-$(Arg)_3$-$NH_2$;

(SEQ ID NO: 354)
Ac-Nle-c(Cys-D-Ala-His-D-Phe-Arg-Trp-Pen)-Doc-Tyr-Gly-$(Arg)_5$-Gln-$(Arg)_3$-$NH_2$;

(SEQ ID NO: 355)
Ac-Nle-c(Cys-D-Ala-His-D-Phe-Arg-Trp-Pen)-Doc-Gly-$(Arg)_5$-Gln-$(Arg)_3$-$NH_2$;

(SEQ ID NO: 356)
Ac-Nle-c(Cys-D-Ala-His-D-Phe-Arg-Trp-Pen)-Doc-$(Arg)_5$-Gln-$(Arg)_3$-$NH_2$;

(SEQ ID NO: 357)
Ac-Nle-c(Cys-D-Ala-His-D-Phe-Arg-Trp-Pen)-$(Doc)_2$-Tyr-Gly-$(Arg)_5$-Gln-$(Arg)_3$-$NH_2$;

(SEQ ID NO: 358)
Ac-Nle-c(Cys-D-Ala-His-D-Phe-Arg-Trp-Pen)-$(Doc)_2$-Gly-$(Arg)_5$-Gln-$(Arg)_3$-$NH_2$;

(SEQ ID NO: 359)
Ac-Nle-c(Cys-D-Ala-His-D-Phe-Arg-Trp-Pen)-$(Doc)_2$-$(Arg)_5$-Gln-$(Arg)_3$-$NH_2$;

(SEQ ID NO: 360)
D-Phe-c(Cys-His-D-(Et)Tyr-Arg-Trp-β-Ala-D-Cys)-β-Ala-Tyr-Gly-$(Arg)_5$-Gln-$(Arg)_3$-$NH_2$;

(SEQ ID NO: 361)
D-Phe-c(Cys-His-D-(Et)Tyr-Arg-Trp-β-Ala-D-Cys)-β-Ala-$(Arg)_5$-Gln-$(Arg)_3$-$NH_2$;

(SEQ ID NO: 362)
D-Phe-c(Cys-His-D-(Et)Tyr-Arg-Trp-β-Ala-D-Cys)-β-Ala-Gly-$(Arg)_5$-Gln-$(Arg)_3$-$NH_2$;

(SEQ ID NO: 363)
D-Phe-c(Cys-His-D-(Et)Tyr-Arg-Trp-β-Ala-D-Cys)-β-Ala-$(Arg)_5$-Gln-$(Arg)_4$-$NH_2$;

(SEQ ID NO: 364)
D-Phe-c(Cys-His-D-(Et)Tyr-Arg-Trp-β-Ala-D-Cys)-$(β-Ala)_2$-Tyr-Gly-$(Arg)_5$-Gln-$(Arg)_3$-$NH_2$;

(SEQ ID NO: 365)
D-Phe-c(Cys-His-D-(Et)Tyr-Arg-Trp-β-Ala-D-Cys)-$(β-Ala)_2$-$(Arg)_5$-Gln-$(Arg)_3$-$NH_2$;

(SEQ ID NO: 366)
D-Phe-c(Cys-His-D-(Et)Tyr-Arg-Trp-β-Ala-D-Cys)-$(β-Ala)_2$-Gly-$(Arg)_5$-Gln-$(Arg)_3$-$NH_2$;

(SEQ ID NO: 367)
D-Phe-c(Cys-His-D-(Et)Tyr-Arg-Trp-β-Ala-D-Cys)-$(β-Ala)_2$-$(Arg)_5$-Gln-$(Arg)_4$-$NH_2$;

(SEQ ID NO: 368)
D-Phe-c(Cys-His-D-(Et)Tyr-Arg-Trp-β-Ala-D-Cys)-Doc-Tyr-Gly-$(Arg)_5$-Gln-$(Arg)_3$-$NH_2$;

(SEQ ID NO: 369)
D-Phe-c(Cys-His-D-(Et)Tyr-Arg-Trp-β-Ala-D-Cys)-Doc-$(Arg)_5$-Gln-$(Arg)_3$-$NH_2$;

(SEQ ID NO: 370)
D-Phe-c(Cys-His-D-(Et)Tyr-Arg-Trp-β-Ala-D-Cys)-Doc-Gly-$(Arg)_5$-Gln-$(Arg)_3$-$NH_2$;

(SEQ ID NO: 371)
D-Phe-c(Cys-His-D-(Et)Tyr-Arg-Trp-β-Ala-D-Cys)-Doc-$(Arg)_5$-Gln-$(Arg)_4$-$NH_2$;

-continued (SEQ ID NO: 372)
D-Phe-c(Cys-His-D-(Et)Tyr-Arg-Trp-β-Ala-D-Cys)-(Doc)$_2$-Tyr-Gly-(Arg)$_5$-Gln-(Arg)$_3$-NH$_2$;

(SEQ ID NO: 373)
D-Phe-c(Cys-His-D-(Et)Tyr-Arg-Trp-β-Ala-D-Cys)-(Doc)$_2$-(Arg)$_5$-Gln-(Arg)$_3$-NH$_2$;

(SEQ ID NO: 374)
D-Phe-c(Cys-His-D-(Et)Tyr-Arg-Trp-β-Ala-D-Cys)-(Doc)$_2$-Gly-(Arg)$_5$-Gln-(Arg)$_3$-NH$_2$;

(SEQ ID NO: 375)
D-Phe-c(Cys-His-D-(Et)Tyr-Arg-Trp-β-Ala-D-Cys)-(Doc)$_2$-(Arg)$_5$-Gln(Arg)$_4$-NH$_2$;-

(SEQ ID NO: 376)
D-Phe-c(Cys-His-D-(Et)Tyr-hArg-Trp-β-Ala-D-Cys)-Thr-β-Ala-Tyr-Gly-(Arg)$_5$-Gln-(Arg)$_3$-NH$_2$;

(SEQ ID NO: 377)
D-Phe-c(Cys-His-D-(Et)Tyr-hArg-Trp-β-Ala-D-Cys)-Thr-β-Ala-(Arg)$_5$-Gln-(Arg)$_3$-NH$_2$;

(SEQ ID NO: 378)
D-Phe-c(Cys-His-D-(Et)Tyr-hArg-Trp-β-Ala-D-Cys)-Thr-(β-Ala)$_2$-Tyr-Gly-(Arg)$_5$-Gln-(Arg)$_3$-NH$_2$;

(SEQ ID NO: 379)
D-Phe-c(Cys-His-D-(Et)Tyr-hArg-Trp-β-Ala-D-Cys)-Thr-(β-Ala)$_2$-(Arg)$_5$-Gln-(Arg)$_3$-NH$_2$;

(SEQ ID NO: 380)
D-Phe-c(Cys-His-D-(Et)Tyr-hArg-Trp-β-Ala-D-Cys)-Thr-Doc-Tyr-Gly-(Arg)$_5$-Gln-(Arg)$_3$-NH$_2$;

(SEQ ID NO: 381)
D-Phe-c(Cys-His-D-(Et)Tyr-hArg-Trp-β-Ala-D-Cys)-Thr-Doc-(Arg)$_5$-Gln-(Arg)$_3$-NH$_2$;

(SEQ ID NO: 382)
D-Phe-c(Cys-His-D-(Et)Tyr-hArg-Trp-β-Ala-D-Cys)-Thr-(Doc)$_2$-Tyr-Gly-(Arg)$_5$-Gln-(Arg)$_3$-NH$_2$;

(SEQ ID NO: 383)
D-Phe-c(Cys-His-D-(Et)Tyr-hArg-Trp-β-Ala-D-Cys)-Thr-β-Ala-Tyr-Gly-(Arg)$_5$-Gln-(Arg)$_4$-NH$_2$;

(SEQ ID NO: 384)
D-Phe-c(Cys-His-D-(Et)Tyr-hArg-Trp-β-Ala-D-Cys)-Thr-β-Ala-(Arg)$_5$-Gln-(Arg)$_4$-NH$_2$;

(SEQ ID NO: 385)
D-Phe-c(Cys-His-D-(Et)Tyr-hArg-Trp-β-Ala-D-Cys)-Thr-(β-Ala)$_2$-Tyr-Gly-(Arg)$_5$-Gln-(Arg)$_4$-NH$_2$;

(SEQ ID NO: 386)
D-Phe-c(Cys-His-D-(Et)Tyr-hArg-Trp-β-Ala-D-Cys)-Thr-(β-Ala)$_2$-(Arg)$_5$-Gln-(Arg)$_4$-NH$_2$;

(SEQ ID NO: 387)
D-Phe-c(Cys-His-D-(Et)Tyr-hArg-Trp-β-Ala-D-Cys)-Thr-Doc-Tyr-Gly-(Arg)$_5$-Gln-(Arg)$_4$-NH$_2$;

(SEQ ID NO: 388)
D-Phe-c(Cys-His-D-(Et)Tyr-hArg-Trp-β-Ala-D-Cys)-Thr-Doc-(Arg)$_5$-Gln-(Arg)$_4$-NH$_2$;

(SEQ ID NO: 389)
D-Phe-c(Cys-His-D-(Et)Tyr-hArg-Trp-β-Ala-D-Cys)-Thr-(Doc)$_2$-Tyr-Gly-(Arg)$_5$-Gln-(Arg)$_4$-NH$_2$;

(SEQ ID NO: 390)
D-Phe-c(Cys-His-D-(Et)Tyr-hArg-Trp-β-Ala-D-Cys)-Thr-(Doc)$_2$-(Arg)$_5$-Gln-(Arg)$_4$-NH$_2$;

(SEQ ID NO: 391)
D-Phe-c(Cys-His-D-(Et)Tyr-hArg-Bip-β-Ala-D-Cys)-Thr-β-Ala-Tyr-Gly-(Arg)$_5$-Gln-(Arg)$_3$-NH$_2$;

(SEQ ID NO: 392)
D-Phe-c(Cys-His-D-(Et)Tyr-hArg-Bip-β-Ala-D-Cys)-Thr-β-Ala-Tyr-Gly-(Arg)$_5$-Gln-(Arg)$_4$-NH$_2$;

(SEQ ID NO: 393)
D-Phe-c(Cys-His-D-(Et)Tyr-hArg-Bip-β-Ala-D-Cys)-Thr-β-Ala-(Arg)$_5$-Gln-(Arg)$_3$-NH$_2$;

-continued (SEQ ID NO: 394)
D-Phe-c(Cys-His-D-(Et)Tyr-hArg-Bip-β-Ala-D-Cys)-Thr-(β-Ala)$_2$-Tyr-Gly-(Arg)$_5$-Gln-(Arg)$_3$-NH$_2$;

(SEQ ID NO: 395)
D-Phe-c(Cys-His-D-(Et)Tyr-hArg-Bip-β-Ala-D-Cys)-Thr-(β-Ala)$_2$-(Arg)$_5$-Gln-(Arg)$_3$-NH$_2$;

(SEQ ID NO: 396)
D-Phe-c(Cys-His-D-(Et)Tyr-hArg-Bip-β-Ala-D-Cys)-Thr-Doc-Tyr-Gly-(Arg)$_5$-Gln-(Arg)$_3$-NH$_2$;

(SEQ ID NO: 397)
D-Phe-c(Cys-His-D-(Et)Tyr-hArg-Bip-β-Ala-D-Cys)-Thr-Doc-Tyr-Gly-(Arg)$_5$-Gln-(Arg)$_4$-NH$_2$;

(SEQ ID NO: 398)
D-Phe-c(Cys-His-D-(Et)Tyr-hArg-Bip-β-Ala-D-Cys)-Thr-Doc-(Arg)$_5$-Gln-(Arg)$_3$-NH$_2$;

(SEQ ID NO: 399)
D-Phe-c(Cys-His-D-(Et)Tyr-hArg-Bip-β-Ala-D-Cys)-Thr-(Doc)$_2$-Tyr-Gly-(Arg)$_5$-Gln-(Arg)$_3$-NH$_2$;

(SEQ ID NO: 400)
D-Phe-c(Cys-His-D-(Et)Tyr-hArg-Bip-β-Ala-D-Cys)-Thr-(Doc)$_2$-(Arg)$_5$-Gln-(Arg)$_3$-NH$_2$;

(SEQ ID NO: 401)
Ac-Nle-c(Cys-D-Ala-His-D-Phe-Arg-Trp-Gly-Cys)-β-Ala-Tyr-Gly-(Arg)$_5$-Gln-(Arg)$_3$-NH$_2$;

(SEQ ID NO: 402)
Ac-Nle-c(Cys-D-Ala-His-D-Phe-Arg-Trp-Gly-Cys)-β-Ala-(Arg)$_5$-Gln-(Arg)$_3$-NH$_2$;

(SEQ ID NO: 403)
Nle-c(Cys-His-D-Phe-Arg-Trp-Apn-Cys)-β-Ala-Tyr-Gly-(Arg)$_5$-Gln-(Arg)$_3$-NH$_2$;

(SEQ ID NO: 404)
Nle-c(Cys-His-D-Phe-Arg-Trp-Apn-Cys)-β-Ala-(Arg)$_5$-Gln-(Arg)$_3$-NH$_2$;

(SEQ ID NO: 405)
Nle-c(Cys-His-D-Phe-Arg-Trp-Apn-Cys)-(β-Ala)$_2$-Tyr-Gly-(Arg)$_5$-Gln-(Arg)$_3$-NH$_2$;

(SEQ ID NO: 406)
Nle-c(Cys-His-D-Phe-Arg-Trp-Apn-Cys)-(β-Ala)$_2$-(Arg)$_5$-Gln-(Arg)$_3$-NH$_2$;

(SEQ ID NO: 407)
Nle-c(Cys-His-D-Phe-Arg-Trp-Apn-Cys)-β-Ala-Tyr-Gly-(Arg)$_5$-Gln-(Arg)$_4$-NH$_2$;

(SEQ ID NO: 408)
Nle-c(Cys-His-D-Phe-Arg-Trp-Apn-Cys)-β-Ala-(Arg)$_5$-Gln-(Arg)$_4$-NH$_2$;

(SEQ ID NO: 409)
Nle-c(Cys-His-D-Phe-Arg-Trp-Apn-Cys)-(β-Ala)$_2$-Tyr-Gly-(Arg)$_5$-Gln-(Arg)$_4$-NH$_2$;

(SEQ ID NO: 410)
Nle-c(Cys-His-D-Phe-Arg-Trp-Apn-Cys)-(β-Ala)$_2$-(Arg)$_5$-Gln-(Arg)$_4$-NH$_2$;

(SEQ ID NO: 411)
Nle-c(Cys-His-D-Phe-Arg-Trp-Apn-Cys)-Doc-Tyr-Gly-(Arg)$_5$-Gln-(Arg)$_3$-NH$_2$;

(SEQ ID NO: 412)
Nle-c(Cys-His-D-Phe-Arg-Trp-Apn-Cys)-Doc-(Arg)$_5$-Gln-(Arg)$_3$-NH$_2$;

(SEQ ID NO: 413)
Nle-c(Cys-His-D-Phe-Arg-Trp-Apn-Cys)-(Doc)$_2$-Tyr-Gly-(Arg)$_5$-Gln-(Arg)$_3$-NH$_2$;

(SEQ ID NO: 414)
Nle-c(Cys-His-D-Phe-Arg-Trp-Apn-Cys)-(Doc)$_2$-(Arg)$_5$-Gln-(Arg)$_3$-NH$_2$;

(SEQ ID NO: 415)
Nle-c(Cys-His-D-Phe-Arg-Trp-Apn-Cys)-Doc-Tyr-Gly-(Arg)$_5$-Gln-(Arg)$_4$-NH$_2$;

(SEQ ID NO: 416)
Nle-c(Cys-His-D-Phe-Arg-Trp-Apn-Cys)-Doc-(Arg)$_5$-Gln-(Arg)$_4$-NH$_2$;

(SEQ ID NO: 417)
Nle-c(Cys-His-D-Phe-Arg-Trp-Apn-Cys)-(Doc)$_2$-Tyr-Gly-(Arg)$_5$-Gln-(Arg)$_4$-NH$_2$;

(SEQ ID NO: 418)
Nle-c(Cys-His-D-Phe-Arg-Trp-Apn-Cys)-(Doc)$_2$-(Arg)5-Gln-(Arg)$_4$-NH$_2$;

-continued (SEQ ID NO: 419)
Ac-Nle-c(Cys-D-Leu-His-D-Phe-Arg-Trp-Cys)-β-Ala-Tyr-Gly-$(Arg)_5$-Gln-$(Arg)_3$-$NH_2$;

(SEQ ID NO: 420)
Ac-Nle-c(Cys-D-Leu-His-D-Phe-Arg-Trp-Cys)-β-Ala-$(Arg)_5$-Gln-$(Arg)_3$-$NH_2$;

(SEQ ID NO: 421)
Ac-Nle-c(Cys-D-Leu-His-D-Phe-Arg-Trp-Cys)-$(β\text{-Ala})_2$-Tyr-Gly-$(Arg)_5$-Gln-$(Arg)_3$-$NH_2$;

(SEQ ID NO: 422)
Ac-Nle-c(Cys-D-Leu-His-D-Phe-Arg-Trp-Cys)-$(β\text{-Ala})_2$-$(Arg)_5$-Gln-$(Arg)_3$-$NH_2$;

(SEQ ID NO: 423)
Ac-Nle-c(Cys-D-Leu-His-D-Phe-Arg-Trp-Cys)-Doc-Tyr-Gly-$(Arg)_5$-Gln-$(Arg)_3$-$NH_2$;

(SEQ ID NO: 424)
Ac-Nle-c(Cys-D-Leu-His-D-Phe-Arg-Trp-Cys)-Doc-$(Arg)_5$-Gln-$(Arg)_3$-$NH_2$;

(SEQ ID NO: 425)
Ac-Nle-c(Cys-D-Leu-His-D-Phe-Arg-Trp-Cys)-$(Doc)_2$-Tyr-Gly-$(Arg)_5$-Gln-$(Arg)_3$-$NH_2$;

(SEQ ID NO: 426)
Ac-Nle-c(Cys-D-Leu-His-D-Phe-Arg-Trp-Cys)-$(Doc)_2$-$(Arg)_5$-Gln-$(Arg)_3$-$NH_2$;

(SEQ ID NO: 427)
Ac-Nle-c(Cys-D-Leu-His-D-Phe-Arg-Trp-Cys)-β-Ala-Tyr-Gly-$(Arg)_5$-Gln-$(Arg)_4$-$NH_2$;

(SEQ ID NO: 428)
Ac-Nle-c(Cys-D-Leu-His-D-Phe-Arg-Trp-Cys)-β-Ala-$(Arg)_5$-Gln-$(Arg)_4$-$NH_2$;

(SEQ ID NO: 429)
Ac-Nle-c(Cys-D-Leu-His-D-Phe-Arg-Trp-Cys)-$(β\text{-Ala})_2$-Tyr-Gly-$(Arg)_5$-Gln-$(Arg)_4$-$NH_2$;

(SEQ ID NO: 430)
Ac-Nle-c(Cys-D-Leu-His-D-Phe-Arg-Trp-Cys)-$(β\text{-Ala})_2$-$(Arg)_5$-Gln-$(Arg)_4$-$NH_2$;

(SEQ ID NO: 431)
Ac-Nle-c(Cys-D-Leu-His-D-Phe-Arg-Trp-Cys)-Doc-Tyr-Gly-$(Arg)_5$-Gln-$(Arg)_4$-$NH_2$;

(SEQ ID NO: 432)
Ac-Nle-c(Cys-D-Leu-His-D-Phe-Arg-Trp-Cys)-Doc-$(Arg)_5$-Gln-$(Arg)_4$-$NH_2$;

(SEQ ID NO: 433)
Ac-Nle-c(Cys-D-Leu-His-D-Phe-Arg-Trp-Cys)-$(Doc)_2$-Tyr-Gly-$(Arg)_5$-Gln-$(Arg)_4$-$NH_2$;

(SEQ ID NO: 434)
Ac-Nle-c(Cys-D-Leu-His-D-Phe-Arg-Trp-Cys)-$(Doc)_2$-$(Arg)_5$-Gln-$(Arg)_4$-$NH_2$;

(SEQ ID NO: 435)
Ac-Nle-c(Cys-D-Cha-His-D-Phe-Arg-Trp-Cys)-β-Ala-Tyr-Gly-$(Arg)_5$-Gln-$(Arg)_3$-$NH_2$;

(SEQ ID NO: 436)
Ac-Nle-c(Cys-D-Cha-His-D-Phe-Arg-Trp-Cys)-β-Ala-$(Arg)_5$-Gln-$(Arg)_3$-$NH_2$;

(SEQ ID NO: 437)
Ac-Nle-c(Cys-D-Cha-His-D-Phe-Arg-Trp-Cys)-$(β\text{-Ala})_2$-Tyr-Gly-$(Arg)_5$-Gln-$(Arg)_3$-$NH_2$;

(SEQ ID NO: 438)
Ac-Nle-c(Cys-D-Cha-His-D-Phe-Arg-Trp-Cys)-$(β\text{-Ala})_2$-$(Arg)_5$-Gln-$(Arg)_3$-$NH_2$;

(SEQ ID NO: 439)
Ac-Nle-c(Cys-D-Cha-His-D-Phe-Arg-Trp-Cys)-Doc-Tyr-Gly-$(Arg)_5$-Gln-$(Arg)_3$-$NH_2$;

(SEQ ID NO: 440)
Ac-Nle-c(Cys-D-Cha-His-D-Phe-Arg-Trp-Cys)-Doc-$(Arg)_5$-Gln-$(Arg)_3$-$NH_2$;

(SEQ ID NO: 441)
Ac-Nle-c(Cys-D-Cha-His-D-Phe-Arg-Trp-Cys)-$(Doc)_2$-Tyr-Gly-$(Arg)_5$-Gln-$(Arg)_3$-$NH_2$;

(SEQ ID NO: 442)
Ac-Nle-c(Cys-D-Cha-His-D-Phe-Arg-Trp-Cys)-$(Doc)_2$-$(Arg)_5$-Gln-$(Arg)_3$-$NH_2$;

(SEQ ID NO: 443)
Ac-Nle-c(Cys-D-Cha-His-D-Phe-Arg-Trp-Cys)-β-Ala-Tyr-Gly-$(Arg)_5$-Gln-$(Arg)_4$-$NH_2$;

(SEQ ID NO: 444)
Ac-Nle-c(Cys-D-Cha-His-D-Phe-Arg-Trp-Cys)-β-Ala-$(Arg)_5$-Gln-$(Arg)_4$-$NH_2$;

(SEQ ID NO: 445)
Ac-Nle-c(Cys-D-Cha-His-D-Phe-Arg-Trp-Cys)-$(β\text{-Ala})_2$-Tyr-Gly-$(Arg)_5$-Gln-(Arg)4-$NH_2$;

-continued (SEQ ID NO: 446)
Ac-Nle-c(Cys-D-Cha-His-D-Phe-Arg-Trp-Cys)-($\beta$-Ala)$_2$-(Arg)$_5$-Gln-(Arg)$_4$-$NH_2$;

(SEQ ID NO: 447)
Ac-Nle-c(Cys-D-Cha-His-D-Phe-Arg-Trp-Cys)-Doc-Tyr-Gly-(Arg)$_5$-Gln-(Arg)$_4$-$NH_2$;

(SEQ ID NO: 448)
Ac-Nle-c(Cys-D-Cha-His-D-Phe-Arg-Trp-Cys)-Doc-(Arg)$_5$-Gln-(Arg)$_4$-$NH_2$;

(SEQ ID NO: 449)
Ac-Nle-c(Cys-D-Cha-His-D-Phe-Arg-Trp-Cys)-(Doc)$_2$-Tyr-Gly-(Arg)$_5$-Gln-(Arg)$_4$-$NH_2$;

(SEQ ID NO: 450)
Ac-Nle-c(Cys-D-Cha-His-D-Phe-Arg-Trp-Cys)-(Doc)$_2$-(Arg)$_5$-Gln-(Arg)$_4$-$NH_2$;

(SEQ ID NO: 451)
Nle-c(Cys-His-D-Phe-Arg-Trp-Gaba-Cys)-$\beta$-Ala-Tyr-Gly-(Arg)$_5$-Gln-(Arg)$_3$-$NH_2$;

(SEQ ID NO: 452)
Nle-c(Cys-His-D-Phe-Arg-Trp-Gaba-Cys)-$\beta$-Ala-(Arg)$_5$-Gln-(Arg)$_3$-$NH_2$;

(SEQ ID NO: 453)
Nle-c(Cys-His-D-Phe-Arg-Trp-Gaba-Cys)-($\beta$-Ala)$_2$-Tyr-Gly-(Arg)$_5$-Gln-(Arg)$_3$-$NH_2$;

(SEQ ID NO: 454)
Nle-c(Cys-His-D-Phe-Arg-Trp-Gaba-Cys)-($\beta$-Ala)$_2$-(Arg)$_5$-Gln-(Arg)$_3$-$NH_2$;

(SEQ ID NO: 455)
Nle-c(Cys-His-D-Phe-Arg-Trp-Gaba-Cys)-$\beta$-Ala-Tyr-Gly-(Arg)$_5$-Gln-(Arg)$_4$-$NH_2$;

(SEQ ID NO: 456)
Nle-c(Cys-His-D-Phe-Arg-Trp-Gaba-Cys)-$\beta$-Ala-(Arg)$_5$-Gln-(Arg)$_4$-$NH_2$;

(SEQ ID NO: 457)
Nle-c(Cys-His-D-Phe-Arg-Trp-Gaba-Cys)-($\beta$-Ala)$_2$-Tyr-Gly-(Arg)$_5$-Gln-(Arg)$_4$-$NH_2$;

(SEQ ID NO: 458)
Nle-c(Cys-His-D-Phe-Arg-Trp-Gaba-Cys)-($\beta$-Ala)$_2$-(Arg)$_5$-Gln-(Arg)$_4$-$NH_2$;

(SEQ ID NO: 459)
Nle-c(Cys-His-D-Phe-Arg-Trp-Gaba-Cys)-Doc-Tyr-Gly-(Arg)$_5$-Gln-(Arg)$_3$-$NH_2$;

(SEQ ID NO: 460)
Nle-c(Cys-His-D-Phe-Arg-Trp-Gaba-Cys)-Doc-(Arg)$_5$-Gln-(Arg)$_3$-$NH_2$;

(SEQ ID NO: 461)
Nle-c(Cys-His-D-Phe-Arg-Trp-Gaba-Cys)-(Doc)$_2$-Tyr-Gly-(Arg)$_5$-Gln-(Arg)$_3$-$NH_2$;

(SEQ ID NO: 462)
Nle-c(Cys-His-D-Phe-Arg-Trp-Gaba-Cys)-(Doc)$_2$-(Arg)$_5$-Gln-(Arg)$_3$-$NH_2$;

(SEQ ID NO: 463)
Nle-c(Cys-His-D-Phe-Arg-Trp-Gaba-Cys)-Doc-Tyr-Gly-(Arg)$_5$-Gln-(Arg)$_4$-$NH_2$;

(SEQ ID NO: 464)
Nle-c(Cys-His-D-Phe-Arg-Trp-Gaba-Cys)-Doc-(Arg)$_5$-Gln-(Arg)$_4$-$NH_2$;

(SEQ ID NO: 465)
Nle-c(Cys-His-D-Phe-Arg-Trp-Gaba-Cys)-(Doc)$_2$-Tyr-Gly-(Arg)$_5$-Gln-(Arg)$_4$-$NH_2$;
or (SEQ ID NO: 466)
Nle-c(Cys-His-D-Phe-Arg-Trp-Gaba-Cys)-(Doc)$_2$-(Arg)$_5$-Gln-(Arg)$_4$-$NH_2$, or pharmaceutically acceptable salts thereof.

In an example embodiment, the compounds useful for practicing the methods described herein are the compounds of Formula (IV):

Ac-*c*(Cys-Glu-His-$A^1$-Arg-$A^2$-$A^3$-Cys)-$(Pro)_2$-Lys-Asp-$NH_2$ (IV)

or pharmaceutically acceptable salts thereof. In Formula (IV):

$A^1$ is the D-isomer of X-Phe or 2-Nal where X is halogen;

$A^2$ is Bal, 1-Nal, 2-Nal, or Trp; and $A^3$ is Aib, Ala, β-Ala or Gly,

In an example embodiments, the at least one of the following compounds is used:

(SEQ ID NO: 467)
Ac-c(Cys-Glu-His-D-4-Br-Phe-Arg-Trp-Gly-Cys)-$(Pro)_2$-Lys-Asp-$NH_2$;

(SEQ ID NO: 468)
Ac-c(Cys-Glu-His-D-2-Nal-Arg-Trp-Ala-Cys)-$(Pro)_2$-Lys-Asp-$NH_2$;

(SEQ ID NO: 469)
Ac-c(Cys-Glu-His-D-2-Nal-Arg-2-Nal-Ala-Cys)-$(Pro)_2$-Lys-Asp-$NH_2$;

(SEQ ID NO: 470)
Ac-c(Cys-Glu-His-D-2-Nal-Arg-1-Nal-Ala-Cys)-$(Pro)_2$-Lys-Asp-$NH_2$;

(SEQ ID NO: 471)
Ac-c(Cys-Glu-His-D-2-Nal-Arg-Bal-Ala-Cys)-$(Pro)_2$-Lys-Asp-$NH_2$;

(SEQ ID NO: 472)
Ac-c(Cys-Glu-His-D-2-Nal-Arg-2-Nal-β-Ala-Cys)-$(Pro)_2$-Lys-Asp-$NH_2$;
or (SEQ ID NO: 473)
Ac-c(Cy s-Glu-His-D-2-Nal-Arg-2-Nal-Aib-Cys)-$(Pro)_2$-Lys-Asp-$NH_2$;

or pharmaceutically acceptable salts thereof.

In example embodiments, an MC4R agonist useful for practicing the methods described herein is at least one compound modified with a hydantoin moiety according to Formula (V), (VI) or (VII), or a pharmaceutically acceptable salt, hydrate, solvate or a prodrug thereof.

Formula (V) is described below: (see International Patent Application Number PCT/US08/06675 incorporated herein by reference in its entirety).

(V)

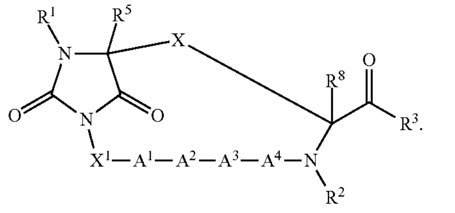

In Formula (V):

X is selected from the group consisting of $—CH_2—S—S—CH_2—$, $—C(CH_3)_2—S—S—CH_2$, $—CH_2—S—S—C(CH_3)_2—$, $—C(CH_3)_2—S—S—C(CH_3)_2—$, $—(CH_2)_2—S—S—CH_2—$, $—CH_2—S—S—(CH_2)_2—$, $—S—S—(CH_2)_2—S—S—(CH_2)_2—$, $—C(CH_3)_2—S—S—(CH_2)_2—$, $—(CH_2)_2—S—S—C(CH_3)_2—$, $—(CH_2)_tC(O)—NR^8—(CH_2)_r—$ and $—(CH_2)_r—NR^8—C(O)—(CH_2)_t—$;

$R^2$ each is, independently, H, $(C_1\text{-}C_{10})$alkyl or substituted $(C_1\text{-}C_{10})$alkyl;

$R^3$ is —OH or $—NH_2$;

$R^4$ and $R^5$ each is, independently, H, $(C_1\text{-}C_{10})$alkyl or substituted $(C_1\text{-}C_{10})$alkyl;

$X^1$ is

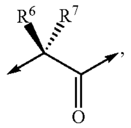

$A^1$ is His, 2-Pal, 3-Pal, 4-Pal, ($X^1$, $X^2$, $X^3$, $X^4$, $X^5$) Phe, Taz, 2-Thi, 3-Thi or is deleted;

$A^2$ is D-Bal, D-1-Nal, D-2-Nal, D-Phe or D-($X^1$, $X^2$, $X^3$, $X^4$, $X^5$) Phe;

$A^3$ is Arg, hArg, Dab, Dap, Lys or Orn;

$A^4$ is Bal, 1-Nal, 2-Nal, ($X^1$, $X^2$, $X^3$, $X^4$, $X^5$) Phe or Trp;

$R^6$ and $R^7$ each is, independently for each occurrence thereof, H, $(C_1\text{-}C_{10})$ heteroalkyl, aryl$(C_1\text{-}C_5)$alkyl, substituted $(C_1\text{-}C_{10})$alkyl, substituted $(C_1\text{-}C_{10})$ heteroalkyl or substituted aryl$(C_1\text{-}C_5)$alkyl provided that $R^6$ and $R^7$ may be joined together to form a ring;

$R^8$ is H, $(C_1\text{-}C_{10})$alkyl or substituted $(C_1\text{-}C_{10})$alkyl;

r is, independently for each occurrence thereof, 1, 2, 3, 4 or 5; and t is, independently for each occurrence thereof, 1 or 2.

Compounds according the foregoing formula can include compounds wherein $X^1$ is selected from the group consisting of:

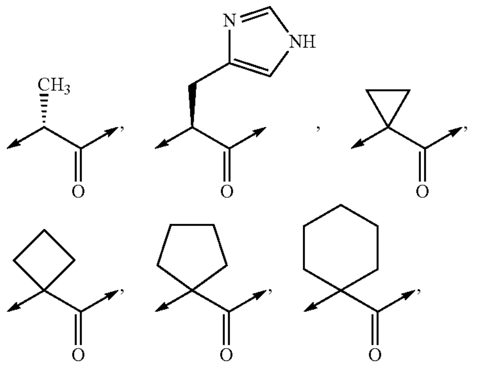

-continued

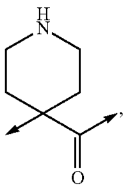, and

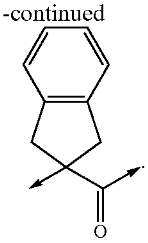.

Representative embodiments of the foregoing class of compounds are as follows:

(SEQ ID NO: 474
c[Hydantoin(C(O)-(Cys-D-Ala))-His-D-Phe-Arg-Trp-Cys]-$NH_2$;

(SEQ ID NO: 475)
c[Hydantoin(C(O)-(hCys-D-Ala))-His-D-Phe-Arg-Trp-Cys]-$NH_2$;

(SEQ ID NO: 476)
c[Hydantoin(C(O)-(Cys-D-Ala))-His-D-2-Nal-Arg-Trp-Cys]-$NH_2$;

(SEQ ID NO: 477)
c[Hydantoin(C(O)-(hCys-D-Ala))-His-D-2-Nal-Arg-Trp-Cys]-$NH_2$;

(SEQ ID NO: 478)
c[Hydantoin(C(O)-(Asp-D-Ala))-His-D-Phe-Arg-Trp-Lys]-$NH_2$;

(SEQ ID NO: 479)
c[Hydantoin(C(O)-(Asp-D-Ala))-His-D-Phe-Arg-Trp-Orn]-$NH_2$;

(SEQ ID NO: 480)
c[Hydantoin(C(O)-(Asp-D-Ala))-His-D-Phe-Arg-Trp-Dab]-$NH_2$;

(SEQ ID NO: 481)
c[Hydantoin(C(O)-(Asp-D-Ala))-His-D-Phe-Arg-Trp-Dap]-$NH_2$;

(SEQ ID NO: 482)
c[Hydantoin(C(O)-(Asp-His))-D-2-Nal-Arg-Trp-Lys]-$NH_2$;

(SEQ ID NO: 483)
c[Hydantoin(C(O)-(Asp-His))-D-Phe-Arg-Trp-Lys]-$NH_2$;

(SEQ ID NO: 484)
c[Hydantoin(C(O)-(Asp-A3c))-D-Phe-Arg-Trp-Lys]-$NH_2$;

(SEQ ID NO: 485)
c[Hydantoin(C(O)-(Asp-A5c))-D-Phe-Arg-Trp-Lys]-$NH_2$;

(SEQ ID NO: 486)
c[Hydantoin(C(O)-(Asp-A6c))-D-Phe-Arg-Trp-Lys]-$NH_2$;

(SEQ ID NO: 487)
c[Hydantoin(C(O)-(Asp-A3c))-D-2-Nal-Arg-Trp-Lys]-$NH_2$;

(SEQ ID NO: 488)
c[Hydantoin(C(O)-(Asp-A5c))-D-2-Nal-Arg-Trp-Lys]-$NH_2$;

(SEQ ID NO: 489)
c[Hydantoin(C(O)-(Asp-A6c))-D-2-Nal-Arg-Trp-Lys]-$NH_2$;

(SEQ ID NO: 490)
c[Hydantoin(C(O)-(Asp-Aic))-D-Phe-Arg-Trp-Lys]-$NH_2$;

(SEQ ID NO: 491)
c[Hydantoin(C(O)-(Asp-Apc))-D-Phe-Arg-Trp-Lys]-$NH_2$;

(SEQ ID NO: 492)
c[Hydantoin(C(O)-(Asp-Aic))-D-2-Nal-Arg-Trp-Lys]-$NH_2$;

(SEQ ID NO: 493)
c[Hydantoin(C(O)-(Asp-Apc))-D-2-Nal-Arg-Trp-Lys]-$NH_2$;

(SEQ ID NO: 494)
c[Hydantoin(C(O)-(Glu-D-Ala))-His-D-Phe-Arg-Trp-Orn]-$NH_2$;

-continued (SEQ ID NO: 495)
c[Hydantoin(C(O)-(Glu-D-Ala))-His-D-Phe-Arg-Trp-DaN-$NH_2$;

(SEQ ID NO: 496)
c[Hydantoin(C(O)-(Glu-D-Ala))-His-D-Phe-Arg-Trp-Dap]-$NH_2$;

(SEQ ID NO: 497)
c[Hydantoin(C(O)-(Glu-D-Ala))-His-D-Phe-Arg-Trp-Lys]-$NH_2$;

(SEQ ID NO: 498)
c[Hydantoin(C(O)-(Glu-His))-D-Phe-Arg-Trp-Dap]-$NH_2$;
or (SEQ ID NO: 499)
c[Hydantoin(C(O)-(Glu-His))-D-Phe-Arg-Trp-Lys]-$NH_2$.

In an example embodiment, an MC4R agonist useful for practicing the methods described herein is at least one compound of Formula (VI), a pharmaceutically-acceptable salt, hydrate, solvate and/or prodrugs thereof (see International Patent Application Number PCT/US08/06675 which is incorporated herein by reference in its entirety):

(VI)

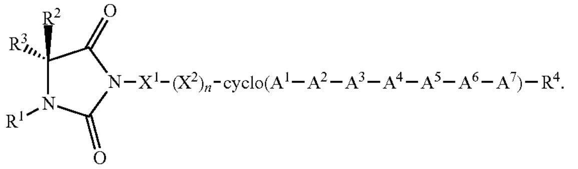

In Formula (VI):

$X^1$ is

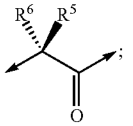

$X^2$ is

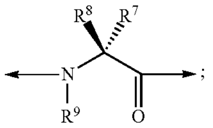

$A^1$ is Asp, Cys, D-Cys, Dab, Dap, Glu, Lys, Orn, Pen or D-Pen;

$A^2$ is an L- or D-amino acid;

$A^3$ is His, 2-Pal, 3-Pal, 4-Pal, ($X^1$, $X^2$, $X^3$, $X^4$, $X^5$) Phe, Taz, 2-Thi or 3-Thi;

$A^4$ is D-Bal, D-1-Nal, D-2-Nal, D-Phe or D-($X^1$, $X^2$, $X^3$, $X^4$, $X^5$) Phe;

$A^5$ is Arg, hArg, Dab, Dap, Lys or Orn;

$A^6$ is Bal, 1-Nal, 2-Nal, ($X^1$, $X^2$, $X^3$, $X^4$, $X^5$) Phe or Trp;

$A^7$ is Asp, Cys, D-Cys, Dab, Dap, Glu, Lys, Orn, Pen or D-Pen;

$R^1$ is H, ($C_1$-$C_{10}$)alkyl or substituted ($C_1$-$C_{10}$)alkyl;

$R^2$ and $R^3$ each is, independently, H, ($C_1$-$C_{10}$)alkyl, ($C_1$-$C_{10}$) heteroalkyl, aryl($C_1$-$C_5$)alkyl, substituted ($C_1$-$C_{10}$)alkyl, substituted ($C_1$-$C_{10}$) heteroalkyl or substituted aryl($C_1$-$C_5$)alkyl or $R^2$ and $R^3$ may be fused together form a cyclic moiety;

$R^4$ is $CO_2H$ or $C(O)NH_2$;

$R^5$ and $R^6$ each is, independently, H, ($C_1$-00)alkyl, ($C_1$-$C_{10}$) heteroalkyl, aryl($C_1$-$C_5$)alkyl, substituted ($C_1$-$C_{10}$)alkyl, substituted ($C_1$-$C_{10}$) heteroalkyl or substituted aryl($C_1$-$C_5$)alkyl or $R^5$ and $R^6$ may be fused together form a cyclic moiety;

$R^7$ and $R^8$ each is, independently, H, ($C_1$-$C_{10}$)alkyl, ($C_1$-$C_{10}$) heteroalkyl, aryl($C_1$-$C_5$)alkyl, substituted ($C_1$-$C_{10}$)alkyl, substituted ($C_1$-$C_{10}$) heteroalkyl or substituted aryl($C_1$-$C_5$)alkyl; or $R^7$ and $R^8$ may be fused together form a cyclic moiety;

$R^9$ is H, ($C_1$-$C_{10}$)alkyl or substituted ($C_1$-$C_{10}$)alkyl; and n is, independently for each occurrence thereof, 1, 2, 3, 4, 5, 6 or 7;

or a pharmaceutically acceptable salt thereof.

Exemplary embodiments of the compounds of Formula (VI) are those compounds wherein:

$A^1$ is Cys, $A^2$ is D-Ala, Asn, Asp, Gln, Glu or D-Phe;

$A^3$ is His;

$A^4$ is D-2-Nal or D-Phe;

$A^5$ is Arg;

$A^6$ is Trp; and $A^7$ is Cys or Pen;

each of R', $R^2$, $R^3$, and $R^9$ is, independently, H;

$R^4$ is $C(O)NH_2$;

each of $R^5$ and $R^6$ is, independently, H, ($C_1$-$C_{10}$) heteroalkyl, substituted ($C_1$-$C_{10}$)alkyl or substituted ($C_1$-$C_{10}$) heteroalkyl or $R^5$ and $R^6$ may be fused together form a cyclic moiety; and each of $R^7$ and $R^8$ is, independently, H, ($C_1$-$C_{10}$)alkyl, ($C_1$-$C_{10}$) heteroalkyl, substituted ($C_1$-$C_{10}$)alkyl or substituted ($C_1$-$C_{10}$) heteroalkyl; or pharmaceutically acceptable salts thereof.

Example compounds of the immediately foregoing Formula (VI) include:

(SEQ ID NO: 500)
Hydantoin(C(O)-(Arg-Gly))-c(Cys-Glu-His-D-Phe-Arg-Trp-Cys)-$NH_2$;

(SEQ ID NO: 501)
Hydantoin(C(O)-(Nle-Gly))-c(Cys-Glu-His-D-Phe-Arg-Trp-Cys)-$NH_2$;

-continued (SEQ ID NO: 502)
Hydantoin(C(O)-(Gly-Gly))-c(Cys-Glu-His-D-Phe-Arg-Trp-Cys)-$NH_2$;

(SEQ ID NO: 503)
Hydantoin(C(O)-(Nle-Gly))-c(Cys-D-Ala-His-D-Phe-Arg-Trp-Cys)-$NH_2$;

(SEQ ID NO: 504)
Hydantoin(C(O)-(Gly-Gly))-c(Cys-D-Ala-His-D-Phe-Arg-Trp-Cys)-$NH_2$;

(SEQ ID NO: 505)
Hydantoin(C(O)-(Nle-Gly))-c(Cys-D-Ala-His-D-Phe-Arg-Trp-Pen)-$NH_2$;

(SEQ ID NO: 506)
Hydantoin(C(O)-(Gly-Gly))-c(Cys-D-Ala-His-D-Phe-Arg-Trp-Pen)-$NH_2$;

(SEQ ID NO: 507)
Hydantoin(C(O)-(Ala-Gly))-c(Cys-D-Ala-His-D-Phe-Arg-Trp-Cys)-$NH_2$;

(SEQ ID NO: 508)
Hydantoin(C(O)-(D-Ala-Gly))-c(Cys-D-Ala-His-D-Phe-Arg-Trp-Cys)-$NH_2$;

(SEQ ID NO: 509)
Hydantoin(C(O)-(Aib-Gly))-c(Cys-D-Ala-His-D-Phe-Arg-Trp-Cys)-$NH_2$;

(SEQ ID NO: 510)
Hydantoin(C(O)-(Val-Gly))-c(Cys-D-Ala-His-D-Phe-Arg-Trp-Cys)-$NH_2$;

(SEQ ID NO: 511)
Hydantoin(C(O)-(Ile-Gly))-c(Cys-D-Ala-His-D-Phe-Arg-Trp-Cys)-$NH_2$;

(SEQ ID NO: 512)
Hydantoin(C(O)-(Leu-Gly))-c(Cys-D-Ala-His-D-Phe-Arg-Trp-Cys)-$NH_2$;

(SEQ ID NO: 513)
Hydantoin(C(O)-(Gly-Gly))-c(Cys-Glu-His-D-2-Nal-Arg-Trp-Cys)-$NH_2$;

(SEQ ID NO: 514)
Hydantoin(C(O)-(Nle-Gly))-c(Cys-Glu-His-D-2-Nal-Arg-Trp-Cys)-$NH_2$;

(SEQ ID NO: 515)
Hydantoin(C(O)-(D-Arg-Gly))-c(Cys-Glu-His-D-Phe-Arg-Trp-Cys)-$NH_2$;

(SEQ ID NO: 516)
Hydantoin(C(O)-(D-Arg-Gly))-c(Cys-D-Ala-His-D-Phe-Arg-Trp-Cys)-$NH_2$;

(SEQ ID NO: 517)
Hydantoin(C(O)-(Arg-Gly))-c(Cys-D-Ala-His-D-Phe-Arg-Trp-Cys)-$NH_2$;

(SEQ ID NO: 518)
Hydantoin(C(O)-(D-Arg-Gly))-c(Cys-D-Ala-His-D-2-Nal-Arg-Trp-Cys)-$NH_2$;

(SEQ ID NO: 519)
Hydantoin(C(O)-(Arg-Gly))-c(Cys-D-Ala-His-D-2-Nal-Arg-Trp-Cys)-$NH_2$;

(SEQ ID NO: 520)
Hydantoin(C(O)-(Ala-Nle))-c(Cys-Glu-His-D-Phe-Arg-Trp-Cys)-$NH_2$;

(SEQ ID NO: 521)
Hydantoin(C(O)-(Val-Nle))-c(Cys-Glu-His-D-Phe-Arg-Trp-Cys)-$NH_2$;

(SEQ ID NO: 522)
Hydantoin(C(O)-(Gly-Nle))-c(Cys-Glu-His-D-Phe-Arg-Trp-Cys)-$NH_2$;

(SEQ ID NO: 523)
Hydantoin(C(O)-(A6c-Nle))-c(Cys-D-Ala-His-D-Phe-Arg-Trp-Cys)-$NH_2$;

(SEQ ID NO: 524)
Hydantoin(C(O)-(Gly-Nle))-c(Cys-D-Ala-His-D-Phe-Arg-Trp-Cys)-$NH_2$;

(SEQ ID NO: 525)
Hydantoin(C(O)-(Ala-Nle))-c(Cys-D-Ala-His-D-Phe-Arg-Trp-Cys)-$NH_2$;

(SEQ ID NO: 526)
Hydantoin(C(O)-(D-Ala-Nle))-c(Cys-D-Ala-His-D-Phe-Arg-Trp-Cys)-$NH_2$;

(SEQ ID NO: 527)
Hydantoin(C(O)-(Val-Nle))-c(Cys-D-Ala-His-D-Phe-Arg-Trp-Cys)-$NH_2$;

(SEQ ID NO: 528)
Hydantoin(C(O)-(Leu-Nle))-c(Cys-D-Ala-His-D-Phe-Arg-Trp-Cys)-$NH_2$;

-continued (SEQ ID NO: 529)
Hydantoin(C(O)-(Cha-Nle))-c(Cys-D-Ala-His-D-Phe-Arg-Trp-Cys)-$NH_2$;

(SEQ ID NO: 530)
Hydantoin(C(O)-(Aib-Nle))-c(Cys-D-Ala-His-D-Phe-Arg-Trp-Cys)-$NH_2$;

(SEQ ID NO: 531)
Hydantoin(C(O)-(Gly-Arg))-c(Cys-Glu-His-D-Phe-Arg-Trp-Cys)-$NH_2$;

(SEQ ID NO: 532)
Hydantoin(C(O)-(Gly-Arg))-c(Cys-Glu-His-D-2-Nal-Arg-Trp-Cys)-$NH_2$;

(SEQ ID NO: 533)
Hydantoin(C(O)-(Gly-Arg))-c(Cys-D-Ala-His-D-Phe-Arg-Trp-Cys)-$NH_2$;

(SEQ ID NO: 534)
Hydantoin(C(O)-(Gly-Arg))-c(Cys-D-Ala-His-D-2-Nal-Arg-Trp-Cys)-$NH_2$;

(SEQ ID NO: 535)
Hydantoin(C(O)-(Gly-D-Arg))-c(Cys-Glu-His-D-Phe-Arg-Trp-Cys)-$NH_2$;

(SEQ ID NO: 536)
Hydantoin(C(O)-(Gly-D-Arg))-c(Cys-D-Ala-His-D-Phe-Arg-Trp-Cys)-$NH_2$;

(SEQ ID NO: 537)
Hydantoin(C(O)-(Gly-D-Arg))-c(Cys-D-Ala-His-D-2-Nal-Arg-Trp-Cys)-$NH_2$;
or (SEQ ID NO: 538)
Hydantoin(C(O)-(Nle-Ala))-c(Cys-Glu-His-D-Phe-Arg-Trp-Cys)-$NH_2$;

or a pharmaceutically acceptable salt thereof.

In an example embodiment, the MC4R agonists useful for practicing the methods described herein are compounds having a structure according to Formula (VII) as depicted below (see International Patent Application Number PCT/US08/06675 which is incorporated herein by reference in its entirety):

(VII)

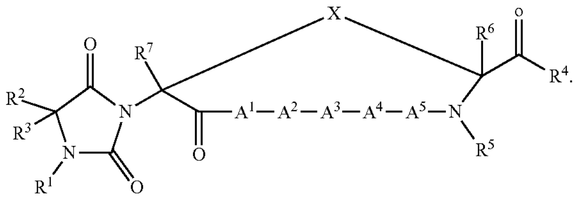

wherein:

X is selected from the group consisting of $-CH_2-S-S-CH_2-$, $-C(CH_3)_2SSCH_2-$, $-CH_2-S-S-C(CH_3)_2-$, $-C(CH_3)_2-S-S-C(CH_3)_2-$, $-(CH_2)_2-S-S-CH_2-$, $-CH_2-S-S-(CH_2)_2$, $(CH_2)_2-S-S-(CH_2)_2-$, $-C(CH_3)_2-S-S-(CH_2)_2$, $-(CH_2)_2-S-S-C(CH_3)_2-$, $-(CH_2)_t-C(O)-NR^8-(CH_2)_r-$ and $-(CH_2)_r-NR^8-C(O)-(CH_2)_t-$;

each of $R^1$ and $R^5$ is, independently, H, $(C_1\text{-}C_{10})$alkyl or substituted $(C_1\text{-}C_{10})$alkyl;

each of $R^2$ and $R^3$ is, independently, H, $(C_1\text{-}C_{10})$alkyl, $(C_1$-00) heteroalkyl, aryl$(C_1\text{-}C_5)$alkyl, substituted $(C_1\text{-}C_{10})$alkyl, substituted $(C_1\text{-}C_{10})$ heteroalkyl or substituted aryl$(C_1\text{-}C_5)$alkyl or $R^2$ and $R^3$ may be fused together to form a ring;

$R^4$ is OH or $NH_2$;

each of $R^6$ and $R^7$ is, independently, H, $(C_1\text{-}C_{10})$alkyl or substituted $(C_1\text{-}C_{10})$alkyl;

$A^1$ is an L- or D-amino acid or deleted;

$A^2$ is His, 2-Pal, 3-Pal, 4-Pal, $(X^1, X^2, X^3, X^4, X^5)$ Phe, Taz, 2-Thi or 3-Thi;

$A^3$ is D-Bal, D-1-Nal, D-2-Nal, D-Phe or D-$(X^1, X^2, X^3, X^4, X^5)$ Phe;

$A^4$ is Arg, hArg, Dab, Dap, Lys or Orn;

$A^5$ is Bal, 1-Nal, 2-Nal, $(X^1, X^2, X^3, X^4, X^5)$ Phe or Trp;

r is, independently for each occurrence thereof, 1, 2, 3, 4 or 5; and t is, independently for each occurrence thereof, 1 or 2;

or pharmaceutically acceptable salts thereof.

In an example embodiment of the compounds of Formula (VII), $A^1$ is Ala, D-Ala, Asn, Asp, Gln, Glu or Gly.

Example compounds according to Formula (VII) include the following compounds:

(SEQ ID NO: 539)
c[Hydantoin(C(O)-(Nle-Cys))-D-Ala-His-D-Phe-Arg-Trp-Cys]-$NH_2$;

(SEQ ID NO: 540)
c[Hydantoin(C(O)-(Ala-Cys))-D-Ala-His-D-Phe-Arg-Trp-Cys]-$NH_2$;

(SEQ ID NO: 541)
c[Hydantoin(C(O)-(D-Ala-Cys))-D-Ala-His-D-Phe-Arg-Trp-Cys]-$NH_2$;

(SEQ ID NO: 542)
c[Hydantoin(C(O)-(Aib-Cys))-D-Ala-His-D-Phe-Arg-Trp-Cys]-$NH_2$;

-continued (SEQ ID NO: 543)
c[Hydantoin(C(O)-(Val-Cys))-D-Ala-His-D-Phe-Arg-Trp-Cys]-$NH_2$;

(SEQ ID NO: 544)
c[Hydantoin(C(O)-(Abu-Cys))-D-Ala-His-D-Phe-Arg-Trp-Cys]-$NH_2$;

(SEQ ID NO: 545)
c[Hydantoin(C(O)-(Leu-Cys))-D-Ala-His-D-Phe-Arg-Trp-Cys]-$NH_2$;

(SEQ ID NO: 546)
c[Hydantoin(C(O)-(Ile-Cys))-D-Ala-His-D-Phe-Arg-Trp-Cys]-$NH_2$;

(SEQ ID NO: 547)
c[Hydantoin(C(O)-(Cha-Cys))-D-Ala-His-D-Phe-Arg-Trp-Cys]-$NH_2$;

(SEQ ID NO: 548)
c[Hydantoin(C(O)-(A6c-Cys))-D-Ala-His-D-Phe-Arg-Trp-Cys]-$NH_2$;

(SEQ ID NO: 549)
c[Hydantoin(C(O)-(Phe-Cys))-D-Ala-His-D-Phe-Arg-Trp-Cys]-$NH_2$;

(SEQ ID NO: 550)
c[Hydantoin(C(O)-(Gly-Cys))-D-Ala-His-D-Phe-Arg-Trp-Cys]-$NH_2$;
or (SEQ ID NO: 551)
c[Hydantoin(C(O)-(Gly-Cys))-Glu-His-D-Phe-Arg-Trp-Cys]-$NH_2$;

or pharmaceutically acceptable salts thereof.

In an example embodiment, the MC4R agonist useful for practicing the methods described herein is at least one compound according to Formula (VIII) (see International Patent Application Number PCT/US08/07411, incorporated herein by reference in its entirety):

$$(R^2R^3)\text{-}A^0\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \quad \text{(VIII)}$$

In Formula (VIII):

$A^0$ is an aromatic amino acid $A^1$ is Acc, HN—$(CH_2)_m$—C(O), an L- or D-amino acid;

$A^2$ is Asp, Cys, D-Cys, hCys, D-hCys, Glu, Pen, or D-Pen;

$A^3$ is Aib, Ala, β-Ala, Gaba, Gly or a D-amino acid;

$A^4$ is His, 2-Pal, 3-Pal, 4-Pal, ($X^1$, $X^2$, $X^3$, $X^4$, $X^5$) Phe, Taz, 2-Thi, or 3-Thi;

$A^5$ is D-Bal, D-1-Nal, D-2-Nal, D-Phe, L-Phe, D-($X^1$, $X^2$, $X^3$, $X^4$, $X^3$) Phe, L-Phe, D-Trp or D-(Et) Tyr;

$A^6$ is Arg, hArg, Dab, Dap, Lys, Orn, or HN—CH(($CH_2$)$_{rt}$—N($R^4R^5$))—C(O);

$A^7$ is Bal, D-Bal, Bip, D-Bip, 1-Nal, D-1-Nal, 2-Nal, D-2-Nal, or D-Trp;

$A^8$ is Acc, Aha, Ahx, Ala, D-Ala, β-Ala, Apn, Gaba, Gly, HN—$(CH_2)_s$—C(O), or deleted;

$A^9$ is Cys, D-Cys, hCys, D-hCys, Dab, Dap, Lys, Orn, Pen, or D-Pen;

$A^{10}$ is Acc, HN—$(CH_2)_t$—C(O), L- or D-amino acid, or deleted;

$R^1$ is OH, or $NH_2$;

each of $R^2$ and $R^3$ is, independently for each occurrence selected from the group consisting of H, ($C_1$-$C_{30}$)alkyl, ($C_1$-$C_{30}$) heteroalkyl, ($C_1$-$C_{30}$) acyl, ($C_2$-$C_{30}$)alkenyl, ($C_2$-$C_{30}$)alkynyl, aryl($C_1$-$C_{30}$)alkyl, aryl ($C_1$-$C_{30}$) acyl, substituted ($C_1$-$C_{30}$)alkyl, substituted ($C_1$-$C_{30}$) heteroalkyl, substituted ($C_1$-$C_{30}$) acyl, substituted ($C_2$-$C_{30}$)alkenyl, substituted ($C_2$-$C_{30}$)alkynyl, substituted aryl($C_1$-$C_{30}$)alkyl, and substituted aryl($C_1$-$C_{30}$) acyl;

each of $R^4$ and $R^5$ is, independently for each occurrence, H, ($C_1$-$C_{40}$)alkyl, ($C_1$-$C_{40}$) heteroalkyl, ($C_1$-$C_{40}$) acyl, ($C_2$-$C_{40}$)alkenyl, ($C_2$-$C_{40}$)alkynyl, aryl($C_1$-$C_{40}$)alkyl, aryl($C_1$-$C_{40}$) acyl, substituted ($C_1$-$C_{40}$)alkyl, substituted ($C_1$-$C_{40}$) heteroalkyl, substituted ($C_1$-$C_{40}$) acyl, substituted ($C_2$-$C_{40}$)alkenyl, substituted ($C_2$-$C_{40}$)alkynyl, substituted aryl($C_1$-$C_{40}$) allyl, substituted aryl($C_1$-$C_{40}$) acyl, ($C_1$-$C_{40}$)alkylsulfonyl, or —C(NH)—$NH_2$;

m is, independently for each occurrence, 1, 2, 3, 4, 5, 6 or 7;

n is, independently for each occurrence, 1, 2, 3, 4 or 5;

s is, independently for each occurrence, 1, 2, 3, 4, 5, 6, or 7;

t is, independently for each occurrence, 1, 2, 3, 4, 5, 6, or 7;

$X^1$, $X^2$, $X^3$, $X^4$, and $X^5$ each is, independently for each occurrence, H, F, Cl, Br, I, ($C_{1-10}$)alkyl, substituted ($C_{1-10}$)alkyl, ($C_{2-10}$)alkenyl, substituted ($C_{2-10}$)alkenyl, ($C_{2-10}$)alkynyl, substituted ($C_{2-10}$)alkynyl, aryl, substituted aryl, OH, $NH_2$, $NO_2$, or CN.

In example embodiments of Formula (VIII), (I) when $R^4$ is ($C_1$-$C_{40}$) acyl, aryl($C_1$-$C_{40}$) acyl, substituted ($C_1$-$C_{40}$) acyl, substituted aryl($C_1$-$C_{40}$) acyl, ($C_1$-$C_{40}$)alkylsulfonyl, or —C(NH)—$NH_2$, then $R^5$ is H or ($C_1$-$C_{40}$)alkyl, ($C_1$-$C_{40}$) heteroalkyl, ($C_2$-$C_{40}$)alkenyl, ($C_2$-$C_{40}$)alkynyl, aryl($C_1$-$C_{40}$)alkyl, substituted ($C_1$-$C_{40}$)alkyl, substituted ($C_1$-$C_{40}$) heteroalkyl, substituted ($C_2$-$C_{40}$)alkenyl, substituted ($C_2$-$C_{40}$)alkynyl, or substituted aryl($C_1$-$C_{40}$)alkyl;

(II) when $R^2$ is ($C_1$-$C_{30}$) acyl, aryl($C_1$-$C_{30}$) acyl, substituted ($C_1$-$C_{30}$) acyl, or substituted aryl($C_1$-$C_{30}$) acyl, then $R^3$ is H, ($C_1$-$C_{30}$)alkyl, ($C_1$-$C_{30}$) heteroalkyl, ($C_2$-$C_{30}$)alkenyl, ($C_2$-$C_{30}$)alkynyl, aryl($C_1$-$C_{30}$)alkyl, substituted ($C_1$-$C_{30}$)alkyl, substituted ($C_1$-$C_{30}$) heteroalkyl, substituted ($C_2$-$C_{30}$)alkenyl, substituted ($C_2$-$C_{30}$) alkynyl, or substituted aryl($C_1$-$C_{30}$)alkyl;

(III) when $A^2$ is Cys, D-Cys, hCys, D-hCys, Pen, or D-Pen, then $A^9$ is Cys, D-Cys, hCys, D-hCys, Pen, or D-Pen;

(IV) when $A^2$ is Asp or Glu, then $A^9$ is Dab, Dap, Orn, or Lys;

(V) when $A^8$ is Ala or Gly, then $A^1$ is not Nle; or pharmaceutically acceptable salts thereof.

In example embodiments of compounds of Formula (VIII):

$A^0$ is 1-Nal, 2-Nal, His, Pff, Phe, Trp, or Tyr;

$A^1$ is Arg;

$A^2$ is Cys;
$A^3$ is D-Ala;
$A^4$ is His;
$A^5$ is D-Phe
$A^6$ is Arg;
$A^7$ is Trp
$A^8$ is deleted;
$A^9$ is Cys; and
$A^{10}$ is deleted;

or pharmaceutically acceptable salts thereof.

Particular compounds of the immediately foregoing group of compounds are of the formula:

(SEQ ID NO: 552)
Ac-Tyr-Arg-c(Cys-D-Ala-His-D-Phe-Arg-Trp-Cys)-$NH_2$;

(SEQ ID NO: 553)
Ac-2-Nal-Arg-c(Cys-D-Ala-His-D-Phe-Arg-Trp-Cys)-$NH_2$;

(SEQ ID NO: 554)
Ac-1-Nal-Arg-c(Cys-D-Ala-His-DPhe-Arg-Trp-Cys)-$NH_2$;

(SEQ ID NO: 555)
Ac-Phe-Arg-c(Cys-D-Ala-His-D-Phe-Arg-Trp-Cys)-$NH_2$;

(SEQ ID NO: 556)
Ac-Trp-Arg-c(Cys-D-Ala-His-D-Phe-Arg-Trp-Cys)-$NH_2$;

(SEQ ID NO: 557)
Ac-Pff-Arg-c(Cys-D-Ala-His-D-Phe-Arg-Trp-Cys)-$NH_2$;

(SEQ ID NO: 558)
H-His-Arg-c(Cys-D-Ala-His-D-Phe-Arg-Trp-Cys)-$NH_2$;
or (SEQ ID NO: 559)
Ac-His-Arg-c(Cys-D-Ala-His-D-Phe-Arg-Trp-Cys)-$NH_2$;

or a pharmaceutically acceptable salt thereof.

In one example embodiment, the MC4R agonist is Ac-Arg-c(Cys-D-Ala-His-D-Phe-Arg-Trp-Cys)-$NH_2$ (SEQ ID NO: 140) or a pharmaceutically acceptable salt thereof. In another example embodiment, the MC4R agonist is Hydantoin(C(O)-(Arg-Gly))-c(Cys-Glu-His-D-Phe-Arg-Trp-Cys)-$NH_2$ (SEQ ID NO: 500) or a pharmaceutically acceptable salt thereof.

Administration of a compound or pharmaceutically acceptable salt thereof or a composition comprising a compound or pharmaceutical salt of a compound of the invention useful to practice the methods described herein, can be continuous, hourly, four times daily, three time daily, twice daily, once daily, once every other day, twice weekly, once weekly, once every two weeks, once a month, or once every two months, or longer or some other intermittent dosing regimen.

Examples of administration of a compound or composition comprising a compound or pharmaceutical salt of a compound of the invention include peripheral administration. Examples of peripheral administration include oral, subcutaneous, intraperitoneal, intramuscular, intravenous, rectal, transdermal or intranasal forms of administration.

As used herein, peripheral administration includes all forms of administration of a compound or a composition comprising a compound of the instant invention which excludes intracranial administration. Examples of peripheral administration include, but are not limited to, oral, parenteral (e.g., intramuscular, intraperitoneal, intravenous or subcutaneous injection, extended release, slow release implant, depot and the like), nasal, vaginal, rectal, sublingual or topical routes of administration, including transdermal patch applications and the like.

The nomenclature used to define the peptides is that typically used in the art wherein the amino group at the N-terminus appears to the left and the carboxyl group at the C-terminus appears to the right. Where the amino acid has D and L isomeric forms, it is the L form of the amino acid that is represented unless otherwise explicitly indicated.

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention. For example, a claim to 2-hydroxypyridinyl would also cover its tautomeric form, α-pyridonyl.

Unless defined otherwise, all technical and scientific terms used herein have the same meaning as commonly understood by one of ordinary skill in the art to which this invention belongs. Also, all publications, patent applications, patents and other references mentioned herein are incorporated by reference in their entirety.

| Symbol | Meaning |
|---|---|
| Abu | α-aminobutyric acid |
| Ac | acyl group |
| Acc | 1-amino-1-cyclo($C_3$-$C_9$)alkyl carboxylic acid |
| A3c | 1-amino-1cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Aha | 7-aminoheptanoic acid |
| Ahx | 6-aminohexanoic acid |
| Aib | α-aminoisobutyric acid |
| Aic | 2-aminoindan-2-carboxylic acid |
| Ala or A | alanine |
| β-Ala | β-alanine |
| Apc | denotes the structure: 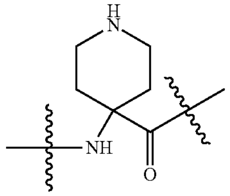 [SMILES: *NC1(C(*)=O)CCNCC1] |
| Apn | 5-aminopentanoic acid (HN—$(CH2)_4$—C(O) |
| Arg or R | arginine |
| hArg | homoarginine |
| Asn or N | asparagine |
| Asp or D | aspartic acid |
| Bal | 3-benzothienylalanine |

-continued

| Symbol | Meaning |
|---|---|
| Bip | 4,4'-biphenylalanine, represented by the structure 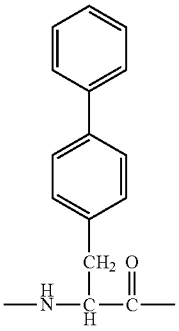 [SMILES: CNC(Cc1ccc(-c2ccccc2)cc1)C(C)=O] |
| Bpa | 4-benzoylphenylalanine |
| 4-Br-Phe | 4-bromo-phenylalanine |
| Cha | β-cyclohexylalanine |
| hCha | homo-cyclohexylalanine |
| Chg | cyclohexylglycine |
| Cys or C | cysteine |
| hCys | homocysteine |
| Dab | 2,4-diaminobutyric acid |
| Dap | 2,3-diaminopropionic acid |
| Dip | β,β-diphenylalanine |
| Doc | 8-amino-3,6-dioxaoctanoic acid with the structure of: 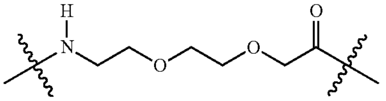 [SMILES: *NCCOCCOCC(*)=O] |
| 2-Fua | β-(2-furyl)-alanine |
| Gaba | 4-aminobutyric acid |
| Gln or Q | glutamine |
| Glu or E | glutamic acid |
| Gly or G | glycine |
| His or H | histidine |
| 3-Hyp | trans-3-hydroxy-L-proline, i.e., (2S,3S)-3-hydroxy-pyrrolidine-2-carboxylic acid |
| 4-Hyp | 4-hydroxyproline, i.e., (2S,4R)-4-hydorxypyrrolidine-2-carboxylic acid |
| Ile or 1 | isoleucine |
| Leu or L | leucine |
| hLeu | homoleucine |
| Lys or K | lysine |
| Met or M | methionine |
| β-hMet | β-homomethionine |
| 1-Nal | β-(1-naphthyl)alanine |
| 2-Nal | β-(2-naphthyl)alanine |
| Nip | nipecotic acid |
| Nle | norleucine |
| Ole | octahydroindole-2-carboxylic acid |
| Orn | ornithine |
| 2-Pal | β-(2-pyridiyl)alanine |
| 3-Pal | β-(3-pyridiyl)alanine |
| 4-Pal | β-(4-pyridiyl)alanine |
| Pen | penicillamine |
| Pff | (S)-pentafluorophenylalanine |
| Phe or F | phenylalanine |
| hPhe | homophenylalanine |
| Pro or P | proline |
| hProP | homoproline |
| Ser or S | Serine |
| Tle | tert-Leucine |
| Taz | β-(4-thiazolyl)alanine |
| 2-Thi | β-(2-thienyl)alanine |
| 3-Thi | β-(3-thienyl)alanine |
| Thr or T | threonine |
| Trp or W | tryptopham |
| Tyr or Y | tyrosine |

-continued

| Symbol | Meaning |
|---|---|
| D-(Et) Tyr | has a structure of 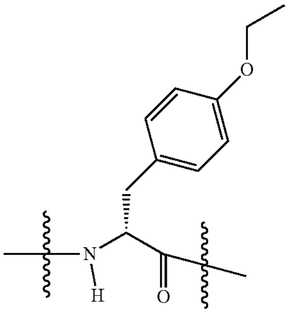 [SMILES: *N[C@H](Cc1ccc(OCC)cc1)C(*)=O] |
| Val or V | Valine |

Certain other abbreviations used herein are defined as follows:

| | |
|---|---|
| Boc: | tert-butyloxycarbonyl |
| Bzl: | benzyl |
| DCM: | dichloromethane |
| DIC: | N,N-diisopropylcarbodiimide |
| DIEA: | diisopropylethyl amine |
| Dmab: | 4-{N-(1-(4,4-dimethyl-2,6-dioxocyclohexylidene)-3-methylbutyl)-amino}benzyl |
| DMAP: | 4-(dimethylamino)pyridine |
| DMF: | dimethylformamide |
| DNP: | 2,4-dinitrophenyl |
| Fm: | fluorenylmethyl |
| Fmoc: | fluorenylmethyloxycarbonyl |
| For: | formyl |
| HBTU: | 2-(1H-benzotriazole-1-yl)-1,1,3,3-tetramethyl-uronium hexafluorophosphate |
| cHex | cyclohexyl |
| HOAT: | O-(7-azabenzotriazol-1-yl)-1,1,3,3-tetramethyl-uronium hexafluorophosphate |
| HOBt: | 1-hydroxy-benzotriazole |
| MBNA | 4-methylbenzhydrylamine |
| Mmt: | 4-methoxytrityl |
| NMP: | N-methylpyrrolidone |
| O-tBu | oxy-tert-butyl |
| Pbf: | 2,2,4,6,7-pentamethyldihydrobenzofuran-5-sulfonyl |
| PyBroP | bromo-tris-pyrrolidino-phosphonium hexafluoro-phosphate |
| tBu: | tert-butyl |
| TIS: | triisopropylsilane |
| TOS: | tosyl |
| Trt | trityl |
| TFA: | trifluoro acetic acide |
| TFFH: | tetramethylfluoroforamidiaium hexafluorophosphate |
| Z: | benzyloxycarbonyl |

Unless otherwise indicated, with the exception of the N-terminal amino acid, all abbreviations (e.g. Ala) of amino acids in this disclosure stand for the structure of —NH—C(R)(R')—CO—, wherein R and R' each is, independently, hydrogen or the side chain of an amino acid (e.g., $R=CH_3$ and R'=H for Ala), or R and R' may be joined to form a ring system.

For the N-terminal amino acid, the abbreviation stands for the structure of:

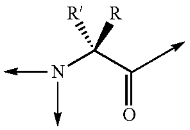

The designation "$NH_2$" in e.g., Ac-Nle-c(Cys-D-Ala-His-D-Phe-Arg-Trp-Cys)-$NH_2$ (SEQ ID NO:13), indicates that the C-terminus of the peptide is amidated. Ac-Nle-c(Cys-D-Ala-His-D-Phe-Arg-Trp-Cys) (SEQ ID NO:107), or alternatively Ac-Nle-c(Cys-D-Ala-His-D-Phe-Arg-Trp-Cys)-OH (SEQ ID NO:107), indicates that the C-terminus is the free acid.

"-c(Cys-Cys)-" or "-cyclo(Cys-Cys)-" denotes the structure:

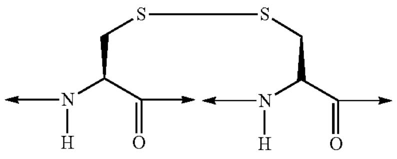

"-c(Cys-Pen)-" or "-cyclo(Cys-Pen)-" denotes the structure:

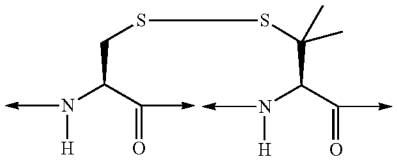

"-c(Asp-Lys)-" or "-cyclo(Asp-Lys)-" denotes the structure:

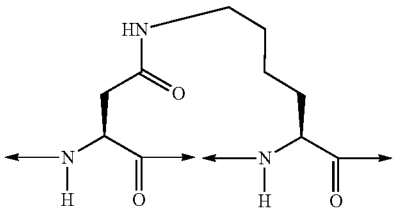 [SMILES: N[C@H](C=O)CCCCNC(=O)C[C@H](N)C=O]

Applicants have devised the following shorthand used in naming the specific embodiments and/or species:

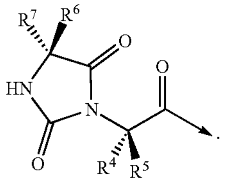

"HydantoinC(O)-($A^a$-$A^b$)" denotes the structure: wherein amino acid "$A^a$" has the structure:

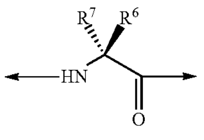

and amino acid "$A^b$" the structure:

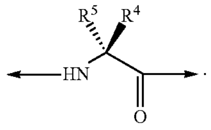

For example, a compound represented as "c[Hydantoin (C(O)-(Cys-$A^b$))-$A^1$-$A^2$-$A^3$-$A^4$-Cys]-" would have the following the structure:

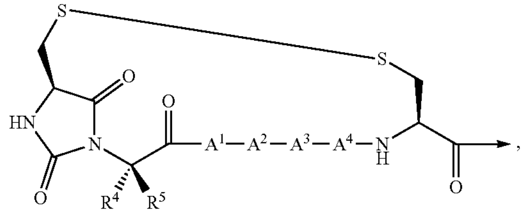

whereas a compound represented as "c[Hydantoin(C(O)-($A^b$-Cys))-$A^1$-$A^2$-$A^3$-$A^4$-Cys]-" would have the structure:

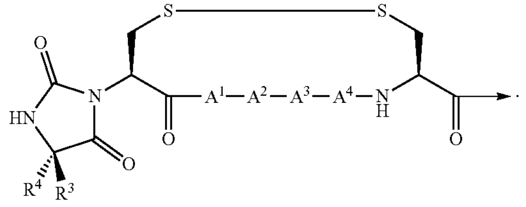

For further guidance, "c[Hydantoin(C(O)-(Asp-$A^b$))-$A^1$-$A^2$-$A^3$-$A^4$-Lys]-" represents the following compound:

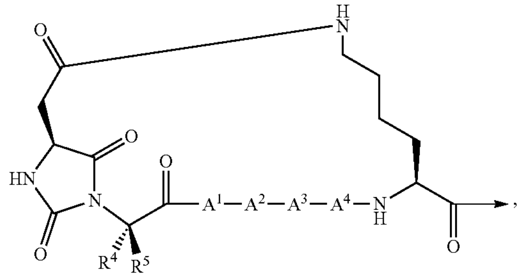

whereas "c[Hydantoin(C(O)-(Dap-$A^b$))-$A^1$-$A^2$-$A^3$-$A^4$-Asp]-" has the following formula:

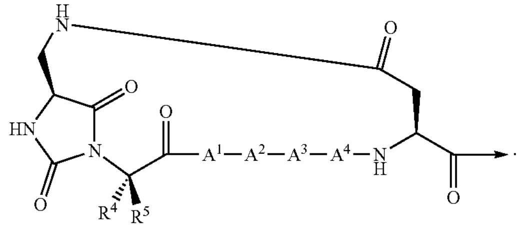

"Acyl" refers to R"—C(O)—, where R" is H, alkyl, substituted alkyl, heteroalkyl, substituted heteroalkyl, alkenyl, substituted alkenyl, aryl, alkylaryl, or substituted alklyaryl, and is indicated in the general formula of a particular embodiment as "Ac".

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Hydroxyalkyl" refers to an alkyl group wherein one or more hydrogen atoms of the hydrocarbon group are substituted with one or more hydroxy radicals, such as hydroxymethyl, hydroxyethyl, hydroxypropyl, hydroxybutyl, hydroxypentyl, hydroxyhexyl and the like.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, $—NH_2$, $—NHCH_3$, $—NO_2$, and $—C_{1-20}$ alkyl, wherein said-$C_{1-20}$ alkyl optionally may be substituted with one or more substituents selected, independently for each occurrence, from the group consisting of halogens, $—CF_3$, $—OCH_3$, $—OCF_3$, and $—(CH_2)_{0-20}—COOH)$. In different embodiments 1, 2, 3 or 4 substituents are present. The presence of $—(CH_2)_{0-20}—COOH)$ results in the production of an alkyl acid. Non-limiting examples of alkyl acids containing, or consisting of, $—(CH_2)_{0-20}—COOH)$ include 2-norbornane acetic acid, tert-butyric acid, 3-cyclopentyl propionic acid, and the like.

The term "halo" encompasses fluoro, chloro, bromo and iodo.

"Heteroalkyl" refers to an alkyl wherein one of more of the carbon atoms in the hydrocarbon group is replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, $—NH_2$, $—NHCH_3$, $—NO_2$, and $—C_{1-20}$ alkyl, wherein said-$C_{1-20}$ alkyl optionally may be substituted with one or more substituents selected, independently for each occurrence, from the group consisting of halogens, $—CF_3$, $—OCH_3$, $—OCF_3$, and $—(CH_2)_{0-20}—COOH)$. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, $—NH_2$, $—NHCH_3$, $—NO_2$, and $—C_{1-20}$ alkyl, wherein said $—C_{1-20}$ alkyl optionally may be substituted with one or more substituents selected, independently for each occurrence, from the group consisting of halogens, $—CF_3$, $—OCH_3$, $—OCF_3$, and $—(CH_2)_{0-20}—COOH)$. In different embodiments 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5- or 6-membered ring. Preferred atoms for a heterocyclic aryl are one or more sulfur, oxygen, and/or nitrogen. Non-limiting examples of aryl include phenyl, 1-naphthyl, 2-naphthyl, indole, quinoline, 2-imidazole, 9-anthracene, and the like. Aryl substituents are selected from the group consisting of $—C_{1-20}$ alkyl, $—C_{1-20}$ alkoxy, halogen (i.e., fluorine, chlorine, bromine, and iodine), —OH, —CN, —SH, $—NH_2$, $—NO_2$, $—C_{1-20}$ alkyl substituted with halogens, $—CF_3$, $—OCF_3$, and $—(CH_2)_{0-20}—COOH)$. In different embodiments the aryl contains 0, 1, 2, 3, or 4 substituents.

"Alkylaryl" refers to an "alkyl" joined to an "aryl".

The term "$(C_{1-12})$ hydrocarbon moiety" encompasses alkyl, alkenyl and alkynyl and in the case of alkenyl and alkynyl there is $C_2$-$C_{12}$.

For the avoidance of doubt, unless otherwise indicated, the term substituted means substituted by one or more defined groups. In the case where groups may be selected from a number of alternative groups, the selected groups may be the same or different. For the avoidance of doubt, the term independently means that where more than one substituent is selected from a number of possible substituents, those substituents may be the same or different.

The pharmaceutically acceptable salts of the compounds of the invention which contain a basic center are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically acceptable metal salts, in particular non-toxic alkali and alkaline earth metal salts, with bases. Examples include the sodium, potassium, aluminum, calcium, magnesium, zinc and diethanolamine salts (Berge, S. M. et al., *J. Pharm. Sci.,* 66:1-19 (1977); Gould, P. L., *Int'l J. Pharmaceutics,* 33:201-17 (1986); and Bighley, L. D. et al., *Encyclo. Pharma. Tech.*, Marcel Dekker Inc, New York, 13:453-97 (1996).

The pharmaceutically acceptable solvates of the compounds of the invention include the hydrates thereof. Also included within the scope of the invention and various salts of the invention are polymorphs thereof. Hereinafter, compounds their pharmaceutically acceptable salts, their solvates or polymorphs, defined in any aspect of the invention (except intermediate compounds in chemical processes) are referred to as "compounds of the invention".

Designation "(amino acid) n" means that an amino acid is repeated n times. For example, designation "$(Pro)_2$" or "$(Arg)_3$" mean that proline or arginine residues are repeated, respectively, two or three times.

MC4R agonists and pharmaceutically acceptable salts thereof described herein can also be used to treat individuals, including human subjects defective melanocortin receptor signaling, due to mutations/defects upstream of the MC4R. MC4R agonists and pharmaceutically acceptable salts thereof described herein can also be used to treat individuals, including human subjects that carry mutations in the genes coding for pro-opiomelanocortin (POMC) and leptin such that these mutations result in POMC haplo-insufficiency or haplo-deficiency and/or leptin haplo-insufficiency or haplo-deficiency.

In one example embodiment, an MC4R agonist is a compound represented by structural formula (X):

(X)

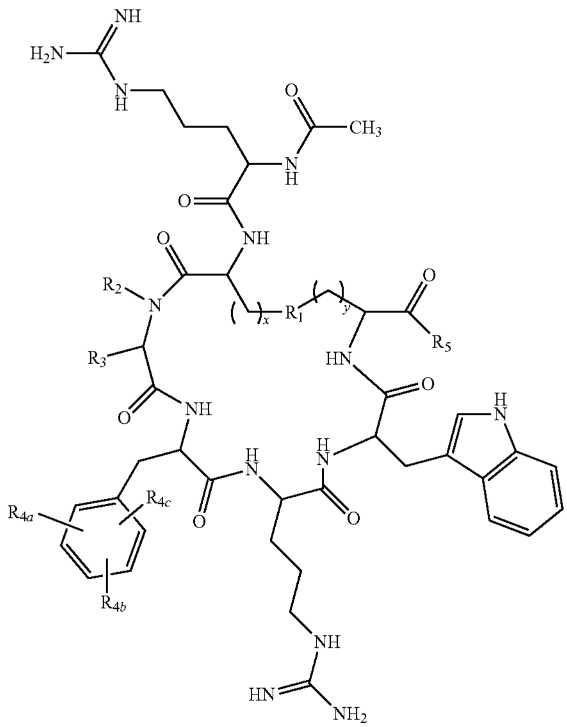

or a pharmaceutically acceptable salt thereof. In structural formula (X), the chemical substituents are defined as follows:

$R_1$ is —NH—C(O)— or —C(O)—NH—;

$R_2$ is —H, —$CH_2$—, or, $R_2$, together with $R_3$, forms a pyrrolidine ring optionally substituted with —OH;

$R_3$ is —$(CH_2)_2$— if $R_2$ is —$CH_2$—, and otherwise $R_3$ is selected from

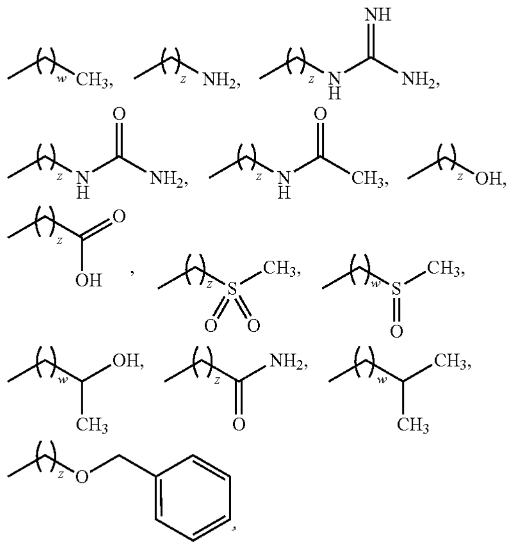

-continued

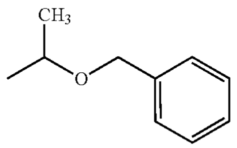

, and

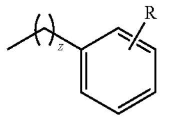

,

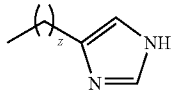

;

$R_{4a}$, $R_{4b}$, and $R_{4c}$ are each independently selected from hydrogen, halo, $(C_1\text{-}C_{10})$alkyl-halo, $(C_1\text{-}C_{10})$alkyl-dihalo, $(C_1\text{-}C_{10})$alkyl-trihalo, $(C_1\text{-}C_{10})$alkyl, $(C_1\text{-}C_{10})$alkoxy, $(C_1\text{-}C_{10})$alkylthio, aryl, aryloxy, nitro, nitrile, sulfoniamide, amino, hydroxyl, carboxy, and alkoxycarbonyl. In one example embodiment, $R_{4a}$, $R_{4b}$, and $R_{4c}$ is not hydrogen.

$R_5$ is —OH or —$N(R_{6a})(R_{6b})$;

$R_{6a}$ and $R_{6b}$ are each independently H or $C_1$ to $C_4$ linear, branched or cyclic alkyl chain;

$R^7$ is —H or —C(O)—$NH_2$;

w is in each instance independently 0 to 5;

x is 1 to 5;

y is 1 to 5;

z is in each instance independently 1 to 5.

An example of a compound of structural formula (X) is a cyclic peptide defined by structural formula (XI):

(XI)

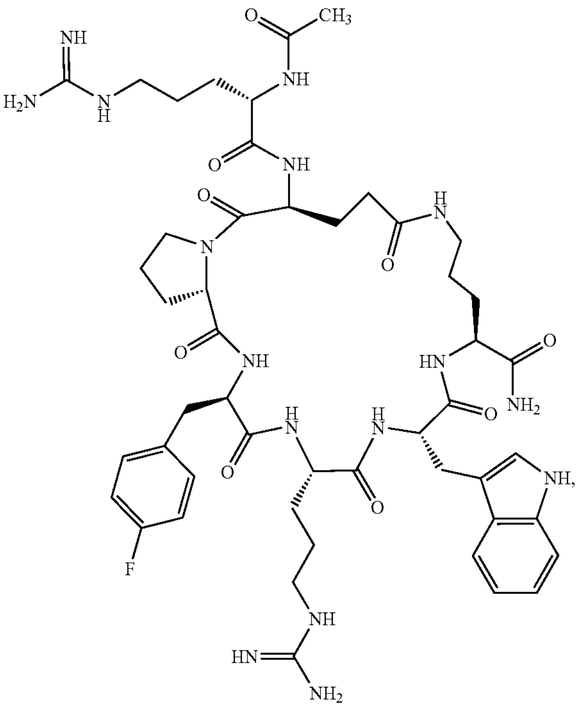

or a pharmaceutically acceptable salt thereof.

EXEMPLIFICATION

Example 1: Model for Evaluating Whether Obese MC4R+/− Heterozygotic Mice are Responsive to Treatment with Compound of SEQ ID NO: 140

The effect of MC4R agonist administration on a subject can be evaluated according to the following procedure.

The effects of a MC4 agonist in heterozygous MC4+/− mice and in weight-matched diet-induced-obesity (DIO) mice is evaluated. Heterozygous MC4+/− mice express a mild hyperphagic and obese phenotype when compared to the homozygous MC4−/− mice while retaining a putative response to MC4 stimulation. Weight-matched DIO mice are expressing the MC4 receptor (wild-type). In the course of the study, the effect of MC4 agonism on food intake and body weight in mice that are phenotypically obese but differ genetically in terms of the expression of the MC4 receptor is being characterized.

Pre-Study activities: $C_{57}$BL/6 mice (N=50, males, 4 weeks of age) are pre-fed a high fat (HF) diet, commercially available from Research Diets Inc, New Brunswick, NJ, for 10 weeks prior to enrollment onto study. The HF diet (D12492) is fed to the animals ad libitum.

Species (number, sex, age/weight): C57BL/6 mice (N=40, males, 14 weeks of age at initiation of dose administration). Study criteria for animal enrollment based on body weight. B6-129/S-MC4+/− heterozygous mice (Jackson Labs or Taconic; N=40, males, body weight matching the DIO mice, 12-14 weeks of age).

Formulations: all test materials are formulated once weekly.

Treatment: All animals are surgically implanted with a subcutaneous osmotic minipump (infusion duration of 14 days).

The design of this study is symmarized in Table A:

TABLE A

Study Design:

| Group No. | Mice | Animals per Group | Treatment | Dose Level and Volume | Treatment Regimen | Observation Period |
|---|---|---|---|---|---|---|
| 1 | $MC4^{+/-}$ | 10 | Vehicle | 0 | Chronic | 14 |
| 2 | DIO | 10 | | | Constant | days |
| 3 | $MC4^{+/-}$ | 10 | Peptide | Low | Infusion by | |
| 4 | DIO | 10 | drug | | Osmotic | |
| 5 | $MC4^{+/-}$ | 10 | | Mid | Minipump | |
| 6 | DIO | 10 | | | (Option 2) | |
| 7 | $MC4^{+/-}$ | 10 | | High | | |
| 8 | DIO | 10 | | | | |

Cage side and clinical observations are performed daily, clinical observations are noted per exception. Food intake by mice is permitted daily. Body Weights: All animals have body weights measured once weekly during the pre-feed and twice weekly during administration, initiating prior to the initial dose administration. Doses are based on most recently collected body weight.

Fasting Whole Blood Glucose Levels and Plasma Sample Collection: Following an overnight fast, all animals have a fasting whole blood glucose level (via glucometer) and blood sample collected (~100 μL) on Days −1 and 14.

Euthanasia and Tissue Collection: All animals are scheduled for euthanasia on Day 15 in the AM. All animals have a maximum terminal blood collection made. Blood samples are processed for plasma for insulin measurement. All animals have the retroperitoneal adipose tissue and liver excised and weighed.

Insulin measurement: Insulin levels are determined in terminal plasma samples using a mouse insulin ELISA assay by the testing facility.

Reporting: Data submission including clinical observations, food intakes, body weights, insulin levels, fasting blood glucose and plasma collections, mortality record (if applicable), the study protocol and associated amendments, and all protocol deviations.

Example 2: Models for Clinical Evaluation of the Efficacy of Treatment of MC4R-Mediated Obesity Using Compounds Disclosed Herein 1. Randomized, Double-Blind, Placebo-Controlled, Multiple Ascending Dose Study to Evaluate the Safety, Tolerability, Pharmacokinetics and Pharmacodynamics of Compounds of the Present Invention Administered to Healthy Obese Non-Diabetic Volunteers Objectives Primary:

Investigate the safety and tolerability of multiple dose levels of the compounds of the present invention when given by continuous subcutaneous (SC) infusion for 14 or 28 days.

Secondary:

Evaluate the pharmacokinetics (PK) of multiple dose levels of the compounds of the present invention when given by SC continuous infusion for 14 or 28 days.

Exploratory pharmacodynamic (PD) objectives of this study are to evaluate the effect of multiple dose levels of the compounds of the present invention when given by SC continuous infusion for 14 or 28 days on:

Caloric intake, weight and waist circumference.

Insulin sensitivity as measured by a Meal Tolerance Test (MTT).

Hunger and satiety as measured by a Hunger/Satiety Questionnaire.

Resting energy expenditure (REE) as measured by indirect calorimetry (to be performed at select centers with this capability).

Study Design

The study is designed to evaluate safety and tolerability of the compounds of the present invention administered up to 1 mg/kg/day for 14 or 28 days as a SC continuous infusion. The highest dose proposed to use in the study is no higher than 1 mg/kg. This is a randomized, double-blind, placebo-controlled, multiple ascending dose study during which 5 sequential cohorts of subjects will receive the compounds of the present invention or placebo by SC continuous infusion for 14 (Cohorts dosed for 14 days) or 28 days (Cohorts dosed for 28 days). Nine subjects will be enrolled in each cohort and subjects will be randomly allocated to receive the compounds of the present invention or placebo in a 6:3 ratio.

All subjects will remain confined to the Phase 1 clinical unit during treatment and under observation for at least 24 hours after the end of the study drug infusion.

A Clinical Safety Committee (CSC) will review blinded interim safety data from each dose level. Dose escalation will be recommended only if the previous dose level was deemed to be safe and well tolerated. Where appropriate, for safety reasons, additional interim dose levels (lower than the next scheduled dose) may be administered. Additionally, a sub-set of the general obese population may be enrolled. These subjects will meet all inclusion and exclusion criteria outlined in below, as well as one additional criterion: subjects must be heterozygous with a loss-of-function mutation in one of their two copies of the MC4 receptor gene. These subjects will have been pre-identified as having an MC4 receptor mutation. The rationale for this cohort is the lesser MC4 tone that is seen in heterozygous subjects, may give an altered sensitivity for these subjects to MC4 agonists such as the compounds of the present invention. If this cohort is enrolled, it is anticipated to be at a select site, nearer the end of the study.

Number of Subjects Planned

A sufficient number of healthy obese adult male and female subjects will be screened so that approximately 45 eligible subjects qualify for the study and are randomized. It is expected that approximately 45 subjects will be enrolled in approximately 5 dose groups to evaluate multiple days of dosing (14 or 28 days) of the compounds of the present invention administered by SC continuous infusion. Up to an additional 63 subjects may be enrolled to further characterize the compounds of the present invention with a maximum of approximately 108 subjects planned for treatment in the study. The additional subjects will be recruited in the event a subject needs to be replaced, a cohort is to be expanded or an intermediate dose is recommended by the CSC. It is intended that most cohorts will consist of 9 subjects (in a ratio of 2 active: 1 placebo). However some cohorts may be increased in order to enhance the sample size and further define any prior findings.

Diagnosis and Main Criteria for Inclusion

Subjects must meet all of the following inclusion criteria to be eligible for the study.

Inclusion Criteria.

- Able to provide voluntary, written informed consent with comprehension of all aspects of the protocol, prior to any study procedures.
- Healthy obese male and female volunteers aged 18 to 55 years, inclusive.
- In good general health, without significant medical history, physical examination findings, or clinical laboratory abnormalities.
- Body Mass Index of 30-40 kg/$m^2$, inclusive.
- Stable body weight during the previous 6 months, based on Investigator judgment.
- Blood pressure <140/90 mmHg at Screening and D-1. Measurement may be repeated once within 24 hours, based on Investigator judgment.
- Females must not be pregnant and must have a negative serum pregnancy test result at the Screening Visit and Day −1.
- Females of childbearing potential must agree to be abstinent or else use any two of the following medically acceptable forms of contraception from the Screening Period through the Final Study Visit: hormonal, condom with spermicidal jelly, diaphragm or cervical cap with spermicidal jelly, or IUD. Hormonal contraception must have started at least 3 months prior to screening. A female whose male partner has had a vasectomy must agree to use one additional form of medically acceptable contraception. Subjects must agree to practice the above birth control methods for 30 days from the final visit as a safety precaution.
- Females of non-childbearing potential, defined as surgically sterile (status post hysterectomy, bilateral oophorectomy, or bilateral tubal ligation) or postmenopausal for at least 12 months (and confirmed with a screening FSH level in the post-menopausal range), do not require contraception during the study.
- Males with female partners of childbearing potential must agree to use two medically acceptable forms of contraception as described above, with one of the two forms being condom with spermicide, from the Screening Period through the Final Study Visit. Males with female partners of childbearing potential who themselves are surgically sterile (status post vasectomy) must agree to use condoms with spermicide over the same period of time. Male subjects must agree to practice the above birth control methods for 30 days from the final visit as a safety precaution.

Additional Inclusion Criteria for Heterozygous MC4 Receptor Mutation Cohort:

- Mutation of MC4R gene resulting in partial loss or complete loss of function of one of the MC4 receptor genes.

Exclusion criteria

- Fasting blood glucose >126 mg/dL at screening.
- Resting heart rate <45 bpm or >90 bpm at screening.
- Abnormal thyroid stimulating hormone (TSH) or thyroxine ($T_4$) levels on screening.
- Elevated ALT or serum creatinine on screening or any clinically significant abnormalities on screening laboratory tests as determined by the Investigator.
- History of diabetes or of treated or medically diagnosed hypertension.
- Presence of a skin lesion suspicious for malignancy.
- History of malignancy except for treated cervical carcinoma in situ in the past 5 years.
- Active or history of any clinically significant medical condition including renal, hepatic, pulmonary, gastrointestinal, cardiovascular, genitourinary, endocrine, immunologic, metabolic, neurologic, psychiatric or hematological disease, based on Investigator judgment.
- Acute illness or history of illness, which in the opinion of the Investigator, could pose a threat or harm to the subject or obscure interpretation of laboratory test results or interpretation of study data.
- Positive hepatitis B surface antigen, positive hepatitis C antibody or positive HIV test at screening or a history of positive testing (e.g. liver biopsy, serology) suggesting acute or chronic hepatitis.
- Abnormal 12-lead electrocardiogram (ECG) at screening or pre-dose (Day −1 or Day 1), except minor deviations deemed to be of no clinical significance by the Investigator.
- Received any experimental drugs or devices within 30 days or 5 half lives, whichever is longer, prior to dosing.
- Ongoing participation in a prior clinical study at the time of screening.
- Blood donation within 60 days prior to screening or intent to donate within 60 days after Final Study Visit.
- Hospitalization for major surgery including but not limited to abdominal, thoracic, or cardiovascular surgery within the past 3 months prior to screening, or for a clinically significant non-surgical illness, based on Investigator judgment, within the past 3 months.
- Planned elective surgery within 30 days of the Final Study Visit.
- Poor venous access or inability to tolerate venipuncture.
- History of drug hypersensitivity or anaphylaxis.
- History of hypersensitivity to proteins (e.g., allergy shots).
- Use of prescription medications on a regular basis. The last use of any prescription medication must have been greater than 5 half-lives for the specific medication or at least 14 days prior to admission (Day −1), whichever is longer. Hormonal contraception is allowed for female subjects.

Use of a non-prescription drug and herbal substances during the study (through the Final Study Visit). The last dose of any non-prescription drug must have been taken greater than 5 half-lives for that drug before receiving study drug.

Inability to attend all study visits or to comply with protocol requirements including fasting and restrictions on alcohol, caffeine, nicotine and concomitant medication intake.

A significant history of drug/solvent abuse within 5 years of screening or a positive test for drugs of abuse test at screening or on Day −1.

Positive alcohol (breath test) or nicotine screen at Screening Visit or Day −1.

History of alcohol abuse (defined as average intake of three or more units of alcohol per day) within 5 years of the Screening Visit.

History of tobacco or tobacco product use unless abstinent for at least one year prior to the Screening Visit.

Previously randomized and dosed in this study.

Any other reason, which in the opinion of the Investigator would confound proper evaluation of the study.

Test Products, Doses, and Mode of Administration

The compounds of the present invention and the placebo are formulated for administration by SC continuous infusion using an infusion pump.

The 5 dose levels planned, in ascending order, are:

0.01 mg/kg/24 hrs 0.1 mg/kg/24 hrs 0.25 mg/kg/24 hrs 0.5 mg/kg/24 hrs 1.0 mg/kg/24 hrs The compounds of the present invention or placebo will be given by SC continuous infusion for 14 or 28 days. The dose levels evaluated may be modified based upon data from the single ascending dose study, or the prior MAD cohort.

Duration of Treatment

Overall study duration will be approximately 7 months. Individual subject participation in the study (screening, dosing, post-dosing assessments, follow-up) will be approximately 72 and 86 days for Cohorts dosed for 14 days and dosed for 28 days respectively.

The study will consist of a Screening Period, a Treatment Period and a Follow-up Period. The Screening Period will occur within 30 days prior to enrollment. The Treatment Period will consist of administration of a SC continuous infusion initiated on Day 1 and completed on Day 15 or Day 29 for Cohorts dosed for 14 days and Cohorts dosed for 28 days, respectively. Subjects will remain confined in the clinical research center (CRC) for approximately 24 hours following completion of the infusion and will be discharged from the CRC on Day 16 or 30 after all study procedures have been completed. Follow-up study visits are scheduled 1 and 4 weeks after the end of the study drug infusion.

Study Procedures

The procedures for each study period are briefly outlined below and are depicted in detail in the Schedule of Assessments (SOA).

Screening Period (Days −30 to −1)

After informed consent is obtained and eligibility assessed, screening assessments will be performed including: medical history; pregnancy test (all females); drug, nicotine and alcohol screen; safety laboratory tests (including clinical chemistry, hematology and urinalysis), HbA1c and fructosamine, full physical examination (including weight, waist circumference and height), comprehensive skin examination performed by a Dermatologist, vital signs (including supine systolic and diastolic blood pressure, pulse rate, respiratory rate and body temperature); 12-lead electrocardiogram (ECG); HBsAg, HCV-Ab, HIV screening; samples of antibodies against the compounds of the present invention; Fitzpatrick scale; dietary recall review, indirect calorimetry (within 3 days of Day 1); previous and concomitant medication use.

Treatment Period

Subjects will be admitted to the research unit on Day −1. After continued eligibility is confirmed, the following assessments will be performed: abbreviated physical exams including weight and waist circumference; vital signs; 12 lead ECG; safety laboratory tests (including clinical chemistry, hematology and urinalysis); lipid profile; level of antibodies against the compounds of the present invention; serum sample for storage; quantitative skin color measurement; photographic skin evaluation; Hunger/Satiety questionnaire; initiation of cardiac telemetry and ambulatory blood pressure (ABPM) monitoring; sample collection for 24 hour urine catecholamine and cortisol level determination; estimated caloric intake; Meal Tolerance Test (MTT), randomization; monitoring for AEs and concomitant medications.

Upon initiation of study treatment on Day 1, the following assessments will be performed on Days 1-16 (Cohorts dosed for 14 days) or Days 1-29 (Cohorts dosed for 28 days) according to the SOA: abbreviated physical exam including weight and waist circumference; vital signs; cardiac telemetry, ABPM, 12-lead ECG, safety laboratory tests; lipid profile; sample collection for 24 hour urine catecholamine and cortisol level determination; sample collection for plasma free metanephrine levels, PK blood and urine sampling, melanocortin receptor genotyping; infusion site evaluation; quantitative skin color measurement; photographic skin evaluation; estimated caloric intake; MTT; HbA1c and fructosamine; Hunger/Satiety questionnaire; indirect calorimetry, monitoring for AEs and concomitant medications. Prior to discharge from the research unit, a serum pregnancy test will be performed on all females, and a comprehensive skin evaluation will be performed by a Dermatologist.

Follow-Up Period

One and 4 weeks after completion of the study treatment infusion, subjects will return to the research unit for the following assessments: complete physical exam including weight and waist circumference; comprehensive skin exam performed by a Dermatologist, quantitative skin color measurement; photographic skin evaluation; infusion site evaluation; vital signs; safety laboratory tests; lipid profile; HbA1c and fructosamine; levels of antibodies against the compounds of the present invention; Hunger/Satiety questionnaire, monitoring for AEs and concomitant medications.

Study Endpoints

Safety

Safety will be evaluated by assessment of adverse events, ECGs, cardiac telemetry, ambulatory blood pressure monitoring, clinical laboratory evaluations (hematology, clinical chemistry including fasting blood glucose levels and urinalysis), lipid profile; levels of antibodies against the compounds of the present invention, urinary catecholamine levels, urinary free cortisol levels, plasma free metanephrine levels, vital signs (including blood pressure, respiratory rate, heart rate, and body temperature), physical examinations including infusion site evaluations and concomitant medication review.

Pharmacokinetic

Serial blood sampling and urine collections for measurement of plasma and urinary levels of the compounds of the present invention will be conducted. All samples will be assayed for the compounds of the present invention from which the following PK parameters will be computed for each subject: $AUC_{0-\tau}$, $C_{ave}$, $C_{max}$, $T_{max}$, λz, $T_{1/2}$, CL/F, Vz/F, accumulation ratios, total urinary excretion and renal clearance.

Pharmacodynamic

Caloric intake, weight and waist circumference, insulin sensitivity (as measured by MTT), hunger and satiety (using a Hunger/Satiety Questionnaire) and REE (using indirect calorimetry) will be assessed as exploratory PD endpoints. HbAc1 and fructosamine levels will also be assessed.

Sample Size Determination

The sample size for this Phase 1 first multiple-dose study in humans was not based on formal statistical determinations. The sample size for this study was chosen in consideration of limiting exposure to this new compound while providing information to evaluate the safety and effect of the compounds of the present invention in a Phase 1 first multiple-dose study.

Statistical Methods

Continuous variables will be summarized by dose (all placebo pooled) with descriptive statistics (number of observations, mean, SD, median, maximum, and minimum). Categorical variables will be tabulated by frequency of subjects by dose (all placebo pooled) and for the active treatment doses combined. The PD endpoints may be analyzed via analysis of variance if appropriate. All subject information and safety measurements will be based on the Safety Population.

CSC Data Review and Stopping Rules

The study design is such that successively higher doses will be administered to different groups of subjects after the safety and tolerability of the preceding dose has been established. Dose escalation recommendations are to be made by the CSC based upon a review of clinical safety data through Day 16 (Cohorts dosed for 14 days) or Day 30 (Cohorts dosed for 28 days).

Rules for Suspension of Dosing for a Subject:

- An increase in SBP, sustained for a minimum of 30 minutes, either to >35 mmHg above mean baseline pre-dose SBP, or to >165 mmHg;
- An increase in DBP, sustained for a minimum of 30 minutes, either to >20 mmHg above mean baseline pre-dose DBP, or to >100 mmHg;
- Any increase in BP that is judged to be symptomatic, per the Investigator, regardless of duration;
- An increase in HR, sustained for a minimum of 30 minutes (or less in the judgment of the Investigator), to >35 bpm above mean baseline pre-dose HR;
- A prolonged spontaneous erection lasting more than 60 minutes, or a spontaneous painful erection of any duration based on Investigator judgment;
- Any other treatment-emergent AE that in the judgment of the Investigator poses a significant safety risk for that subject in the context of continued infusion of study drug.

Rules for Suspension or Termination of Dose Escalation:

- An SAE that is deemed by the Investigator to be possibly or probably related to study drug occurs in any subject treated with the compounds of the present invention;
- A CTCAE Grade 3 (severe treatment emergent AE) or higher that is possibly or probably related occurs in a subject treated with the compounds of the present invention;
- A possibly or probably related treatment emergent AE not listed by the CTCAE occurs in a subject treated with the compounds of the present invention that is graded as severe or life threatening.

The CSC may also recommend suspension of the compounds of the present invention dose escalation based upon other conditions as deemed medically appropriate.

Rules for Suspension of Further Dosing:

The study may be immediately suspended and no additional doses administered if one or more subjects at any dose level develop any of the following adverse events deemed to be possibly or probably attributable to study drug:

- Anaphylaxis (i.e., angioedema, hypotension, bronchospasm, hypoxia or respiratory distress) in a subject treated with the compounds of the present invention;
- Any clinically significant treatment-related AE that poses an undue risk to subjects in the opinion of the CSC.

2. Randomized, Double-Blind, Placebo-Controlled Study to Evaluate the Safety and Efficacy of the Compound of the Present Invention in Patients with Obesity Due to an MC4R Mutation Objectives The primary objective is to assess the effect of the compounds of the present invention vs. placebo on mean percent body weight loss when administered for 90 days by continuous SC infusion.

Secondary Objectives are to Assess:

- The mean body weight (BW) loss in the active treatment group compared to the placebo group from baseline to Day 90.
- The proportion of patients who lose ≥5% of their baseline body weight in the active treatment group compared to the placebo group from baseline to Day 90.
- The pharmacokinetics (PK) of the compounds of the present invention when given by continuous SC infusion for 90 days.
- The safety and tolerability of the compounds of the present invention when given by continuous SC infusion for 90 days.
- The effect of the compounds of the present invention versus placebo on ambulatory blood pressure monitoring parameters (ABPM) when given by continuous SC infusion for 90 days (sub-study).
- The mean percent weight loss, mean weight loss, and proportion of patients who lose ≥5% of their baseline body weight in the active treatment group compared to the placebo group from baseline to Day 90 in patients who are severely obese (e.g., BMI ≥40 $Kg/m^2$, sub-study).

Exploratory pharmacodynamic objectives of this study are to evaluate the effect of the compounds of the present invention when given by SC continuous infusion for 90 days in all patients, and those in the severely obese sub-study, on:

- The proportion of patients who achieve a ≥10% decrease in body weight in the active treatment group compared to placebo from baseline to Day 90.
- The change in glucose and insulin during a Meal Tolerance Test (MTT) from Baseline to Day 90.
- Change in fasting glucose, insulin, insulin sensitivity, triglycerides, cholesterol, HDL, LDL, hs-CRP and HbA1c from Baseline to Day 90.
- Change in waist circumference from Baseline to Day 90.

Change in body composition (assessed by Dual Energy X-Ray Absorptiometry (DXA)) from Baseline to Day 90 (sub-study).

Change in hunger and satiety from Baseline to Day 90.

Change in Impact of Weight on Quality of Life-Lite questionnaire (IWQOL-Lite) total score from Baseline to Day 90.

Change in depression/suicidality score (assessed by PHQ-9 and C—SSRS) from Baseline to Day 90.

Change in skin pigmentation (assessed by mexameter) from Baseline to Day 90.

Study Design

This is a randomized, double-blind, placebo-controlled study designed to evaluate the efficacy and safety of the compounds of the present invention when administered for 90 days to obese patients, inclusive of a sub-set of patients who are severely obese (BMI ≥40 $Kg/m^2$).

Patients who are obese (BMI between 35-50 $Kg/m^2$), but otherwise healthy, will be enrolled. This study will be conducted on an outpatient basis. All patients will be required to self-administer study drug via an approved insulin infusion pump (OmniPod®) during the ~7 day placebo practice period. Patients with continued eligibility who have demonstrated the ability to successfully manage self-administration of placebo during the practice period will be randomized to the double blind 90 day Treatment Period.

Number of Patients Planned

Approximately 70 patients will be enrolled into the study. There will be three sub-studies within the protocol. The first will include those patients who are severely obese (BMI ≥40 $Kg/m^2$, who will be stratified separately). Approximately severely obese patients will be enrolled into this sub-study; these subjects will be recruited at all sites. The two remaining sub-studies will be enrolled at select sites. The first will be an ABPM sub-study where approximately 30 patients will be enrolled, and the final sub-study will include DXA scans on approximately 20 patients.

Diagnosis and Main Criteria for Inclusion

Patients must meet all of the following inclusion criteria to be eligible for the study:

1. MC4R heterozygous patients: mutation of MC4R gene.
2. Be between the age of 18 and 65.
3. Able to provide voluntary, written informed consent with comprehension of all aspects of the protocol, prior to any study procedures.
4. In good general health, without significant medical history, physical examination findings, or clinical laboratory abnormalities.
5. Body Mass Index: 35-50 $Kg/m^2$, inclusive. It is planned that approximately 20 of these patients will have a BMI ≥40 $Kg/m^2$.
6. Stable body weight (+/−5 Kg) during previous 6 months.
7. Blood pressure (<140/90 mmHg); may include stable dose (>30 days of use) of up to two anti-hypertensive medications to achieve control that are intended to remain on a stable dose during the protocol.
8. Willingness and demonstrates ability to self administer study medication subcutaneously via a continuous infusion pump during the placebo practice period.
9. Willing to maintain a healthy diet and exercise regime throughout study as recommended by counseling at study start.
10. Females of childbearing potential must agree to be abstinent or else use any two of the following medically acceptable forms of contraception from the Screening Period through the completion of study treatment: hormonal, condom with spermicidal jelly, diaphragm or cervical cap with spermicidal jelly, or IUD. Hormonal contraception must have started at least 3 months prior to screening. A female whose male partner has had a vasectomy must agree to use one additional form of medically acceptable contraception. Patients must agree to practice the above birth control methods for 30 days after completion of study treatment as a safety precaution.
11. Females of non-childbearing potential, defined as surgically sterile (status post hysterectomy, bilateral oophorectomy, or bilateral tubal ligation) or post-menopausal for at least 12 months (and confirmed with a screening FSH level in the post-menopausal range), do not require contraception during the study.
12. Males with female partners of childbearing potential must agree to use two medically acceptable forms of contraception as described above, with one of the two forms being condom with spermicide, from the Screening Period through 90 days after completion of study treatment. Males with female partners of childbearing potential who themselves are surgically sterile (status post vasectomy) must agree to use condoms with spermicide over the same period of time.

If any of the following exclusion criteria are met, the patient is not eligible for the study:

1. Fasting blood glucose greater than 140 mg/dL.
2. HbA1c ≥6.5%.
3. TSH level outside the normal range.
4. Creatinine >1.5 times the upper limit of normal.
5. Liver function tests >2 times the upper limit of normal.
6. Active or history of any significant medical condition including renal, hepatic, pulmonary, gastrointestinal, cardiovascular, genitourinary, endocrine, immunologic, metabolic, neurologic or hematological disease.
7. Patients with a history of the following:
   a. Uncontrolled hypertension;
   b. Diabetes requiring medical treatment, presently or in the past;
   c. Major depressive disorder within the last 2 years;
   d. Any lifetime history of a suicide attempt;
   c. Any suicidal behavior in the last month;
   f. Other severe psychiatric disorders (e.g. schizophrenia, bipolar disorder, severe eating disorders including bulimia).
8. A PHQ-9 score of ≥15.
9. Any suicidal ideation of type 4 or 5 on the C—SSRS.
10. Prior bariatric surgery.
11. History or close family history (parents or siblings) of melanoma.
12. Significant dermatologic findings as part of the Screening comprehensive skin evaluation performed by the dermatologist. Any concerning lesions identified during the screening period will be biopsied and results known to be benign prior to randomization. If the pre-treatment biopsy results are of concern, the patient will be excluded from the study.
13. Treated with anorectic agents or drugs with anorexia as a frequent side event.
14. Taking 3 or more anti-hypertensive medications.
15. Acute illness or history of illness, which in the opinion of the Investigator, could pose a threat or harm to the patient or obscure interpretation of laboratory test results or interpretation of study data.
16. History of any malignancy, past or present, including skin cancer, multiple severely dysplastic nevi, or nevoid basal cell carcinoma.

17. History of HIV infection.
18. History of significant drug hypersensitivity or anaphylaxis.
19. History of hypersensitivity to proteins (e.g., allergy shots).
20. Any clinically significant abnormalities on screening laboratories as determined by the Investigator.
21. Abnormal 12-lead electrocardiogram (ECG) at screening or pre-dose (Day 1), except minor deviations deemed to be of no clinical significance by the Investigator. QTc must be <450 ms.
22. Received any experimental drugs or devices or have participated in a clinical study within 30 days prior to dosing.
23. Blood donation within 60 days prior to screening or intent to donate up to 60 days after Final Study Visit.
24. Hospitalization for surgery within the 3 months prior to screening except for minor outpatient procedures, or any planned hospitalizations during the study period.
25. Poor venous access or inability to tolerate venipuncture.
26. Inability to attend all study visits or comply with protocol requirements including fasting and restrictions on concomitant medication intake.
27. Participation in weight loss programs during the study period, including nutritional supplements/replacements other than as recommended by nutritional counseling provided at study start
28. Use of prescription medications on a regular basis with the following exceptions:
    a. Contraceptives (must be on for ≥3 months);
    b. Hormone replacement therapy (must be on stable dose for ≥3 months);
    c. Antihypertensives (<3 medications on a stable dose for ≥30 days);
    d. Statins (dose must be ≤half the maximum dose; must be on a stable dose ≥3 months);
    e. Fibrates (must be on stable dose for ≥3 months);
    f. Niacin (must be on stable dose for >3 months);
    g. Thyroxin (stable dose for ≥30 days);
    h. The last use of any other prescription medication must have been greater than 5 half-lives for the specific medication or at least 14 days prior to randomization, whichever is longer.
29. Women who are pregnant or are breast feeding.
30. Previously randomized and dosed in this study or previously exposed to the compounds of the present invention.
31. History of alcohol or drug abuse within 5 years of Screening Visit.
32. Any other reason, which in the opinion of the Investigator would confound proper evaluation of the study.

Test Products, Doses, and Mode of Administration

The compounds of the present invention will be supplied as sterile solutions for infusion. The product will be manufactured at a concentration of 2.0 mg/mL at pH 5 with a fill volume of 11 mL/vial. Placebo will be vehicle. Drug products and placebo consist of sodium phosphate and citric acid, including 0.5% phenol as a preservative. Both the compounds of the present invention and placebo multiuse vials may be punctured multiple times under sterile conditions. The compounds of the present invention and placebo will be administered as a continuous subcutaneous infusion using the FDA approved insulin infusion pump, Insulet's OmniPod® (infusion pump which is wireless/tubeless and does not require a traditional infusion set, inclusive of an auto-injector whereby the patient never sees the needle or cannula). A total daily dose of 1 mg/24 hours of the compounds of the present invention, or equivalent volume of placebo, will be self-administered via continuous SC infusion during the treatment period.

Duration of Treatment

The overall study duration will be approximately 9 months, as currently planned. Individual patient participation in the study (Screening Period, Treatment Period and Follow-up Period) will be approximately 7 months. Screening, inclusive of the placebo practice period, will occur within 30 days prior to randomization. Patients who successfully complete the open label placebo practice period will be randomized to double blind treatment for 90 days. The Final Visit will occur approximately 90 days after the last dose of study drug is administered (Day 180).

Study Procedures

The study will consist of a Screening Period inclusive of 2 visits. Patients who demonstrate compliance with the continuous infusion will be randomized to a double-blind treatment regimen (at Visit 3) and will begin 90 days of double-blind, self-administered SC continuous infusion, outpatient treatment. Additional clinic visits are scheduled on approximately Day 7 (Visit 4), Day 14 (Visit 5), Day 28 (Visit 6), Day 56 (Visit 7) and at the end of treatment (Day 90, Visit 8). Patients will also be contacted by telephone weekly during the first month of treatment, followed by bi-weekly contact during the remaining Treatment Period to encourage compliance and to assess adverse events. Follow up Visits will be scheduled monthly for 3 months after completion of the 90-day Treatment Period. The Final Visit will occur ~90 days after the last dose of study drug is administered (Day 180, Visit 11).

Screening Period (Days −30 to −1)

The Screening Period consists of 2 visits; the first where patients will be assessed for study qualification. Eligible patients will then proceed onto the second screening visit which will consist of an open label placebo practice period to ensure study patients can self-administer placebo drug via an FDA approved SC insulin infusion pump for approximately 1 week.

Visit 1

During Visit 1, following signed, written informed consent, confirmation of eligibility will be performed. Medical history, physical examination (including vital signs, height and weight and waist circumference measurements), a comprehensive skin exam will be conducted by the Dermatologist, quantitative skin measurement, Fitzpatrick scale and Edmond Obesity Staging System (EOSS) assessments, concomitant medication review, clinical laboratory tests including HbA1c, serum pregnancy test or follicle-stimulating hormone test, and a 12-lead ECG will be performed at this visit. The PHQ-9 and C—SSRS will be administered. Hunger and satiety questionnaire will also be administered.

Visit 2

During visit 2, patients confirmed to be eligible at Visit 1 and who continue to meet the inclusion and exclusion criteria upon review of medical history since the prior visit as well as AE and concomitant medication review, will have their weight and waist circumference measured and vital signs measured. Study staff will train patients and instruct them on proper technique of how to use the OmniPod® at this visit. Patients will be required to demonstrate understanding by successfully filling the OmniPod® with placebo, successfully placing the pod on an appropriate body area, and starting the infusion while at site. The study patients will change the OmniPod® approximately 2-3 times during the ~7 day period between Visits 2 and 3.

For those patients participating in the ABPM sub-study, an additional clinic visit will be necessary.

Treatment Period (Days 1-90)

Patients will return to the clinic approximately 7 days after starting the placebo practice period. Study patients who successfully complete the open label placebo practice period will return for Visit 3 (Day 1), and be randomized to 90 days of double-blind study treatment. Additional clinic visits are scheduled on approximately Day 7 (Visit 4), Day 14 (Visit 5), Day 28 (Visit 6), Day 56 (Visit 7) and at the end of treatment (Day 90, Visit 8). During these visits, a variety of efficacy, safety and exploratory assessments will be performed, according to the SOA.

Efficacy will be evaluated by measuring body weight. Safety will be evaluated by assessment of adverse events, vital signs (including blood pressure, respiratory rate, heart rate, and body temperature), ECGs, ABPM (sub-study), clinical laboratory evaluations (hematology, clinical chemistry including fasting blood glucose and insulin levels and urinalysis), lipid profile; levels of antibodies against the compounds of the present invention, quantitative skin assessments (mexameter) and photographic skin evaluation, protocol defined pigmented skin lesion biopsies, physical examinations including infusion site evaluations and concomitant medication review. Additionally, changes in depression/suicidality as assessed by the C—SSRS and PHQ-9 will be monitored. Plasma concentrations of the compounds of the present invention will be summarized and may be compared to PD parameters.

Exploratory measurements will be assessed by insulin sensitivity (as measured by MTT and HOMA-IR), effects on Hs—CRP and HbA1c, hunger and satiety (using a Hunger/Satiety Questionnaire), body composition (using DXA at select sites), changes in waist circumference, and changes in IWQOL-Lite, PHQ-9 and C—SSRS will be assessed as exploratory endpoints.

For patients who do not complete the full 90 day treatment period, attempts will be made to have the patient return for continued follow-up visits in order to monitor patient safety, as well as any effects on pharmacodynamic assessments.

Follow-Up Period (Days 91-180)

Upon completion of the 90 day Treatment Period, Patients will enter a 90 day post-treatment Follow-up Period consisting of 3 monthly visits, where a variety of safety and efficacy assessments according to the SOA. The Final Study Visit will occur on approximately Day 180.

In the event an AE is ongoing at the time of the Final Visit, additional visits should be scheduled, at a frequency deemed appropriate by the Investigator, in order to follow the event to resolution. If a patient experiences a Serious Adverse Event for which follow-up laboratories and review are required, the Investigator will schedule additional post-treatment visits as necessary.

Study Endpoints

The primary endpoint will be evaluated by assessment of mean percent body weight loss. Secondary endpoints will be evaluated by assessments of weight, as well as safety and tolerability, including the ABPM sub-study. Plasma concentrations of the compounds of the present invention will be summarized and may be compared to various endpoints. In addition, weight loss parameters will be summarized in the severely obese patient sub-study.

Safety

Safety will be evaluated by assessment of adverse events, vital signs (including blood pressure, respiratory rate, heart rate, and body temperature), ECGs, clinical laboratory evaluations (hematology, clinical chemistry including fasting blood glucose and insulin levels and urinalysis), lipid profile; levels of antibodies against the compounds of the present invention, quantitative skin assessments (mexameter) and photographic skin evaluation, protocol defined pigmented skin lesion biopsies, physical examinations including infusion site evaluations and concomitant medication review. Additionally, changes in depression/suicidality as assessed by the C—SSRS and PHQ-9 will be monitored.

Pharmacokinetic

Plasma concentrations of the compounds of the present invention will summarized and may be compared to PD endpoints.

Exploratory

Exploratory measurements will be assessed by insulin sensitivity (as measured by MTT and HOMA-IR), effects on Hs—CRP and HbA1c, hunger and satiety (using a Hunger/Satiety Questionnaire), body composition (using DXA at select sites), changes in waist circumference, and changes in IWQOL-Lite and C—SSRS will be assessed as exploratory endpoints.

Sample Size Determination

Sample size per arm was calculated to target a 5 percentage point difference in mean weight change between a treatment arm and the placebo arm. From data reported by Gadde (2011), an SD of 5.7% was computed for weight change after 16 weeks of treatment. Assuming the SD in this study will be 5% to 6%, the sample size of N=30 completing subjects (accounting for 5 dropouts per dose group) has 97% power to yield a statistically significant (alpha=0.025, 1-sided) difference between an active dose group and placebo if the true underlying difference in means is 5 percentage points, and the SD is 5%. If the SD is 6%, there is 89% power.

Statistical Methods

Continuous variables will be summarized by dose group with descriptive statistics (e.g., number of observations, mean, SD, median, maximum, and minimum). Categorical variables will be tabulated by frequency of patients per dose group. All patient information and safety measurements will be based on the Safety Population, which will include all patients who receive a dose of study drug and have a post baseline observation.

Analyses will be based on observed data only; no data will be imputed.

Continuous efficacy endpoints will be assessed via a longitudinal mixed analysis of variance model which will include fixed effects terms for treatment, timepoint, treatment-by-timepoint interaction, and baseline covariate, and random effect for subjects. The assumption of normality will be assessed via the Shapiro-Wilk statistic. If substantial departure from normality is observed, a transformation such as log (post/pre) or rank may be used to analyze the data.

The comparison of the compounds of the present invention with placebo will be carried out via 1-sided statistical test at alpha-0.025.

Guidelines for Additional Safety Monitoring and Suspension of Dosing of a Patient Patients will be monitored carefully during the treatment period during on site clinic visits as well as periodic telephone calls made to the patients by the study staff. In the event a patient is withdrawn from treatment due to an AE, the patient should be encouraged to complete the remaining study visits in order to monitor the event to resolution and obtain additional protocol defined safety assessments. Additionally, guidance will be provided for any worsening of depression or suicidality during the study. At all times, this guidance is subject to the clinical judgment of the Investigator and study consultants (if applicable).

The Investigator shall notify the Medical Monitor in the event any study participant fulfills any of the criteria defined in the appendices noted above, or undergoes additional monitoring for any of the events defined herein.

Example 3: Treatment of Obese MC4R+/− Heterozygotic Mice with Compound of SEQ ID NO: 140

Diet induced obesity (DIO) littermate C57Bl/6J mice that were either wild type with respect to MC4R gene (+/+), or heterozygous for the MC4R gene (+/−), or homozygous MC4R knockout mice that do not express the MC4R gene at all (−/−) were exposed to the compound of SEQ ID NO: 140: Ac-Arg-c(Cys-D-Ala-His-D-Phe-Arg-Trp-Cys)-$NH_2$ by Alzet pump infusion of at a concentration of 1200 nmol/kg/day for 8 days. Body weight was measured.

Figure 3:
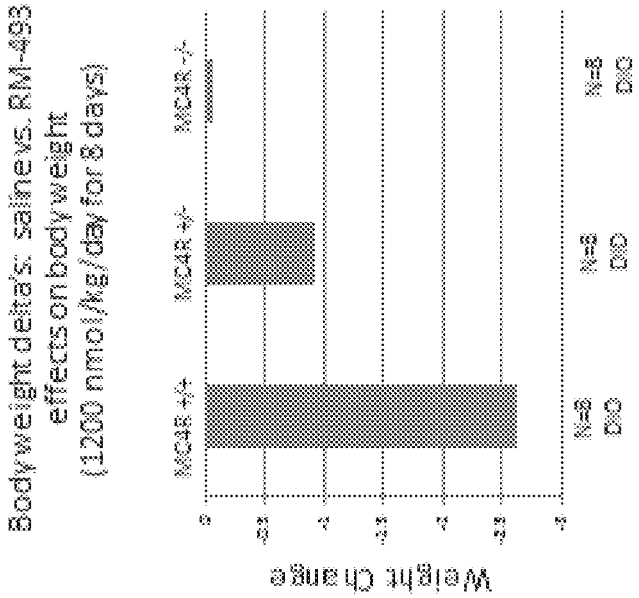
FIG. 3 is a bar plot showing the effect of administration of a compound of SEQ ID NO: 140 to mice as described in Example 1.

The data is presented in FIG. 3. The data shows that mice that were heterozygous for the MC4R gene (+/−) lost significant body weight (about 1 gram) over the treatment period while rodents that did not express the MC4R gene, did not show significant weight loss over this time period.

The weight change due to the exposure to the compound of SEQ ID NO: 140 in mice that are either wild type for the MC4R gene, or express only a single MC4R allele, or mice without any MC4R protein expression were compared. The data suggests that human patients with one functional MC4R allele, where their obesity is caused by the loss of function of the MC4R allele, will respond to the SEQ ID NO: 140, resulting in weight loss.

While this invention has been particularly shown and described with references to example embodiments thereof, it will be understood by those skilled in the art that various changes in form and details may be made therein without departing from the scope of the invention encompassed by the appended claims.

SEQUENCE LISTING

```
Sequence total quantity: 559
SEQ ID NO: 1            moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine,
MOD_RES                 7
                        note = bAla
source                  1..8
                        mol_type = protein
                        organism = synthetic construct
SEQUENCE: 1
XDHFRWAK                                                                8

SEQ ID NO: 2            moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = A6c
source                  1..8
                        mol_type = protein
                        organism = synthetic construct
SEQUENCE: 2
XDHFRWXK                                                                8

SEQ ID NO: 3            moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
```

-continued

```
SITE                    1
                        note = Nle
REGION                  2..8
                        note = Cyclic
SITE                    4
                        note = D-Phenylalanine
MOD_RES                 7
                        note = 6-aminohexanoic acid
source                  1..8
                        mol_type = protein
                        organism = synthetic construct
SEQUENCE: 3
XCHFRWXC                                                    8

SEQ ID NO: 4            moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
SITE                    8
                        note = D-Cystine
source                  1..9
                        mol_type = protein
                        organism = synthetic construct
SEQUENCE: 4
FCHFRWACT                                                   9

SEQ ID NO: 5            moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
MOD_RES                 7
                        note = bAla
SITE                    8
                        note = D-Cystine
source                  1..9
                        mol_type = protein
                        organism = synthetic construct
SEQUENCE: 5
FCHFRWACT                                                   9

SEQ ID NO: 6            moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
MOD_RES                 7
                        note = 4abu
SITE                    8
                        note = D-Cystine
source                  1..9
                        mol_type = protein
                        organism = synthetic construct
SEQUENCE: 6
FCHFRWXCT                                                   9

SEQ ID NO: 7            moltype = AA  length = 8
```

-continued

```
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 5-aminopentanoic acid
source                  1..8
                        mol_type = protein
                        organism = synthetic construct
SEQUENCE: 7
XCHFRWXC                                                    8

SEQ ID NO: 8            moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 5-aminopentanoic acid
source                  1..8
                        mol_type = protein
                        organism = synthetic construct
SEQUENCE: 8
XDHFRWXK                                                    8

SEQ ID NO: 9            moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = A6c
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 9
XDHFRWXK                                                    8

SEQ ID NO: 10           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = D-P-(2-naphthyl)alanine
REGION                  2..8
                        note = Cyclic
SITE                    4
                        note = D-Phenylalanine
```

-continued

```
MOD_RES                 7
                        note = 4abu
source                  1..8
                        mol_type = protein
                        organism = synthetic construct
SEQUENCE: 10
XDHFRWXK                                                                   8

SEQ ID NO: 11           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = Beta-cyclohexylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 11
XDHFRWXK                                                                   8

SEQ ID NO: 12           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 12
XDHFRWXK                                                                   8

SEQ ID NO: 13           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
source                  1..8
                        mol_type = protein
                        organism = synthetic construct
SEQUENCE: 13
XCAHFRWC                                                                   8

SEQ ID NO: 14           moltype = AA  length = 8
FEATURE                 Location/Qualifiers
SITE                    8
                        note = C-terminal is: NH2
```

```
REGION              1..8
                    note = Description of Sequence: MC4R agonist
SITE
                    note = N-terminal is: Acetylated
SITE                1
                    note = Nle
REGION              2..8
                    note = Cyclic
MOD_RES             3
                    note = bAla
SITE                5
                    note = D-Phenylalanine
source              1..8
                    mol_type = protein
                    organism = synthetic construct
SEQUENCE: 14
XCAHFRWC                                                  8

SEQ ID NO: 15       moltype = AA  length = 8
FEATURE             Location/Qualifiers
SITE                8
                    note = C-terminal is: NH2
REGION              1..8
                    note = Description of Sequence: MC4R agonist
SITE
                    note = N-terminal is: Acetylated
SITE                1
                    note = Nle
REGION              2..8
                    note = Cyclic
MOD_RES             3
                    note = 4abu
SITE                5
                    note = D-Phenylalanine
source              1..8
                    mol_type = protein
                    organism = synthetic construct
SEQUENCE: 15
XCXHFRWC                                                  8

SEQ ID NO: 16       moltype = AA  length = 8
FEATURE             Location/Qualifiers
SITE                8
                    note = C-terminal is: NH2
REGION              1..8
                    note = Description of Sequence: MC4R agonist
SITE
                    note = N-terminal is: Acetylated
SITE                1
                    note = Nle
REGION              2..8
                    note = Cyclic
MOD_RES             3
                    note = a-aminoisobutyric acid
SITE                5
                    note = D-Phenylalanine
source              1..8
                    mol_type = protein
                    organism = synthetic construct
SEQUENCE: 16
XCXHFRWC                                                  8

SEQ ID NO: 17       moltype = AA  length = 8
FEATURE             Location/Qualifiers
SITE                8
                    note = C-terminal is: NH2
REGION              1..8
                    note = Description of Sequence: MC4R agonist
SITE
                    note = N-terminal is: Acetylated
SITE                1
                    note = Nle
REGION              2..8
                    note = Cyclic
SITE                5
                    note = D-Phenylalanine
source              1..8
                    mol_type = protein
                    organism = synthetic construct
```

```
SEQUENCE: 17
XCGHFRWC                                                    8

SEQ ID NO: 18           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    2
                        note = D-Cystine
SITE                    5
                        note = D-Phenylalanine
source                  1..8
                        mol_type = protein
                        organism = synthetic construct
SEQUENCE: 18
XCAHFRWC                                                    8

SEQ ID NO: 19           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    2
                        note = D-Cystine
SITE                    3
                        note = D-Alanine
SITE                    5
                        note = D-Phenylalanine
source                  1..8
                        mol_type = protein
                        organism = synthetic construct
SEQUENCE: 19
XCAHFRWC                                                    8

SEQ ID NO: 20           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    2
                        note = D-Cystine
MOD_RES                 3
                        note = bAla
SITE                    5
                        note = D-Phenylalanine
source                  1..8
                        mol_type = protein
                        organism = synthetic construct
SEQUENCE: 20
XCAHFRWC                                                    8

SEQ ID NO: 21           moltype = AA  length = 8
FEATURE                 Location/Qualifiers
SITE                    8
                        note = C-terminal is: NH2
REGION                  1..8
                        note = Description of Sequence: MC4R agonist
```

-continued

```
SITE
                       note = N-terminal is: Acetylated
SITE                   1
                       note = Nle
REGION                 2..8
                       note = Cyclic
SITE                   2
                       note = D-Cystine
MOD_RES                3
                       note = 4abu
SITE                   5
                       note = D-Phenylalanine
source                 1..8
                       mol_type = protein
                       organism = synthetic construct
SEQUENCE: 21
XCXHFRWC                                                  8

SEQ ID NO: 22          moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
SITE                   1
                       note = Nle
REGION                 2..8
                       note = Cyclic
SITE                   2
                       note = D-Cystine
MOD_RES                3
                       note = a-aminoisobutyric acid
SITE                   5
                       note = D-Phenylalanine
source                 1..8
                       mol_type = protein
                       organism = synthetic construct
SEQUENCE: 22
XCXHFRWC                                                  8

SEQ ID NO: 23          moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
SITE                   1
                       note = Nle
REGION                 2..8
                       note = Cyclic
SITE                   2
                       note = D-Cystine
SITE                   5
                       note = D-Phenylalanine
source                 1..8
                       mol_type = protein
                       organism = synthetic construct
SEQUENCE: 23
XCGHFRWC                                                  8

SEQ ID NO: 24          moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Alanine
```

-continued

```
SITE                    5
                        note = D-Phenylalanine
SITE                    8
                        note = D-Cystine
source                  1..8
                        mol_type = protein
                        organism = synthetic construct
SEQUENCE: 24
XCAHFRWC                                                                   8

SEQ ID NO: 25           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = bAla
SITE                    5
                        note = D-Phenylalanine
SITE                    8
                        note = D-Cystine
source                  1..8
                        mol_type = protein
                        organism = synthetic construct
SEQUENCE: 25
XCAHFRWC                                                                   8

SEQ ID NO: 26           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = 4abu
SITE                    5
                        note = D-Phenylalanine
SITE                    8
                        note = D-Cystine
source                  1..8
                        mol_type = protein
                        organism = synthetic construct
SEQUENCE: 26
XCXHFRWC                                                                   8

SEQ ID NO: 27           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = a-aminoisobutyric acid
SITE                    5
                        note = D-Phenylalanine
SITE                    8
                        note = D-Cystine
source                  1..8
                        mol_type = protein
                        organism = synthetic construct
```

-continued

```
SEQUENCE: 27
XCXHFRWC                                                    8

SEQ ID NO: 28           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    5
                        note = D-Phenylalanine
SITE                    8
                        note = D-Cystine
source                  1..8
                        mol_type = protein
                        organism = synthetic construct
SEQUENCE: 28
XCGHFRWC                                                    8

SEQ ID NO: 29           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    2
                        note = D-Cystine
SITE                    5
                        note = D-Phenylalanine
SITE                    8
                        note = D-Cystine
source                  1..8
                        mol_type = protein
                        organism = synthetic construct
SEQUENCE: 29
XCAHFRWC                                                    8

SEQ ID NO: 30           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    2
                        note = D-Cystine
SITE                    3
                        note = D-Alanine
SITE                    5
                        note = D-Phenylalanine
SITE                    8
                        note = D-Cystine
source                  1..8
                        mol_type = protein
                        organism = synthetic construct
SEQUENCE: 30
XCAHFRWC                                                    8

SEQ ID NO: 31           moltype = AA  length = 8
FEATURE                 Location/Qualifiers
SITE                    8
                        note = C-terminal is: NH2
```

```
REGION                1..8
                      note = Description of Sequence: MC4R agonist
SITE
                      note = N-terminal is: Acetylated
SITE                  1
                      note = Nle
REGION                2..8
                      note = Cyclic
SITE                  2
                      note = D-Cystine
MOD_RES               3
                      note = bAla
SITE                  5
                      note = D-Phenylalanine
SITE                  8
                      note = D-Cystine
source                1..8
                      mol_type = protein
                      organism = synthetic construct
SEQUENCE: 31
XCAHFRWC                                                       8

SEQ ID NO: 32         moltype = AA  length = 8
FEATURE               Location/Qualifiers
SITE                  8
                      note = C-terminal is: NH2
REGION                1..8
                      note = Description of Sequence: MC4R agonist
SITE
                      note = N-terminal is: Acetylated
SITE                  1
                      note = Nle
REGION                2..8
                      note = Cyclic
SITE                  2
                      note = D-Cystine
MOD_RES               3
                      note = 4abu
SITE                  5
                      note = D-Phenylalanine
SITE                  8
                      note = D-Cystine
source                1..8
                      mol_type = protein
                      organism = synthetic construct
SEQUENCE: 32
XCXHFRWC                                                       8

SEQ ID NO: 33         moltype = AA  length = 8
FEATURE               Location/Qualifiers
SITE                  8
                      note = C-terminal is: NH2
REGION                1..8
                      note = Description of Sequence: MC4R agonist
SITE
                      note = N-terminal is: Acetylated
SITE                  1
                      note = Nle
REGION                2..8
                      note = Cyclic
SITE                  2
                      note = D-Cystine
MOD_RES               3
                      note = a-aminoisobutyric acid
SITE                  5
                      note = D-Phenylalanine
SITE                  8
                      note = D-Cystine
source                1..8
                      mol_type = protein
                      organism = synthetic construct
SEQUENCE: 33
XCXHFRWC                                                       8

SEQ ID NO: 34         moltype = AA  length = 8
FEATURE               Location/Qualifiers
SITE                  8
                      note = C-terminal is: NH2
```

```
REGION                  1..8
                        note = Description of Sequence: MC4R agonist
SITE
                        note = N-terminal is: Acetylated
MOD_RES                 1
                        note = Octahydroindole-2-carboxylic acid
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 34
XDHFRWXK                                                                    8

SEQ ID NO: 35           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = Cyclohexylglycine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 35
XDHFRWXK                                                                    8

SEQ ID NO: 36           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 36
XDHFRWXK                                                                    8

SEQ ID NO: 37           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = D-Beta-cyclohexylalanine
REGION                  2..8
                        note = Cyclic
SITE                    4
                        note = D-Phenylalanine
MOD_RES                 7
                        note = 4abu
```

-continued

```
source                  1..8
                        mol_type = protein
                        organism = synthetic construct
SEQUENCE: 37
XDHFRWXK                                                                  8

SEQ ID NO: 38           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = D-homo-cyclohexylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 38
XDHFRWXK                                                                  8

SEQ ID NO: 39           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = Nipecotic acid
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 39
XDHFRWXK                                                                  8

SEQ ID NO: 40           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Homoproline
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 40
PDHFRWXK                                                                  8

SEQ ID NO: 41           moltype = AA  length = 8
FEATURE                 Location/Qualifiers
SITE                    8
                        note = C-terminal is: NH2
REGION                  1..8
                        note = Description of Sequence: MC4R agonist
```

```
SITE
                        note = N-terminal is: Acetylated
SITE                    1
                        note = Homoleucine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 41
LDHFRWXK                                                      8

SEQ ID NO: 42           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 42
FDHFRWXK                                                      8

SEQ ID NO: 43           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = D-Phenylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 43
FDHFRWXK                                                      8

SEQ ID NO: 44           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = D-Chg
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 44
XDHFRWXK                                                      8
```

```
SEQ ID NO: 45           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-term is: n-butanoyl
MOD_RES                 1
                        note = Beta-cyclohexylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 45
XDHFRWXK                                                                  8

SEQ ID NO: 46           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-term is: n-butyryl
MOD_RES                 1
                        note = Beta-cyclohexylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 46
XDHFRWXK                                                                  8

SEQ ID NO: 47           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Homophenylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 47
FDHFRWXK                                                                  8

SEQ ID NO: 48           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = Beta-hMet
REGION                  2..8
                        note = Cyclic
```

-continued

```
SITE                 4
                     note = D-Phenylalanine
MOD_RES              7
                     note = 4abu
source               1..8
                     mol_type = protein
                     organism = synthetic construct
SEQUENCE: 48
MDHFRWXK                                                                8

SEQ ID NO: 49        moltype = AA  length = 8
FEATURE              Location/Qualifiers
SITE                 8
                     note = C-terminal is: NH2
REGION               1..8
                     note = Description of Sequence: MC4R agonist
SITE
                     note = N-terminal is: Acetylated
MOD_RES              1
                     note = 4abu
REGION               2..8
                     note = Cyclic
SITE                 4
                     note = D-Phenylalanine
MOD_RES              7
                     note = 4abu
source               1..8
                     mol_type = protein
                     organism = synthetic construct
SEQUENCE: 49
XDHFRWXK                                                                8

SEQ ID NO: 50        moltype = AA  length = 8
FEATURE              Location/Qualifiers
SITE                 8
                     note = C-terminal is: NH2
REGION               1..8
                     note = Description of Sequence: MC4R agonist
SITE
                     note = N-terminal is: Acetylated
MOD_RES              1
                     note = Beta-cyclohexylalanine
REGION               2..8
                     note = Cyclic
SITE                 4
                     note = D-Phenylalanine
SITE                 6
                     note = D-Trp
source               1..8
                     mol_type = protein
                     organism = synthetic construct
SEQUENCE: 50
XDHFRWAK                                                                8

SEQ ID NO: 51        moltype = AA  length = 8
FEATURE              Location/Qualifiers
SITE                 8
                     note = C-terminal is: NH2
REGION               1..8
                     note = Description of Sequence: MC4R agonist
SITE
                     note = N-terminal is: Acetylated
MOD_RES              1
                     note = Homo-cyclohexylalanine
REGION               2..8
                     note = Cyclic
SITE                 4
                     note = D-Phenylalanine
SITE                 6
                     note = D-Trp
source               1..8
                     mol_type = protein
                     organism = synthetic construct
SEQUENCE: 51
XDHFRWAK                                                                8
```

```
SEQ ID NO: 52           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  2..8
                        note = Cyclic
SITE                    4
                        note = D-Phenylalanine
SITE                    6
                        note = D-Trp
source                  1..8
                        mol_type = protein
                        organism = synthetic construct
SEQUENCE: 52
LDHFRWAK                                                        8

SEQ ID NO: 53           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Homoleucine
REGION                  2..8
                        note = Cyclic
SITE                    4
                        note = D-Phenylalanine
SITE                    6
                        note = D-Trp
source                  1..8
                        mol_type = protein
                        organism = synthetic construct
SEQUENCE: 53
LDHFRWAK                                                        8

SEQ ID NO: 54           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  2..8
                        note = Cyclic
SITE                    4
                        note = D-Phenylalanine
SITE                    6
                        note = D-Trp
source                  1..8
                        mol_type = protein
                        organism = synthetic construct
SEQUENCE: 54
FDHFRWAK                                                        8

SEQ ID NO: 55           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
```

-continued

```
SITE                    7
                        note = D-Alanine
source                  1..8
                        mol_type = protein
                        organism = synthetic construct
SEQUENCE: 55
XDHFRWAK                                                                   8

SEQ ID NO: 56           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = bAla
source                  1..8
                        mol_type = protein
                        organism = synthetic construct
SEQUENCE: 56
XDHFRWAK                                                                   8

SEQ ID NO: 57           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = 4abu
source                  1..8
                        mol_type = protein
                        organism = synthetic construct
SEQUENCE: 57
XDHFRWXK                                                                   8

SEQ ID NO: 58           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = Aha
source                  1..8
                        mol_type = protein
                        organism = synthetic construct
SEQUENCE: 58
XDHFRWXK                                                                   8
```

-continued

```
SEQ ID NO: 59            moltype = AA  length = 8
FEATURE                  Location/Qualifiers
SITE                     8
                         note = C-terminal is: NH2
REGION                   1..8
                         note = Description of Sequence: MC4R agonist
SITE
                         note = N-terminal is: Acetylated
SITE                     1
                         note = Nle
REGION                   2..8
                         note = Cyclic
SITE                     4
                         note = D-Phenylalanine
SITE                     6
                         note = D-Trp
MOD_RES                  7
                         note = 5-aminopentanoic acid
source                   1..8
                         mol_type = protein
                         organism = synthetic construct
SEQUENCE: 59
XDHFRWXK                                                           8

SEQ ID NO: 60            moltype = AA  length = 8
FEATURE                  Location/Qualifiers
SITE                     8
                         note = C-terminal is: NH2
REGION                   1..8
                         note = Description of Sequence: MC4R agonist
SITE
                         note = N-terminal is: Acetylated
SITE                     1
                         note = Nle
REGION                   2..8
                         note = Cyclic
SITE                     4
                         note = D-Phenylalanine
SITE                     6
                         note = D-Trp
MOD_RES                  7
                         note = 5-aminopentanoic acid
source                   1..8
                         mol_type = protein
                         organism = synthetic construct
SEQUENCE: 60
XCHFRWXC                                                           8

SEQ ID NO: 61            moltype = AA  length = 8
FEATURE                  Location/Qualifiers
SITE                     8
                         note = C-terminal is: NH2
REGION                   1..8
                         note = Description of Sequence: MC4R agonist
SITE
                         note = N-terminal is: Acetylated
SITE                     1
                         note = Nle
REGION                   2..8
                         note = Cyclic
SITE                     4
                         note = D-Phenylalanine
SITE                     6
                         note = D-Trp
MOD_RES                  7
                         note = 4abu
source                   1..8
                         mol_type = protein
                         organism = synthetic construct
SEQUENCE: 61
XCHFRWXC                                                           8

SEQ ID NO: 62            moltype = AA  length = 8
FEATURE                  Location/Qualifiers
SITE                     8
                         note = C-terminal is: NH2
REGION                   1..8
                         note = Description of Sequence: MC4R agonist
```

-continued

```
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = 6-aminohexanoic acid
source                  1..8
                        mol_type = protein
                        organism = synthetic construct
SEQUENCE: 62
XCHFRWXC                                                      8

SEQ ID NO: 63           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = bAla
source                  1..8
                        mol_type = protein
                        organism = synthetic construct
SEQUENCE: 63
XCHFRWAC                                                      8

SEQ ID NO: 64           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
SITE                    7
                        note = D-Alanine
source                  1..8
                        mol_type = protein
                        organism = synthetic construct
SEQUENCE: 64
XCHFRWAC                                                      8

SEQ ID NO: 65           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
```

-continued

```
SITE                    3
                        note = D-Alanine
MOD_RES                 5
                        note = D-P-(2-naphthyl)alanine
source                  1..8
                        mol_type = protein
                        organism = synthetic construct
SEQUENCE: 65
XCAHXRWC                                                                    8

SEQ ID NO: 66           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
MOD_RES                 5
                        note = D-P-(2-naphthyl)alanine
MOD_RES                 7
                        note = P-(2-naphthyl)alanine
source                  1..8
                        mol_type = protein
                        organism = synthetic construct
SEQUENCE: 66
XCAHXRXC                                                                    8

SEQ ID NO: 67           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
MOD_RES                 5
                        note = D-P-(2-naphthyl)alanine
MOD_RES                 7
                        note = 1-Nal
source                  1..8
                        mol_type = protein
                        organism = synthetic construct
SEQUENCE: 67
XCAHXRXC                                                                    8

SEQ ID NO: 68           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-term is: n-butanoyl
SITE                    1
                        note = Nle
REGION                  2..8
                        note = Cyclic
SITE                    3
                        note = D-Alanine
SITE                    5
                        note = D-Phenylalanine
MOD_RES                 7
                        note = P-(2-naphthyl)alanine
source                  1..8
                        mol_type = protein
                        organism = synthetic construct
```

```
SEQUENCE: 68
XCAHFRXC                                                   8

SEQ ID NO: 69           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-term is: n-butanoyl
SITE                    1
                        note = Nle
REGION                  2..8
                        note = Cyclic
SITE                    3
                        note = D-Alanine
SITE                    5
                        note = D-Phenylalanine
source                  1..8
                        mol_type = protein
                        organism = synthetic construct
SEQUENCE: 69
XCAHFRWC                                                   8

SEQ ID NO: 70           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 7
                        note = P-(2-naphthyl)alanine
source                  1..8
                        mol_type = protein
                        organism = synthetic construct
SEQUENCE: 70
XCAHFRXC                                                   8

SEQ ID NO: 71           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 7
                        note = 1-Nal
source                  1..8
                        mol_type = protein
                        organism = synthetic construct
SEQUENCE: 71
XCAHFRXC                                                   8

SEQ ID NO: 72           moltype = AA  length = 8
FEATURE                 Location/Qualifiers
SITE                    8
                        note = C-terminal is: NH2
```

-continued

```
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 7
                        note = 3-benzothienylaaanine
source                  1..8
                        mol_type = protein
                        organism = synthetic construct
SEQUENCE: 72
XCAHFRXC                                                            8

SEQ ID NO: 73           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Glu
SITE                    5
                        note = D-Phenylalanine
source                  1..8
                        mol_type = protein
                        organism = synthetic construct
SEQUENCE: 73
XCEHFRWC                                                            8

SEQ ID NO: 74           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    7
                        note = D-Alanine
source                  1..8
                        mol_type = protein
                        organism = synthetic construct
SEQUENCE: 74
XDHFRWAK                                                            8

SEQ ID NO: 75           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
```

```
MOD_RES                 5
                        note = D-P-(2-naphthyl)alanine
MOD_RES                 7
                        note = 3-benzothienylaaanine
source                  1..8
                        mol_type = protein
                        organism = synthetic construct
SEQUENCE: 75
XCAHXRXC                                                                8

SEQ ID NO: 76           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 2
                        note = Penicillamine
SITE                    3
                        note = D-Alanine
SITE                    5
                        note = D-Phenylalanine
source                  1..8
                        mol_type = protein
                        organism = synthetic construct
SEQUENCE: 76
XXAHFRWC                                                                8

SEQ ID NO: 77           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 8
                        note = Penicillamine
source                  1..8
                        mol_type = protein
                        organism = synthetic construct
SEQUENCE: 77
XCAHFRWX                                                                8

SEQ ID NO: 78           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 2
                        note = Penicillamine
SITE                    3
                        note = D-Alanine
SITE                    5
                        note = D-Phenylalanine
MOD_RES                 8
                        note = Penicillamine
```

-continued

```
source                  1..8
                        mol_type = protein
                        organism = synthetic construct
SEQUENCE: 78
XXAHFRWX                                                                   8

SEQ ID NO: 79           moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
SITE                    5
                        note = Homoarginine
MOD_RES                 7
                        note = bAla
SITE                    8
                        note = D-Cystine
source                  1..9
                        mol_type = protein
                        organism = synthetic construct
SEQUENCE: 79
FCHFRWACT                                                                  9

SEQ ID NO: 80           moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-(Et)Tyr
MOD_RES                 7
                        note = bAla
SITE                    8
                        note = D-Cystine
source                  1..9
                        mol_type = protein
                        organism = synthetic construct
SEQUENCE: 80
FCHYRWACT                                                                  9

SEQ ID NO: 81           moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
MOD_RES                 6
                        note = 4,4'-biphenylalanine
MOD_RES                 7
                        note = bAla
SITE                    8
                        note = D-Cystine
source                  1..9
                        mol_type = protein
                        organism = synthetic construct
SEQUENCE: 81
FCHFRXACT                                                                  9
```

```
SEQ ID NO: 82           moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
source                  1..9
                        mol_type = protein
                        organism = synthetic construct
SEQUENCE: 82
FCHYRWACT                                                                 9

SEQ ID NO: 83           moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
SITE                    5
                        note = Homoarginine
MOD_RES                 6
                        note = 4,4'-biphenylalanine
MOD_RES                 7
                        note = bAla
SITE                    8
                        note = D-Cystine
source                  1..9
                        mol_type = protein
                        organism = synthetic construct
SEQUENCE: 83
FCHFRXACT                                                                 9

SEQ ID NO: 84           moltype = AA  length = 9
FEATURE                 Location/Qualifiers
SITE                    9
                        note = C-terminal is: NH2
REGION                  1..9
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 6
                        note = 4,4'-biphenylalanine
MOD_RES                 7
                        note = bAla
SITE                    8
                        note = D-Cystine
source                  1..9
                        mol_type = protein
                        organism = synthetic construct
SEQUENCE: 84
FCHYRXACT                                                                 9

SEQ ID NO: 85           moltype = AA  length = 8
FEATURE                 Location/Qualifiers
```

-continued

```
SITE                    8
                        note = C-terminal is: NH2
REGION                  1..8
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
source                  1..8
                        mol_type = protein
                        organism = synthetic construct
SEQUENCE: 85
XCHFRWXC                                                                8

SEQ ID NO: 86           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
source                  1..8
                        mol_type = protein
                        organism = synthetic construct
SEQUENCE: 86
XDAHFRWK                                                                8

SEQ ID NO: 87           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 7
                        note = 3-benzothienylaaanine
source                  1..8
                        mol_type = protein
                        organism = synthetic construct
SEQUENCE: 87
XDAHFRXK                                                                8

SEQ ID NO: 88           moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
```

-continued

```
SITE                    5
                        note = D-Phenylalanine
MOD_RES                 8
                        note = Penicillamine
source                  1..8
                        mol_type = protein
                        organism = synthetic construct
SEQUENCE: 88
XCAHFRWX                                                                    8

SEQ ID NO: 89           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Abu
SITE                    5
                        note = D-Phenylalanine
source                  1..8
                        mol_type = protein
                        organism = synthetic construct
SEQUENCE: 89
XCXHFRWC                                                                    8

SEQ ID NO: 90           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Val
SITE                    5
                        note = D-Phenylalanine
source                  1..8
                        mol_type = protein
                        organism = synthetic construct
SEQUENCE: 90
XCVHFRWC                                                                    8

SEQ ID NO: 91           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Ile
SITE                    5
                        note = D-Phenylalanine
source                  1..8
                        mol_type = protein
                        organism = synthetic construct
SEQUENCE: 91
XCIHFRWC                                                                    8
```

```
SEQ ID NO: 92           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
source                  1..8
                        mol_type = protein
                        organism = synthetic construct
SEQUENCE: 92
XCLHFRWC                                                        8

SEQ ID NO: 93           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Tle
SITE                    5
                        note = D-Phenylalanine
source                  1..8
                        mol_type = protein
                        organism = synthetic construct
SEQUENCE: 93
XCXHFRWC                                                        8

SEQ ID NO: 94           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
source                  1..8
                        mol_type = protein
                        organism = synthetic construct
SEQUENCE: 94
XCXHFRWC                                                        8

SEQ ID NO: 95           moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
```

-continued

```
MOD_RES                2
                       note = Penicillamine
SITE                   4
                       note = D-Phenylalanine
MOD_RES                7
                       note = 4abu
source                 1..8
                       mol_type = protein
                       organism = synthetic construct
SEQUENCE: 95
XXHFRWXC                                                    8

SEQ ID NO: 96          moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
SITE                   1
                       note = Nle
REGION                 2..8
                       note = Cyclic
SITE                   4
                       note = D-Phenylalanine
MOD_RES                7
                       note = 4abu
MOD_RES                8
                       note = Penicillamine
source                 1..8
                       mol_type = protein
                       organism = synthetic construct
SEQUENCE: 96
XCHFRWXX                                                    8

SEQ ID NO: 97          moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
SITE                   1
                       note = Nle
REGION                 2..8
                       note = Cyclic
MOD_RES                2
                       note = Penicillamine
SITE                   4
                       note = D-Phenylalanine
MOD_RES                7
                       note = 4abu
MOD_RES                8
                       note = Penicillamine
source                 1..8
                       mol_type = protein
                       organism = synthetic construct
SEQUENCE: 97
XXHFRWXX                                                    8

SEQ ID NO: 98          moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
REGION                 2..8
                       note = Cyclic
SITE                   4
                       note = D-Phenylalanine
MOD_RES                7
                       note = 4abu
source                 1..8
                       mol_type = protein
                       organism = synthetic construct
```

```
SEQUENCE: 98
LCHFRWXC                                                   8

SEQ ID NO: 99          moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
MOD_RES                1
                       note = Beta-cyclohexylalanine
REGION                 2..8
                       note = Cyclic
SITE                   4
                       note = D-Phenylalanine
MOD_RES                7
                       note = 4abu
source                 1..8
                       mol_type = protein
                       organism = synthetic construct
SEQUENCE: 99
XCHFRWXC                                                   8

SEQ ID NO: 100         moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
REGION                 2..8
                       note = Cyclic
SITE                   4
                       note = D-Phenylalanine
MOD_RES                7
                       note = 4abu
source                 1..8
                       mol_type = protein
                       organism = synthetic construct
SEQUENCE: 100
ICHFRWXC                                                   8

SEQ ID NO: 101         moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
REGION                 2..8
                       note = Cyclic
SITE                   4
                       note = D-Phenylalanine
MOD_RES                7
                       note = 4abu
source                 1..8
                       mol_type = protein
                       organism = synthetic construct
SEQUENCE: 101
FCHFRWXC                                                   8

SEQ ID NO: 102         moltype = AA  length = 8
FEATURE                Location/Qualifiers
SITE                   8
                       note = C-terminal is: NH2
REGION                 1..8
                       note = Description of Sequence: MC4R agonist
SITE
                       note = N-terminal is: Acetylated
REGION                 2..8
                       note = Cyclic
SITE                   4
                       note = D-Phenylalanine
MOD_RES                7
                       note = 4abu
```

```
source                  1..8
                        mol_type = protein
                        organism = synthetic construct
SEQUENCE: 102
VCHFRWXC                                                                    8

SEQ ID NO: 103          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = P-(2-naphthyl)alanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 103
XCHFRWXC                                                                    8

SEQ ID NO: 104          moltype = AA  length = 8
FEATURE                 Location/Qualifiers
SITE                    8
                        note = C-terminal is: NH2
REGION                  1..8
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 104
XCHFRWXC                                                                    8

SEQ ID NO: 105          moltype = AA  length = 8
FEATURE                 Location/Qualifiers
SITE                    8
                        note = C-terminal is: NH2
REGION                  1..8
                        note = Description of Sequence: MC4R agonist
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 105
FCHFRWXC                                                                    8

SEQ ID NO: 106          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
```

```
MOD_RES                 3
                        note = 3-Pal
SITE                    4
                        note = D-Phenylalanine
MOD_RES                 7
                        note = 4abu
source                  1..8
                        mol_type = protein
                        organism = synthetic construct
SEQUENCE: 106
XCXFRWXC                                                                      8

SEQ ID NO: 107          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
source                  1..8
                        mol_type = protein
                        organism = synthetic construct
SEQUENCE: 107
XCAHFRWC                                                                      8

SEQ ID NO: 108          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    6
                        note = D-Trp
MOD_RES                 7
                        note = 4abu
source                  1..8
                        mol_type = protein
                        organism = synthetic construct
SEQUENCE: 108
XCHFRWXC                                                                      8

SEQ ID NO: 109          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 4
                        note = D-P-(2-naphthyl)alanine
source                  1..8
                        mol_type = protein
                        organism = synthetic construct
SEQUENCE: 109
XDHXRWAK                                                                      8
```

```
SEQ ID NO: 110          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 4
                        note = D-P-(2-naphthyl)alanine
MOD_RES                 7
                        note = bAla
source                  1..8
                        mol_type = protein
                        organism = synthetic construct
SEQUENCE: 110
XDHXRWAK                                                      8

SEQ ID NO: 111          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 4
                        note = D-P-(2-naphthyl)alanine
MOD_RES                 7
                        note = 4abu
source                  1..8
                        mol_type = protein
                        organism = synthetic construct
SEQUENCE: 111
XCHXRWXC                                                      8

SEQ ID NO: 112          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 4
                        note = D-P-(2-naphthyl)alanine
MOD_RES                 7
                        note = 6-aminohexanoic acid
source                  1..8
                        mol_type = protein
                        organism = synthetic construct
SEQUENCE: 112
XCHXRWXC                                                      8

SEQ ID NO: 113          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = Homophenylalanine
REGION                  2..8
                        note = Cyclic
```

```
MOD_RES                 4
                        note = D-P-(2-naphthyl)alanine
MOD_RES                 7
                        note = 4abu
source                  1..8
                        mol_type = protein
                        organism = synthetic construct
SEQUENCE: 113
FDHXRWXK                                                                  8

SEQ ID NO: 114          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
MOD_RES                 1
                        note = Beta-cyclohexylalanine
REGION                  2..8
                        note = Cyclic
MOD_RES                 4
                        note = D-P-(2-naphthyl)alanine
MOD_RES                 7
                        note = 4abu
source                  1..8
                        mol_type = protein
                        organism = synthetic construct
SEQUENCE: 114
XDHXRWXK                                                                  8

SEQ ID NO: 115          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = bAla
source                  1..8
                        mol_type = protein
                        organism = synthetic construct
SEQUENCE: 115
XDHFRWAK                                                                  8

SEQ ID NO: 116          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 6-aminohexanoic acid
source                  1..8
                        mol_type = protein
                        organism = synthetic construct
SEQUENCE: 116
XCHFRWXC                                                                  8
```

```
SEQ ID NO: 117          moltype = AA  length = 9
FEATURE                 Location/Qualifiers
SITE                    9
                        note = C-terminal is: OH
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
SITE                    8
                        note = D-Cystine
source                  1..9
                        mol_type = protein
                        organism = synthetic construct
SEQUENCE: 117
FCHFRWACT                                                     9

SEQ ID NO: 118          moltype = AA  length = 9
FEATURE                 Location/Qualifiers
SITE                    9
                        note = C-terminal is: OH
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
MOD_RES                 7
                        note = bAla
SITE                    8
                        note = D-Cystine
source                  1..9
                        mol_type = protein
                        organism = synthetic construct
SEQUENCE: 118
FCHFRWACT                                                     9

SEQ ID NO: 119          moltype = AA  length = 9
FEATURE                 Location/Qualifiers
SITE                    9
                        note = C-terminal is: OH
REGION                  1..9
                        note = Description of Sequence: MC4R agonist
SITE                    1
                        note = D-Phenylalanine
REGION                  2..8
                        note = Cyclic
SITE                    4
                        note = D-Phenylalanine
MOD_RES                 7
                        note = 4abu
SITE                    8
                        note = D-Cystine
source                  1..9
                        mol_type = protein
                        organism = synthetic construct
SEQUENCE: 119
FCHFRWXCT                                                     9

SEQ ID NO: 120          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
```

```
MOD_RES                 7
                        note = 5-aminopentanoic acid
source                  1..8
                        mol_type = protein
                        organism = synthetic construct
SEQUENCE: 120
XCHFRWXC                                                                   8

SEQ ID NO: 121          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 5-aminopentanoic acid
source                  1..8
                        mol_type = protein
                        organism = synthetic construct
SEQUENCE: 121
XDHFRWXK                                                                   8

SEQ ID NO: 122          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
MOD_RES                 1
                        note = Beta-cyclohexylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 122
XDHFRWXK                                                                   8

SEQ ID NO: 123          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 123
XDHFRWXK                                                                   8

SEQ ID NO: 124          moltype = AA  length = 8
FEATURE                 Location/Qualifiers
SITE                    8
                        note = C-terminal is: OH
```

```
REGION                  1..8
                        note = Description of Sequence: MC4R agonist
SITE
                        note = N-terminal is: Acetylated
MOD_RES                 1
                        note = Cyclohexylglycine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 124
XDHFRWXK                                                                 8

SEQ ID NO: 125          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
MOD_RES                 1
                        note = D-Beta-cyclohexylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 125
XDHFRWXK                                                                 8

SEQ ID NO: 126          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 126
XDHFRWXK                                                                 8

SEQ ID NO: 127          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = D-Chg
REGION                  2..8
                        note = Cyclic
SITE                    4
                        note = D-Phenylalanine
MOD_RES                 7
                        note = 4abu
```

```
source                  1..8
                        mol_type = protein
                        organism = synthetic construct
SEQUENCE: 127
XDHFRWXK                                                                    8

SEQ ID NO: 128          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Homophenylalanine
REGION                  2..8
                        note = Cyclic
SITE                    4
                        note = D-Phenylalanine
MOD_RES                 7
                        note = 4abu
source                  1..8
                        mol_type = protein
                        organism = synthetic construct
SEQUENCE: 128
FDHFRWXK                                                                    8

SEQ ID NO: 129          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = 4abu
source                  1..8
                        mol_type = protein
                        organism = synthetic construct
SEQUENCE: 129
XCHFRWXC                                                                    8

SEQ ID NO: 130          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = 6-aminohexanoic acid
source                  1..8
                        mol_type = protein
                        organism = synthetic construct
SEQUENCE: 130
XCHFRWXC                                                                    8
```

```
SEQ ID NO: 131          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = bAla
source                  1..8
                        mol_type = protein
                        organism = synthetic construct
SEQUENCE: 131
XCHFRWAC                                                                8

SEQ ID NO: 132          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
SITE                    7
                        note = D-Alanine
source                  1..8
                        mol_type = protein
                        organism = synthetic construct
SEQUENCE: 132
XCHFRWAC                                                                8

SEQ ID NO: 133          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
MOD_RES                 5
                        note = D-P-(2-naphthyl)alanine
source                  1..8
                        mol_type = protein
                        organism = synthetic construct
SEQUENCE: 133
XCAHXRWC                                                                8

SEQ ID NO: 134          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
```

```
SITE                    1
                        note = Nle
REGION                  2..8
                        note = Cyclic
SITE                    3
                        note = D-Alanine
MOD_RES                 5
                        note = D-P-(2-naphthyl)alanine
MOD_RES                 7
                        note = P-(2-naphthyl)alanine
source                  1..8
                        mol_type = protein
                        organism = synthetic construct
SEQUENCE: 134
XCAHXRXC                                                    8

SEQ ID NO: 135          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
MOD_RES                 5
                        note = D-P-(2-naphthyl)alanine
MOD_RES                 7
                        note = 1-Nal
source                  1..8
                        mol_type = protein
                        organism = synthetic construct
SEQUENCE: 135
XCAHXRXC                                                    8

SEQ ID NO: 136          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
MOD_RES                 5
                        note = D-P-(2-naphthyl)alanine
MOD_RES                 7
                        note = 3-benzothienylaaanine
source                  1..8
                        mol_type = protein
                        organism = synthetic construct
SEQUENCE: 136
XCAHXRXC                                                    8

SEQ ID NO: 137          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
MOD_RES                 2
                        note = Penicillamine
```

```
SITE                    3
                        note = D-Alanine
SITE                    5
                        note = D-Phenylalanine
source                  1..8
                        mol_type = protein
                        organism = synthetic construct
SEQUENCE: 137
XXAHFRWC                                                                    8

SEQ ID NO: 138          moltype = AA  length = 8
FEATURE                 Location/Qualifiers
SITE                    8
                        note = C-terminal is: OH
REGION                  1..8
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 4abu
MOD_RES                 8
                        note = Penicillamine
source                  1..8
                        mol_type = protein
                        organism = synthetic construct
SEQUENCE: 138
XCHFRWXX                                                                    8

SEQ ID NO: 139          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  2..8
                        note = Cyclic
SITE                    3
                        note = D-Alanine
MOD_RES                 5
                        note = D-P-(2-naphthyl)alanine
source                  1..8
                        mol_type = protein
                        organism = synthetic construct
SEQUENCE: 139
RCAHXRWC                                                                    8

SEQ ID NO: 140          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  2..8
                        note = Cyclic
SITE                    3
                        note = D-Alanine
SITE                    5
                        note = D-Phenylalanine
source                  1..8
                        mol_type = protein
                        organism = synthetic construct
SEQUENCE: 140
RCAHFRWC                                                                    8

SEQ ID NO: 141          moltype = AA  length = 8
FEATURE                 Location/Qualifiers
SITE                    8
                        note = C-terminal is: NH2
```

```
REGION                  1..8
                        note = Description of Sequence: MC4R agonist
SITE
                        note = N-terminal is: Acetylated
SITE                    1
                        note = D-Arg
REGION                  2..8
                        note = Cyclic
MOD_RES                 3
                        note = D-Alanine
SITE                    5
                        note = D-Phenylalanine
source                  1..8
                        mol_type = protein
                        organism = synthetic construct
SEQUENCE: 141
RCAHFRWC                                                                    8

SEQ ID NO: 142          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = D-Arg
REGION                  2..8
                        note = Cyclic
SITE                    3
                        note = D-Alanine
SITE                    5
                        note = D-Phenylalanine
MOD_RES                 8
                        note = Penicillamine
source                  1..8
                        mol_type = protein
                        organism = synthetic construct
SEQUENCE: 142
RCAHFRWX                                                                    8

SEQ ID NO: 143          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = D-Arg
REGION                  2..8
                        note = Cyclic
SITE                    4
                        note = D-Phenylalanine
MOD_RES                 7
                        note = 4abu
MOD_RES                 8
                        note = Penicillamine
source                  1..8
                        mol_type = protein
                        organism = synthetic construct
SEQUENCE: 143
RCHFRWXX                                                                    8

SEQ ID NO: 144          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  2..8
                        note = Cyclic
SITE                    4
                        note = D-Phenylalanine
```

```
MOD_RES                 7
                        note = 4abu
MOD_RES                 8
                        note = Penicillamine
source                  1..8
                        mol_type = protein
                        organism = synthetic construct
SEQUENCE: 144
RCHFRWXX                                                                  8

SEQ ID NO: 145          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  2..8
                        note = Cyclic
SITE                    3
                        note = D-Alanine
SITE                    5
                        note = D-Phenylalanine
MOD_RES                 8
                        note = Penicillamine
source                  1..8
                        mol_type = protein
                        organism = synthetic construct
SEQUENCE: 145
RCAHFRWX                                                                  8

SEQ ID NO: 146          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
SITE                    1
                        note = D-Arg
REGION                  2..8
                        note = Cyclic
SITE                    4
                        note = D-Phenylalanine
source                  1..8
                        mol_type = protein
                        organism = synthetic construct
SEQUENCE: 146
RDHFRWAK                                                                  8

SEQ ID NO: 147          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  2..8
                        note = Cyclic
SITE                    4
                        note = D-Phenylalanine
source                  1..8
                        mol_type = protein
                        organism = synthetic construct
SEQUENCE: 147
RDHFRWAK                                                                  8

SEQ ID NO: 148          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
```

```
SITE                    1
                        note = Nle
REGION                  2..9
                        note = Cyclic
SITE                    3
                        note = D-Alanine
SITE                    5
                        note = D-Phenylalanine
source                  1..9
                        mol_type = protein
                        organism = synthetic construct
SEQUENCE: 148
XCAHFRWGC                                                       9

SEQ ID NO: 149          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
SITE                    1
                        note = Nle
REGION                  2..9
                        note = Cyclic
SITE                    3
                        note = D-Alanine
SITE                    5
                        note = D-Phenylalanine
MOD_RES                 8
                        note = D-Alanine
source                  1..9
                        mol_type = protein
                        organism = synthetic construct
SEQUENCE: 149
XCAHFRWAC                                                       9

SEQ ID NO: 150          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
SITE                    1
                        note = Nle
REGION                  2..9
                        note = Cyclic
SITE                    3
                        note = D-Alanine
SITE                    5
                        note = D-Phenylalanine
MOD_RES                 8
                        note = bAla
source                  1..9
                        mol_type = protein
                        organism = synthetic construct
SEQUENCE: 150
XCAHFRWAC                                                       9

SEQ ID NO: 151          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
SITE                    1
                        note = Nle
REGION                  2..9
                        note = Cyclic
SITE                    3
                        note = D-Alanine
SITE                    5
                        note = D-Phenylalanine
```

-continued

```
MOD_RES                 8
                        note = 4abu
source                  1..9
                        mol_type = protein
                        organism = synthetic construct
SEQUENCE: 151
XCAHFRWXC                                                                9

SEQ ID NO: 152          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
SITE                    1
                        note = Nle
REGION                  2..9
                        note = Cyclic
SITE                    3
                        note = D-Alanine
SITE                    5
                        note = D-Phenylalanine
MOD_RES                 8
                        note = 5-aminopentanoic acid
source                  1..9
                        mol_type = protein
                        organism = synthetic construct
SEQUENCE: 152
XCAHFRWXC                                                                9

SEQ ID NO: 153          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  1..8
                        note = Cyclic
SITE                    4
                        note = D-Phenylalanine
source                  1..8
                        mol_type = protein
                        organism = synthetic construct
SEQUENCE: 153
CEHFRWAC                                                                 8

SEQ ID NO: 154          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  1..8
                        note = Cyclic
SITE                    4
                        note = D-Phenylalanine
MOD_RES                 6
                        note = P-(2-naphthyl)alanine
source                  1..8
                        mol_type = protein
                        organism = synthetic construct
SEQUENCE: 154
CEHFRXAC                                                                 8

SEQ ID NO: 155          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
```

-continued

```
REGION                  1..8
                        note = Cyclic
SITE                    2
                        note = D-Alanine
SITE                    4
                        note = D-Phenylalanine
source                  1..8
                        mol_type = protein
                        organism = synthetic construct
SEQUENCE: 155
CAHFRWAC                                                                    8

SEQ ID NO: 156          moltype = AA  length = 8
FEATURE                 Location/Qualifiers
SITE                    8
                        note = C-terminal is: NH2
REGION                  1..8
                        note = Description of Sequence: MC4R agonist
SITE
                        note = N-terminal is: Acetylated
REGION                  1..8
                        note = Cyclic
SITE                    2
                        note = D-Alanine
SITE                    4
                        note = D-Phenylalanine
MOD_RES                 6
                        note = P-(2-naphthyl)alanine
source                  1..8
                        mol_type = protein
                        organism = synthetic construct
SEQUENCE: 156
CAHFRXAC                                                                    8

SEQ ID NO: 157          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
SITE                    1
                        note = Nle
REGION                  2..9
                        note = Cyclic
SITE                    3
                        note = D-Alanine
SITE                    5
                        note = D-Phenylalanine
source                  1..9
                        mol_type = protein
                        organism = synthetic construct
SEQUENCE: 157
XCAHFRWAC                                                                   9

SEQ ID NO: 158          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
SITE                    1
                        note = Nle
REGION                  2..9
                        note = Cyclic
SITE                    3
                        note = D-Alanine
SITE                    5
                        note = D-Phenylalanine
MOD_RES                 7
                        note = 3-benzothienylaaanine
source                  1..9
                        mol_type = protein
                        organism = synthetic construct
SEQUENCE: 158
XDAHFRXAK                                                                   9
```

```
SEQ ID NO: 159         moltype = AA  length = 18
FEATURE                Location/Qualifiers
SITE                   18
                       note = C-terminal is: NH2
REGION                 1..18
                       note = Description of Sequence: MC4R agonist
SITE                   12
                       note = Nle
REGION                 13..18
                       note = Cyclic
MOD_RES                15
                       note = D-2-Nal
source                 1..18
                       mol_type = protein
                       organism = synthetic construct
SEQUENCE: 159
YGRKKRRQRR RXDHXRWK                                                18

SEQ ID NO: 160         moltype = AA  length = 19
FEATURE                Location/Qualifiers
SITE                   19
                       note = C-terminal is: NH2
REGION                 1..19
                       note = Description of Sequence: MC4R agonist
MOD_RES                12
                       note = 8-amino-3,6-dioxaoctanoic acid
SITE                   13
                       note = Nle
REGION                 14..19
                       note = Cyclic
MOD_RES                16
                       note = D-2-Nal
source                 1..19
                       mol_type = protein
                       organism = synthetic construct
SEQUENCE: 160
YGRKKRRQRR RXXDHXRWK                                               19

SEQ ID NO: 161         moltype = AA  length = 19
FEATURE                Location/Qualifiers
SITE                   19
                       note = C-terminal is: NH2
REGION                 1..19
                       note = Description of Sequence: MC4R agonist
SITE                   1
                       note = Nle
REGION                 2..7
                       note = Cyclic
MOD_RES                4
                       note = D-P-(2-naphthyl)alanine
MOD_RES                8
                       note = bAla
source                 1..19
                       mol_type = protein
                       organism = synthetic construct
SEQUENCE: 161
XDHXRWKAYG RKKRRQRRR                                               19

SEQ ID NO: 162         moltype = AA  length = 19
FEATURE                Location/Qualifiers
SITE                   19
                       note = C-terminal is: NH2
REGION                 1..19
                       note = Description of Sequence: MC4R agonist
SITE
                       note = N-terminal is: Acetylated
SITE                   1
                       note = Nle
REGION                 2..7
                       note = Cyclic
MOD_RES                4
                       note = D-P-(2-naphthyl)alanine
MOD_RES                8
                       note = bAla
source                 1..19
                       mol_type = protein
                       organism = synthetic construct
```

```
SEQUENCE: 162
XDHXRWKAYG RKKRRQRRR                                              19

SEQ ID NO: 163          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = Nle
REGION                  2..7
                        note = Cyclic
MOD_RES                 4
                        note = D-P-(2-naphthyl)alanine
MOD_RES                 8..9
                        note = 8-amino-3,6-dioxaoctanoic acid
source                  1..20
                        mol_type = protein
                        organism = synthetic construct
SEQUENCE: 163
XDHXRWKXXY GRKKRRQRRR                                             20

SEQ ID NO: 164          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
SITE                    1
                        note = Nle
REGION                  2..7
                        note = Cyclic
MOD_RES                 4
                        note = D-P-(2-naphthyl)alanine
source                  1..22
                        mol_type = protein
                        organism = synthetic construct
SEQUENCE: 164
XDHXRWKPPK DYGRKKRRQR RR                                          22

SEQ ID NO: 165          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
source                  1..23
                        mol_type = protein
                        organism = synthetic construct
SEQUENCE: 165
CEHXRWGCPP KDYGRKKRRQ RRR                                         23

SEQ ID NO: 166          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..7
                        note = Cyclic
MOD_RES                 4
                        note = D-P-(2-naphthyl)alanine
MOD_RES                 8..9
                        note = bAla
```

-continued

```
source                  1..20
                        mol_type = protein
                        organism = synthetic construct
SEQUENCE: 166
XDHXRWKAAY GRKKRRQRRR                                                   20

SEQ ID NO: 167          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
SITE                    1
                        note = Nle
REGION                  2..7
                        note = Cyclic
MOD_RES                 4
                        note = D-P-(2-naphthyl)alanine
MOD_RES                 12
                        note = 8-amino-3,6-dioxaoctanoic acid
source                  1..23
                        mol_type = protein
                        organism = synthetic construct
SEQUENCE: 167
XDHXRWKPPK DXYGRKKRRQ RRR                                               23

SEQ ID NO: 168          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 13
                        note = 8-amino-3,6-dioxaoctanoic acid
source                  1..24
                        mol_type = protein
                        organism = synthetic construct
SEQUENCE: 168
CEHXRWGCPP KDXYGRKKRR QRRR                                              24

SEQ ID NO: 169          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 13
                        note = bAla
source                  1..24
                        mol_type = protein
                        organism = synthetic construct
SEQUENCE: 169
CEHXRWACPP KDAYGRKKRR QRRR                                              24

SEQ ID NO: 170          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
```

```
MOD_RES                 4
                        note = D-P-(2-naphthyl)alanine
MOD_RES                 13
                        note = 8-amino-3,6-dioxaoctanoic acid
source                  1..24
                        mol_type = protein
                        organism = synthetic construct
SEQUENCE: 170
CEHXRWACPP KDXYGRKKRR QRRR                                          24

SEQ ID NO: 171          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..7
                        note = Cyclic
MOD_RES                 4
                        note = D-P-(2-naphthyl)alanine
MOD_RES                 8..9
                        note = 8-amino-3,6-dioxaoctanoic acid
source                  1..20
                        mol_type = protein
                        organism = synthetic construct
SEQUENCE: 171
XDHXRWKXXY GRKKRRQRRR                                               20

SEQ ID NO: 172          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..24
                        mol_type = protein
                        organism = synthetic construct
SEQUENCE: 172
CEHXRXACPP KDAYGRKKRR QRRR                                          24

SEQ ID NO: 173          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..22
                        mol_type = protein
                        organism = synthetic construct
SEQUENCE: 173
CEHXRXACPP KDARRRRRQR RR                                            22
```

```
SEQ ID NO: 174          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..23
                        mol_type = protein
                        organism = synthetic construct
SEQUENCE: 174
CEHXRXACPP KDAGRRRRRQ RRR                                          23

SEQ ID NO: 175          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..24
                        mol_type = protein
                        organism = synthetic construct
SEQUENCE: 175
CEHXRXACPP KDAYGRRRRR QRRR                                         24

SEQ ID NO: 176          moltype = AA  length = 24
FEATURE                 Location/Qualifiers
SITE                    24
                        note = C-terminal is: NH2
REGION                  1..24
                        note = Description of Sequence: MC4R agonist
REGION                  1..8
                        note = Cyclic
MOD_RES                 4
                        note = D-P-(2-naphthyl)alanine
MOD_RES                 13
                        note = bAla
source                  1..24
                        mol_type = protein
                        organism = synthetic construct
SEQUENCE: 176
CEHXRWACPP KDAYGRKKRQ RRRR                                         24

SEQ ID NO: 177          moltype = AA  length = 24
FEATURE                 Location/Qualifiers
SITE                    24
                        note = C-terminal is: NH2
REGION                  1..24
                        note = Description of Sequence: MC4R agonist
REGION                  1..8
                        note = Cyclic
MOD_RES                 4
                        note = D-P-(2-naphthyl)alanine
MOD_RES                 13
                        note = bAla
source                  1..24
                        mol_type = protein
                        organism = synthetic construct
```

```
SEQUENCE: 177
CEHXRWACPP KDAYGRKKQR RRRR                                          24

SEQ ID NO: 178          moltype = AA  length = 24
FEATURE                 Location/Qualifiers
SITE                    24
                        note = C-terminal is: NH2
REGION                  1..24
                        note = Description of Sequence: MC4R agonist
REGION                  1..8
                        note = Cyclic
MOD_RES                 4
                        note = D-P-(2-naphthyl)alanine
MOD_RES                 13
                        note = bAla
source                  1..24
                        mol_type = protein
                        organism = synthetic construct
SEQUENCE: 178
CEHXRWACPP KDAYGRKQKR RRRR                                          24

SEQ ID NO: 179          moltype = AA  length = 24
FEATURE                 Location/Qualifiers
SITE                    24
                        note = C-terminal is: NH2
REGION                  1..24
                        note = Description of Sequence: MC4R agonist
REGION                  1..8
                        note = Cyclic
MOD_RES                 4
                        note = D-P-(2-naphthyl)alanine
MOD_RES                 13
                        note = bAla
source                  1..24
                        mol_type = protein
                        organism = synthetic construct
SEQUENCE: 179
CEHXRWACPP KDAYGRKKRR RRQR                                          24

SEQ ID NO: 180          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
MOD_RES                 15
                        note = a-aminoisobutyric acid
source                  1..24
                        mol_type = protein
                        organism = synthetic construct
SEQUENCE: 180
CEHXRXACPP KDAYXRKKRR QRRR                                          24

SEQ ID NO: 181          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
```

```
source                  1..22
                        mol_type = protein
                        organism = synthetic construct
SEQUENCE: 181
CEHXRXACPP RDARRRRRQR RR                                           22

SEQ ID NO: 182          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..22
                        mol_type = protein
                        organism = synthetic construct
SEQUENCE: 182
CEHXRXACPP KDARRRRRQR RR                                           22

SEQ ID NO: 183          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..23
                        mol_type = protein
                        organism = synthetic construct
SEQUENCE: 183
CEHXRXACPP KDARRRRRRQ RRR                                          23

SEQ ID NO: 184          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..22
                        mol_type = protein
                        organism = synthetic construct
SEQUENCE: 184
CEHXRXACPP RDARRRRRQR RR                                           22

SEQ ID NO: 185          moltype = AA  length = 22
FEATURE                 Location/Qualifiers
SITE                    22
                        note = C-terminal is: NH2
REGION                  1..22
                        note = Description of Sequence: MC4R agonist
```

-continued

```
SITE
                       note = N-terminal is: Acetylated
REGION                 1..8
                       note = Cyclic
MOD_RES                4
                       note = D-P-(2-naphthyl)alanine
MOD_RES                6
                       note = P-(2-naphthyl)alanine
MOD_RES                13
                       note = bAla
source                 1..22
                       mol_type = protein
                       organism = synthetic construct
SEQUENCE: 185
CEHXRXACPP KDARRRRRQR RR                                             22

SEQ ID NO: 186         moltype = AA  length = 23
FEATURE                Location/Qualifiers
SITE                   23
                       note = C-terminal is: NH2
REGION                 1..23
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                6
                       note = P-(2-naphthyl)alanine
MOD_RES                13
                       note = bAla
source                 1..23
                       mol_type = protein
                       organism = synthetic construct
SEQUENCE: 186
CEHXRXACPP KDARRRRRRQ RRR                                            23

SEQ ID NO: 187         moltype = AA  length = 23
FEATURE                Location/Qualifiers
SITE                   23
                       note = C-terminal is: NH2
REGION                 1..23
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                6
                       note = 3-benzothienylaaanine
MOD_RES                13
                       note = bAla
source                 1..23
                       mol_type = protein
                       organism = synthetic construct
SEQUENCE: 187
CEHXRXACPP RDARRRRRRQ RRR                                            23

SEQ ID NO: 188         moltype = AA  length = 22
FEATURE                Location/Qualifiers
SITE                   22
                       note = C-terminal is: NH2
REGION                 1..22
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                6
                       note = 3-benzothienylaaanine
MOD_RES                13
                       note = bAla
source                 1..22
                       mol_type = protein
                       organism = synthetic construct
```

```
SEQUENCE: 188
CEHXRXACPP RDARRRRRQR RR                                          22

SEQ ID NO: 189         moltype = AA  length = 23
FEATURE                Location/Qualifiers
SITE                   23
                       note = C-terminal is: NH2
REGION                 1..23
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                6
                       note = 3-benzothienylaaanine
MOD_RES                13
                       note = bAla
source                 1..23
                       mol_type = protein
                       organism = synthetic construct
SEQUENCE: 189
CEHXRXACPP KDARRRRRRQ RRR                                         23

SEQ ID NO: 190         moltype = AA  length = 24
FEATURE                Location/Qualifiers
SITE                   24
                       note = C-terminal is: NH2
REGION                 1..24
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                13
                       note = bAla
source                 1..24
                       mol_type = protein
                       organism = synthetic construct
SEQUENCE: 190
CEHXRWACPP KDAYGRKKRR RQRR                                        24

SEQ ID NO: 191         moltype = AA  length = 24
FEATURE                Location/Qualifiers
SITE                   24
                       note = C-terminal is: NH2
REGION                 1..24
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                13
                       note = bAla
source                 1..24
                       mol_type = protein
                       organism = synthetic construct
SEQUENCE: 191
CEHXRWACPP KDAYGRQKKR RRRR                                        24

SEQ ID NO: 192         moltype = AA  length = 24
FEATURE                Location/Qualifiers
SITE                   24
                       note = C-terminal is: NH2
REGION                 1..24
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                13
                       note = bAla
```

```
source                  1..24
                        mol_type = protein
                        organism = synthetic construct
SEQUENCE: 192
CEHXRWACPP KDAYGRKKRR RRRQ                                          24

SEQ ID NO: 193          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..24
                        mol_type = protein
                        organism = synthetic construct
SEQUENCE: 193
CEHXRXACPP KDAYGRKKRR QRRR                                          24

SEQ ID NO: 194          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..24
                        mol_type = protein
                        organism = synthetic construct
SEQUENCE: 194
CEHXRXACPP KDAYGRKKRR QRRR                                          24

SEQ ID NO: 195          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..22
                        mol_type = protein
                        organism = synthetic construct
SEQUENCE: 195
CEHXRXACPP KDARRKRRQR RR                                            22

SEQ ID NO: 196          moltype = AA  length = 22
FEATURE                 Location/Qualifiers
SITE                    22
                        note = C-terminal is: NH2
REGION                  1..22
                        note = Description of Sequence: MC4R agonist
```

```
SITE
                      note = N-terminal is: Acetylated
REGION                1..8
                      note = Cyclic
MOD_RES               4
                      note = D-P-(2-naphthyl)alanine
MOD_RES               6
                      note = 1-Nal
MOD_RES               13
                      note = bAla
source                1..22
                      mol_type = protein
                      organism = synthetic construct
SEQUENCE: 196
CEHXRXACPP KDARKRRRQR RR                                          22

SEQ ID NO: 197        moltype = AA  length = 22
FEATURE               Location/Qualifiers
SITE                  22
                      note = C-terminal is: NH2
REGION                1..22
                      note = Description of Sequence: MC4R agonist
SITE
                      note = N-terminal is: Acetylated
REGION                1..8
                      note = Cyclic
MOD_RES               4
                      note = D-P-(2-naphthyl)alanine
MOD_RES               6
                      note = P-(2-naphthyl)alanine
MOD_RES               13
                      note = bAla
source                1..22
                      mol_type = protein
                      organism = synthetic construct
SEQUENCE: 197
CEHXRXACPP KDARRKRRQR RR                                          22

SEQ ID NO: 198        moltype = AA  length = 24
FEATURE               Location/Qualifiers
SITE                  24
                      note = C-terminal is: NH2
REGION                1..24
                      note = Description of Sequence: MC4R agonist
SITE
                      note = N-terminal is: Acetylated
REGION                1..8
                      note = Cyclic
MOD_RES               4
                      note = D-P-(2-naphthyl)alanine
MOD_RES               6
                      note = P-(2-naphthyl)alanine
MOD_RES               13
                      note = bAla
source                1..24
                      mol_type = protein
                      organism = synthetic construct
SEQUENCE: 198
CEHXRXACPP KDAYGRRKRR QRRR                                        24

SEQ ID NO: 199        moltype = AA  length = 23
FEATURE               Location/Qualifiers
SITE                  23
                      note = C-terminal is: NH2
REGION                1..23
                      note = Description of Sequence: MC4R agonist
SITE
                      note = N-terminal is: Acetylated
REGION                1..8
                      note = Cyclic
MOD_RES               4
                      note = D-P-(2-naphthyl)alanine
MOD_RES               6
                      note = P-(2-naphthyl)alanine
MOD_RES               13
                      note = bAla
source                1..23
                      mol_type = protein
                      organism = synthetic construct
```

```
SEQUENCE: 199
CEHXRXACPP KDAGRRKRRQ RRR                                         23

SEQ ID NO: 200          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..23
                        mol_type = protein
                        organism = synthetic construct
SEQUENCE: 200
CEHXRXACPP KDAGRKRRRQ RRR                                         23

SEQ ID NO: 201          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..24
                        mol_type = protein
                        organism = synthetic construct
SEQUENCE: 201
CEHXRXACPP KDAYGRRKRR QRRR                                        24

SEQ ID NO: 202          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..24
                        mol_type = protein
                        organism = synthetic construct
SEQUENCE: 202
CEHXRXACPP KDAYGRKRRR QRRR                                        24

SEQ ID NO: 203          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
```

```
MOD_RES                 4
                        note = D-P-(2-naphthyl)alanine
MOD_RES                 6
                        note = 1-Nal
MOD_RES                 13
                        note = bAla
source                  1..23
                        mol_type = protein
                        organism = synthetic construct
SEQUENCE: 203
CEHXRXACPP KDAGRRKRRQ RRR                                           23

SEQ ID NO: 204          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..23
                        mol_type = protein
                        organism = synthetic construct
SEQUENCE: 204
CEHXRXACPP KDAGRKRRRQ RRR                                           23

SEQ ID NO: 205          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..22
                        mol_type = protein
                        organism = synthetic construct
SEQUENCE: 205
CEHXRXACPP KDARRKRRQR RR                                            22

SEQ ID NO: 206          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..22
                        mol_type = protein
                        organism = synthetic construct
SEQUENCE: 206
CEHXRXACPP KDARKRRRQR RR                                            22

SEQ ID NO: 207          moltype = AA  length = 24
```

-continued

```
FEATURE                Location/Qualifiers
SITE                   24
                       note = C-terminal is: NH2
REGION                 1..24
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                6
                       note = P-(2-naphthyl)alanine
MOD_RES                13
                       note = bAla
source                 1..24
                       mol_type = protein
                       organism = synthetic construct
SEQUENCE: 207
CEHXRXACPP KDAYGRKRRR QRRR                                             24

SEQ ID NO: 208         moltype = AA  length = 22
FEATURE                Location/Qualifiers
SITE                   22
                       note = C-terminal is: NH2
REGION                 1..22
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                6
                       note = 3-benzothienylaaanine
MOD_RES                13
                       note = bAla
source                 1..22
                       mol_type = protein
                       organism = synthetic construct
SEQUENCE: 208
CEHXRXACPP KDARRKRRQR RR                                               22

SEQ ID NO: 209         moltype = AA  length = 22
FEATURE                Location/Qualifiers
SITE                   22
                       note = C-terminal is: NH2
REGION                 1..22
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                6
                       note = 3-benzothienylaaanine
MOD_RES                13
                       note = bAla
source                 1..22
                       mol_type = protein
                       organism = synthetic construct
SEQUENCE: 209
CEHXRXACPP KDARKRRRQR RR                                               22

SEQ ID NO: 210         moltype = AA  length = 24
FEATURE                Location/Qualifiers
SITE                   24
                       note = C-terminal is: NH2
REGION                 1..24
                       note = Description of Sequence: MC4R agonist
SITE
                       note = N-terminal is: Acetylated
REGION                 1..8
                       note = Cyclic
MOD_RES                4
                       note = D-P-(2-naphthyl)alanine
MOD_RES                6
                       note = 3-benzothienylaaanine
```

```
MOD_RES                 13
                        note = bAla
source                  1..24
                        mol_type = protein
                        organism = synthetic construct
SEQUENCE: 210
CEHXRXACPP KDAYGRRKRR QRRR                                           24

SEQ ID NO: 211          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..24
                        mol_type = protein
                        organism = synthetic construct
SEQUENCE: 211
CEHXRXACPP KDAYGRKRRR QRRR                                           24

SEQ ID NO: 212          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..23
                        mol_type = protein
                        organism = synthetic construct
SEQUENCE: 212
CEHXRXACPP KDAGRRKRRQ RRR                                            23

SEQ ID NO: 213          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..23
                        mol_type = protein
                        organism = synthetic construct
SEQUENCE: 213
CEHXRXACPP KDAGRKRRRQ RRR                                            23

SEQ ID NO: 214          moltype = AA  length = 22
FEATURE                 Location/Qualifiers
SITE                    22
                        note = C-terminal is: NH2
```

```
REGION                1..22
                      note = Description of Sequence: MC4R agonist
SITE
                      note = N-terminal is: Acetylated
REGION                1..8
                      note = Cyclic
MOD_RES               4
                      note = D-P-(2-naphthyl)alanine
MOD_RES               13
                      note = bAla
source                1..22
                      mol_type = protein
                      organism = synthetic construct
SEQUENCE: 214
CEHXRWACPP KDARRRRRQR RR                                          22

SEQ ID NO: 215        moltype = AA  length = 22
FEATURE               Location/Qualifiers
SITE                  22
                      note = C-terminal is: NH2
REGION                1..22
                      note = Description of Sequence: MC4R agonist
SITE
                      note = N-terminal is: Acetylated
REGION                1..8
                      note = Cyclic
MOD_RES               4
                      note = D-2-Nal
MOD_RES               13
                      note = bAla
source                1..22
                      mol_type = protein
                      organism = synthetic construct
SEQUENCE: 215
CEHXRWACPP RDARRRRRQR RR                                          22

SEQ ID NO: 216        moltype = AA  length = 24
FEATURE               Location/Qualifiers
SITE                  24
                      note = C-terminal is: NH2
REGION                1..24
                      note = Description of Sequence: MC4R agonist
SITE
                      note = N-terminal is: Acetylated
REGION                1..8
                      note = Cyclic
MOD_RES               4
                      note = D-P-(2-naphthyl)alanine
MOD_RES               13
                      note = bAla
source                1..24
                      mol_type = protein
                      organism = synthetic construct
SEQUENCE: 216
CEHXRWACPP KDAYGRRRRR QRRR                                        24

SEQ ID NO: 217        moltype = AA  length = 24
FEATURE               Location/Qualifiers
SITE                  24
                      note = C-terminal is: NH2
REGION                1..24
                      note = Description of Sequence: MC4R agonist
SITE
                      note = N-terminal is: Acetylated
REGION                1..8
                      note = Cyclic
MOD_RES               4
                      note = D-P-(2-naphthyl)alanine
MOD_RES               13
                      note = bAla
source                1..24
                      mol_type = protein
                      organism = synthetic construct
SEQUENCE: 217
CEHXRWACPP RDAYGRRRRR QRRR                                        24
```

```
SEQ ID NO: 218          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 13
                        note = bAla
source                  1..23
                        mol_type = protein
                        organism = synthetic construct
SEQUENCE: 218
CEHXRWACPP KDARRRRRQR RRR                                          23

SEQ ID NO: 219          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 13
                        note = bAla
source                  1..23
                        mol_type = protein
                        organism = synthetic construct
SEQUENCE: 219
CEHXRWACPP RDARRRRRQR RRR                                          23

SEQ ID NO: 220          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 13
                        note = bAla
source                  1..25
                        mol_type = protein
                        organism = synthetic construct
SEQUENCE: 220
CEHXRWACPP KDAYGRRRRR QRRRR                                        25

SEQ ID NO: 221          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 13
                        note = bAla
source                  1..25
                        mol_type = protein
                        organism = synthetic construct
```

```
SEQUENCE: 221
CEHXRWACPP RDAYGRRRRR QRRRR                                            25

SEQ ID NO: 222          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..23
                        mol_type = protein
                        organism = synthetic construct
SEQUENCE: 222
CEHXRXACPP KDARRRRRQR RRR                                              23

SEQ ID NO: 223          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..23
                        mol_type = protein
                        organism = synthetic construct
SEQUENCE: 223
CEHXRXACPP RDARRRRRQR RRR                                              23

SEQ ID NO: 224          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..23
                        mol_type = protein
                        organism = synthetic construct
SEQUENCE: 224
CEHXRXACPP RDARRRRRRQ RRR                                              23

SEQ ID NO: 225          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
```

```
MOD_RES                 4
                        note = D-P-(2-naphthyl)alanine
MOD_RES                 6
                        note = 1-Nal
MOD_RES                 13
                        note = bAla
source                  1..24
                        mol_type = protein
                        organism = synthetic construct
SEQUENCE: 225
CEHXRXACPP KDAYGRRRRR QRRR                                              24

SEQ ID NO: 226          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..24
                        mol_type = protein
                        organism = synthetic construct
SEQUENCE: 226
CEHXRXACPP RDAYGRRRRR QRRR                                              24

SEQ ID NO: 227          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..25
                        mol_type = protein
                        organism = synthetic construct
SEQUENCE: 227
CEHXRXACPP KDAYGRRRRR QRRRR                                             25

SEQ ID NO: 228          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..25
                        mol_type = protein
                        organism = synthetic construct
SEQUENCE: 228
CEHXRXACPP RDAYGRRRRR QRRRR                                             25

SEQ ID NO: 229          moltype = AA  length = 25
```

-continued

```
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..25
                        mol_type = protein
                        organism = synthetic construct
SEQUENCE: 229
CEHXRXACPP KDAYGRRRRR RQRRR                                        25

SEQ ID NO: 230          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
MOD_RES                 13
                        note = bAla
source                  1..25
                        mol_type = protein
                        organism = synthetic construct
SEQUENCE: 230
CEHXRXACPP RDAYGRRRRR RQRRR                                        25

SEQ ID NO: 231          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..23
                        mol_type = protein
                        organism = synthetic construct
SEQUENCE: 231
CEHXRXACPP RDARRRRRRQ RRR                                          23

SEQ ID NO: 232          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
```

```
MOD_RES                 13
                        note = bAla
source                  1..23
                        mol_type = protein
                        organism = synthetic construct
SEQUENCE: 232
CEHXRXACPP KDARRRRRQR RRR                                          23

SEQ ID NO: 233          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..23
                        mol_type = protein
                        organism = synthetic construct
SEQUENCE: 233
CEHXRXACPP RDARRRRRQR RRR                                          23

SEQ ID NO: 234          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..24
                        mol_type = protein
                        organism = synthetic construct
SEQUENCE: 234
CEHXRXACPP KDAYGRRRRR QRRR                                         24

SEQ ID NO: 235          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..24
                        mol_type = protein
                        organism = synthetic construct
SEQUENCE: 235
CEHXRXACPP RDAYGRRRRR QRRR                                         24

SEQ ID NO: 236          moltype = AA  length = 25
FEATURE                 Location/Qualifiers
SITE                    25
                        note = C-terminal is: NH2
```

-continued

```
REGION                  1..25
                        note = Description of Sequence: MC4R agonist
SITE
                        note = N-terminal is: Acetylated
REGION                  1..8
                        note = Cyclic
MOD_RES                 4
                        note = D-2-Nal
MOD_RES                 6
                        note = P-(2-naphthyl)alanine
MOD_RES                 13
                        note = bAla
source                  1..25
                        mol_type = protein
                        organism = synthetic construct
SEQUENCE: 236
CEHXRXACPP KDAYGRRRRR RQRRR                                        25

SEQ ID NO: 237          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..25
                        mol_type = protein
                        organism = synthetic construct
SEQUENCE: 237
CEHXRXACPP RDAYGRRRRR RQRRR                                        25

SEQ ID NO: 238          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
source                  1..25
                        mol_type = protein
                        organism = synthetic construct
SEQUENCE: 238
CEHXRXACPP KDAYGRRRRR QRRRR                                        25

SEQ ID NO: 239          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 13
                        note = bAla
```

```
source                  1..25
                        mol_type = protein
                        organism = synthetic construct
SEQUENCE: 239
CEHXRXACPP RDAYGRRRRR QRRRR                                          25

SEQ ID NO: 240          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..23
                        mol_type = protein
                        organism = synthetic construct
SEQUENCE: 240
CEHXRXACPP KDARRRRRQR RRR                                            23

SEQ ID NO: 241          moltype = AA  length = 23
FEATURE                 Location/Qualifiers
SITE                    23
                        note = C-terminal is: NH2
REGION                  1..23
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..23
                        mol_type = protein
                        organism = synthetic construct
SEQUENCE: 241
CEHXRXACPP RDARRRRRQR RRR                                            23

SEQ ID NO: 242          moltype = AA  length = 24
FEATURE                 Location/Qualifiers
SITE                    24
                        note = C-terminal is: NH2
REGION                  1..24
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..24
                        mol_type = protein
                        organism = synthetic construct
SEQUENCE: 242
CEHXRXACPP RDAYGRRRRR QRRR                                           24

SEQ ID NO: 243          moltype = AA  length = 25
FEATURE                 Location/Qualifiers
SITE                    25
                        note = C-terminal is: NH2
REGION                  1..25
                        note = Description of Sequence: MC4R agonist
```

```
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..25
                        mol_type = protein
                        organism = synthetic construct
SEQUENCE: 243
CEHXRXACPP KDAYGRRRRR QRRRR                                          25

SEQ ID NO: 244          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..25
                        mol_type = protein
                        organism = synthetic construct
SEQUENCE: 244
CEHXRXACPP RDAYGRRRRR QRRRR                                          25

SEQ ID NO: 245          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..25
                        mol_type = protein
                        organism = synthetic construct
SEQUENCE: 245
CEHXRXACPP KDAYGRRRRR RQRRR                                          25

SEQ ID NO: 246          moltype = AA  length = 25
FEATURE                 Location/Qualifiers
SITE                    25
                        note = C-terminal is: NH2
REGION                  1..25
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
MOD_RES                 13
                        note = bAla
source                  1..25
                        mol_type = protein
                        organism = synthetic construct
```

```
SEQUENCE: 246
CEHXRXACPP RDAYGRRRRR RQRRR                                         25

SEQ ID NO: 247          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = 8-amino-3,6-dioxaoctanoic acid
source                  1..21
                        mol_type = protein
                        organism = synthetic construct
SEQUENCE: 247
XCAHFRWCXX YGRKKRRQRR R                                             21

SEQ ID NO: 248          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
MOD_RES                 5
                        note = D-Phenylalanine
MOD_RES                 9
                        note = bAla
source                  1..20
                        mol_type = protein
                        organism = synthetic construct
SEQUENCE: 248
XCAHFRWCAY GRKKRQRRRR                                               20

SEQ ID NO: 249          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = 8-amino-3,6-dioxaoctanoic acid
source                  1..20
                        mol_type = protein
                        organism = synthetic construct
SEQUENCE: 249
XCAHFRWCXY GRKKRRQRRR                                               20

SEQ ID NO: 250          moltype = AA  length = 18
FEATURE                 Location/Qualifiers
SITE                    18
                        note = C-terminal is: NH2
```

-continued

```
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = bAla
source                  1..18
                        mol_type = protein
                        organism = synthetic construct
SEQUENCE: 250
XCAHFRWCAR RRRRQRRR                                                18

SEQ ID NO: 251          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = bAla
source                  1..19
                        mol_type = protein
                        organism = synthetic construct
SEQUENCE: 251
XCAHFRWCAG RRRRRQRRR                                               19

SEQ ID NO: 252          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = bAla
source                  1..20
                        mol_type = protein
                        organism = synthetic construct
SEQUENCE: 252
XCAHFRWCAY GRRRRRQRRR                                              20

SEQ ID NO: 253          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
```

-continued

```
REGION                  2..8
                        note = Cyclic
SITE                    3
                        note = D-Alanine
SITE                    5
                        note = D-Phenylalanine
MOD_RES                 9
                        note = bAla
source                  1..20
                        mol_type = protein
                        organism = synthetic construct
SEQUENCE: 253
XCAHFRWCAG RRRRRQRRRR                                              20

SEQ ID NO: 254          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = bAla
source                  1..20
                        mol_type = protein
                        organism = synthetic construct
SEQUENCE: 254
XCAHFRWCAY GRRKRRQRRR                                              20

SEQ ID NO: 255          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = bAla
source                  1..20
                        mol_type = protein
                        organism = synthetic construct
SEQUENCE: 255
XCAHFRWCAY GRKRRRQRRR                                              20

SEQ ID NO: 256          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
```

-continued

```
MOD_RES                9
                       note = bAla
source                 1..19
                       mol_type = protein
                       organism = synthetic construct
SEQUENCE: 256
XCAHFRWCAG RRKRRQRRR                                        19

SEQ ID NO: 257         moltype = AA  length = 19
FEATURE                Location/Qualifiers
SITE                   19
                       note = C-terminal is: NH2
REGION                 1..19
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Alanine
SITE                   5
                       note = D-Phenylalanine
MOD_RES                9
                       note = bAla
source                 1..19
                       mol_type = protein
                       organism = synthetic construct
SEQUENCE: 257
XCAHFRWCAG RKRRRQRRR                                        19

SEQ ID NO: 258         moltype = AA  length = 18
FEATURE                Location/Qualifiers
SITE                   18
                       note = C-terminal is: NH2
REGION                 1..18
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Alanine
SITE                   5
                       note = D-Phenylalanine
MOD_RES                9
                       note = bAla
source                 1..18
                       mol_type = protein
                       organism = synthetic construct
SEQUENCE: 258
XCAHFRWCAR RKRRQRRR                                         18

SEQ ID NO: 259         moltype = AA  length = 18
FEATURE                Location/Qualifiers
SITE                   18
                       note = C-terminal is: NH2
REGION                 1..18
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Alanine
SITE                   5
                       note = D-Phenylalanine
MOD_RES                9
                       note = bAla
source                 1..18
                       mol_type = protein
                       organism = synthetic construct
SEQUENCE: 259
XCAHFRWCAR KRRRQRRR                                         18
```

```
SEQ ID NO: 260          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = bAla
source                  1..19
                        mol_type = protein
                        organism = synthetic construct
SEQUENCE: 260
XCAHFRWCAA RRRRRQRRR                                              19

SEQ ID NO: 261          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = bAla
source                  1..20
                        mol_type = protein
                        organism = synthetic construct
SEQUENCE: 261
XCAHFRWCAA GRRRRRQRRR                                             20

SEQ ID NO: 262          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = bAla
source                  1..21
                        mol_type = protein
                        organism = synthetic construct
SEQUENCE: 262
XCAHFRWCAA YGRRRRRQRR R                                           21

SEQ ID NO: 263          moltype = AA  length = 18
FEATURE                 Location/Qualifiers
SITE                    18
                        note = C-terminal is: NH2
```

-continued

```
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = 8-amino-3,6-dioxaoctanoic acid
source                  1..18
                        mol_type = protein
                        organism = synthetic construct
SEQUENCE: 263
XCAHFRWCXR RRRRQRRR                                                18

SEQ ID NO: 264          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = 8-amino-3,6-dioxaoctanoic acid
source                  1..19
                        mol_type = protein
                        organism = synthetic construct
SEQUENCE: 264
XCAHFRWCXG RRRRRQRRR                                               19

SEQ ID NO: 265          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = 8-amino-3,6-dioxaoctanoic acid
source                  1..20
                        mol_type = protein
                        organism = synthetic construct
SEQUENCE: 265
XCAHFRWCXY GRRRRRQRRR                                              20

SEQ ID NO: 266          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
```

```
REGION                2..8
                      note = Cyclic
SITE                  3
                      note = D-Alanine
SITE                  5
                      note = D-Phenylalanine
MOD_RES               9..10
                      note = 8-amino-3,6-dioxaoctanoic acid
source                1..19
                      mol_type = protein
                      organism = synthetic construct
SEQUENCE: 266
XCAHFRWCXX RRRRRQRRR                                              19

SEQ ID NO: 267        moltype = AA  length = 20
FEATURE               Location/Qualifiers
SITE                  20
                      note = C-terminal is: NH2
REGION                1..20
                      note = Description of Sequence: MC4R agonist
SITE
                      note = N-terminal is: Acetylated
SITE                  1
                      note = Nle
REGION                2..8
                      note = Cyclic
SITE                  3
                      note = D-Alanine
SITE                  5
                      note = D-Phenylalanine
MOD_RES               9..10
                      note = 8-amino-3,6-dioxaoctanoic acid
source                1..20
                      mol_type = protein
                      organism = synthetic construct
SEQUENCE: 267
XCAHFRWCXX GRRRRRQRRR                                             20

SEQ ID NO: 268        moltype = AA  length = 21
FEATURE               Location/Qualifiers
SITE                  21
                      note = C-terminal is: NH2
REGION                1..21
                      note = Description of Sequence: MC4R agonist
SITE
                      note = N-terminal is: Acetylated
SITE                  1
                      note = Nle
REGION                2..8
                      note = Cyclic
SITE                  3
                      note = D-Alanine
SITE                  5
                      note = D-Phenylalanine
MOD_RES               9..10
                      note = 8-amino-3,6-dioxaoctanoic acid
source                1..21
                      mol_type = protein
                      organism = synthetic construct
SEQUENCE: 268
XCAHFRWCXX YGRRRRRQRR R                                           21

SEQ ID NO: 269        moltype = AA  length = 19
FEATURE               Location/Qualifiers
SITE                  19
                      note = C-terminal is: NH2
REGION                1..19
                      note = Description of Sequence: MC4R agonist
SITE
                      note = N-terminal is: Acetylated
SITE                  1
                      note = Nle
REGION                2..8
                      note = Cyclic
SITE                  3
                      note = D-Alanine
SITE                  5
                      note = D-Phenylalanine
```

```
MOD_RES                 9
                        note = bAla
source                  1..19
                        mol_type = protein
                        organism = synthetic construct
SEQUENCE: 269
XCAHFRWCAR RRRRQRRRR                                          19

SEQ ID NO: 270          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = bAla
source                  1..21
                        mol_type = protein
                        organism = synthetic construct
SEQUENCE: 270
XCAHFRWCAY GRRRRRQRRR R                                       21

SEQ ID NO: 271          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = bAla
source                  1..20
                        mol_type = protein
                        organism = synthetic construct
SEQUENCE: 271
XCAHFRWCAA RRRRRQRRRR                                         20

SEQ ID NO: 272          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = bAla
source                  1..21
                        mol_type = protein
                        organism = synthetic construct
SEQUENCE: 272
XCAHFRWCAA GRRRRRQRRR R                                       21
```

```
SEQ ID NO: 273          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = bAla
source                  1..22
                        mol_type = protein
                        organism = synthetic construct
SEQUENCE: 273
XCAHFRWCAA YGRRRRRQRR RR                                            22

SEQ ID NO: 274          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = 8-amino-3,6-dioxaoctanoic acid
source                  1..19
                        mol_type = protein
                        organism = synthetic construct
SEQUENCE: 274
XCAHFRWCXR RRRRQRRRR                                                19

SEQ ID NO: 275          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = 8-amino-3,6-dioxaoctanoic acid
source                  1..20
                        mol_type = protein
                        organism = synthetic construct
SEQUENCE: 275
XCAHFRWCXG RRRRRQRRRR                                               20

SEQ ID NO: 276          moltype = AA  length = 21
FEATURE                 Location/Qualifiers
SITE                    21
                        note = C-terminal is: NH2
```

```
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9
                        note = 8-amino-3,6-dioxaoctanoic acid
source                  1..21
                        mol_type = protein
                        organism = synthetic construct
SEQUENCE: 276
XCAHFRWCXY GRRRRRQRRR R                                             21

SEQ ID NO: 277          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = 8-amino-3,6-dioxaoctanoic acid
source                  1..20
                        mol_type = protein
                        organism = synthetic construct
SEQUENCE: 277
XCAHFRWCXX RRRRRQRRRR                                               20

SEQ ID NO: 278          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 9..10
                        note = 8-amino-3,6-dioxaoctanoic acid
source                  1..21
                        mol_type = protein
                        organism = synthetic construct
SEQUENCE: 278
XCAHFRWCXX GRRRRRQRRR R                                             21

SEQ ID NO: 279          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
SITE                    1
                        note = Nle
```

-continued

```
REGION                  2..8
                        note = Cyclic
SITE                    3
                        note = D-Alanine
SITE                    5
                        note = D-Phenylalanine
MOD_RES                 9..10
                        note = 8-amino-3,6-dioxaoctanoic acid
source                  1..22
                        mol_type = protein
                        organism = synthetic construct
SEQUENCE: 279
XCAHFRWCXX YGRRRRRQRR RR                                                22

SEQ ID NO: 280          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 4abu
MOD_RES                 9
                        note = bAla
source                  1..20
                        mol_type = protein
                        organism = synthetic construct
SEQUENCE: 280
XCHFRWXCAY GRRRRRQRRR                                                   20

SEQ ID NO: 281          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 4abu
MOD_RES                 9
                        note = bAla
source                  1..18
                        mol_type = protein
                        organism = synthetic construct
SEQUENCE: 281
XCHFRWXCAR RRRRQRRR                                                     18

SEQ ID NO: 282          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 9
                        note = bAla
```

```
source                  1..20
                        mol_type = protein
                        organism = synthetic construct
SEQUENCE: 282
XDHFRWAKAY GRRRRRQRRR                                               20

SEQ ID NO: 283          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 9
                        note = bAla
source                  1..18
                        mol_type = protein
                        organism = synthetic construct
SEQUENCE: 283
XDHFRWAKAR RRRRQRRR                                                 18

SEQ ID NO: 284          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8
                        note = bAla
source                  1..19
                        mol_type = protein
                        organism = synthetic construct
SEQUENCE: 284
XDHFRWKAYG RRRRRQRRR                                                19

SEQ ID NO: 285          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8
                        note = bAla
source                  1..18
                        mol_type = protein
                        organism = synthetic construct
SEQUENCE: 285
XDHFRWKAGR RRRRQRRR                                                 18

SEQ ID NO: 286          moltype = AA  length = 17
FEATURE                 Location/Qualifiers
SITE                    17
                        note = C-terminal is: NH2
REGION                  1..17
                        note = Description of Sequence: MC4R agonist
```

```
SITE
                       note = N-terminal is: Acetylated
SITE                   1
                       note = Nle
REGION                 2..7
                       note = Cyclic
SITE                   4
                       note = D-Phenylalanine
MOD_RES                8
                       note = bAla
source                 1..17
                       mol_type = protein
                       organism = synthetic construct
SEQUENCE: 286
XDHFRWKARR RRRQRRR                                              17

SEQ ID NO: 287         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
REGION                 2..7
                       note = Cyclic
SITE                   4
                       note = D-Phenylalanine
MOD_RES                8..9
                       note = bAla
source                 1..20
                       mol_type = protein
                       organism = synthetic construct
SEQUENCE: 287
XDHFRWKAAY GRRRRRQRRR                                           20

SEQ ID NO: 288         moltype = AA  length = 19
FEATURE                Location/Qualifiers
SITE                   19
                       note = C-terminal is: NH2
REGION                 1..19
                       note = Description of Sequence: MC4R agonist
SITE
                       note = N-terminal is: Acetylated
SITE                   1
                       note = Nle
REGION                 2..7
                       note = Cyclic
SITE                   4
                       note = D-Phenylalanine
MOD_RES                8..9
                       note = bAla
source                 1..19
                       mol_type = protein
                       organism = synthetic construct
SEQUENCE: 288
XDHFRWKAAG RRRRRQRRR                                            19

SEQ ID NO: 289         moltype = AA  length = 18
FEATURE                Location/Qualifiers
SITE                   18
                       note = C-terminal is: NH2
REGION                 1..18
                       note = Description of Sequence: MC4R agonist
SITE
                       note = N-terminal is: Acetylated
SITE                   1
                       note = Nle
REGION                 2..7
                       note = Cyclic
SITE                   4
                       note = D-Phenylalanine
MOD_RES                8..9
                       note = bAla
source                 1..18
                       mol_type = protein
                       organism = synthetic construct
```

```
SEQUENCE: 289
XDHFRWKAAR RRRRQRRR                                              18

SEQ ID NO: 290          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8
                        note = 8-amino-3,6-dioxaoctanoic acid
source                  1..19
                        mol_type = protein
                        organism = synthetic construct
SEQUENCE: 290
XDHFRWKXYG RRRRRQRRR                                             19

SEQ ID NO: 291          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8
                        note = 8-amino-3,6-dioxaoctanoic acid
source                  1..18
                        mol_type = protein
                        organism = synthetic construct
SEQUENCE: 291
XDHFRWKXGR RRRRQRRR                                              18

SEQ ID NO: 292          moltype = AA  length = 17
FEATURE                 Location/Qualifiers
SITE                    17
                        note = C-terminal is: NH2
REGION                  1..17
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8
                        note = 8-amino-3,6-dioxaoctanoic acid
source                  1..17
                        mol_type = protein
                        organism = synthetic construct
SEQUENCE: 292
XDHFRWKXRR RRRQRRR                                               17

SEQ ID NO: 293          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
```

-continued

```
REGION                  2..7
                        note = Cyclic
SITE                    4
                        note = D-Phenylalanine
MOD_RES                 8..9
                        note = 8-amino-3,6-dioxaoctanoic acid
source                  1..20
                        mol_type = protein
                        organism = synthetic construct
SEQUENCE: 293
XDHFRWKXXY GRRRRRQRRR                                             20

SEQ ID NO: 294          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8..9
                        note = 8-amino-3,6-dioxaoctanoic acid
source                  1..19
                        mol_type = protein
                        organism = synthetic construct
SEQUENCE: 294
XDHFRWKXXG RRRRRQRRR                                              19

SEQ ID NO: 295          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8..9
                        note = 8-amino-3,6-dioxaoctanoic acid
source                  1..18
                        mol_type = protein
                        organism = synthetic construct
SEQUENCE: 295
XDHFRWKXXR RRRRQRRR                                               18

SEQ ID NO: 296          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8
                        note = bAla
source                  1..20
                        mol_type = protein
                        organism = synthetic construct
SEQUENCE: 296
XDHFRWKAYG RRRRRQRRRR                                             20

SEQ ID NO: 297          moltype = AA  length = 19
```

-continued

```
FEATURE                Location/Qualifiers
SITE                   19
                       note = C-terminal is: NH2
REGION                 1..19
                       note = Description of Sequence: MC4R agonist
SITE
                       note = N-terminal is: Acetylated
SITE                   1
                       note = Nle
REGION                 2..7
                       note = Cyclic
SITE                   4
                       note = D-Phenylalanine
MOD_RES                8
                       note = bAla
source                 1..19
                       mol_type = protein
                       organism = synthetic construct
SEQUENCE: 297
XDHFRWKAGR RRRRQRRRR                                            19

SEQ ID NO: 298         moltype = AA  length = 18
FEATURE                Location/Qualifiers
SITE                   18
                       note = C-terminal is: NH2
REGION                 1..18
                       note = Description of Sequence: MC4R agonist
SITE
                       note = N-terminal is: Acetylated
SITE                   1
                       note = Nle
REGION                 2..7
                       note = Cyclic
SITE                   4
                       note = D-Phenylalanine
MOD_RES                8
                       note = bAla
source                 1..18
                       mol_type = protein
                       organism = synthetic construct
SEQUENCE: 298
XDHFRWKARR RRRQRRRR                                             18

SEQ ID NO: 299         moltype = AA  length = 21
FEATURE                Location/Qualifiers
SITE                   21
                       note = C-terminal is: NH2
REGION                 1..21
                       note = Description of Sequence: MC4R agonist
SITE
                       note = N-terminal is: Acetylated
SITE                   1
                       note = Nle
REGION                 2..7
                       note = Cyclic
SITE                   4
                       note = D-Phenylalanine
MOD_RES                8..9
                       note = bAla
source                 1..21
                       mol_type = protein
                       organism = synthetic construct
SEQUENCE: 299
XDHFRWKAAY GRRRRRQRRR R                                         21

SEQ ID NO: 300         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
REGION                 2..7
                       note = Cyclic
SITE                   4
                       note = D-Phenylalanine
```

-continued

```
MOD_RES                 8..9
                        note = bAla
source                  1..20
                        mol_type = protein
                        organism = synthetic construct
SEQUENCE: 300
XDHFRWKAAG RRRRRQRRRR                                              20

SEQ ID NO: 301          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8..9
                        note = bAla
source                  1..19
                        mol_type = protein
                        organism = synthetic construct
SEQUENCE: 301
XDHFRWKAAR RRRRQRRRR                                               19

SEQ ID NO: 302          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8
                        note = 8-amino-3,6-dioxaoctanoic acid
source                  1..20
                        mol_type = protein
                        organism = synthetic construct
SEQUENCE: 302
XDHFRWKXYG RRRRRQRRRR                                              20

SEQ ID NO: 303          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..7
                        note = Cyclic
SITE                    4
                        note = D-Phenylalanine
MOD_RES                 8
                        note = 8-amino-3,6-dioxaoctanoic acid
source                  1..19
                        mol_type = protein
                        organism = synthetic construct
SEQUENCE: 303
XDHFRWKXGR RRRRQRRRR                                               19

SEQ ID NO: 304          moltype = AA  length = 18
FEATURE                 Location/Qualifiers
SITE                    18
                        note = C-terminal is: NH2
```

```
REGION                1..18
                      note = Description of Sequence: MC4R agonist
SITE
                      note = N-terminal is: Acetylated
SITE                  1
                      note = Nle
REGION                2..7
                      note = Cyclic
SITE                  4
                      note = D-Phenylalanine
MOD_RES               8
                      note = 8-amino-3,6-dioxaoctanoic acid
source                1..18
                      mol_type = protein
                      organism = synthetic construct
SEQUENCE: 304
XDHFRWKXRR RRRQRRRR                                          18

SEQ ID NO: 305        moltype = AA  length = 21
FEATURE               Location/Qualifiers
SITE                  21
                      note = C-terminal is: NH2
REGION                1..21
                      note = Description of Sequence: MC4R agonist
SITE
                      note = N-terminal is: Acetylated
SITE                  1
                      note = Nle
REGION                2..7
                      note = Cyclic
SITE                  4
                      note = D-Phenylalanine
MOD_RES               8..9
                      note = 8-amino-3,6-dioxaoctanoic acid
source                1..21
                      mol_type = protein
                      organism = synthetic construct
SEQUENCE: 305
XDHFRWKXXY GRRRRRQRRR R                                      21

SEQ ID NO: 306        moltype = AA  length = 20
FEATURE               Location/Qualifiers
SITE                  20
                      note = C-terminal is: NH2
REGION                1..20
                      note = Description of Sequence: MC4R agonist
SITE
                      note = N-terminal is: Acetylated
SITE                  1
                      note = Nle
REGION                2..7
                      note = Cyclic
SITE                  4
                      note = D-Phenylalanine
MOD_RES               8..9
                      note = 8-amino-3,6-dioxaoctanoic acid
source                1..20
                      mol_type = protein
                      organism = synthetic construct
SEQUENCE: 306
XDHFRWKXXG RRRRRQRRRR                                        20

SEQ ID NO: 307        moltype = AA  length = 19
FEATURE               Location/Qualifiers
SITE                  19
                      note = C-terminal is: NH2
REGION                1..19
                      note = Description of Sequence: MC4R agonist
SITE
                      note = N-terminal is: Acetylated
SITE                  1
                      note = Nle
REGION                2..7
                      note = Cyclic
SITE                  4
                      note = D-Phenylalanine
MOD_RES               8..9
                      note = 8-amino-3,6-dioxaoctanoic acid
```

```
source                  1..19
                        mol_type = protein
                        organism = synthetic construct
SEQUENCE: 307
XDHFRWKXXR RRRRQRRRR                                                19

SEQ ID NO: 308          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = bAla
MOD_RES                 9
                        note = bAla
source                  1..20
                        mol_type = protein
                        organism = synthetic construct
SEQUENCE: 308
XDHFRWAKAY GRRRRRQRRR                                               20

SEQ ID NO: 309          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = bAla
MOD_RES                 9
                        note = bAla
source                  1..18
                        mol_type = protein
                        organism = synthetic construct
SEQUENCE: 309
XDHFRWAKAR RRRRQRRR                                                 18

SEQ ID NO: 310          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 6-aminohexanoic acid
MOD_RES                 9
                        note = bAla
source                  1..20
                        mol_type = protein
                        organism = synthetic construct
SEQUENCE: 310
XCHFRWXCAY GRRRRRQRRR                                               20

SEQ ID NO: 311          moltype = AA  length = 18
```

-continued

```
FEATURE                Location/Qualifiers
SITE                   18
                       note = C-terminal is: NH2
REGION                 1..18
                       note = Description of Sequence: MC4R agonist
SITE
                       note = N-terminal is: Acetylated
SITE                   1
                       note = Nle
REGION                 2..8
                       note = Cyclic
SITE                   4
                       note = D-Phenylalanine
MOD_RES                7
                       note = 6-aminohexanoic acid
MOD_RES                9
                       note = bAla
source                 1..18
                       mol_type = protein
                       organism = synthetic construct
SEQUENCE: 311
XCHFRWXCAR RRRRQRRR                                                18

SEQ ID NO: 312         moltype = AA  length = 21
FEATURE                Location/Qualifiers
SITE                   21
                       note = C-terminal is: NH2
REGION                 1..21
                       note = Description of Sequence: MC4R agonist
SITE                   1
                       note = D-Phenylalanine
REGION                 2..8
                       note = Cyclic
SITE                   4
                       note = D-Phenylalanine
MOD_RES                7
                       note = bAla
SITE                   8
                       note = D-Cystine
MOD_RES                10
                       note = bAla
source                 1..21
                       mol_type = protein
                       organism = synthetic construct
SEQUENCE: 312
FCHFRWACTA YGRRRRRQRR R                                            21

SEQ ID NO: 313         moltype = AA  length = 19
FEATURE                Location/Qualifiers
SITE                   19
                       note = C-terminal is: NH2
REGION                 1..19
                       note = Description of Sequence: MC4R agonist
SITE                   1
                       note = D-Phenylalanine
REGION                 2..8
                       note = Cyclic
SITE                   4
                       note = D-Phenylalanine
MOD_RES                7
                       note = bAla
SITE                   8
                       note = D-Cystine
MOD_RES                10
                       note = bAla
source                 1..19
                       mol_type = protein
                       organism = synthetic construct
SEQUENCE: 313
FCHFRWACTA RRRRRQRRR                                               19

SEQ ID NO: 314         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
```

```
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9
                        note = bAla
source                  1..20
                        mol_type = protein
                        organism = synthetic construct
SEQUENCE: 314
XCHFRWXCAY GRRRRRQRRR                                                20

SEQ ID NO: 315          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9
                        note = bAla
source                  1..18
                        mol_type = protein
                        organism = synthetic construct
SEQUENCE: 315
XCHFRWXCAR RRRRQRRR                                                  18

SEQ ID NO: 316          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
MOD_RES                 1
                        note = Beta-cyclohexylalanine
REGION                  2..8
                        note = Cyclic
SITE                    4
                        note = D-Phenylalanine
MOD_RES                 7
                        note = 4abu
MOD_RES                 9
                        note = bAla
source                  1..20
                        mol_type = protein
                        organism = synthetic construct
SEQUENCE: 316
XDHFRWXKAY GRRRRRQRRR                                                20

SEQ ID NO: 317          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
MOD_RES                 1
                        note = Beta-cyclohexylalanine
REGION                  2..8
                        note = Cyclic
SITE                    4
                        note = D-Phenylalanine
```

-continued

```
MOD_RES                 7
                        note = 4abu
MOD_RES                 9
                        note = bAla
source                  1..18
                        mol_type = protein
                        organism = synthetic construct
SEQUENCE: 317
XDHFRWXKAR RRRRQRRR                                                18

SEQ ID NO: 318          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 4abu
MOD_RES                 9
                        note = bAla
source                  1..20
                        mol_type = protein
                        organism = synthetic construct
SEQUENCE: 318
XDHFRWXKAY GRRRRRQRRR                                              20

SEQ ID NO: 319          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
MOD_RES                 7
                        note = 4abu
MOD_RES                 9
                        note = bAla
source                  1..18
                        mol_type = protein
                        organism = synthetic construct
SEQUENCE: 319
XDHFRWXKAR RRRRQRRR                                                18

SEQ ID NO: 320          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
MOD_RES                 1
                        note = Cyclohexylglycine
REGION                  2..8
                        note = Cyclic
SITE                    4
                        note = D-Phenylalanine
MOD_RES                 7
                        note = 4abu
MOD_RES                 9
                        note = bAla
source                  1..20
                        mol_type = protein
                        organism = synthetic construct
```

```
SEQUENCE: 320
XDHFRWXKAY GRRRRRQRRR                                              20

SEQ ID NO: 321          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
MOD_RES                 1
                        note = Cyclohexylglycine
REGION                  2..8
                        note = Cyclic
SITE                    4
                        note = D-Phenylalanine
MOD_RES                 7
                        note = 4abu
MOD_RES                 9
                        note = bAla
source                  1..18
                        mol_type = protein
                        organism = synthetic construct
SEQUENCE: 321
XDHFRWXKAR RRRRQRRR                                                18

SEQ ID NO: 322          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9
                        note = bAla
source                  1..20
                        mol_type = protein
                        organism = synthetic construct
SEQUENCE: 322
XDHFRWXKAY GRRRRRQRRR                                              20

SEQ ID NO: 323          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9
                        note = bAla
source                  1..18
                        mol_type = protein
                        organism = synthetic construct
SEQUENCE: 323
XDHFRWXKAR RRRRQRRR                                                18

SEQ ID NO: 324          moltype = AA  length = 21
FEATURE                 Location/Qualifiers
SITE                    21
                        note = C-terminal is: NH2
```

-continued

```
REGION                  1..21
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9..10
                        note = bAla
source                  1..21
                        mol_type = protein
                        organism = synthetic construct
SEQUENCE: 324
XDHFRWXKAA YGRRRRRQRR R                                                21

SEQ ID NO: 325          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9..10
                        note = bAla
source                  1..19
                        mol_type = protein
                        organism = synthetic construct
SEQUENCE: 325
XDHFRWXKAA RRRRRQRRR                                                   19

SEQ ID NO: 326          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9
                        note = 8-amino-3,6-dioxaoctanoic acid
source                  1..20
                        mol_type = protein
                        organism = synthetic construct
SEQUENCE: 326
XDHFRWXKXY GRRRRRQRRR                                                  20

SEQ ID NO: 327          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
MOD_RES                 1
                        note = Homo-cyclohexylalanine
```

```
REGION                2..8
                      note = Cyclic
SITE                  4
                      note = D-Phenylalanine
MOD_RES               7
                      note = 4abu
MOD_RES               9
                      note = 8-amino-3,6-dioxaoctanoic acid
source                1..18
                      mol_type = protein
                      organism = synthetic construct
SEQUENCE: 327
XDHFRWXKXR RRRRQRRR                                                18

SEQ ID NO: 328        moltype = AA  length = 21
FEATURE               Location/Qualifiers
SITE                  21
                      note = C-terminal is: NH2
REGION                1..21
                      note = Description of Sequence: MC4R agonist
SITE
                      note = N-terminal is: Acetylated
MOD_RES               1
                      note = Homo-cyclohexylalanine
REGION                2..8
                      note = Cyclic
SITE                  4
                      note = D-Phenylalanine
MOD_RES               7
                      note = 4abu
MOD_RES               9..10
                      note = 8-amino-3,6-dioxaoctanoic acid
source                1..21
                      mol_type = protein
                      organism = synthetic construct
SEQUENCE: 328
XDHFRWXKXX YGRRRRRQRR R                                            21

SEQ ID NO: 329        moltype = AA  length = 19
FEATURE               Location/Qualifiers
SITE                  19
                      note = C-terminal is: NH2
REGION                1..19
                      note = Description of Sequence: MC4R agonist
SITE
                      note = N-terminal is: Acetylated
MOD_RES               1
                      note = Homo-cyclohexylalanine
REGION                2..8
                      note = Cyclic
SITE                  4
                      note = D-Phenylalanine
MOD_RES               7
                      note = 4abu
MOD_RES               9..10
                      note = 8-amino-3,6-dioxaoctanoic acid
source                1..19
                      mol_type = protein
                      organism = synthetic construct
SEQUENCE: 329
XDHFRWXKXX RRRRRQRRR                                               19

SEQ ID NO: 330        moltype = AA  length = 21
FEATURE               Location/Qualifiers
SITE                  21
                      note = C-terminal is: NH2
REGION                1..21
                      note = Description of Sequence: MC4R agonist
SITE
                      note = N-terminal is: Acetylated
MOD_RES               1
                      note = Homo-cyclohexylalanine
REGION                2..8
                      note = Cyclic
SITE                  4
                      note = D-Phenylalanine
MOD_RES               7
                      note = 4abu
```

```
MOD_RES                 9
                        note = bAla
source                  1..21
                        mol_type = protein
                        organism = synthetic construct
SEQUENCE: 330
XDHFRWXKAY GRRRRRQRRR R                                     21

SEQ ID NO: 331          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9
                        note = bAla
source                  1..19
                        mol_type = protein
                        organism = synthetic construct
SEQUENCE: 331
XDHFRWXKAR RRRRQRRRR                                        19

SEQ ID NO: 332          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9..10
                        note = bAla
source                  1..22
                        mol_type = protein
                        organism = synthetic construct
SEQUENCE: 332
XDHFRWXKAA YGRRRRRQRR RR                                    22

SEQ ID NO: 333          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9..10
                        note = bAla
source                  1..20
                        mol_type = protein
                        organism = synthetic construct
SEQUENCE: 333
XDHFRWXKAA RRRRRQRRRR                                       20
```

```
SEQ ID NO: 334          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9
                        note = 8-amino-3,6-dioxaoctanoic acid
source                  1..21
                        mol_type = protein
                        organism = synthetic construct
SEQUENCE: 334
XDHFRWXKXY GRRRRRQRRR R                                                21

SEQ ID NO: 335          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9
                        note = 8-amino-3,6-dioxaoctanoic acid
source                  1..19
                        mol_type = protein
                        organism = synthetic construct
SEQUENCE: 335
XDHFRWXKXR RRRRQRRRR                                                   19

SEQ ID NO: 336          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
MOD_RES                 1
                        note = Homo-cyclohexylalanine
REGION                  2..8
                        note = Cyclic
SITE                    4
                        note = D-Phenylalanine
MOD_RES                 7
                        note = 4abu
MOD_RES                 9..10
                        note = 8-amino-3,6-dioxaoctanoic acid
source                  1..22
                        mol_type = protein
                        organism = synthetic construct
SEQUENCE: 336
XDHFRWXKXX YGRRRRRQRR RR                                               22

SEQ ID NO: 337          moltype = AA  length = 20
FEATURE                 Location/Qualifiers
SITE                    20
                        note = C-terminal is: NH2
REGION                  1..20
                        note = Description of Sequence: MC4R agonist
```

-continued

```
SITE
                          note = N-terminal is: Acetylated
MOD_RES                   1
                          note = Homo-cyclohexylalanine
REGION                    2..8
                          note = Cyclic
SITE                      4
                          note = D-Phenylalanine
MOD_RES                   7
                          note = 4abu
MOD_RES                   9..10
                          note = 8-amino-3,6-dioxaoctanoic acid
source                    1..20
                          mol_type = protein
                          organism = synthetic construct
SEQUENCE: 337
XDHFRWXKXX RRRRRQRRRR                                        20

SEQ ID NO: 338            moltype = AA  length = 20
FEATURE                   Location/Qualifiers
SITE                      20
                          note = C-terminal is: NH2
REGION                    1..20
                          note = Description of Sequence: MC4R agonist
SITE
                          note = N-terminal is: Acetylated
SITE                      1
                          note = D-Chg
REGION                    2..8
                          note = Cyclic
SITE                      4
                          note = D-Phenylalanine
MOD_RES                   7
                          note = 4abu
MOD_RES                   9
                          note = bAla
source                    1..20
                          mol_type = protein
                          organism = synthetic construct
SEQUENCE: 338
XDHFRWXKAY GRRRRRQRRR                                        20

SEQ ID NO: 339            moltype = AA  length = 18
FEATURE                   Location/Qualifiers
SITE                      18
                          note = C-terminal is: NH2
REGION                    1..18
                          note = Description of Sequence: MC4R agonist
SITE
                          note = N-terminal is: Acetylated
SITE                      1
                          note = D-Chg
REGION                    2..8
                          note = Cyclic
SITE                      4
                          note = D-Phenylalanine
MOD_RES                   7
                          note = 4abu
MOD_RES                   9
                          note = bAla
source                    1..18
                          mol_type = protein
                          organism = synthetic construct
SEQUENCE: 339
XDHFRWXKAR RRRRQRRR                                          18

SEQ ID NO: 340            moltype = AA  length = 20
FEATURE                   Location/Qualifiers
SITE                      20
                          note = C-terminal is: NH2
REGION                    1..20
                          note = Description of Sequence: MC4R agonist
SITE
                          note = N-terminal is: Acetylated
SITE                      1
                          note = Homophenylalanine
REGION                    2..8
                          note = Cyclic
```

```
SITE                    4
                        note = D-Phenylalanine
MOD_RES                 7
                        note = 4abu
MOD_RES                 9
                        note = bAla
source                  1..20
                        mol_type = protein
                        organism = synthetic construct
SEQUENCE: 340
FDHFRWXKAY GRRRRRQRRR                                               20

SEQ ID NO: 341          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Homophenylalanine
REGION                  2..8
                        note = Cyclic
SITE                    4
                        note = D-Phenylalanine
MOD_RES                 7
                        note = 4abu
MOD_RES                 9
                        note = bAla
source                  1..18
                        mol_type = protein
                        organism = synthetic construct
SEQUENCE: 341
FDHFRWXKAR RRRRQRRR                                                 18

SEQ ID NO: 342          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = 5-aminopentanoic acid
MOD_RES                 9
                        note = bAla
source                  1..20
                        mol_type = protein
                        organism = synthetic construct
SEQUENCE: 342
XCHFRWXCAY GRRRRRQRRR                                               20

SEQ ID NO: 343          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
```

-continued

```
MOD_RES                7
                       note = 5-aminopentanoic acid
MOD_RES                9
                       note = bAla
source                 1..18
                       mol_type = protein
                       organism = synthetic construct
SEQUENCE: 343
XCHFRWXCAR RRRRQRRR                                                18

SEQ ID NO: 344         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
REGION                 2..8
                       note = Cyclic
SITE                   4
                       note = D-Phenylalanine
SITE                   6
                       note = D-Trp
MOD_RES                7
                       note = 6-aminohexanoic acid
MOD_RES                9
                       note = bAla
source                 1..20
                       mol_type = protein
                       organism = synthetic construct
SEQUENCE: 344
XCHFRWXCAY GRRRRRQRRR                                              20

SEQ ID NO: 345         moltype = AA  length = 18
FEATURE                Location/Qualifiers
SITE                   18
                       note = C-terminal is: NH2
REGION                 1..18
                       note = Description of Sequence: MC4R agonist
SITE
                       note = N-terminal is: Acetylated
SITE                   1
                       note = Nle
REGION                 2..8
                       note = Cyclic
SITE                   4
                       note = D-Phenylalanine
SITE                   6
                       note = D-Trp
MOD_RES                7
                       note = 6-aminohexanoic acid
MOD_RES                9
                       note = bAla
source                 1..18
                       mol_type = protein
                       organism = synthetic construct
SEQUENCE: 345
XCHFRWXCAR RRRRQRRR                                                18

SEQ ID NO: 346         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
REGION                 2..8
                       note = Cyclic
SITE                   4
                       note = D-Phenylalanine
SITE                   6
                       note = D-Trp
```

```
MOD_RES                 7
                        note = bAla
MOD_RES                 9
                        note = bAla
source                  1..20
                        mol_type = protein
                        organism = synthetic construct
SEQUENCE: 346
XCHFRWACAY GRRRRRQRRR                                              20

SEQ ID NO: 347          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    4
                        note = D-Phenylalanine
SITE                    6
                        note = D-Trp
MOD_RES                 7
                        note = bAla
MOD_RES                 9
                        note = bAla
source                  1..18
                        mol_type = protein
                        organism = synthetic construct
SEQUENCE: 347
XCHFRWACAR RRRRQRRR                                                18

SEQ ID NO: 348          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 8
                        note = Penicillamine
MOD_RES                 9
                        note = bAla
source                  1..20
                        mol_type = protein
                        organism = synthetic construct
SEQUENCE: 348
XCAHFRWXAY GRRRRRQRRR                                              20

SEQ ID NO: 349          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
```

```
MOD_RES                 8
                        note = Penicillamine
MOD_RES                 9
                        note = bAla
source                  1..19
                        mol_type = protein
                        organism = synthetic construct
SEQUENCE: 349
XCAHFRWXAG RRRRRQRRR                                               19

SEQ ID NO: 350          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 8
                        note = Penicillamine
MOD_RES                 9
                        note = bAla
source                  1..18
                        mol_type = protein
                        organism = synthetic construct
SEQUENCE: 350
XCAHFRWXAR RRRRQRRR                                                18

SEQ ID NO: 351          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 8
                        note = Penicillamine
MOD_RES                 9..10
                        note = bAla
source                  1..21
                        mol_type = protein
                        organism = synthetic construct
SEQUENCE: 351
XCAHFRWXAA YGRRRRRQRR R                                            21

SEQ ID NO: 352          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
```

```
MOD_RES                 8
                        note = Penicillamine
MOD_RES                 9..10
                        note = bAla
source                  1..20
                        mol_type = protein
                        organism = synthetic construct
SEQUENCE: 352
XCAHFRWXAA GRRRRRQRRR                                            20

SEQ ID NO: 353          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 8
                        note = Penicillamine
MOD_RES                 9..10
                        note = bAla
source                  1..19
                        mol_type = protein
                        organism = synthetic construct
SEQUENCE: 353
XCAHFRWXAA RRRRRQRRR                                             19

SEQ ID NO: 354          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 8
                        note = Penicillamine
MOD_RES                 9
                        note = 8-amino-3,6-dioxaoctanoic acid
source                  1..20
                        mol_type = protein
                        organism = synthetic construct
SEQUENCE: 354
XCAHFRWXXY GRRRRRQRRR                                            20

SEQ ID NO: 355          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
```

```
MOD_RES                 8
                        note = Penicillamine
MOD_RES                 9
                        note = 8-amino-3,6-dioxaoctanoic acid
source                  1..19
                        mol_type = protein
                        organism = synthetic construct
SEQUENCE: 355
XCAHFRWXXG RRRRRQRRR                                              19

SEQ ID NO: 356          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 8
                        note = Penicillamine
MOD_RES                 9
                        note = 8-amino-3,6-dioxaoctanoic acid
source                  1..18
                        mol_type = protein
                        organism = synthetic construct
SEQUENCE: 356
XCAHFRWXXR RRRRQRRR                                               18

SEQ ID NO: 357          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
MOD_RES                 8
                        note = Penicillamine
MOD_RES                 9..10
                        note = 8-amino-3,6-dioxaoctanoic acid
source                  1..21
                        mol_type = protein
                        organism = synthetic construct
SEQUENCE: 357
XCAHFRWXXX YGRRRRRQRR R                                           21

SEQ ID NO: 358          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Alanine
SITE                    5
                        note = D-Phenylalanine
```

-continued

```
MOD_RES              8
                     note = Penicillamine
MOD_RES              9..10
                     note = 8-amino-3,6-dioxaoctanoic acid
source               1..20
                     mol_type = protein
                     organism = synthetic construct
SEQUENCE: 358
XCAHFRWXXX GRRRRRQRRR                                        20

SEQ ID NO: 359       moltype = AA  length = 19
FEATURE              Location/Qualifiers
SITE                 19
                     note = C-terminal is: NH2
REGION               1..19
                     note = Description of Sequence: MC4R agonist
SITE
                     note = N-terminal is: Acetylated
SITE                 1
                     note = Nle
REGION               2..8
                     note = Cyclic
SITE                 3
                     note = D-Alanine
SITE                 5
                     note = D-Phenylalanine
MOD_RES              8
                     note = Penicillamine
MOD_RES              9..10
                     note = 8-amino-3,6-dioxaoctanoic acid
source               1..19
                     mol_type = protein
                     organism = synthetic construct
SEQUENCE: 359
XCAHFRWXXX RRRRRQRRR                                         19

SEQ ID NO: 360       moltype = AA  length = 20
FEATURE              Location/Qualifiers
SITE                 20
                     note = C-terminal is: NH2
REGION               1..20
                     note = Description of Sequence: MC4R agonist
SITE                 1
                     note = D-Phenylalanine
REGION               2..8
                     note = Cyclic
SITE                 4
                     note = D-(Et)Tyr
MOD_RES              7
                     note = bAla
SITE                 8
                     note = D-Cystine
MOD_RES              9
                     note = bAla
source               1..20
                     mol_type = protein
                     organism = synthetic construct
SEQUENCE: 360
FCHYRWACAY GRRRRRQRRR                                        20

SEQ ID NO: 361       moltype = AA  length = 18
FEATURE              Location/Qualifiers
SITE                 18
                     note = C-terminal is: NH2
REGION               1..18
                     note = Description of Sequence: MC4R agonist
SITE                 1
                     note = D-Phenylalanine
REGION               2..8
                     note = Cyclic
SITE                 4
                     note = D-(Et)Tyr
MOD_RES              7
                     note = bAla
SITE                 8
                     note = D-Cystine
MOD_RES              9
                     note = bAla
```

-continued

```
source                  1..18
                        mol_type = protein
                        organism = synthetic construct
SEQUENCE: 361
FCHYRWACAR RRRRQRRR                                                   18

SEQ ID NO: 362          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = D-Phenylalanine
REGION                  2..8
                        note = Cyclic
SITE                    4
                        note = D-(Et)Tyr
MOD_RES                 7
                        note = bAla
SITE                    8
                        note = D-Cystine
MOD_RES                 9
                        note = bAla
source                  1..19
                        mol_type = protein
                        organism = synthetic construct
SEQUENCE: 362
FCHYRWACAG RRRRRQRRR                                                  19

SEQ ID NO: 363          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = D-Phenylalanine
REGION                  2..8
                        note = Cyclic
SITE                    4
                        note = D-(Et)Tyr
MOD_RES                 7
                        note = bAla
SITE                    8
                        note = D-Cystine
MOD_RES                 9
                        note = bAla
source                  1..19
                        mol_type = protein
                        organism = synthetic construct
SEQUENCE: 363
FCHYRWACAR RRRRQRRRR                                                  19

SEQ ID NO: 364          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = D-Phenylalanine
REGION                  2..8
                        note = Cyclic
SITE                    4
                        note = D-(Et)Tyr
MOD_RES                 7
                        note = bAla
SITE                    8
                        note = D-Cystine
MOD_RES                 9..10
                        note = bAla
source                  1..21
                        mol_type = protein
                        organism = synthetic construct
SEQUENCE: 364
FCHYRWACAA YGRRRRRQRR R                                               21

SEQ ID NO: 365          moltype = AA  length = 19
```

-continued

```
FEATURE                Location/Qualifiers
SITE                   19
                       note = C-terminal is: NH2
REGION                 1..19
                       note = Description of Sequence: MC4R agonist
SITE                   1
                       note = D-Phenylalanine
REGION                 2..8
                       note = Cyclic
SITE                   4
                       note = D-(Et)Tyr
MOD_RES                7
                       note = bAla
SITE                   8
                       note = D-Cystine
MOD_RES                9..10
                       note = bAla
source                 1..19
                       mol_type = protein
                       organism = synthetic construct
SEQUENCE: 365
FCHYRWACAA RRRRRQRRR                                              19

SEQ ID NO: 366         moltype = AA  length = 20
FEATURE                Location/Qualifiers
SITE                   20
                       note = C-terminal is: NH2
REGION                 1..20
                       note = Description of Sequence: MC4R agonist
SITE                   1
                       note = D-Phenylalanine
REGION                 2..8
                       note = Cyclic
SITE                   4
                       note = D-(Et)Tyr
MOD_RES                7
                       note = bAla
SITE                   8
                       note = D-Cystine
MOD_RES                9..10
                       note = bAla
source                 1..20
                       mol_type = protein
                       organism = synthetic construct
SEQUENCE: 366
FCHYRWACAA GRRRRRQRRR                                             20

SEQ ID NO: 367         moltype = AA  length = 20
FEATURE                Location/Qualifiers
SITE                   20
                       note = C-terminal is: NH2
REGION                 1..20
                       note = Description of Sequence: MC4R agonist
SITE                   1
                       note = D-Phenylalanine
REGION                 2..8
                       note = Cyclic
SITE                   4
                       note = D-(Et)Tyr
MOD_RES                7
                       note = bAla
SITE                   8
                       note = D-Cystine
MOD_RES                9..10
                       note = bAla
source                 1..20
                       mol_type = protein
                       organism = synthetic construct
SEQUENCE: 367
FCHYRWACAA RRRRRQRRRR                                             20

SEQ ID NO: 368         moltype = AA  length = 20
FEATURE                Location/Qualifiers
SITE                   20
                       note = C-terminal is: NH2
REGION                 1..20
                       note = Description of Sequence: MC4R agonist
SITE                   1
                       note = D-Phenylalanine
```

```
REGION                 2..8
                       note = Cyclic
SITE                   4
                       note = D-(Et)Tyr
MOD_RES                7
                       note = bAla
SITE                   8
                       note = D-Cystine
MOD_RES                9
                       note = 8-amino-3,6-dioxaoctanoic acid
source                 1..20
                       mol_type = protein
                       organism = synthetic construct
SEQUENCE: 368
FCHYRWACXY GRRRRRQRRR                                               20

SEQ ID NO: 369         moltype = AA  length = 18
FEATURE                Location/Qualifiers
SITE                   18
                       note = C-terminal is: NH2
REGION                 1..18
                       note = Description of Sequence: MC4R agonist
SITE                   1
                       note = D-Phenylalanine
REGION                 2..8
                       note = Cyclic
SITE                   4
                       note = D-(Et)Tyr
MOD_RES                7
                       note = bAla
SITE                   8
                       note = D-Cystine
MOD_RES                9
                       note = 8-amino-3,6-dioxaoctanoic acid
source                 1..18
                       mol_type = protein
                       organism = synthetic construct
SEQUENCE: 369
FCHYRWACXR RRRRQRRR                                                 18

SEQ ID NO: 370         moltype = AA  length = 19
FEATURE                Location/Qualifiers
SITE                   19
                       note = C-terminal is: NH2
REGION                 1..19
                       note = Description of Sequence: MC4R agonist
SITE                   1
                       note = D-Phenylalanine
REGION                 2..8
                       note = Cyclic
SITE                   4
                       note = D-(Et)Tyr
MOD_RES                7
                       note = bAla
SITE                   8
                       note = D-Cystine
MOD_RES                9
                       note = 8-amino-3,6-dioxaoctanoic acid
source                 1..19
                       mol_type = protein
                       organism = synthetic construct
SEQUENCE: 370
FCHYRWACXG RRRRRQRRR                                                19

SEQ ID NO: 371         moltype = AA  length = 19
FEATURE                Location/Qualifiers
SITE                   19
                       note = C-terminal is: NH2
REGION                 1..19
                       note = Description of Sequence: MC4R agonist
SITE                   1
                       note = D-Phenylalanine
REGION                 2..8
                       note = Cyclic
SITE                   4
                       note = D-(Et)Tyr
MOD_RES                7
                       note = bAla
```

```
SITE                    8
                        note = D-Cystine
MOD_RES                 9
                        note = 8-amino-3,6-dioxaoctanoic acid
source                  1..19
                        mol_type = protein
                        organism = synthetic construct
SEQUENCE: 371
FCHYRWACXR RRRRQRRRR                                                19

SEQ ID NO: 372          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = D-Phenylalanine
REGION                  2..8
                        note = Cyclic
SITE                    4
                        note = D-(Et)Tyr
MOD_RES                 7
                        note = bAla
SITE                    8
                        note = D-Cystine
MOD_RES                 9..10
                        note = 8-amino-3,6-dioxaoctanoic acid
source                  1..21
                        mol_type = protein
                        organism = synthetic construct
SEQUENCE: 372
FCHYRWACXX YGRRRRRQRR R                                             21

SEQ ID NO: 373          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = D-Phenylalanine
REGION                  2..8
                        note = Cyclic
SITE                    4
                        note = D-(Et)Tyr
MOD_RES                 7
                        note = bAla
SITE                    8
                        note = D-Cystine
MOD_RES                 9..10
                        note = 8-amino-3,6-dioxaoctanoic acid
source                  1..19
                        mol_type = protein
                        organism = synthetic construct
SEQUENCE: 373
FCHYRWACXX RRRRRQRRR                                                19

SEQ ID NO: 374          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = D-Phenylalanine
REGION                  2..8
                        note = Cyclic
SITE                    4
                        note = D-(Et)Tyr
MOD_RES                 7
                        note = bAla
SITE                    8
                        note = D-Cystine
MOD_RES                 9..10
                        note = 8-amino-3,6-dioxaoctanoic acid
source                  1..20
                        mol_type = protein
                        organism = synthetic construct
```

```
SEQUENCE: 374
FCHYRWACXX GRRRRRQRRR                                          20

SEQ ID NO: 375         moltype = AA  length = 20
FEATURE                Location/Qualifiers
SITE                   20
                       note = C-terminal is: NH2
REGION                 1..20
                       note = Description of Sequence: MC4R agonist
SITE                   1
                       note = D-Phenylalanine
REGION                 2..8
                       note = Cyclic
SITE                   4
                       note = D-(Et)Tyr
MOD_RES                7
                       note = bAla
SITE                   8
                       note = D-Cystine
MOD_RES                9..10
                       note = 8-amino-3,6-dioxaoctanoic acid
source                 1..20
                       mol_type = protein
                       organism = synthetic construct
SEQUENCE: 375
FCHYRWACXX RRRRRQRRRR                                          20

SEQ ID NO: 376         moltype = AA  length = 21
FEATURE                Location/Qualifiers
SITE                   21
                       note = C-terminal is: NH2
REGION                 1..21
                       note = Description of Sequence: MC4R agonist
SITE                   1
                       note = D-Phenylalanine
REGION                 2..8
                       note = Cyclic
SITE                   4
                       note = D-(Et)Tyr
SITE                   5
                       note = Homoarginine
MOD_RES                7
                       note = bAla
SITE                   8
                       note = D-Cystine
MOD_RES                10
                       note = bAla
source                 1..21
                       mol_type = protein
                       organism = synthetic construct
SEQUENCE: 376
FCHYRWACTA YGRRRRRQRR R                                        21

SEQ ID NO: 377         moltype = AA  length = 19
FEATURE                Location/Qualifiers
SITE                   19
                       note = C-terminal is: NH2
REGION                 1..19
                       note = Description of Sequence: MC4R agonist
SITE                   1
                       note = D-Phenylalanine
REGION                 2..8
                       note = Cyclic
SITE                   4
                       note = D-(Et)Tyr
SITE                   5
                       note = Homoarginine
MOD_RES                7
                       note = bAla
SITE                   8
                       note = D-Cystine
MOD_RES                10
                       note = bAla
source                 1..19
                       mol_type = protein
                       organism = synthetic construct
SEQUENCE: 377
FCHYRWACTA RRRRRQRRR                                           19
```

-continued

```
SEQ ID NO: 378          moltype = AA  length = 22
FEATURE                 Location/Qualifiers
SITE                    22
                        note = C-terminal is: NH2
REGION                  1..22
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10..11
                        note = bAla
source                  1..22
                        mol_type = protein
                        organism = synthetic construct
SEQUENCE: 378
FCHYRWACTA AYGRRRRRQR RR                                              22

SEQ ID NO: 379          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10..11
                        note = bAla
source                  1..20
                        mol_type = protein
                        organism = synthetic construct
SEQUENCE: 379
FCHYRWACTA ARRRRRQRRR                                                 20

SEQ ID NO: 380          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10
                        note = 8-amino-3,6-dioxaoctanoic acid
source                  1..21
                        mol_type = protein
                        organism = synthetic construct
SEQUENCE: 380
FCHYRWACTX YGRRRRRQRR R                                               21

SEQ ID NO: 381          moltype = AA  length = 19
```

-continued

```
FEATURE              Location/Qualifiers
SITE                 19
                     note = C-terminal is: NH2
REGION               1..19
                     note = Description of Sequence: MC4R agonist
SITE                 1
                     note = D-Phenylalanine
REGION               2..8
                     note = Cyclic
SITE                 4
                     note = D-(Et)Tyr
SITE                 5
                     note = Homoarginine
MOD_RES              7
                     note = bAla
SITE                 8
                     note = D-Cystine
MOD_RES              10
                     note = 8-amino-3,6-dioxaoctanoic acid
source               1..19
                     mol_type = protein
                     organism = synthetic construct
SEQUENCE: 381
FCHYRWACTX RRRRRQRRR                                                19

SEQ ID NO: 382       moltype = AA  length = 22
FEATURE              Location/Qualifiers
SITE                 22
                     note = C-terminal is: NH2
REGION               1..22
                     note = Description of Sequence: MC4R agonist
SITE                 1
                     note = D-Phenylalanine
REGION               2..8
                     note = Cyclic
SITE                 4
                     note = D-(Et)Tyr
SITE                 5
                     note = Homoarginine
MOD_RES              7
                     note = bAla
SITE                 8
                     note = D-Cystine
MOD_RES              10..11
                     note = 8-amino-3,6-dioxaoctanoic acid
source               1..22
                     mol_type = protein
                     organism = synthetic construct
SEQUENCE: 382
FCHYRWACTX XYGRRRRRQR RR                                            22

SEQ ID NO: 383       moltype = AA  length = 22
FEATURE              Location/Qualifiers
SITE                 22
                     note = C-terminal is: NH2
REGION               1..22
                     note = Description of Sequence: MC4R agonist
SITE                 1
                     note = D-Phenylalanine
REGION               2..8
                     note = Cyclic
SITE                 4
                     note = D-(Et)Tyr
SITE                 5
                     note = Homoarginine
MOD_RES              7
                     note = bAla
SITE                 8
                     note = D-Cystine
MOD_RES              10
                     note = bAla
source               1..22
                     mol_type = protein
                     organism = synthetic construct
SEQUENCE: 383
FCHYRWACTA YGRRRRRQRR RR                                            22

SEQ ID NO: 384       moltype = AA  length = 20
FEATURE              Location/Qualifiers
```

```
SITE                    20
                        note = C-terminal is: NH2
REGION                  1..20
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10
                        note = bAla
source                  1..20
                        mol_type = protein
                        organism = synthetic construct
SEQUENCE: 384
FCHYRWACTA RRRRRQRRRR                                            20

SEQ ID NO: 385          moltype = AA  length = 23
FEATURE                 Location/Qualifiers
SITE                    23
                        note = C-terminal is: NH2
REGION                  1..23
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10..11
                        note = bAla
source                  1..23
                        mol_type = protein
                        organism = synthetic construct
SEQUENCE: 385
FCHYRWACTA AYGRRRRRQR RRR                                        23

SEQ ID NO: 386          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10..11
                        note = bAla
source                  1..21
                        mol_type = protein
                        organism = synthetic construct
SEQUENCE: 386
FCHYRWACTA ARRRRRQRRR R                                          21
```

```
SEQ ID NO: 387          moltype = AA  length = 22
FEATURE                 Location/Qualifiers
SITE                    22
                        note = C-terminal is: NH2
REGION                  1..22
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10
                        note = 8-amino-3,6-dioxaoctanoic acid
source                  1..22
                        mol_type = protein
                        organism = synthetic construct
SEQUENCE: 387
FCHYRWACTX YGRRRRRQRR RR                                            22

SEQ ID NO: 388          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10
                        note = 8-amino-3,6-dioxaoctanoic acid
source                  1..20
                        mol_type = protein
                        organism = synthetic construct
SEQUENCE: 388
FCHYRWACTX RRRRRQRRRR                                               20

SEQ ID NO: 389          moltype = AA  length = 23
FEATURE                 Location/Qualifiers
SITE                    23
                        note = C-terminal is: NH2
REGION                  1..23
                        note = Description of Sequence: MC4R agonist
SITE                    1
                        note = D-Phenylalanine
REGION                  2..8
                        note = Cyclic
MOD_RES                 4
                        note = D-(Et)Tyr
SITE                    5
                        note = Homoarginine
MOD_RES                 7
                        note = bAla
SITE                    8
                        note = D-Cystine
MOD_RES                 10..11
                        note = 8-amino-3,6-dioxaoctanoic acid
source                  1..23
                        mol_type = protein
                        organism = synthetic construct
SEQUENCE: 389
FCHYRWACTX XYGRRRRRQR RRR                                           23
```

-continued

```
SEQ ID NO: 390          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 7
                        note = bAla
SITE                    8
                        note = D-Cystine
MOD_RES                 10..11
                        note = 8-amino-3,6-dioxaoctanoic acid
source                  1..21
                        mol_type = protein
                        organism = synthetic construct
SEQUENCE: 390
FCHYRWACTX XRRRRRQRRR R                                             21

SEQ ID NO: 391          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 6
                        note = 4,4'-biphenylalanine
MOD_RES                 7
                        note = bAla
SITE                    8
                        note = D-Cystine
MOD_RES                 10
                        note = bAla
source                  1..21
                        mol_type = protein
                        organism = synthetic construct
SEQUENCE: 391
FCHYRXACTA YGRRRRRQRR R                                             21

SEQ ID NO: 392          moltype = AA  length = 22
FEATURE                 Location/Qualifiers
SITE                    22
                        note = C-terminal is: NH2
REGION                  1..22
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 6
                        note = 4,4'-biphenylalanine
MOD_RES                 7
                        note = bAla
SITE                    8
                        note = D-Cystine
MOD_RES                 10
                        note = bAla
source                  1..22
                        mol_type = protein
                        organism = synthetic construct
```

```
SEQUENCE: 392
FCHYRXACTA YGRRRRRQRR RR                                          22

SEQ ID NO: 393          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 6
                        note = 4,4'-biphenylalanine
MOD_RES                 7
                        note = bAla
SITE                    8
                        note = D-Cystine
MOD_RES                 10
                        note = bAla
source                  1..19
                        mol_type = protein
                        organism = synthetic construct
SEQUENCE: 393
FCHYRXACTA RRRRRQRRR                                              19

SEQ ID NO: 394          moltype = AA  length = 22
FEATURE                 Location/Qualifiers
SITE                    22
                        note = C-terminal is: NH2
REGION                  1..22
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 6
                        note = 4,4'-biphenylalanine
MOD_RES                 7
                        note = bAla
SITE                    8
                        note = D-Cystine
MOD_RES                 10..11
                        note = bAla
source                  1..22
                        mol_type = protein
                        organism = synthetic construct
SEQUENCE: 394
FCHYRXACTA AYGRRRRRQR RR                                          22

SEQ ID NO: 395          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 6
                        note = 4,4'-biphenylalanine
MOD_RES                 7
                        note = bAla
SITE                    8
                        note = D-Cystine
```

```
MOD_RES                 10..11
                        note = bAla
source                  1..20
                        mol_type = protein
                        organism = synthetic construct
SEQUENCE: 395
FCHYRXACTA ARRRRRQRRR                                              20

SEQ ID NO: 396          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 6
                        note = 4,4'-biphenylalanine
MOD_RES                 7
                        note = bAla
SITE                    8
                        note = D-Cystine
MOD_RES                 10
                        note = 8-amino-3,6-dioxaoctanoic acid
source                  1..21
                        mol_type = protein
                        organism = synthetic construct
SEQUENCE: 396
FCHYRXACTX YGRRRRRQRR R                                            21

SEQ ID NO: 397          moltype = AA  length = 22
FEATURE                 Location/Qualifiers
SITE                    22
                        note = C-terminal is: NH2
REGION                  1..22
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
MOD_RES                 6
                        note = 4,4'-biphenylalanine
MOD_RES                 7
                        note = bAla
SITE                    8
                        note = D-Cystine
MOD_RES                 10
                        note = 8-amino-3,6-dioxaoctanoic acid
source                  1..22
                        mol_type = protein
                        organism = synthetic construct
SEQUENCE: 397
FCHYRXACTX YGRRRRRQRR RR                                           22

SEQ ID NO: 398          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = D-Phenylalanine
REGION                  2..8
                        note = Cyclic
SITE                    4
                        note = D-(Et)Tyr
SITE                    5
                        note = Homoarginine
```

-continued

```
MOD_RES                6
                       note = 4,4'-biphenylalanine
MOD_RES                7
                       note = bAla
SITE                   8
                       note = D-Cystine
MOD_RES                10
                       note = 8-amino-3,6-dioxaoctanoic acid
source                 1..19
                       mol_type = protein
                       organism = synthetic construct
SEQUENCE: 398
FCHYRXACTX RRRRRQRRR                                              19

SEQ ID NO: 399         moltype = AA  length = 22
FEATURE                Location/Qualifiers
SITE                   22
                       note = C-terminal is: NH2
REGION                 1..22
                       note = Description of Sequence: MC4R agonist
SITE                   1
                       note = D-Phenylalanine
REGION                 2..8
                       note = Cyclic
SITE                   4
                       note = D-(Et)Tyr
SITE                   5
                       note = Homoarginine
MOD_RES                6
                       note = 4,4'-biphenylalanine
MOD_RES                7
                       note = bAla
SITE                   8
                       note = D-Cystine
MOD_RES                10..11
                       note = 8-amino-3,6-dioxaoctanoic acid
source                 1..22
                       mol_type = protein
                       organism = synthetic construct
SEQUENCE: 399
FCHYRXACTX XYGRRRRRQR RR                                          22

SEQ ID NO: 400         moltype = AA  length = 20
FEATURE                Location/Qualifiers
SITE                   20
                       note = C-terminal is: NH2
REGION                 1..20
                       note = Description of Sequence: MC4R agonist
SITE                   1
                       note = D-Phenylalanine
REGION                 2..8
                       note = Cyclic
SITE                   4
                       note = D-(Et)Tyr
SITE                   5
                       note = Homoarginine
MOD_RES                6
                       note = 4,4'-biphenylalanine
MOD_RES                7
                       note = bAla
SITE                   8
                       note = D-Cystine
MOD_RES                10..11
                       note = 8-amino-3,6-dioxaoctanoic acid
source                 1..20
                       mol_type = protein
                       organism = synthetic construct
SEQUENCE: 400
FCHYRXACTX XRRRRRQRRR                                             20

SEQ ID NO: 401         moltype = AA  length = 21
FEATURE                Location/Qualifiers
SITE                   21
                       note = C-terminal is: NH2
REGION                 1..21
                       note = Description of Sequence: MC4R agonist
SITE
                       note = N-terminal is: Acetylated
```

-continued

```
SITE                    1
                        note = Nle
REGION                  2..9
                        note = Cyclic
SITE                    3
                        note = D-Alanine
SITE                    5
                        note = D-Phenylalanine
MOD_RES                 10
                        note = bAla
source                  1..21
                        mol_type = protein
                        organism = synthetic construct
SEQUENCE: 401
XCAHFRWGCA YGRRRRRQRR R                                                21

SEQ ID NO: 402          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..9
                        note = Cyclic
SITE                    3
                        note = D-Alanine
SITE                    5
                        note = D-Phenylalanine
MOD_RES                 10
                        note = bAla
source                  1..19
                        mol_type = protein
                        organism = synthetic construct
SEQUENCE: 402
XCAHFRWGCA RRRRRQRRR                                                   19

SEQ ID NO: 403          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9
                        note = bAla
source                  1..20
                        mol_type = protein
                        organism = synthetic construct
SEQUENCE: 403
XCHFRWXCAY GRRRRRQRRR                                                  20

SEQ ID NO: 404          moltype = AA  length = 18
FEATURE                 Location/Qualifiers
SITE                    18
                        note = C-terminal is: NH2
REGION                  1..18
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9
                        note = bAla
```

```
source                1..18
                      mol_type = protein
                      organism = synthetic construct
SEQUENCE: 404
XCHFRWXCAR RRRRQRRR                                                18

SEQ ID NO: 405        moltype = AA  length = 21
FEATURE               Location/Qualifiers
SITE                  21
                      note = C-terminal is: NH2
REGION                1..21
                      note = Description of Sequence: MC4R agonist
SITE                  1
                      note = Nle
REGION                2..8
                      note = Cyclic
SITE                  4
                      note = D-Phenylalanine
MOD_RES               7
                      note = 5-aminopentanoic acid
MOD_RES               9..10
                      note = bAla
source                1..21
                      mol_type = protein
                      organism = synthetic construct
SEQUENCE: 405
XCHFRWXCAA YGRRRRRQRR R                                            21

SEQ ID NO: 406        moltype = AA  length = 19
FEATURE               Location/Qualifiers
SITE                  19
                      note = C-terminal is: NH2
REGION                1..19
                      note = Description of Sequence: MC4R agonist
SITE                  1
                      note = Nle
REGION                2..8
                      note = Cyclic
SITE                  4
                      note = D-Phenylalanine
MOD_RES               7
                      note = 5-aminopentanoic acid
MOD_RES               9..10
                      note = bAla
source                1..19
                      mol_type = protein
                      organism = synthetic construct
SEQUENCE: 406
XCHFRWXCAA RRRRRQRRR                                               19

SEQ ID NO: 407        moltype = AA  length = 21
FEATURE               Location/Qualifiers
SITE                  21
                      note = C-terminal is: NH2
REGION                1..21
                      note = Description of Sequence: MC4R agonist
SITE                  1
                      note = Nle
REGION                2..8
                      note = Cyclic
SITE                  4
                      note = D-Phenylalanine
MOD_RES               7
                      note = 5-aminopentanoic acid
MOD_RES               9
                      note = bAla
source                1..21
                      mol_type = protein
                      organism = synthetic construct
SEQUENCE: 407
XCHFRWXCAY GRRRRRQRRR R                                            21

SEQ ID NO: 408        moltype = AA  length = 19
FEATURE               Location/Qualifiers
SITE                  19
                      note = C-terminal is: NH2
REGION                1..19
                      note = Description of Sequence: MC4R agonist
```

-continued

```
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9
                        note = bAla
source                  1..19
                        mol_type = protein
                        organism = synthetic construct
SEQUENCE: 408
XCHFRWXCAR RRRRQRRRR                                                19

SEQ ID NO: 409          moltype = AA  length = 22
FEATURE                 Location/Qualifiers
SITE                    22
                        note = C-terminal is: NH2
REGION                  1..22
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9..10
                        note = bAla
source                  1..22
                        mol_type = protein
                        organism = synthetic construct
SEQUENCE: 409
XCHFRWXCAA YGRRRRRQRR RR                                            22

SEQ ID NO: 410          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9..10
                        note = bAla
source                  1..20
                        mol_type = protein
                        organism = synthetic construct
SEQUENCE: 410
XCHFRWXCAA RRRRRQRRRR                                               20

SEQ ID NO: 411          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9
                        note = 8-amino-3,6-dioxaoctanoic acid
source                  1..20
                        mol_type = protein
                        organism = synthetic construct
```

```
SEQUENCE: 411
XCHFRWXCXY GRRRRRQRRR                                              20

SEQ ID NO: 412          moltype = AA  length = 18
FEATURE                 Location/Qualifiers
SITE                    18
                        note = C-terminal is: NH2
REGION                  1..18
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9
                        note = 8-amino-3,6-dioxaoctanoic acid
source                  1..18
                        mol_type = protein
                        organism = synthetic construct
SEQUENCE: 412
XCHFRWXCXR RRRRQRRR                                                18

SEQ ID NO: 413          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9..10
                        note = 8-amino-3,6-dioxaoctanoic acid
source                  1..21
                        mol_type = protein
                        organism = synthetic construct
SEQUENCE: 413
XCHFRWXCXX YGRRRRRQRR R                                            21

SEQ ID NO: 414          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9..10
                        note = 8-amino-3,6-dioxaoctanoic acid
source                  1..19
                        mol_type = protein
                        organism = synthetic construct
SEQUENCE: 414
XCHFRWXCXX RRRRRQRRR                                               19

SEQ ID NO: 415          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = Nle
REGION                  2..8
                        note = Cyclic
```

```
SITE                    4
                        note = D-Phenylalanine
MOD_RES                 7
                        note = 5-aminopentanoic acid
MOD_RES                 9
                        note = 8-amino-3,6-dioxaoctanoic acid
source                  1..21
                        mol_type = protein
                        organism = synthetic construct
SEQUENCE: 415
XCHFRWXCXY GRRRRRQRRR R                                                  21

SEQ ID NO: 416          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9
                        note = 8-amino-3,6-dioxaoctanoic acid
source                  1..19
                        mol_type = protein
                        organism = synthetic construct
SEQUENCE: 416
XCHFRWXCXR RRRRQRRRR                                                     19

SEQ ID NO: 417          moltype = AA  length = 22
FEATURE                 Location/Qualifiers
SITE                    22
                        note = C-terminal is: NH2
REGION                  1..22
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9..10
                        note = 8-amino-3,6-dioxaoctanoic acid
source                  1..22
                        mol_type = protein
                        organism = synthetic construct
SEQUENCE: 417
XCHFRWXCXX YGRRRRRQRR RR                                                 22

SEQ ID NO: 418          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 5-aminopentanoic acid
MOD_RES                 9..10
                        note = 8-amino-3,6-dioxaoctanoic acid
source                  1..20
                        mol_type = protein
                        organism = synthetic construct
SEQUENCE: 418
XCHFRWXCXX RRRRRQRRRR                                                    20

SEQ ID NO: 419          moltype = AA  length = 20
```

```
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Leu
SITE                   5
                       note = D-Phenylalanine
MOD_RES                9
                       note = bAla
source                 1..20
                       mol_type = protein
                       organism = synthetic construct
SEQUENCE: 419
XCLHFRWCAY GRRRRRQRRR                                          20

SEQ ID NO: 420         moltype = AA  length = 18
FEATURE                Location/Qualifiers
SITE                   18
                       note = C-terminal is: NH2
REGION                 1..18
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Leu
SITE                   5
                       note = D-Phenylalanine
MOD_RES                9
                       note = bAla
source                 1..18
                       mol_type = protein
                       organism = synthetic construct
SEQUENCE: 420
XCLHFRWCAR RRRRQRRR                                            18

SEQ ID NO: 421         moltype = AA  length = 21
FEATURE                Location/Qualifiers
SITE                   21
                       note = C-terminal is: NH2
REGION                 1..21
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Leu
SITE                   5
                       note = D-Phenylalanine
MOD_RES                9..10
                       note = bAla
source                 1..21
                       mol_type = protein
                       organism = synthetic construct
SEQUENCE: 421
XCLHFRWCAA YGRRRRRQRR R                                        21

SEQ ID NO: 422         moltype = AA  length = 19
FEATURE                Location/Qualifiers
SITE                   19
                       note = C-terminal is: NH2
REGION                 1..19
                       note = Description of Sequence: MC4R agonist
SITE
                       note = N-terminal is: Acetylated
```

```
SITE                    1
                        note = Nle
REGION                  2..8
                        note = Cyclic
SITE                    3
                        note = D-Leu
SITE                    5
                        note = D-Phenylalanine
MOD_RES                 9..10
                        note = bAla
source                  1..19
                        mol_type = protein
                        organism = synthetic construct
SEQUENCE: 422
XCLHFRWCAA RRRRRQRRR                                            19

SEQ ID NO: 423          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
MOD_RES                 9
                        note = 8-amino-3,6-dioxaoctanoic acid
source                  1..20
                        mol_type = protein
                        organism = synthetic construct
SEQUENCE: 423
XCLHFRWCXY GRRRRRQRRR                                           20

SEQ ID NO: 424          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
MOD_RES                 9
                        note = 8-amino-3,6-dioxaoctanoic acid
source                  1..18
                        mol_type = protein
                        organism = synthetic construct
SEQUENCE: 424
XCLHFRWCXR RRRRQRRR                                             18

SEQ ID NO: 425          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
```

```
SITE                    5
                        note = D-Phenylalanine
MOD_RES                 9..10
                        note = 8-amino-3,6-dioxaoctanoic acid
source                  1..21
                        mol_type = protein
                        organism = synthetic construct
SEQUENCE: 425
XCLHFRWCXX YGRRRRRQRR R                                              21

SEQ ID NO: 426          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
MOD_RES                 9..10
                        note = 8-amino-3,6-dioxaoctanoic acid
source                  1..19
                        mol_type = protein
                        organism = synthetic construct
SEQUENCE: 426
XCLHFRWCXX RRRRRQRRR                                                 19

SEQ ID NO: 427          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
MOD_RES                 9
                        note = bAla
source                  1..21
                        mol_type = protein
                        organism = synthetic construct
SEQUENCE: 427
XCLHFRWCAY GRRRRRQRRR R                                              21

SEQ ID NO: 428          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
MOD_RES                 9
                        note = bAla
source                  1..19
                        mol_type = protein
                        organism = synthetic construct
```

```
SEQUENCE: 428
XCLHFRWCAR RRRRQRRRR                                              19

SEQ ID NO: 429          moltype = AA  length = 22
FEATURE                 Location/Qualifiers
SITE                    22
                        note = C-terminal is: NH2
REGION                  1..22
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
MOD_RES                 9..10
                        note = bAla
source                  1..22
                        mol_type = protein
                        organism = synthetic construct
SEQUENCE: 429
XCLHFRWCAA YGRRRRRQRR RR                                          22

SEQ ID NO: 430          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
MOD_RES                 9..10
                        note = bAla
source                  1..20
                        mol_type = protein
                        organism = synthetic construct
SEQUENCE: 430
XCLHFRWCAA RRRRRQRRRR                                             20

SEQ ID NO: 431          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
SITE                    3
                        note = D-Leu
SITE                    5
                        note = D-Phenylalanine
MOD_RES                 9
                        note = 8-amino-3,6-dioxaoctanoic acid
source                  1..21
                        mol_type = protein
                        organism = synthetic construct
SEQUENCE: 431
XCLHFRWCXY GRRRRRQRRR R                                           21

SEQ ID NO: 432          moltype = AA  length = 19
FEATURE                 Location/Qualifiers
SITE                    19
                        note = C-terminal is: NH2
```

```
REGION                 1..19
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Leu
SITE                   5
                       note = D-Phenylalanine
MOD_RES                9
                       note = 8-amino-3,6-dioxaoctanoic acid
source                 1..19
                       mol_type = protein
                       organism = synthetic construct
SEQUENCE: 432
XCLHFRWCXR RRRRQRRRR                                             19

SEQ ID NO: 433         moltype = AA  length = 22
FEATURE                Location/Qualifiers
SITE                   22
                       note = C-terminal is: NH2
REGION                 1..22
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Leu
SITE                   5
                       note = D-Phenylalanine
MOD_RES                9..10
                       note = 8-amino-3,6-dioxaoctanoic acid
source                 1..22
                       mol_type = protein
                       organism = synthetic construct
SEQUENCE: 433
XCLHFRWCXX YGRRRRRQRR RR                                         22

SEQ ID NO: 434         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
REGION                 2..8
                       note = Cyclic
SITE                   3
                       note = D-Leu
SITE                   5
                       note = D-Phenylalanine
MOD_RES                9..10
                       note = 8-amino-3,6-dioxaoctanoic acid
source                 1..20
                       mol_type = protein
                       organism = synthetic construct
SEQUENCE: 434
XCLHFRWCXX RRRRRQRRRR                                            20

SEQ ID NO: 435         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
```

```
REGION                  2..8
                        note = Cyclic
MOD_RES                 3
                        note = D-Beta-cyclohexylalanine
SITE                    5
                        note = D-Phenylalanine
MOD_RES                 9
                        note = bAla
source                  1..20
                        mol_type = protein
                        organism = synthetic construct
SEQUENCE: 435
XCXHFRWCAY GRRRRRQRRR                                          20

SEQ ID NO: 436          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
MOD_RES                 9
                        note = bAla
source                  1..18
                        mol_type = protein
                        organism = synthetic construct
SEQUENCE: 436
XCXHFRWCAR RRRRQRRR                                            18

SEQ ID NO: 437          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
MOD_RES                 9..10
                        note = bAla
source                  1..21
                        mol_type = protein
                        organism = synthetic construct
SEQUENCE: 437
XCXHFRWCAA YGRRRRRQRR R                                        21

SEQ ID NO: 438          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
```

```
MOD_RES                 9..10
                        note = bAla
source                  1..19
                        mol_type = protein
                        organism = synthetic construct
SEQUENCE: 438
XCXHFRWCAA RRRRRQRRR                                        19

SEQ ID NO: 439          moltype = AA  length = 20
FEATURE                 Location/Qualifiers
SITE                    20
                        note = C-terminal is: NH2
REGION                  1..20
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
MOD_RES                 9
                        note = 8-amino-3,6-dioxaoctanoic acid
source                  1..20
                        mol_type = protein
                        organism = synthetic construct
SEQUENCE: 439
XCXHFRWCXY GRRRRRQRRR                                       20

SEQ ID NO: 440          moltype = AA  length = 18
FEATURE                 Location/Qualifiers
SITE                    18
                        note = C-terminal is: NH2
REGION                  1..18
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
MOD_RES                 9
                        note = 8-amino-3,6-dioxaoctanoic acid
source                  1..18
                        mol_type = protein
                        organism = synthetic construct
SEQUENCE: 440
XCXHFRWCXR RRRRQRRR                                         18

SEQ ID NO: 441          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
MOD_RES                 9..10
                        note = 8-amino-3,6-dioxaoctanoic acid
source                  1..21
                        mol_type = protein
                        organism = synthetic construct
SEQUENCE: 441
XCXHFRWCXX YGRRRRRQRR R                                     21
```

```
SEQ ID NO: 442          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
MOD_RES                 9..10
                        note = 8-amino-3,6-dioxaoctanoic acid
source                  1..19
                        mol_type = protein
                        organism = synthetic construct
SEQUENCE: 442
XCXHFRWCXX RRRRRQRRR                                                19

SEQ ID NO: 443          moltype = AA  length = 21
FEATURE                 Location/Qualifiers
SITE                    21
                        note = C-terminal is: NH2
REGION                  1..21
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
MOD_RES                 9
                        note = bAla
source                  1..21
                        mol_type = protein
                        organism = synthetic construct
SEQUENCE: 443
XCXHFRWCAY GRRRRRQRRR R                                             21

SEQ ID NO: 444          moltype = AA  length = 19
FEATURE                 Location/Qualifiers
SITE                    19
                        note = C-terminal is: NH2
REGION                  1..19
                        note = Description of Sequence: MC4R agonist
SITE
                        note = N-terminal is: Acetylated
SITE                    1
                        note = Nle
REGION                  2..8
                        note = Cyclic
MOD_RES                 3
                        note = D-Beta-cyclohexylalanine
SITE                    5
                        note = D-Phenylalanine
MOD_RES                 9
                        note = bAla
source                  1..19
                        mol_type = protein
                        organism = synthetic construct
SEQUENCE: 444
XCXHFRWCAR RRRRQRRRR                                                19

SEQ ID NO: 445          moltype = AA  length = 22
FEATURE                 Location/Qualifiers
SITE                    22
                        note = C-terminal is: NH2
REGION                  1..22
                        note = Description of Sequence: MC4R agonist
```

```
SITE
                       note = N-terminal is: Acetylated
SITE                   1
                       note = Nle
REGION                 2..8
                       note = Cyclic
MOD_RES                3
                       note = D-Beta-cyclohexylalanine
SITE                   5
                       note = D-Phenylalanine
MOD_RES                9..10
                       note = bAla
source                 1..22
                       mol_type = protein
                       organism = synthetic construct
SEQUENCE: 445
XCXHFRWCAA YGRRRRRQRR RR                                            22

SEQ ID NO: 446         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
REGION                 2..8
                       note = Cyclic
MOD_RES                3
                       note = D-Beta-cyclohexylalanine
SITE                   5
                       note = D-Phenylalanine
MOD_RES                9..10
                       note = bAla
source                 1..20
                       mol_type = protein
                       organism = synthetic construct
SEQUENCE: 446
XCXHFRWCAA RRRRRQRRRR                                               20

SEQ ID NO: 447         moltype = AA  length = 21
FEATURE                Location/Qualifiers
SITE                   21
                       note = C-terminal is: NH2
REGION                 1..21
                       note = Description of Sequence: MC4R agonist
SITE
                       note = N-terminal is: Acetylated
SITE                   1
                       note = Nle
REGION                 2..8
                       note = Cyclic
MOD_RES                3
                       note = D-Beta-cyclohexylalanine
SITE                   5
                       note = D-Phenylalanine
MOD_RES                9
                       note = 8-amino-3,6-dioxaoctanoic acid
source                 1..21
                       mol_type = protein
                       organism = synthetic construct
SEQUENCE: 447
XCXHFRWCXY GRRRRRQRRR R                                             21

SEQ ID NO: 448         moltype = AA  length = 19
FEATURE                Location/Qualifiers
SITE                   19
                       note = C-terminal is: NH2
REGION                 1..19
                       note = Description of Sequence: MC4R agonist
SITE
                       note = N-terminal is: Acetylated
SITE                   1
                       note = Nle
REGION                 2..8
                       note = Cyclic
```

-continued

```
MOD_RES                3
                       note = D-Beta-cyclohexylalanine
SITE                   5
                       note = D-Phenylalanine
MOD_RES                9
                       note = 8-amino-3,6-dioxaoctanoic acid
source                 1..19
                       mol_type = protein
                       organism = synthetic construct
SEQUENCE: 448
XCXHFRWCXR RRRRQRRRR                                            19

SEQ ID NO: 449         moltype = AA  length = 22
FEATURE                Location/Qualifiers
SITE                   22
                       note = C-terminal is: NH2
REGION                 1..22
                       note = Description of Sequence: MC4R agonist
SITE
                       note = N-terminal is: Acetylated
SITE                   1
                       note = Nle
REGION                 2..8
                       note = Cyclic
MOD_RES                3
                       note = D-Beta-cyclohexylalanine
SITE                   5
                       note = D-Phenylalanine
MOD_RES                9..10
                       note = 8-amino-3,6-dioxaoctanoic acid
source                 1..22
                       mol_type = protein
                       organism = synthetic construct
SEQUENCE: 449
XCXHFRWCXX YGRRRRRQRR RR                                        22

SEQ ID NO: 450         moltype = AA  length = 20
FEATURE                Location/Qualifiers
SITE                   20
                       note = C-terminal is: NH2
REGION                 1..20
                       note = Description of Sequence: MC4R agonist
SITE
                       note = N-terminal is: Acetylated
SITE                   1
                       note = Nle
REGION                 2..8
                       note = Cyclic
MOD_RES                3
                       note = D-Beta-cyclohexylalanine
SITE                   5
                       note = D-Phenylalanine
MOD_RES                9..10
                       note = 8-amino-3,6-dioxaoctanoic acid
source                 1..20
                       mol_type = protein
                       organism = synthetic construct
SEQUENCE: 450
XCXHFRWCXX RRRRRQRRRR                                           20

SEQ ID NO: 451         moltype = AA  length = 20
FEATURE                Location/Qualifiers
SITE                   20
                       note = C-terminal is: NH2
REGION                 1..20
                       note = Description of Sequence: MC4R agonist
SITE                   1
                       note = Nle
REGION                 2..8
                       note = Cyclic
SITE                   4
                       note = D-Phenylalanine
MOD_RES                7
                       note = 4abu
MOD_RES                9
                       note = bAla
source                 1..20
                       mol_type = protein
                       organism = synthetic construct
```

```
SEQUENCE: 451
XCHFRWXCAY GRRRRRQRRR                                              20

SEQ ID NO: 452          moltype = AA  length = 18
FEATURE                 Location/Qualifiers
SITE                    18
                        note = C-terminal is: NH2
REGION                  1..18
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 4abu
MOD_RES                 9
                        note = bAla
source                  1..18
                        mol_type = protein
                        organism = synthetic construct
SEQUENCE: 452
XCHFRWXCAR RRRRQRRR                                                18

SEQ ID NO: 453          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 4abu
MOD_RES                 9..10
                        note = bAla
source                  1..21
                        mol_type = protein
                        organism = synthetic construct
SEQUENCE: 453
XCHFRWXCAA YGRRRRRQRR R                                            21

SEQ ID NO: 454          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 4abu
MOD_RES                 9..10
                        note = bAla
source                  1..19
                        mol_type = protein
                        organism = synthetic construct
SEQUENCE: 454
XCHFRWXCAA RRRRRQRRR                                               19

SEQ ID NO: 455          moltype = AA  length = 21
FEATURE                 Location/Qualifiers
SITE                    21
                        note = C-terminal is: NH2
REGION                  1..21
                        note = Description of Sequence: MC4R agonist
SITE                    1
                        note = Nle
REGION                  2..8
                        note = Cyclic
```

```
SITE                    4
                        note = D-Phenylalanine
MOD_RES                 7
                        note = 4abu
MOD_RES                 9
                        note = bAla
source                  1..21
                        mol_type = protein
                        organism = synthetic construct
SEQUENCE: 455
XCHFRWXCAY GRRRRRQRRR R                                                21

SEQ ID NO: 456          moltype = AA  length = 19
FEATURE                 Location/Qualifiers
SITE                    19
                        note = C-terminal is: NH2
REGION                  1..19
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 4abu
MOD_RES                 9
                        note = bAla
source                  1..19
                        mol_type = protein
                        organism = synthetic construct
SEQUENCE: 456
XCHFRWXCAR RRRRQRRRR                                                   19

SEQ ID NO: 457          moltype = AA  length = 22
FEATURE                 Location/Qualifiers
SITE                    22
                        note = C-terminal is: NH2
REGION                  1..22
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 4abu
MOD_RES                 9..10
                        note = bAla
source                  1..22
                        mol_type = protein
                        organism = synthetic construct
SEQUENCE: 457
XCHFRWXCAA YGRRRRRQRR RR                                               22

SEQ ID NO: 458          moltype = AA  length = 20
FEATURE                 Location/Qualifiers
SITE                    20
                        note = C-terminal is: NH2
REGION                  1..20
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 4abu
MOD_RES                 9..10
                        note = bAla
source                  1..20
                        mol_type = protein
                        organism = synthetic construct
SEQUENCE: 458
XCHFRWXCAA RRRRRQRRRR                                                  20

SEQ ID NO: 459          moltype = AA  length = 20
```

```
FEATURE                Location/Qualifiers
SITE                   20
                       note = C-terminal is: NH2
REGION                 1..20
                       note = Description of Sequence: MC4R agonist
SITE                   1
                       note = Nle
REGION                 2..8
                       note = Cyclic
SITE                   4
                       note = D-Phenylalanine
MOD_RES                7
                       note = 4abu
MOD_RES                9
                       note = 8-amino-3,6-dioxaoctanoic acid
source                 1..20
                       mol_type = protein
                       organism = synthetic construct
SEQUENCE: 459
XCHFRWXCXY GRRRRRQRRR                                          20

SEQ ID NO: 460         moltype = AA  length = 18
FEATURE                Location/Qualifiers
SITE                   18
                       note = C-terminal is: NH2
REGION                 1..18
                       note = Description of Sequence: MC4R agonist
SITE                   1
                       note = Nle
REGION                 2..8
                       note = Cyclic
SITE                   4
                       note = D-Phenylalanine
MOD_RES                7
                       note = 4abu
MOD_RES                9
                       note = 8-amino-3,6-dioxaoctanoic acid
source                 1..18
                       mol_type = protein
                       organism = synthetic construct
SEQUENCE: 460
XCHFRWXCXR RRRRQRRR                                            18

SEQ ID NO: 461         moltype = AA  length = 21
FEATURE                Location/Qualifiers
SITE                   21
                       note = C-terminal is: NH2
REGION                 1..21
                       note = Description of Sequence: MC4R agonist
SITE                   1
                       note = Nle
REGION                 2..8
                       note = Cyclic
SITE                   4
                       note = D-Phenylalanine
MOD_RES                7
                       note = 4abu
MOD_RES                9..10
                       note = 8-amino-3,6-dioxaoctanoic acid
source                 1..21
                       mol_type = protein
                       organism = synthetic construct
SEQUENCE: 461
XCHFRWXCXX YGRRRRRQRR R                                        21

SEQ ID NO: 462         moltype = AA  length = 19
FEATURE                Location/Qualifiers
SITE                   19
                       note = C-terminal is: NH2
REGION                 1..19
                       note = Description of Sequence: MC4R agonist
SITE                   1
                       note = Nle
REGION                 2..8
                       note = Cyclic
SITE                   4
                       note = D-Phenylalanine
MOD_RES                7
                       note = 4abu
```

-continued

```
MOD_RES                9..10
                       note = 8-amino-3,6-dioxaoctanoic acid
source                 1..19
                       mol_type = protein
                       organism = synthetic construct
SEQUENCE: 462
XCHFRWXCXX RRRRRQRRR                                              19

SEQ ID NO: 463         moltype = AA  length = 21
FEATURE                Location/Qualifiers
SITE                   21
                       note = C-terminal is: NH2
REGION                 1..21
                       note = Description of Sequence: MC4R agonist
SITE                   1
                       note = Nle
REGION                 2..8
                       note = Cyclic
SITE                   4
                       note = D-Phenylalanine
MOD_RES                7
                       note = 4abu
MOD_RES                9
                       note = 8-amino-3,6-dioxaoctanoic acid
source                 1..21
                       mol_type = protein
                       organism = synthetic construct
SEQUENCE: 463
XCHFRWXCXY GRRRRRQRRR R                                           21

SEQ ID NO: 464         moltype = AA  length = 19
FEATURE                Location/Qualifiers
SITE                   19
                       note = C-terminal is: NH2
REGION                 1..19
                       note = Description of Sequence: MC4R agonist
SITE                   1
                       note = Nle
REGION                 2..8
                       note = Cyclic
SITE                   4
                       note = D-Phenylalanine
MOD_RES                7
                       note = 4abu
MOD_RES                9
                       note = 8-amino-3,6-dioxaoctanoic acid
source                 1..19
                       mol_type = protein
                       organism = synthetic construct
SEQUENCE: 464
XCHFRWXCXR RRRRQRRRR                                              19

SEQ ID NO: 465         moltype = AA  length = 22
FEATURE                Location/Qualifiers
SITE                   22
                       note = C-terminal is: NH2
REGION                 1..22
                       note = Description of Sequence: MC4R agonist
SITE                   1
                       note = Nle
REGION                 2..8
                       note = Cyclic
SITE                   4
                       note = D-Phenylalanine
MOD_RES                7
                       note = 4abu
MOD_RES                9..10
                       note = 8-amino-3,6-dioxaoctanoic acid
source                 1..22
                       mol_type = protein
                       organism = synthetic construct
SEQUENCE: 465
XCHFRWXCXX YGRRRRRQRR RR                                          22

SEQ ID NO: 466         moltype = AA  length = 20
FEATURE                Location/Qualifiers
SITE                   20
                       note = C-terminal is: NH2
```

-continued

```
REGION                  1..20
                        note = Description of Sequence: MC4R agonist
SITE                    1
                        note = Nle
REGION                  2..8
                        note = Cyclic
SITE                    4
                        note = D-Phenylalanine
MOD_RES                 7
                        note = 4abu
MOD_RES                 9..10
                        note = 8-amino-3,6-dioxaoctanoic acid
source                  1..20
                        mol_type = protein
                        organism = synthetic construct
SEQUENCE: 466
XCHFRWXCXX RRRRRQRRRR                                              20

SEQ ID NO: 467          moltype = AA  length = 12
FEATURE                 Location/Qualifiers
SITE                    12
                        note = C-terminal is: NH2
REGION                  1..12
                        note = Description of Sequence: MC4R agonist
SITE
                        note = N-terminal is: Acetylated
REGION                  1..8
                        note = Cyclic
MOD_RES                 4
                        note = D-4-Br-Phe
source                  1..12
                        mol_type = protein
                        organism = synthetic construct
SEQUENCE: 467
CEHFRWGCPP KD                                                      12

SEQ ID NO: 468          moltype = AA  length = 12
FEATURE                 Location/Qualifiers
SITE                    12
                        note = C-terminal is: NH2
REGION                  1..12
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
source                  1..12
                        mol_type = protein
                        organism = synthetic construct
SEQUENCE: 468
CEHXRWACPP KD                                                      12

SEQ ID NO: 469          moltype = AA  length = 12
FEATURE                 Location/Qualifiers
SITE                    12
                        note = C-terminal is: NH2
REGION                  1..12
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
source                  1..12
                        mol_type = protein
                        organism = synthetic construct
SEQUENCE: 469
CEHXRXACPP KD                                                      12

SEQ ID NO: 470          moltype = AA  length = 12
FEATURE                 Location/Qualifiers
SITE                    12
                        note = C-terminal is: NH2
```

```
REGION                  1..12
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 1-Nal
source                  1..12
                        mol_type = protein
                        organism = synthetic construct
SEQUENCE: 470
CEHXRXACPP KD                                                           12

SEQ ID NO: 471          moltype = AA  length = 12
FEATURE                 Location/Qualifiers
SITE                    12
                        note = C-terminal is: NH2
REGION                  1..12
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = 3-benzothienylaaanine
source                  1..12
                        mol_type = protein
                        organism = synthetic construct
SEQUENCE: 471
CEHXRXACPP KD                                                           12

SEQ ID NO: 472          moltype = AA  length = 12
FEATURE                 Location/Qualifiers
SITE                    12
                        note = C-terminal is: NH2
REGION                  1..12
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 7
                        note = bAla
source                  1..12
                        mol_type = protein
                        organism = synthetic construct
SEQUENCE: 472
CEHXRXACPP KD                                                           12

SEQ ID NO: 473          moltype = AA  length = 12
FEATURE                 Location/Qualifiers
SITE                    12
                        note = C-terminal is: NH2
REGION                  1..12
                        note = Description of Sequence: MC4R agonist
SITE
                        note = N-terminal is: Acetylated
REGION                  1..8
                        note = Cyclic
MOD_RES                 4
                        note = D-P-(2-naphthyl)alanine
MOD_RES                 6
                        note = P-(2-naphthyl)alanine
MOD_RES                 7
                        note = a-aminoisobutyric acid
source                  1..12
                        mol_type = protein
                        organism = synthetic construct
SEQUENCE: 473
CEHXRXXCPP KD                                                           12
```

```
SEQ ID NO: 474          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(Cys-D-Ala))-His
SITE                    2
                        note = D-Phenylalanine
source                  1..5
                        mol_type = protein
                        organism = synthetic construct
SEQUENCE: 474
HFRWC                                                                       5

SEQ ID NO: 475          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(hCys-D-Ala))-His
SITE                    2
                        note = D-Phenylalanine
source                  1..5
                        mol_type = protein
                        organism = synthetic construct
SEQUENCE: 475
HFRWC                                                                       5

SEQ ID NO: 476          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(Cys-D-Ala))-His
MOD_RES                 2
                        note = D-P-(2-naphthyl)alanine
source                  1..5
                        mol_type = protein
                        organism = synthetic construct
SEQUENCE: 476
HXRWC                                                                       5

SEQ ID NO: 477          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(hCys-D-Ala))-His
MOD_RES                 2
                        note = D-P-(2-naphthyl)alanine
source                  1..5
                        mol_type = protein
                        organism = synthetic construct
SEQUENCE: 477
HXRWC                                                                       5

SEQ ID NO: 478          moltype = AA  length = 5
FEATURE                 Location/Qualifiers
SITE                    5
                        note = C-terminal is: NH2
REGION                  1..5
                        note = Description of Sequence: MC4R agonist
```

```
REGION                  1..5
                        note = Cyclic
MOD_RES                 1
                        note = Hydantoin(C(O)-(Asp-D-Ala))-His
SITE                    2
                        note = D-Phenylalanine
source                  1..5
                        mol_type = protein
                        organism = synthetic construct
SEQUENCE: 478
HFRWK                                                                     5

SEQ ID NO: 479          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(Asp-D-Ala))-His
SITE                    2
                        note = D-Phenylalanine
MOD_RES                 5
                        note = Orn
source                  1..5
                        mol_type = protein
                        organism = synthetic construct
SEQUENCE: 479
HFRWX                                                                     5

SEQ ID NO: 480          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(Asp-D-Ala))-His
SITE                    2
                        note = D-Phenylalanine
MOD_RES                 5
                        note = Dab
source                  1..5
                        mol_type = protein
                        organism = synthetic construct
SEQUENCE: 480
HFRWX                                                                     5

SEQ ID NO: 481          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(Asp-D-Ala))-His
SITE                    2
                        note = D-Phenylalanine
MOD_RES                 5
                        note = Dap
source                  1..5
                        mol_type = protein
                        organism = synthetic construct
SEQUENCE: 481
HFRWX                                                                     5

SEQ ID NO: 482          moltype =   length =
SEQUENCE: 482
000
```

```
SEQ ID NO: 483          moltype = AA  length = 4
FEATURE                 Location/Qualifiers
SITE                    4
                        note = C-terminal is: NH2
REGION                  1..4
                        note = Description of Sequence: MC4R agonist
REGION                  1..4
                        note = Cyclic
MOD_RES                 1
                        note = Hydantoin(C(O)-(Asp-His))-D-Phe
source                  1..4
                        mol_type = protein
                        organism = synthetic construct
SEQUENCE: 483
FRWK                                                                    4

SEQ ID NO: 484          moltype = AA  length = 4
FEATURE                 Location/Qualifiers
SITE                    4
                        note = C-terminal is: NH2
REGION                  1..4
                        note = Description of Sequence: MC4R agonist
REGION                  1..4
                        note = Cyclic
MOD_RES                 1
                        note = Hydantoin(C(O)-(Asp-A3c))-D-Phe
source                  1..4
                        mol_type = protein
                        organism = synthetic construct
SEQUENCE: 484
FRWK                                                                    4

SEQ ID NO: 485          moltype = AA  length = 4
FEATURE                 Location/Qualifiers
SITE                    4
                        note = C-terminal is: NH2
REGION                  1..4
                        note = Description of Sequence: MC4R agonist
REGION                  1..4
                        note = Cyclic
MOD_RES                 1
                        note = Hydantoin(C(O)-(Asp-A5c))-D-Phe
source                  1..4
                        mol_type = protein
                        organism = synthetic construct
SEQUENCE: 485
FRWK                                                                    4

SEQ ID NO: 486          moltype = AA  length = 4
FEATURE                 Location/Qualifiers
SITE                    4
                        note = C-terminal is: NH2
REGION                  1..4
                        note = Description of Sequence: MC4R agonist
REGION                  1..4
                        note = Cyclic
MOD_RES                 1
                        note = Hydantoin(C(O)-(Asp-A6c))-D-Phe
source                  1..4
                        mol_type = protein
                        organism = synthetic construct
SEQUENCE: 486
FRWK                                                                    4

SEQ ID NO: 487          moltype =   length =
SEQUENCE: 487
000

SEQ ID NO: 488          moltype =   length =
SEQUENCE: 488
000

SEQ ID NO: 489          moltype =   length =
SEQUENCE: 489
000

SEQ ID NO: 490          moltype = AA  length = 4
FEATURE                 Location/Qualifiers
```

```
SITE                    4
                        note = C-terminal is: NH2
REGION                  1..4
                        note = Description of Sequence: MC4R agonist
REGION                  1..4
                        note = Cyclic
MOD_RES                 1
                        note = Hydantoin(C(O)-(Asp-Aic))-D-Phe
source                  1..4
                        mol_type = protein
                        organism = synthetic construct
SEQUENCE: 490
FRWK                                                                         4

SEQ ID NO: 491          moltype = AA  length = 4
FEATURE                 Location/Qualifiers
SITE                    4
                        note = C-terminal is: NH2
REGION                  1..4
                        note = Description of Sequence: MC4R agonist
REGION                  1..4
                        note = Cyclic
MOD_RES                 1
                        note = Hydantoin(C(O)-(Asp-Apc))-D-Phe
source                  1..4
                        mol_type = protein
                        organism = synthetic construct
SEQUENCE: 491
FRWK                                                                         4

SEQ ID NO: 492          moltype =   length =
SEQUENCE: 492
000

SEQ ID NO: 493          moltype =   length =
SEQUENCE: 493
000

SEQ ID NO: 494          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(Glu-D-Ala))-His
SITE                    2
                        note = D-Phenylalanine
MOD_RES                 5
                        note = Orn
source                  1..5
                        mol_type = protein
                        organism = synthetic construct
SEQUENCE: 494
HFRWX                                                                        5

SEQ ID NO: 495          moltype = AA  length = 5
FEATURE                 Location/Qualifiers
SITE                    5
                        note = C-terminal is: NH2
REGION                  1..5
                        note = Description of Sequence: MC4R agonist
REGION                  1..5
                        note = Cyclic
MOD_RES                 1
                        note = Hydantoin(C(O)-(Glu-D-Ala))-His
SITE                    2
                        note = D-Phenylalanine
MOD_RES                 5
                        note = Dab
source                  1..5
                        mol_type = protein
                        organism = synthetic construct
SEQUENCE: 495
HFRWX                                                                        5

SEQ ID NO: 496          moltype = AA  length = 5
```

-continued

```
FEATURE                Location/Qualifiers
SITE                   5
                       note = C-terminal is: NH2
REGION                 1..5
                       note = Description of Sequence: MC4R agonist
REGION                 1..5
                       note = Cyclic
MOD_RES                1
                       note = Hydantoin(C(O)-(Glu-D-Ala))-His
SITE                   2
                       note = D-Phenylalanine
MOD_RES                5
                       note = Dap
source                 1..5
                       mol_type = protein
                       organism = synthetic construct
SEQUENCE: 496
HFRWX                                                                5

SEQ ID NO: 497         moltype = AA  length = 5
FEATURE                Location/Qualifiers
SITE                   5
                       note = C-terminal is: NH2
REGION                 1..5
                       note = Description of Sequence: MC4R agonist
REGION                 1..5
                       note = Cyclic
MOD_RES                1
                       note = Hydantoin(C(O)-(Glu-D-Ala))-His
SITE                   2
                       note = D-Phenylalanine
source                 1..5
                       mol_type = protein
                       organism = synthetic construct
SEQUENCE: 497
HFRWK                                                                5

SEQ ID NO: 498         moltype =   length =
SEQUENCE: 498
000

SEQ ID NO: 499         moltype = AA  length = 4
FEATURE                Location/Qualifiers
SITE                   4
                       note = C-terminal is: NH2
REGION                 1..4
                       note = Description of Sequence: MC4R agonist
REGION                 1..4
                       note = Cyclic
MOD_RES                1
                       note = Hydantoin(C(O)-(Glu-His))-D-Phe
source                 1..4
                       mol_type = protein
                       organism = synthetic construct
SEQUENCE: 499
FRWK                                                                 4

SEQ ID NO: 500         moltype = AA  length = 7
FEATURE                Location/Qualifiers
SITE                   7
                       note = C-terminal is: NH2
REGION                 1..7
                       note = Description of Sequence: MC4R agonist
REGION                 1..7
                       note = Cyclic
MOD_RES                1
                       note = Hydantoin(C(O)-(Arg-Gly))-Cys
SITE                   4
                       note = D-Phenylalanine
source                 1..7
                       mol_type = protein
                       organism = synthetic construct
SEQUENCE: 500
CEHFRWC                                                              7

SEQ ID NO: 501         moltype = AA  length = 7
FEATURE                Location/Qualifiers
SITE                   7
                       note = C-terminal is: NH2
```

-continued

```
REGION                  1..7
                        note = Description of Sequence: MC4R agonist
REGION                  1..7
                        note = Cyclic
MOD_RES                 1
                        note = Hydantoin(C(O)-(Nle-Gly))-Cys
SITE                    4
                        note = D-Phenylalanine
source                  1..7
                        mol_type = protein
                        organism = synthetic construct
SEQUENCE: 501
CEHFRWC                                                             7

SEQ ID NO: 502          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-Gly))-Cys
SITE                    4
                        note = D-Phenylalanine
source                  1..7
                        mol_type = protein
                        organism = synthetic construct
SEQUENCE: 502
CEHFRWC                                                             7

SEQ ID NO: 503          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Nle-Gly))-Cys
SITE                    2
                        note = D-Alanine
SITE                    4
                        note = D-Phenylalanine
source                  1..7
                        mol_type = protein
                        organism = synthetic construct
SEQUENCE: 503
CAHFRWC                                                             7

SEQ ID NO: 504          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-Gly))-Cys
SITE                    2
                        note = D-Alanine
SITE                    4
                        note = D-Phenylalanine
source                  1..7
                        mol_type = protein
                        organism = synthetic construct
SEQUENCE: 504
CAHFRWC                                                             7

SEQ ID NO: 505          moltype = AA  length = 7
FEATURE                 Location/Qualifiers
SITE                    7
                        note = C-terminal is: NH2
REGION                  1..7
                        note = Description of Sequence: MC4R agonist
```

```
REGION                  1..7
                        note = Cyclic
MOD_RES                 1
                        note = Hydantoin(C(O)-(Nle-Gly))-Cys
SITE                    2
                        note = D-Alanine
SITE                    4
                        note = D-Phenylalanine
MOD_RES                 7
                        note = Penicillamine
source                  1..7
                        mol_type = protein
                        organism = synthetic construct
SEQUENCE: 505
CAHFRWX                                                                      7

SEQ ID NO: 506          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-Gly))-Cys
SITE                    2
                        note = D-Alanine
SITE                    4
                        note = D-Phenylalanine
MOD_RES                 7
                        note = Penicillamine
source                  1..7
                        mol_type = protein
                        organism = synthetic construct
SEQUENCE: 506
CAHFRWX                                                                      7

SEQ ID NO: 507          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Ala-Gly))-Cys
SITE                    2
                        note = D-Alanine
SITE                    4
                        note = D-Phenylalanine
source                  1..7
                        mol_type = protein
                        organism = synthetic construct
SEQUENCE: 507
CAHFRWC                                                                      7

SEQ ID NO: 508          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(D-Ala-Gly))-Cys
SITE                    2
                        note = D-Alanine
SITE                    4
                        note = D-Phenylalanine
source                  1..7
                        mol_type = protein
                        organism = synthetic construct
SEQUENCE: 508
CAHFRWC                                                                      7

SEQ ID NO: 509          moltype = AA  length = 7
```

-continued

```
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Aib-Gly))-Cys
SITE                    2
                        note = D-Alanine
SITE                    4
                        note = D-Phenylalanine
source                  1..7
                        mol_type = protein
                        organism = synthetic construct
SEQUENCE: 509
CAHFRWC                                                                  7

SEQ ID NO: 510          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Val-Gly))-Cys
SITE                    2
                        note = D-Alanine
SITE                    4
                        note = D-Phenylalanine
source                  1..7
                        mol_type = protein
                        organism = synthetic construct
SEQUENCE: 510
CAHFRWC                                                                  7

SEQ ID NO: 511          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Ile-Gly))-Cys
SITE                    2
                        note = D-Alanine
SITE                    4
                        note = D-Phenylalanine
source                  1..7
                        mol_type = protein
                        organism = synthetic construct
SEQUENCE: 511
CAHFRWC                                                                  7

SEQ ID NO: 512          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Leu-Gly))-Cys
SITE                    2
                        note = D-Alanine
SITE                    4
                        note = D-Phenylalanine
source                  1..7
                        mol_type = protein
                        organism = synthetic construct
SEQUENCE: 512
CAHFRWC                                                                  7
```

-continued

```
SEQ ID NO: 513          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-Gly))-Cys
MOD_RES                 4
                        note = D-P-(2-naphthyl)alanine
source                  1..7
                        mol_type = protein
                        organism = synthetic construct
SEQUENCE: 513
CEHXRWC                                                                   7

SEQ ID NO: 514          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Nle-Gly))-Cys
MOD_RES                 4
                        note = D-P-(2-naphthyl)alanine
source                  1..7
                        mol_type = protein
                        organism = synthetic construct
SEQUENCE: 514
CEHXRWC                                                                   7

SEQ ID NO: 515          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(D-Arg-Gly))-Cys
SITE                    4
                        note = D-Phenylalanine
source                  1..7
                        mol_type = protein
                        organism = synthetic construct
SEQUENCE: 515
CEHFRWC                                                                   7

SEQ ID NO: 516          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(D-Arg-Gly))-Cys
SITE                    2
                        note = D-Alanine
SITE                    4
                        note = D-Phenylalanine
source                  1..7
                        mol_type = protein
                        organism = synthetic construct
SEQUENCE: 516
CAHFRWC                                                                   7

SEQ ID NO: 517          moltype = AA  length = 7
FEATURE                 Location/Qualifiers
SITE                    7
                        note = C-terminal is: NH2
```

```
REGION              1..7
                    note = Description of Sequence: MC4R agonist
REGION              1..7
                    note = Cyclic
MOD_RES             1
                    note = Hydantoin(C(O)-(Arg-Gly))-Cys
SITE                2
                    note = D-Alanine
SITE                4
                    note = D-Phenylalanine
source              1..7
                    mol_type = protein
                    organism = synthetic construct
SEQUENCE: 517
CAHFRWC                                                  7

SEQ ID NO: 518      moltype = AA  length = 7
FEATURE             Location/Qualifiers
SITE                7
                    note = C-terminal is: NH2
REGION              1..7
                    note = Description of Sequence: MC4R agonist
REGION              1..7
                    note = Cyclic
MOD_RES             1
                    note = Hydantoin(C(O)-(D-Arg-Gly))-Cys
SITE                2
                    note = D-Alanine
MOD_RES             4
                    note = D-P-(2-naphthyl)alanine
source              1..7
                    mol_type = protein
                    organism = synthetic construct
SEQUENCE: 518
CAHXRWC                                                  7

SEQ ID NO: 519      moltype = AA  length = 7
FEATURE             Location/Qualifiers
SITE                7
                    note = C-terminal is: NH2
REGION              1..7
                    note = Description of Sequence: MC4R agonist
REGION              1..7
                    note = Cyclic
MOD_RES             1
                    note = Hydantoin(C(O)-(Arg-Gly))-Cys
SITE                2
                    note = D-Alanine
MOD_RES             4
                    note = D-P-(2-naphthyl)alanine
source              1..7
                    mol_type = protein
                    organism = synthetic construct
SEQUENCE: 519
CAHXRWC                                                  7

SEQ ID NO: 520      moltype = AA  length = 7
FEATURE             Location/Qualifiers
SITE                7
                    note = C-terminal is: NH2
REGION              1..7
                    note = Description of Sequence: MC4R agonist
REGION              1..7
                    note = Cyclic
MOD_RES             1
                    note = Hydantoin(C(O)-(Ala-Nle))-Cys
SITE                4
                    note = D-Phenylalanine
source              1..7
                    mol_type = protein
                    organism = synthetic construct
SEQUENCE: 520
CEHFRWC                                                  7

SEQ ID NO: 521      moltype = AA  length = 7
FEATURE             Location/Qualifiers
SITE                7
                    note = C-terminal is: NH2
```

```
REGION                 1..7
                       note = Description of Artificial Sequence: Synthetic peptide
REGION                 1..7
                       note = Cyclic
MOD_RES                1
                       note = Hydantoin(C(O)-(Val-Nle))-Cys
SITE                   4
                       note = D-Phenylalanine
source                 1..7
                       mol_type = protein
                       organism = synthetic construct
SEQUENCE: 521
CEHFRWC                                                                   7

SEQ ID NO: 522         moltype = AA  length = 7
FEATURE                Location/Qualifiers
SITE                   7
                       note = C-terminal is: NH2
REGION                 1..7
                       note = Description of Sequence: MC4R agonist
REGION                 1..7
                       note = Cyclic
MOD_RES                1
                       note = Hydantoin(C(O)-(Gly-Nle))-Cys
SITE                   4
                       note = D-Phenylalanine
source                 1..7
                       mol_type = protein
                       organism = synthetic construct
SEQUENCE: 522
CEHFRWC                                                                   7

SEQ ID NO: 523         moltype = AA  length = 7
FEATURE                Location/Qualifiers
SITE                   7
                       note = C-terminal is: NH2
REGION                 1..7
                       note = Description of Sequence: MC4R agonist
REGION                 1..7
                       note = Cyclic
MOD_RES                1
                       note = Hydantoin(C(O)-(A6c-Nle))-Cys
SITE                   2
                       note = D-Alanine
SITE                   4
                       note = D-Phenylalanine
source                 1..7
                       mol_type = protein
                       organism = synthetic construct
SEQUENCE: 523
CAHFRWC                                                                   7

SEQ ID NO: 524         moltype = AA  length = 7
FEATURE                Location/Qualifiers
SITE                   7
                       note = C-terminal is: NH2
REGION                 1..7
                       note = Description of Sequence: MC4R agonist
REGION                 1..7
                       note = Cyclic
MOD_RES                1
                       note = Hydantoin(C(O)-(Gly-Nle))-Cys
SITE                   2
                       note = D-Alanine
SITE                   4
                       note = D-Phenylalanine
source                 1..7
                       mol_type = protein
                       organism = synthetic construct
SEQUENCE: 524
CAHFRWC                                                                   7

SEQ ID NO: 525         moltype = AA  length = 7
FEATURE                Location/Qualifiers
SITE                   7
                       note = C-terminal is: NH2
REGION                 1..7
                       note = Description of Sequence: MC4R agonist
```

```
REGION                  1..7
                        note = Cyclic
MOD_RES                 1
                        note = Hydantoin(C(O)-(Ala-Nle))-Cys
SITE                    2
                        note = D-Alanine
SITE                    4
                        note = D-Phenylalanine
source                  1..7
                        mol_type = protein
                        organism = synthetic construct
SEQUENCE: 525
CAHFRWC                                                                    7

SEQ ID NO: 526          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(D-Ala-Nle))-Cys
SITE                    2
                        note = D-Alanine
SITE                    4
                        note = D-Phenylalanine
source                  1..7
                        mol_type = protein
                        organism = synthetic construct
SEQUENCE: 526
CAHFRWC                                                                    7

SEQ ID NO: 527          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Val-Nle))-Cys
SITE                    2
                        note = D-Alanine
SITE                    4
                        note = D-Phenylalanine
source                  1..7
                        mol_type = protein
                        organism = synthetic construct
SEQUENCE: 527
CAHFRWC                                                                    7

SEQ ID NO: 528          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Leu-Nle))-Cys
SITE                    2
                        note = D-Alanine
SITE                    4
                        note = D-Phenylalanine
source                  1..7
                        mol_type = protein
                        organism = synthetic construct
SEQUENCE: 528
CAHFRWC                                                                    7

SEQ ID NO: 529          moltype = AA  length = 7
FEATURE                 Location/Qualifiers
SITE                    7
                        note = C-terminal is: NH2
```

```
REGION                  1..7
                        note = Description of Sequence: MC4R agonist
REGION                  1..7
                        note = Cyclic
MOD_RES                 1
                        note = Hydantoin(C(O)-(Cha-Nle))-Cys
SITE                    2
                        note = D-Alanine
SITE                    4
                        note = D-Phenylalanine
source                  1..7
                        mol_type = protein
                        organism = synthetic construct
SEQUENCE: 529
CAHFRWC                                                                     7

SEQ ID NO: 530          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Aib-Nle))-Cys
SITE                    2
                        note = D-Alanine
SITE                    4
                        note = D-Phenylalanine
source                  1..7
                        mol_type = protein
                        organism = synthetic construct
SEQUENCE: 530
CAHFRWC                                                                     7

SEQ ID NO: 531          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-Arg))-Cys
SITE                    4
                        note = D-Phenylalanine
source                  1..7
                        mol_type = protein
                        organism = synthetic construct
SEQUENCE: 531
CEHFRWC                                                                     7

SEQ ID NO: 532          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-Arg))-Cys
MOD_RES                 4
                        note = D-P-(2-naphthyl)alanine
source                  1..7
                        mol_type = protein
                        organism = synthetic construct
SEQUENCE: 532
CEHXRWC                                                                     7

SEQ ID NO: 533          moltype = AA  length = 7
FEATURE                 Location/Qualifiers
SITE                    7
                        note = C-terminal is: NH2
REGION                  1..7
                        note = Description of Sequence: MC4R agonist
```

```
REGION                  1..7
                        note = Cyclic
MOD_RES                 1
                        note = Hydantoin(C(O)-(Gly-Arg))-Cys
SITE                    2
                        note = D-Alanine
SITE                    4
                        note = D-Phenylalanine
source                  1..7
                        mol_type = protein
                        organism = synthetic construct
SEQUENCE: 533
CAHFRWC                                                                    7

SEQ ID NO: 534          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-Arg))-Cys
SITE                    2
                        note = D-Alanine
MOD_RES                 4
                        note = D-P-(2-naphthyl)alanine
source                  1..7
                        mol_type = protein
                        organism = synthetic construct
SEQUENCE: 534
CAHXRWC                                                                    7

SEQ ID NO: 535          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-D-Arg))-Cys
SITE                    4
                        note = D-Phenylalanine
source                  1..7
                        mol_type = protein
                        organism = synthetic construct
SEQUENCE: 535
CEHFRWC                                                                    7

SEQ ID NO: 536          moltype = AA  length = 7
FEATURE                 Location/Qualifiers
SITE                    7
                        note = C-terminal is: NH2
REGION                  1..7
                        note = Description of Sequence: MC4R agonist
REGION                  1..7
                        note = Cyclic
MOD_RES                 1
                        note = Hydantoin(C(O)-(Gly-D-Arg))-Cys
SITE                    2
                        note = D-Alanine
SITE                    4
                        note = D-Phenylalanine
source                  1..7
                        mol_type = protein
                        organism = synthetic construct
SEQUENCE: 536
CAHFRWC                                                                    7

SEQ ID NO: 537          moltype = AA  length = 7
FEATURE                 Location/Qualifiers
SITE                    7
                        note = C-terminal is: NH2
REGION                  1..7
                        note = Description of Sequence: MC4R agonist
```

```
REGION                1..7
                      note = Cyclic
MOD_RES               1
                      note = Hydantoin(C(O)-(Gly-D-Arg))-Cys
SITE                  2
                      note = D-Alanine
MOD_RES               4
                      note = D-P-(2-naphthyl)alanine
source                1..7
                      mol_type = protein
                      organism = synthetic construct
SEQUENCE: 537
CAHXRWC                                                              7

SEQ ID NO: 538        moltype = AA  length = 7
FEATURE               Location/Qualifiers
SITE                  7
                      note = C-terminal is: NH2
REGION                1..7
                      note = Description of Sequence: MC4R agonist
REGION                1..7
                      note = Cyclic
MOD_RES               1
                      note = Hydantoin(C(O)-(Nle-Ala))-Cys
SITE                  4
                      note = D-Phenylalanine
source                1..7
                      mol_type = protein
                      organism = synthetic construct
SEQUENCE: 538
CEHFRWC                                                              7

SEQ ID NO: 539        moltype = AA  length = 6
FEATURE               Location/Qualifiers
SITE                  6
                      note = C-terminal is: NH2
REGION                1..6
                      note = Description of Sequence: MC4R agonist
REGION                1..6
                      note = Cyclic
MOD_RES               1
                      note = Hydantoin(C(O)-(Nle-Cys))-D-Ala
SITE                  3
                      note = D-Phenylalanine
source                1..6
                      mol_type = protein
                      organism = synthetic construct
SEQUENCE: 539
AHFRWC                                                               6

SEQ ID NO: 540        moltype = AA  length = 6
FEATURE               Location/Qualifiers
SITE                  6
                      note = C-terminal is: NH2
REGION                1..6
                      note = Description of Sequence: MC4R agonist
REGION                1..6
                      note = Cyclic
MOD_RES               1
                      note = Hydantoin(C(O)-(Ala-Cys))-D-Ala
SITE                  3
                      note = D-Phenylalanine
source                1..6
                      mol_type = protein
                      organism = synthetic construct
SEQUENCE: 540
AHFRWC                                                               6

SEQ ID NO: 541        moltype = AA  length = 6
FEATURE               Location/Qualifiers
SITE                  6
                      note = C-terminal is: NH2
REGION                1..6
                      note = Description of Sequence: MC4R agonist
REGION                1..6
                      note = Cyclic
MOD_RES               1
                      note = Hydantoin(C(O)-(D-Ala-Cys))-D-Ala
```

```
SITE                  3
                      note = D-Phenylalanine
source                1..6
                      mol_type = protein
                      organism = synthetic construct
SEQUENCE: 541
AHFRWC                                                                    6

SEQ ID NO: 542        moltype = AA  length = 6
FEATURE               Location/Qualifiers
SITE                  6
                      note = C-terminal is: NH2
REGION                1..6
                      note = Description of Sequence: MC4R agonist
REGION                1..6
                      note = Cyclic
MOD_RES               1
                      note = Hydantoin(C(O)-(Aib-Cys))-D-Ala
SITE                  3
                      note = D-Phenylalanine
source                1..6
                      mol_type = protein
                      organism = synthetic construct
SEQUENCE: 542
AHFRWC                                                                    6

SEQ ID NO: 543        moltype = AA  length = 6
FEATURE               Location/Qualifiers
SITE                  6
                      note = C-terminal is: NH2
REGION                1..6
                      note = Description of Sequence: MC4R agonist
REGION                1..6
                      note = Cyclic
MOD_RES               1
                      note = Hydantoin(C(O)-(Val-Cys))-D-Ala
SITE                  3
                      note = D-Phenylalanine
source                1..6
                      mol_type = protein
                      organism = synthetic construct
SEQUENCE: 543
AHFRWC                                                                    6

SEQ ID NO: 544        moltype = AA  length = 6
FEATURE               Location/Qualifiers
SITE                  6
                      note = C-terminal is: NH2
REGION                1..6
                      note = Description of Sequence: MC4R agonist
REGION                1..6
                      note = Cyclic
MOD_RES               1
                      note = Hydantoin(C(O)-(Abu-Cys))-D-Ala
SITE                  3
                      note = D-Phenylalanine
source                1..6
                      mol_type = protein
                      organism = synthetic construct
SEQUENCE: 544
AHFRWC                                                                    6

SEQ ID NO: 545        moltype = AA  length = 6
FEATURE               Location/Qualifiers
SITE                  6
                      note = C-terminal is: NH2
REGION                1..6
                      note = Description of Sequence: MC4R agonist
REGION                1..6
                      note = Cyclic
MOD_RES               1
                      note = Hydantoin(C(O)-(Leu-Cys))-D-Ala
SITE                  3
                      note = D-Phenylalanine
source                1..6
                      mol_type = protein
                      organism = synthetic construct
SEQUENCE: 545
AHFRWC                                                                    6
```

-continued

```
SEQ ID NO: 546          moltype = AA  length = 6
FEATURE                 Location/Qualifiers
SITE                    6
                        note = C-terminal is: NH2
REGION                  1..6
                        note = Description of Sequence: MC4R agonist
REGION                  1..6
                        note = Cyclic
MOD_RES                 1
                        note = Hydantoin(C(O)-(Ile-Cys))-D-Ala
SITE                    3
                        note = D-Phenylalanine
source                  1..6
                        mol_type = protein
                        organism = synthetic construct
SEQUENCE: 546
AHFRWC                                                                        6

SEQ ID NO: 547          moltype = AA  length = 6
FEATURE                 Location/Qualifiers
SITE                    6
                        note = C-terminal is: NH2
REGION                  1..6
                        note = Description of Sequence: MC4R agonist
REGION                  1..6
                        note = Cyclic
MOD_RES                 1
                        note = Hydantoin(C(O)-(Cha-Cys))-D-Ala
SITE                    3
                        note = D-Phenylalanine
source                  1..6
                        mol_type = protein
                        organism = synthetic construct
SEQUENCE: 547
AHFRWC                                                                        6

SEQ ID NO: 548          moltype = AA  length = 6
FEATURE                 Location/Qualifiers
SITE                    6
                        note = C-terminal is: NH2
REGION                  1..6
                        note = Description of Sequence: MC4R agonist
REGION                  1..6
                        note = Cyclic
MOD_RES                 1
                        note = Hydantoin(C(O)-(A6c-Cys))-D-Ala
SITE                    3
                        note = D-Phenylalanine
source                  1..6
                        mol_type = protein
                        organism = synthetic construct
SEQUENCE: 548
AHFRWC                                                                        6

SEQ ID NO: 549          moltype = AA  length = 6
FEATURE                 Location/Qualifiers
SITE                    6
                        note = C-terminal is: NH2
REGION                  1..6
                        note = Description of Sequence: MC4R agonist
REGION                  1..6
                        note = Cyclic
MOD_RES                 1
                        note = Hydantoin(C(O)-(Phe-Cys))-D-Ala
SITE                    3
                        note = D-Phenylalanine
source                  1..6
                        mol_type = protein
                        organism = synthetic construct
SEQUENCE: 549
AHFRWC                                                                        6

SEQ ID NO: 550          moltype = AA  length = 6
FEATURE                 Location/Qualifiers
SITE                    6
                        note = C-terminal is: NH2
```

```
REGION                  1..6
                        note = Description of Sequence: MC4R agonist
REGION                  1..6
                        note = Cyclic
MOD_RES                 1
                        note = Hydantoin(C(O)-(Gly-Cys))-D-Ala
SITE                    3
                        note = D-Phenylalanine
source                  1..6
                        mol_type = protein
                        organism = synthetic construct
SEQUENCE: 550
AHFRWC                                                                       6

SEQ ID NO: 551          moltype = AA  length = 6
FEATURE                 Location/Qualifiers
SITE                    6
                        note = C-terminal is: NH2
REGION                  1..6
                        note = Description of Sequence: MC4R agonist
REGION                  1..6
                        note = Cyclic
MOD_RES                 1
                        note = Hydantoin(C(O)-(Gly-Cys))-Glu
SITE                    3
                        note = D-Phenylalanine
source                  1..6
                        mol_type = protein
                        organism = synthetic construct
SEQUENCE: 551
EHFRWC                                                                       6

SEQ ID NO: 552          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
REGION                  3..9
                        note = Cyclic
SITE                    4
                        note = D-Alanine
SITE                    6
                        note = D-Phenylalanine
source                  1..9
                        mol_type = protein
                        organism = synthetic construct
SEQUENCE: 552
YRCAHFRWC                                                                    9

SEQ ID NO: 553          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
MOD_RES                 1
                        note = P-(2-naphthyl)alanine
REGION                  3..9
                        note = Cyclic
SITE                    4
                        note = D-Alanine
SITE                    6
                        note = D-Phenylalanine
source                  1..9
                        mol_type = protein
                        organism = synthetic construct
SEQUENCE: 553
XRCAHFRWC                                                                    9

SEQ ID NO: 554          moltype = AA  length = 9
FEATURE                 Location/Qualifiers
SITE                    9
                        note = C-terminal is: NH2
```

```
REGION                  1..9
                        note = Description of Sequence: MC4R agonist
SITE
                        note = N-terminal is: Acetylated
MOD_RES                 1
                        note = 1-Nal
REGION                  3..9
                        note = Cyclic
SITE                    4
                        note = D-Alanine
SITE                    6
                        note = D-Phenylalanine
source                  1..9
                        mol_type = protein
                        organism = synthetic construct
SEQUENCE: 554
XRCAHFRWC                                                                  9

SEQ ID NO: 555          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
REGION                  3..9
                        note = Cyclic
SITE                    4
                        note = D-Alanine
SITE                    6
                        note = D-Phenylalanine
source                  1..9
                        mol_type = protein
                        organism = synthetic construct
SEQUENCE: 555
FRCAHFRWC                                                                  9

SEQ ID NO: 556          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
REGION                  3..9
                        note = Cyclic
SITE                    4
                        note = D-Alanine
SITE                    6
                        note = D-Phenylalanine
source                  1..9
                        mol_type = protein
                        organism = synthetic construct
SEQUENCE: 556
WRCAHFRWC                                                                  9

SEQ ID NO: 557          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated
MOD_RES                 1
                        note = Pff
REGION                  3..9
                        note = Cyclic
SITE                    4
                        note = D-Alanine
SITE                    6
                        note = D-Phenylalanine
source                  1..9
                        mol_type = protein
                        organism = synthetic construct
SEQUENCE: 557
XRCAHFRWC                                                                  9
```

-continued

```
SEQ ID NO: 558          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-term is: H
REGION                  3..9
                        note = Cyclic
SITE                    4
                        note = D-Alanine
SITE                    6
                        note = D-Phenylalanine
source                  1..9
                        mol_type = protein
                        organism = synthetic construct
SEQUENCE: 558
HRCAHFRWC                                                      9

SEQ ID NO: 559          moltype = AA  length = 9
FEATURE                 Location/Qualifiers
SITE                    9
                        note = C-terminal is: NH2
REGION                  1..9
                        note = Description of Sequence: MC4R agonist
SITE
                        note = N-terminal is: Acetylated etylated
REGION                  3..9
                        note = Cyclic
SITE                    4
                        note = D-Alanine
SITE                    6
                        note = D-Phenylalanine
source                  1..9
                        mol_type = protein
                        organism = synthetic construct
SEQUENCE: 559
HRCAHFRWC                                                      9
```

The invention claimed is:

1. A method of treating a disorder in a subject in need thereof, comprising:

administering to said subject an effective amount of an agonist of the melanocortin-4 receptor (MC4R), wherein the MC4R agonist is a peptide that includes D-Phe-Arg-Trp (SEQ ID NO: 560) or a pharmaceutical salt thereof, wherein the subject is a heterozygous carrier of an MC4R mutation, and wherein the disorder results from an attenuated response of MC4R to α-melanocortin stimulating hormone (α-MSH).

2. The method of claim 1, wherein the disorder is obesity.

3. The method of claim 1, wherein the disorder is a metabolic syndrome.

4. The method of claim 1, wherein the MC4R agonist is not an adrenocorticotropic hormone (ACTH).

5. The method of claim 1, wherein said MC4R agonist is Ac-Arg-c(Cys-D-Ala-His-D-Phe-Arg-Trp-Cys)-$NH_2$ (SEQ ID NO: 140) or a pharmaceutically acceptable salt thereof.

6. The method of claim 1, wherein said MC4R agonist is Hydantoin(C(O)-(Arg-Gly))-c(Cys-Glu-His-D-Phe-Arg-Trp-Cys)-$NH_2$ (SEQ ID NO: 500) or a pharmaceutically acceptable salt thereof.

7. The method of claim 1, wherein said MC4R agonist is a peptide that includes an acetylated tripeptide Ac-D-Phe-Arg-Trp-$NH_2$ (SEQ ID NO: 561) or a pharmaceutical salt thereof.

8. The method of claim 1, wherein said MC4R agonist is a peptide selected from:

(SEQ ID NO: 1)
Ac-Nle-c(Asp-His-D-Phe-Arg-Trp-β-Ala-Lys)-$NH_2$;

(SEQ ID NO: 2)
Ac-Nle-c(Asp-His-D-Phe-Arg-Trp-A6c-Lys)-$NH_2$;

(SEQ ID NO: 3)
Ac-Nle-c(Cys-His-D-Phe-Arg-Trp-Ahx-Cys)-$NH_2$;

(SEQ ID NO: 4)
D-Phe-c(Cys-His-D-Phe-Arg-Trp-Ala-D-Cys)-Thr-$NH_2$;

(SEQ ID NO: 5)
D-Phe-c(Cys-His-D-Phe-Arg-Trp-β-Ala-D-Cys)-Thr-$NH_2$;

-continued (SEQ ID NO: 6)
D-Phe-c(Cys-His-D-Phe-Arg-Trp-Gaba-D-Cys)-Thr-$NH_2$;

(SEQ ID NO: 7)
Ac-Nle-c(Cys-His-D-Phe-Arg-Trp-Apn-Cys)-$NH_2$;

(SEQ ID NO: 8)
Ac-Nle-c(Asp-His-D-Phe-Arg-Trp-Apn-Lys)-$NH_2$;

(SEQ ID NO: 9)
Ac-A6c-c(Asp-His-D-Phe-Arg-Trp-Gaba-Lys)-$NH_2$;

(SEQ ID NO: 10)
Ac-D-2-Nal-c(Asp-His-D-Phe-Arg-Trp-Gaba-Lys)-$NH_2$;

(SEQ ID NO: 11)
Ac-Cha-c(Asp-His-D-Phe-Arg-Trp-Gaba-Lys)-$NH_2$;

(SEQ ID NO: 12)
Ac-Nle-c(Asp-His-D-Phe-Arg-Trp-Gaba-Lys)-$NH_2$;

(SEQ ID NO: 13)
Ac-Nle-c(Cys-D-Ala-His-D-Phe-Arg-Trp-Cys)-$NH_2$;

(SEQ ID NO: 14)
Ac-Nle-c(Cys-β-Ala-His-D-Phe-Arg-Trp-Cys)-$NH_2$;

(SEQ ID NO: 15)
Ac-Nle-c(Cys-Gaba-His-D-Phe-Arg-Trp-Cys)-$NH_2$;

(SEQ ID NO: 16)
Ac-Nle-c(Cys-Aib-His-D-Phe-Arg-Trp-Cys)-$NH_2$;

(SEQ ID NO: 17)
Ac-Nle-c(Cys-Gly-His-D-Phe-Arg-Trp-Cys)-$NH_2$;

(SEQ ID NO: 18)
Ac-Nle-c(D-Cys-Ala-His-D-Phe-Arg-Trp-Cys)-$NH_2$;

(SEQ ID NO: 19)
Ac-Nle-c(D-Cys-D-Ala-His-D-Phe-Arg-Trp-Cys)-$NH_2$;

(SEQ ID NO: 20)
Ac-Nle-c(D-Cys-β-Ala-His-D-Phe-Arg-Trp-Cys)-$NH_2$;

(SEQ ID NO: 21)
Ac-Nle-c(D-Cys-Gaba-His-D-Phe-Arg-Trp-Cys)-$NH_2$;

(SEQ ID NO: 22)
Ac-Nle-c(D-Cys-Aib-His-D-Phe-Arg-Trp-Cys)-$NH_2$;

(SEQ ID NO: 23)
Ac-Nle-c(D-Cys-Gly-His-D-Phe-Arg-Trp-Cys)-$NH_2$;

(SEQ ID NO: 24)
Ac-Nle-c(Cys-D-Ala-His-D-Phe-Arg-Trp-D-Cys)-$NH_2$;

(SEQ ID NO: 25)
Ac-Nle-c(Cys-β-Ala-His-D-Phe-Arg-Trp-D-Cys)-$NH_2$;

(SEQ ID NO: 26)
Ac-Nle-c(Cys-Gaba-His-D-Phe-Arg-Trp-D-Cys)-$NH_2$;

(SEQ ID NO: 27)
Ac-Nle-c(Cys-Aib-His-D-Phe-Arg-Trp-D-Cys)-$NH_2$;

(SEQ ID NO: 28)
Ac-Nle-c(Cys-Gly-His-D-Phe-Arg-Trp-D-Cys)-$NH_2$;

(SEQ ID NO: 29)
Ac-Nle-c(D-Cys-Ala-His-D-Phe-Arg-Trp-D-Cys)-$NH_2$;

(SEQ ID NO: 30)
Ac-Nle-c(D-Cys-D-Ala-His-D-Phe-Arg-Trp-D-Cys)-$NH_2$;

(SEQ ID NO: 31)
Ac-Nle-c(D-Cys-β-Ala-His-D-Phe-Arg-Trp-D-Cys)-$NH_2$;

(SEQ ID NO: 32)
Ac-Nle-c(D-Cys-Gaba-His-D-Phe-Arg-Trp-D-Cys)-$NH_2$;

-continued (SEQ ID NO: 33)
Ac-Nle-c(D-Cys-Aib-His-D-Phe-Arg-Trp-D-Cys)-$NH_2$;

(SEQ ID NO: 34)
Ac-Oic-c(Asp-His-D-Phe-Arg-Trp-Gaba-Lys)-$NH_2$;

(SEQ ID NO: 35)
Ac-Chg-c(Asp-His-D-Phe-Arg-Trp-Gaba-Lys)-$NH_2$;

(SEQ ID NO: 36)
Ac-hCha-c(Asp-His-D-Phe-Arg-Trp-Gaba-Lys)-$NH_2$;

(SEQ ID NO: 37)
Ac-D-Cha-c(Asp-His-D-Phe-Arg-Trp-Gaba-Lys)-$NH_2$;

(SEQ ID NO: 38)
Ac-D-hCha-c(Asp-His-D-Phe-Arg-Trp-Gaba-Lys)-$NH_2$;

(SEQ ID NO: 39)
Ac-Nip-c(Asp-His-D-Phe-Arg-Trp-Gaba-Lys)-$NH_2$;

(SEQ ID NO: 40)
Ac-hPro-c(Asp-His-D-Phe-Arg-Trp-Gaba-Lys)-$NH_2$;

(SEQ ID NO: 41)
Ac-hLeu-c(Asp-His-D-Phe-Arg-Trp-Gaba-Lys)-$NH_2$;

(SEQ ID NO: 42)
Ac-Phe-c(Asp-His-D-Phe-Arg-Trp-Gaba-Lys)-$NH_2$;

(SEQ ID NO: 43)
Ac-D-Phe-c(Asp-His-D-Phe-Arg-Trp-Gaba-Lys)-$NH_2$;

(SEQ ID NO: 44)
Ac-D-Chg-c(Asp-His-D-Phe-Arg-Trp-Gaba-Lys)-$NH_2$;

(SEQ ID NO: 45)
n-butanoyl-Cha-c(Asp-His-D-Phe-Arg-Trp-Gaba-Lys)-$NH_2$;

(SEQ ID NO: 46)
n-butyryl-Cha-c(Asp-His-D-Phe-Arg-Trp-Gaba-Lys)-$NH_2$;

(SEQ ID NO: 47)
Ac-hPhe-c(Asp-His-D-Phe-Arg-Trp-Gaba-Lys)-$NH_2$;

(SEQ ID NO: 48)
Ac-β-hMet-c(Asp-His-D-Phe-Arg-Trp-Gaba-Lys)-$NH_2$;

(SEQ ID NO: 49)
Ac-Gaba-c(Asp-His-D-Phe-Arg-Trp-Gaba-Lys)-$NH_2$;

(SEQ ID NO: 50)
Ac-Cha-c(Asp-His-D-Phe-Arg-D-Trp-Ala-Lys)-$NH_2$;

(SEQ ID NO: 51)
Ac-hCha-c(Asp-His-D-Phe-Arg-D-Trp-Ala-Lys)-$NH_2$;

(SEQ ID NO: 52)
Ac-Leu-c(Asp-His-D-Phe-Arg-D-Trp-Ala-Lys)-$NH_2$;

(SEQ ID NO: 53)
Ac-hLeu-c(Asp-His-D-Phe-Arg-D-Trp-Ala-Lys)-$NH_2$;

(SEQ ID NO: 54)
Ac-Phe-c(Asp-His-D-Phe-Arg-D-Trp-Ala-Lys)-$NH_2$;

(SEQ ID NO: 55)
Ac-Nle-c(Asp-His-D-Phe-Arg-D-Trp-D-Ala-Lys)-$NH_2$;

(SEQ ID NO: 56)
Ac-Nle-c(Asp-His-D-Phe-Arg-D-Trp-β-Ala-Lys)-$NH_2$;

(SEQ ID NO: 57)
Ac-Nle-c(Asp-His-D-Phe-Arg-D-Trp-Gaba-Lys)-$NH_2$;

(SEQ ID NO: 58)
Ac-Nle-c(Asp-His-D-Phe-Arg-D-Trp-Aha-Lys)-$NH_2$;

(SEQ ID NO: 59)
Ac-Nle-c(Asp-His-D-Phe-Arg-D-Trp-Apn-Lys)-$NH_2$;

-continued (SEQ ID NO: 60)
Ac-Nle-c(Cys-His-D-Phe-Arg-D-Trp-Apn-Cys)-$NH_2$;

(SEQ ID NO: 61)
Ac-Nle-c(Cys-His-D-Phe-Arg-D-Trp-Gaba-Cys)-$NH_2$;

(SEQ ID NO: 62)
Ac-Nle-c(Cys-His-D-Phe-Arg-D-Trp-Ahx-Cys)-$NH_2$;

(SEQ ID NO: 63)
Ac-Nle-c(Cys-His-D-Phe-Arg-D-Trp-β-Ala-Cys)-$NH_2$;

(SEQ ID NO: 64)
Ac-Nle-c(Cys-His-D-Phe-Arg-D-Trp-D-Ala-Cys)-$NH_2$;

(SEQ ID NO: 65)
Ac-Nle-c(Cys-D-Ala-His-D-2-Nal-Arg-Trp-Cys)-$NH_2$;

(SEQ ID NO: 66)
Ac-Nle-c(Cys-D-Ala-His-D-2-Nal-Arg-2-Nal-Cys)-$NH_2$;

(SEQ ID NO: 67)
Ac-Nle-c(Cys-D-Ala-His-D-2-Nal-Arg-1-Nal-Cys)-$NH_2$;

(SEQ ID NO: 68)
n-butanoyl-Nle-c(Cys-D-Ala-His-D-Phe-Arg-2-Nal-Cys)-$NH_2$;

(SEQ ID NO: 69)
n-butanoyl-Nle-c(Cys-D-Ala-His-D-Phe-Arg-Trp-Cys)-$NH_2$;

(SEQ ID NO: 70)
Ac-Nle-c(Cys-D-Ala-His-D-Phe-Arg-2-Nal-Cys)-$NH_2$;

(SEQ ID NO: 71)
Ac-Nle-c(Cys-D-Ala-His-D-Phe-Arg-1-Nal-Cys)-$NH_2$;

(SEQ ID NO: 72)
Ac-Nle-c(Cys-D-Ala-His-D-Phe-Arg-Bal-Cys)-$NH_2$;

(SEQ ID NO: 73)
Ac-Nle-c(Cys-D-Glu-His-D-Phe-Arg-Trp-Cys)-$NH_2$;

(SEQ ID NO: 74)
Ac-Nle-c(Asp-His-D-Phe-Arg-Trp-D-Ala-Lys)-$NH_2$;

(SEQ ID NO: 75)
Ac-Nle-c(Cys-D-Ala-His-D-2-Nal-Arg-Bal-Cys)-$NH_2$;

(SEQ ID NO: 76)
Ac-Nle-c(Pen-D-Ala-His-D-Phe-Arg-Trp-Cys)-$NH_2$;

(SEQ ID NO: 77)
Ac-Nle-c(Cys-D-Ala-His-D-Phe-Arg-Trp-Pen)-$NH_2$;

(SEQ ID NO: 78)
Ac-Nle-c(Pen-D-Ala-His-D-Phe-Arg-Trp-Pen)-$NH_2$;

(SEQ ID NO: 79)
D-Phe-c(Cys-His-D-Phe-hArg-Trp-β-Ala-D-Cys)-Thr-$NH_2$;

(SEQ ID NO: 80)
D-Phe-c(Cys-His-D-(Et)Tyr-Arg-Trp-β-Ala-D-Cys)-Thr-$NH_2$;

(SEQ ID NO: 81)
D-Phe-c(Cys-His-D-Phe-Arg-Bip-β-Ala-D-Cys)-Thr-$NH_2$;

(SEQ ID NO: 82)
D-Phe-c(Cys-His-D-(Et)Tyr-hArg-Trp-β-Ala-D-Cys)-Thr-$NH_2$;

(SEQ ID NO: 83)
D-Phe-c(Cys-His-D-Phe-hArg-Bip-β-Ala-D-Cys)-Thr-$NH_2$;

(SEQ ID NO: 84)
D-Phe-c(Cys-His-D-(Et)Tyr-hArg-Bip-β-Ala-D-Cys)-Thr-$NH_2$;

(SEQ ID NO: 85)
Nle-c(Cys-His-D-Phe-Arg-Trp-Apn-Cys)-$NH_2$;

(SEQ ID NO: 86)
Ac-Nle-c(Asp-D-Ala-His-D-Phe-Arg-Trp-Lys)-$NH_2$;

-continued

Ac-Nle-c(Asp-D-Ala-His-D-Phe-Arg-Bal-Lys)-$NH_2$; (SEQ ID NO: 87)

Ac-Nle-c(Cys-D-Ala-His-D-Phe-Arg-Trp-Pen)-OH; (SEQ ID NO: 88)

Ac-Nle-c(Cys-D-Abu-His-D-Phe-Arg-Trp-Cys)-$NH_2$; (SEQ ID NO: 89)

Ac-Nle-c(Cys-D-Val-His-D-Phe-Arg-Trp-Cys)-$NH_2$; (SEQ ID NO: 90)

Ac-Nle-c(Cys-D-Ile-His-D-Phe-Arg-Trp-Cys)-$NH_2$; (SEQ ID NO: 91)

Ac-Nle-c(Cys-D-Leu-His-D-Phe-Arg-Trp-Cys)-$NH_2$; (SEQ ID NO: 92)

Ac-Nle-c(Cys-D-Tle-His-D-Phe-Arg-Trp-Cys)-$NH_2$; (SEQ ID NO: 93)

Ac-Nle-c(Cys-D-Cha-His-D-Phe-Arg-Trp-Cys)-$NH_2$; (SEQ ID NO: 94)

Ac-Nle-c(Pen-His-D-Phe-Arg-Trp-Gaba-Cys)-$NH_2$; (SEQ ID NO: 95)

Ac-Nle-c(Cys-His-D-Phe-Arg-Trp-Gaba-Pen)-$NH_2$; (SEQ ID NO: 96)

Ac-Nle-c(Pen-His-D-Phe-Arg-Trp-Gaba-Pen)-$NH_2$; (SEQ ID NO: 97)

Ac-Leu-c(Cys-His-D-Phe-Arg-Trp-Gaba-Cys)-$NH_2$; (SEQ ID NO: 98)

Ac-Cha-c(Cys-His-D-Phe-Arg-Trp-Gaba-Cys)-$NH_2$; (SEQ ID NO: 99)

Ac-Ile-c(Cys-His-D-Phe-Arg-Trp-Gaba-Cys)-$NH_2$; (SEQ ID NO: 100)

Ac-Phe-c(Cys-His-D-Phe-Arg-Trp-Gaba-Cys)-$NH_2$; (SEQ ID NO: 101)

Ac-Val-c(Cys-His-D-Phe-Arg-Trp-Gaba-Cys)-$NH_2$; (SEQ ID NO: 102)

Ac-2-Nal-c(Cys-His-D-Phe-Arg-Trp-Gaba-Cys)-$NH_2$; (SEQ ID NO: 103)

Nle-c(Cys-His-D-Phe-Arg-Trp-Gaba-Cys)-$NH_2$; (SEQ ID NO: 104)

Phe-c(Cys-His-D-Phe-Arg-Trp-Gaba-Cys)-$NH_2$; (SEQ ID NO: 105)

Ac-Nle-c(Cys-β-Pal-D-Phe-Arg-Trp-Gaba-Cys)-$NH_2$; (SEQ ID NO: 106)

Ac-Nle-c(Cys-D-Ala-His-D-Phe-Arg-Trp-Cys)-OH; (SEQ ID NO: 107)

Ac-Nle-c(Cys-His-Phe-Arg-D-Trp-Gaba-Cys)-$NH_2$; (SEQ ID NO: 108)

Ac-Nle-c(Asp-His-D-2-Nal-Arg-Trp-Ala-Lys)-$NH_2$; (SEQ ID NO: 109)

Ac-Nle-c(Asp-His-D-2-Nal-Arg-Trp-β-Ala-Lys)-$NH_2$; (SEQ ID NO: 110)

Ac-Nle-c(Cys-His-D-2-Nal-Arg-Trp-Gaba-Cys)-$NH_2$; (SEQ ID NO: 111)

Ac-Nle-c(Cys-His-D-2-Nal-Arg-Trp-Ahx-Cys)-$NH_2$; (SEQ ID NO: 112)

Ac-hPhe-c(Asp-His-D-2-Nal-Arg-Trp-Gaba-Lys)-$NH_2$; (SEQ ID NO: 113)

-continued (SEQ ID NO: 114)
Ac-Cha-c(Asp-His-D-2-Nal-Arg-Trp-Gaba-Lys)-$NH_2$;

(SEQ ID NO: 115)
Ac-Nle-c(Asp-His-D-Phe-Arg-Trp-β-Ala-Lys)-OH;

(SEQ ID NO: 116)
Ac-Nle-c(Cys-His-D-Phe-Arg-Trp-Ahx-Cys)-OH;

(SEQ ID NO: 117)
D-Phe-c(Cys-His-D-Phe-Arg-Trp-Ala-D-Cys)-Thr-OH;

(SEQ ID NO: 118)
D-Phe-c(Cys-His-D-Phe-Arg-Trp-β-Ala-D-Cys)-Thr-OH;

(SEQ ID NO: 119)
D-Phe-c(Cys-His-D-Phe-Arg-Trp-Gaba-D-Cys)-Thr-OH;

(SEQ ID NO: 120)
Ac-Nle-c(Cys-His-D-Phe-Arg-Trp-Apn-Cys)-OH;

(SEQ ID NO: 121)
Ac-Nle-c(Asp-His-D-Phe-Arg-Trp-Apn-Lys)-OH;

(SEQ ID NO: 122)
Ac-Cha-c(Asp-His-D-Phe-Arg-Trp-Gaba-Lys)-OH;

(SEQ ID NO: 123)
Ac-Nle-c(Asp-His-D-Phe-Arg-Trp-Gaba-Lys)-OH;

(SEQ ID NO: 124)
Ac-Chg-c(Asp-His-D-Phe-Arg-Trp-Gaba-Lys)-OH;

(SEQ ID NO: 125)
Ac-D-Cha-c(Asp-His-D-Phe-Arg-Trp-Gaba-Lys)-OH;

(SEQ ID NO: 126)
Ac-hCha-c(Asp-His-D-Phe-Arg-Trp-Gaba-Lys)-OH;

(SEQ ID NO: 127)
Ac-D-Chg-c(Asp-His-D-Phe-Arg-Trp-Gaba-Lys)-OH;

(SEQ ID NO: 128)
Ac-hPhe-c(Asp-His-D-Phe-Arg-Trp-Gaba-Lys)-OH;

(SEQ ID NO: 129)
Ac-Nle-c(Cys-His-D-Phe-Arg-D-Trp-Gaba-Cys)-OH;

(SEQ ID NO: 130)
Ac-Nle-c(Cys-His-D-Phe-Arg-D-Trp-Ahx-Cys)-OH;

(SEQ ID NO: 131)
Ac-Nle-c(Cys-His-D-Phe-Arg-D-Trp-β-Ala-Cys)-OH;

(SEQ ID NO: 132)
Ac-Nle-c(Cys-His-D-Phe-Arg-D-Trp-D-Ala-Cys)-OH;

(SEQ ID NO: 133)
Ac-Nle-c(Cys-D-Ala-His-D-2-Nal-Arg-Trp-Cys)-OH;

(SEQ ID NO: 134)
Ac-Nle-c(Cys-D-Ala-His-D-2-Nal-Arg-2-Nal-Cys)-OH;

(SEQ ID NO: 135)
Ac-Nle-c(Cys-D-Ala-His-D-2-Nal-Arg-1-Nal-Cys)-OH;

(SEQ ID NO: 136)
Ac-Nle-c(Cys-D-Ala-His-D-2-Nal-Arg-Bal-Cys)-OH;

(SEQ ID NO: 137)
Ac-Nle-c(Pen-D-Ala-His-D-Phe-Arg-Trp-Cys)-OH;

(SEQ ID NO: 138)
Ac-Nle-c(Cys-His-D-Phe-Arg-Trp-Gaba-Pen)-OH;

(SEQ ID NO: 139)
Ac-Arg-c(Cys-D-Ala-His-D-2-Nal-Arg-Trp-Cys)-$NH_2$;

(SEQ ID NO: 140)
Ac-Arg-c(Cys-D-Ala-His-D-Phe-Arg-Trp-Cys)-$NH_2$;

-continued (SEQ ID NO: 141)
Ac-D-Arg-c(Cys-D-Ala-His-D-Phe-Arg-Trp-Cys)-$NH_2$;

(SEQ ID NO: 142)
Ac-D-Arg-c(Cys-D-Ala-His-D-Phe-Arg-Trp-Pen)-$NH_2$;

(SEQ ID NO: 143)
Ac-D-Arg-c(Cys-His-D-Phe-Arg-Trp-Gaba-Pen)-$NH_2$;

(SEQ ID NO: 144)
Ac-Arg-c(Cys-His-D-Phe-Arg-Trp-Gaba-Pen)-$NH_2$;

(SEQ ID NO: 145)
Ac-Arg-c(Cys-D-Ala-His-D-Phe-Arg-Trp-Pen)-$NH_2$;

(SEQ ID NO: 146)
Ac-D-Arg-c(Asp-His-D-Phe-Arg-Trp-Ala-Lys)-$NH_2$;

(SEQ ID NO: 147)
Ac-Arg-c(Asp-His-D-Phe-Arg-Trp-Ala-Lys)-$NH_2$;

(SEQ ID NO: 148)
Ac-Nle-c(Cys-D-Ala-His-D-Phe-Arg-Trp-Gly-Cys)-$NH_2$;

(SEQ ID NO: 149)
Ac-Nle-c(Cys-D-Ala-His-D-Phe-Arg-Trp-D-Ala-Cys)-$NH_2$;

(SEQ ID NO: 150)
Ac-Nle-c(Cys-D-Ala-His-D-Phe-Arg-Trp-β-Ala-Cys)-$NH_2$;

(SEQ ID NO: 151)
Ac-Nle-c(Cys-D-Ala-His-D-Phe-Arg-Trp-Gaba-Cys)-$NH_2$;

(SEQ ID NO: 152)
Ac-Nle-c(Cys-D-Ala-His-D-Phe-Arg-Trp-Apn-Cys)-$NH_2$;

(SEQ ID NO: 153)
Ac-c(Cys-Glu-His-D-Phe-Arg-Trp-Ala-Cys)-$NH_2$;

(SEQ ID NO: 154)
Ac-c(Cys-Glu-His-D-Phe-Arg-2-Nal-Ala-Cys)-$NH_2$;

(SEQ ID NO: 155)
Ac-c(Cys-D-Ala-His-D-Phe-Arg-Trp-Ala-Cys)-$NH_2$;

(SEQ ID NO: 156)
Ac-c(Cys-D-Ala-His-D-Phe-Arg-2-Nal-Ala-Cys)-$NH_2$;

(SEQ ID NO: 157)
Ac-Nle-c(Cys-D-Ala-His-D-Phe-Arg-Trp-Ala-Cys)-$NH_2$;

(SEQ ID NO: 158)
Ac-Nle-c(Asp-D-Ala-His-D-Phe-Arg-Bal-Ala-Lys)-$NH_2$;

(SEQ ID NO: 159)
Tyr-Gly-Arg-$(Lys)_2$-$(Arg)_2$-Gln-$(Arg)_3$-Nle-c(Asp-His-D-2-Nal-Arg-Trp-Lys)-$NH_2$;

(SEQ ID NO: 160)
Tyr-Gly-Arg-$(Lys)_2$-$(Arg)_2$-Gln-$(Arg)_3$-Doc-Nle-c(Asp-His-D-2-Nal-Arg-Trp-Lys)-$NH_2$;

(SEQ ID NO: 161)
Nle-c(Asp-His-D-2-Nal-Arg-Trp-Lys)-β-Ala-Tyr-Gly-Arg-$(Lys)_2$-$(Arg)_2$-Gln-$(Arg)_3$-$NH_2$;

(SEQ ID NO: 162)
Ac-Nle-c(Asp-His-D-2-Nal-Arg-Trp-Lys)-β-Ala-Tyr-Gly-Arg-$(Lys)_2$-$(Arg)_2$-Gln-$(Arg)_3$-$NH_2$;

(SEQ ID NO: 163)
Nle-c(Asp-His-D-2-Nal-Arg-Trp-Lys)-$(Doc)_2$-Tyr-Gly-Arg-$(Lys)_2$-$(Arg)_2$-Gln-$(Arg)_3$-$NH_2$;

(SEQ ID NO: 164)
Ac-Nle-c(Asp-His-D-2-Nal-Arg-Trp-Lys)-$(Pro)_2$-Lys-Asp-Tyr-Gly-Arg-$(Lys)_2$-$(Arg)_2$-Gln-$(Arg)_3$-$NH_2$;

-continued (SEQ ID NO: 165)
Ac-c(Cys-Glu-His-D-2-Nal-Arg-Trp-Gly-Cys)-$(Pro)_2$-Lys-Asp-Tyr-Gly-Arg-$(Lys)_2$-$(Arg)_2$-Gln-$(Arg)_3$-$NH_2$;

(SEQ ID NO: 166)
Ac-Nle-c(Asp-His-D-2-Nal-Arg-Trp-Lys)-(β-Ala)2-Tyr-Gly-Arg-$(Lys)_2$-$(Arg)_2$-Gln-$(Arg)_3$-$NH_2$;

(SEQ ID NO: 167)
Ac-Nle-c(Asp-His-D-2-Nal-Arg-Trp-Lys)-$(Pro)_2$-Lys-Asp-Doc-Tyr-Gly-Arg-$(Lys)_2$-$(Arg)_2$-Gln-$(Arg)_3$-$NH_2$;

(SEQ ID NO: 168)
Ac-c(Cys-Glu-His-D-2-Nal-Arg-Trp-Gly-Cys)-$(Pro)_2$-Lys-Asp-Doc-Tyr-Gly-Arg-$(Lys)_2$-$(Arg)_2$-Gln-$(Arg)_3$-$NH_2$;

(SEQ ID NO: 169)
Ac-c(Cys-Glu-His-D-2-Nal-Arg-Trp-Ala-Cys)-$(Pro)_2$-Lys-Asp-β-Ala-Tyr-Gly-Arg-$(Lys)_2$-$(Arg)_2$-Gln-$(Arg)_3$-$NH_2$;

(SEQ ID NO: 170)
Ac-c(Cys-Glu-His-D-2-Nal-Arg-Trp-Ala-Cys)-$(Pro)_2$-Lys-Asp-Doc-Tyr-Gly-Arg-$(Lys)_2$-$(Arg)_2$-Gln-$(Arg)_3$-$NH_2$;

(SEQ ID NO: 171)
Ac-Nle-c(Asp-His-D-2-Nal-Arg-Trp-Lys)-$(Doc)_2$-Tyr-Gly-Arg-$(Lys)_2$-$(Arg)_2$-Gln-$(Arg)_3$-$NH_2$;

(SEQ ID NO: 172)
Ac-c(Cys-Glu-His-D-2-Nal-Arg-2-Nal-Ala-Cys)-$(Pro)_2$-Lys-Asp-β-Ala-Tyr-Gly-Arg-$(Lys)_2$-$(Arg)_2$-Gln-$(Arg)_3$-$NH_2$;

(SEQ ID NO: 173)
Ac-c(Cys-Glu-His-D-2-Nal-Arg-Bal-Ala-Cys)-$(Pro)_2$-Lys-Asp-β-Ala-$(Arg)_5$-Gln-$(Arg)_3$-$NH_2$;

(SEQ ID NO: 174)
Ac-c(Cys-Glu-His-D-2-Nal-Arg-Bal-Ala-Cys)-$(Pro)_2$-Lys-Asp-β-Ala-Gly-$(Arg)_5$-Gln-$(Arg)_3$-$NH_2$;

(SEQ ID NO: 175)
Ac-c(Cys-Glu-His-D-2-Nal-Arg-Bal-Ala-Cys)-$(Pro)_2$-Lys-Asp-β-Ala-Tyr-Gly-$(Arg)_5$-Gln-$(Arg)_3$-$NH_2$;

(SEQ ID NO: 176)
Ac-c(Cys-Glu-His-D-2-Nal-Arg-Trp-Ala-Cys)-$(Pro)_2$-Lys-Asp-β-Ala-Tyr-Gly-Arg-$(Lys)_2$-Arg-Gln-$(Arg)_4$-$NH_2$;

(SEQ ID NO: 177)
Ac-c(Cys-Glu-His-D-2-Nal-Arg-Trp-Ala-Cys)-$(Pro)_2$-Lys-Asp-β-Ala-Tyr-Gly-Arg-$(Lys)_2$-Gln-$(Arg)_5$-$NH_2$;

(SEQ ID NO: 178)
Ac-c(Cys-Glu-His-D-2-Nal-Arg-Trp-Ala-Cys)-$(Pro)_2$-Lys-Asp-β-Ala-Tyr-Gly-Arg-Lys-Gln-Lys-$(Arg)_5$-$NH_2$;

(SEQ ID NO: 179)
Ac-c(Cys-Glu-His-D-2-Nal-Arg-Trp-Ala-Cys)-$(Pro)_2$-Lys-Asp-β-Ala-Tyr-Gly-Arg-$(Lys)_2$-$(Arg)_4$-Gln-Arg-$NH_2$;

(SEQ ID NO: 180)
Ac-c(Cys-Glu-His-D-2-Nal-Arg-Bal-Ala-Cys)-$(Pro)_2$-Lys-Asp-β-Ala-Tyr-Aib-Arg-$(Lys)_2$-$(Arg)_2$-Gln-$(Arg)_3$-$NH_2$;

(SEQ ID NO: 181)
Ac-c(Cys-Glu-His-D-2-Nal-Arg-1-Nal-Ala-Cys)-$(Pro)_2$-Arg-Asp-β-Ala-$(Arg)_5$-Gln-$(Arg)_3$-$NH_2$;

(SEQ ID NO: 182)
Ac-c(Cys-Glu-His-D-2-Nal-Arg-1-Nal-Ala-Cys)-$(Pro)_2$-Lys-Asp-β-Ala-$(Arg)_5$-Gln-$(Arg)_3$-$NH_2$;

(SEQ ID NO: 183)
Ac-c(Cys-Glu-His-D-2-Nal-Arg-1-Nal-Ala-Cys)-$(Pro)_2$-Lys-Asp-β-Ala-$(Arg)_6$-Gln-$(Arg)_3$-$NH_2$;

(SEQ ID NO: 184)
Ac-c(Cys-Glu-His-D-2-Nal-Arg-2-Nal-Ala-Cys)-$(Pro)_2$-Arg-Asp-β-Ala-$(Arg)_5$-Gln-$(Arg)_3$-$NH_2$;

-continued (SEQ ID NO: 185)
Ac-c(Cys-Glu-His-D-2-Nal-Arg-2-Nal-Ala-Cys)-$(Pro)_2$-Lys-Asp-β-Ala-$(Arg)_5$-Gln-$(Arg)_3$-$NH_2$;

(SEQ ID NO: 186)
Ac-c(Cys-Glu-His-D-2-Nal-Arg-2-Nal-Ala-Cys)-$(Pro)_2$-Lys-Asp-β-Ala-$(Arg)_6$-Gln-$(Arg)_3$-$NH_2$;

(SEQ ID NO: 187)
Ac-c(Cys-Glu-His-D-2-Nal-Arg-Bal-Ala-Cys)-$(Pro)_2$-Arg-Asp-β-Ala-$(Arg)_6$-Gln-$(Arg)_3$-$NH_2$;

(SEQ ID NO: 188)
Ac-c(Cys-Glu-His-D-2-Nal-Arg-Bal-Ala-Cys)-$(Pro)_2$-Arg-Asp-β-Ala-$(Arg)_5$-Gln-$(Arg)_3$-$NH_2$;

(SEQ ID NO: 189)
Ac-c(Cys-Glu-His-D-2-Nal-Arg-Bal-Ala-Cys)-$(Pro)_2$-Lys-Asp-β-Ala-$(Arg)_6$-Gln-$(Arg)_3$-$NH_2$;

(SEQ ID NO: 190)
Ac-c(Cys-Glu-His-D-2-Nal-Arg-Trp-Ala-Cys)-$(Pro)_2$-Lys-Asp-β-Ala-Tyr-Gly-Arg-$(Lys)_2$-$(Arg)_3$-Gln-$(Arg)_2$-$NH_2$;

(SEQ ID NO: 191)
Ac-c(Cys-Glu-His-D-2-Nal-Arg-Trp-Ala-Cys)-$(Pro)_2$-Lys-Asp-β-Ala-Tyr-Gly-Arg-Gln-$(Lys)_2$-$(Arg)_5$-$NH_2$;

(SEQ ID NO: 192)
Ac-c(Cys-Glu-His-D-2-Nal-Arg-Trp-Ala-Cys)-$(Pro)_2$-Lys-Asp-β-Ala-Tyr-Gly-Arg-(Lys)2-$(Arg)_5$-Gln-$NH_2$;

(SEQ ID NO: 193)
Ac-c(Cys-Glu-His-D-2-Nal-Arg-1-Nal-Ala-Cys)-$(Pro)_2$-Lys-Asp-β-Ala-Tyr-Gly-Arg-$(Lys)_2$-$(Arg)_2$-Gln-(Arg)3-$NH_2$;;

(SEQ ID NO: 194)
Ac-c(Cys-Glu-His-D-2-Nal-Arg-Bal-Ala-Cys)-$(Pro)_2$-Lys-Asp-β-Ala-Tyr-Gly-Arg-$(Lys)_2$-$(Arg)_2$-Gln-$(Arg)_3$-$NH_2$;

(SEQ ID NO: 195)
Ac-c(Cys-Glu-His-D-2-Nal-Arg-1-Nal-Ala-Cys)-$(Pro)_2$-Lys-Asp-β-Ala-$(Arg)_2$-Lys-$(Arg)_2$-Gln-(Arg)3-$NH_2$;

(SEQ ID NO: 196)
Ac-c(Cys-Glu-His-D-2-Nal-Arg-1-Nal-Ala-Cys)-$(Pro)_2$-Lys-Asp-β-Ala-Arg-Lys-$(Arg)_3$-Gln-$(Arg)_3$-$NH_2$;

(SEQ ID NO: 197)
Ac-c(Cys-Glu-His-D-2-Nal-Arg-2-Nal-Ala-Cys)-$(Pro)_2$-Lys-Asp-β-Ala-$(Arg)_2$-Lys-$(Arg)_2$-Gln-$(Arg)_3$-$NH_2$;

(SEQ ID NO: 198)
Ac-c(Cys-Glu-His-D-2-Nal-Arg-2-Nal-Ala-Cys)-$(Pro)_2$-Lys-Asp-β-Ala-Tyr-Gly-$(Arg)_2$-Lys-$(Arg)_2$-Gln-$(Arg)_3$-$NH_2$;

(SEQ ID NO: 199)
Ac-c(Cys-Glu-His-D-2-Nal-Arg-2-Nal-Ala-Cys)-$(Pro)_2$-Lys-Asp-β-Ala-Gly-$(Arg)_2$-Lys-$(Arg)_2$-Gln-$(Arg)_3$-$NH_2$;

(SEQ ID NO: 200)
Ac-c(Cys-Glu-His-D-2-Nal-Arg-2-Nal-Ala-Cys)-$(Pro)_2$-Lys-Asp-β-Ala-Gly-Arg-Lys-$(Arg)_3$-Gln-$(Arg)_3$-$NH_2$;

(SEQ ID NO: 201)
Ac-c(Cy s-Glu-His-D-2-Nal-Arg-1-Nal-Ala-Cys)-$(Pro)_2$-Lys-Asp-β-Ala-Tyr-Gly-$(Arg)_2$-Lys-$(Arg)_2$-Gln-$(Arg)_3$-$NH_2$;

(SEQ ID NO: 202)
Ac-c(Cys-Glu-His-D-2-Nal-Arg-1-Nal-Ala-Cys)-$(Pro)_2$-Lys-Asp-β-Ala-Tyr-Gly-Arg-Lys-$(Arg)_3$-Gln-$(Arg)_3$-$NH_2$;

(SEQ ID NO: 203)
Ac-c(Cys-Glu-His-D-2-Nal-Arg-1-Nal-Ala-Cys)-$(Pro)_2$-Lys-Asp-β-Ala-Gly-$(Arg)_2$-Lys-$(Arg)_2$-Gln-$(Arg)_3$-$NH_2$;

(SEQ ID NO: 204)
Ac-c(Cys-Glu-His-D-2-Nal-Arg-1-Nal-Ala-Cys)-$(Pro)_2$-Lys-Asp-β-Ala-Gly-Arg-Lys-$(Arg)_3$-Gln-$(Arg)_3$-$NH_2$;

-continued (SEQ ID NO: 205)
Ac-c(Cys-Glu-His-D-2-Nal-Arg-2-Nal-Ala-Cys)-$(Pro)_2$-Lys-Asp-β-Ala-$(Arg)_2$-Lys-$(Arg)_2$-Gln-$(Arg)_3$-$NH_2$;

(SEQ ID NO: 206)
Ac-c(Cys-Glu-His-D-2-Nal-Arg-2-Nal-Ala-Cys)-$(Pro)_2$-Lys-Asp-β-Ala-Arg-Lys-$(Arg)_3$-Gln-$(Arg)_3$-$NH_2$;

(SEQ ID NO: 207)
Ac-c(Cys-Glu-His-D-2-Nal-Arg-2-Nal-Ala-Cys)-$(Pro)_2$-Lys-Asp-β-Ala-Tyr-Gly-Arg-Lys-$(Arg)_3$-Gln-$(Arg)_3$-$NH_2$;

(SEQ ID NO: 208)
Ac-c(Cys-Glu-His-D-2-Nal-Arg-Bal-Ala-Cys)-$(Pro)_2$-Lys-Asp-β-Ala-$(Arg)_2$-Lys-$(Arg)_2$-Gln-$(Arg)_3$-$NH_2$;

(SEQ ID NO: 209)
Ac-c(Cys-Glu-His-D-2-Nal-Arg-Bal-Ala-Cys)-$(Pro)_2$-Lys-Asp-β-Ala-Arg-Lys-$(Arg)_3$-Gln-$(Arg)_3$-$NH_2$;

(SEQ ID NO: 210)
Ac-c(Cys-Glu-His-D-2-Nal-Arg-Bal-Ala-Cys)-$(Pro)_2$-Lys-Asp-β-Ala-Tyr-Gly-$(Arg)_2$-Lys-$(Arg)_2$-Gln-$(Arg)_3$-$NH_2$;

(SEQ ID NO: 211)
Ac-c(Cys-Glu-His-D-2-Nal-Arg-Bal-Ala-Cys)-$(Pro)_2$-Lys-Asp-β-Ala-Tyr-Gly-Arg-Lys-$(Arg)_3$-Gln-$(Arg)_3$-$NH_2$;

(SEQ ID NO: 212)
Ac-c(Cys-Glu-His-D-2-Nal-Arg-Bal-Ala-Cys)-$(Pro)_2$-Lys-Asp-β-Ala-Gly-$(Arg)_2$-Lys-$(Arg)_2$-Gln-$(Arg)_3$-$NH_2$;

(SEQ ID NO: 213)
Ac-c(Cys-Glu-His-D-2-Nal-Arg-Bal-Ala-Cys)-$(Pro)_2$-Lys-Asp-β-Ala-Gly-Arg-Lys-$(Arg)_3$-Gln-$(Arg)_3$-$NH_2$;

(SEQ ID NO: 214)
Ac-c(Cys-Glu-His-D-2-Nal-Arg-Trp-Ala-Cys)-$(Pro)_2$-Lys-Asp-β-Ala-$(Arg)_5$-Gln-$(Arg)_3$-$NH_2$;

(SEQ ID NO: 215)
Ac-c(Cys-Glu-His-D-2-Nal-Arg-Trp-Ala-Cys)-$(Pro)_2$-Arg-Asp-β-Ala-$(Arg)_5$-Gln-$(Arg)_3$-$NH_2$;

(SEQ ID NO: 216)
Ac-c(Cys-Glu-His-D-2-Nal-Arg-Trp-Ala-Cys)-$(Pro)_2$-Lys-Asp-β-Ala-Tyr-Gly-$(Arg)_5$-Gln-$(Arg)_3$-$NH_2$;

(SEQ ID NO: 217)
Ac-c(Cys-Glu-His-D-2-Nal-Arg-Trp-Ala-Cys)-$(Pro)_2$-Arg-Asp-β-Ala-Tyr-Gly-$(Arg)_5$-Gln-$(Arg)_3$-$NH_2$;

(SEQ ID NO: 218)
Ac-c(Cys-Glu-His-D-2-Nal-Arg-Trp-Ala-Cys)-$(Pro)_2$-Lys-Asp-β-Ala-$(Arg)_5$-Gln-$(Arg)_4$-$NH_2$;

(SEQ ID NO: 219)
Ac-c(Cys-Glu-His-D-2-Nal-Arg-Trp-Ala-Cys)-$(Pro)_2$-Arg-Asp-β-Ala-$(Arg)_5$-Gln-$(Arg)_4$-$NH_2$;

(SEQ ID NO: 220)
Ac-c(Cys-Glu-His-D-2-Nal-Arg-Trp-Ala-Cys)-$(Pro)_2$-Lys-Asp-β-Ala-Tyr-Gly-$(Arg)_5$-Gln-$(Arg)_4$-$NH_2$;

(SEQ ID NO: 221)
Ac-c(Cys-Glu-His-D-2-Nal-Arg-Trp-Ala-Cys)-$(Pro)_2$-Arg-Asp-β-Ala-Tyr-Gly-$(Arg)_5$-Gln-$(Arg)_4$-$NH_2$;

(SEQ ID NO: 222)
Ac-c(Cys-Glu-His-D-2-Nal-Arg-1-Nal-Ala-Cys)-$(Pro)_2$-Lys-Asp-β-Ala-$(Arg)_5$-Gln-$(Arg)_4$-$NH_2$;

(SEQ ID NO: 223)
Ac-c(Cys-Glu-His-D-2-Nal-Arg-1-Nal-Ala-Cys)-$(Pro)_2$-Arg-Asp-β-Ala-$(Arg)_5$-Gln-$(Arg)_4$-$NH_2$;

(SEQ ID NO: 224)
Ac-c(Cys-Glu-His-D-2-Nal-Arg-1-Nal-Ala-Cys)-$(Pro)_2$-Arg-Asp-β-Ala-$(Arg)_6$-Gln-$(Arg)_3$-$NH_2$;

-continued (SEQ ID NO: 225)
Ac-c(Cys-Glu-His-D-2-Nal-Arg-1-Nal-Ala-Cys)-$(Pro)_2$-Lys-Asp-β-Ala-Tyr-Gly-$(Arg)_5$-Gln-$(Arg)_3$-$NH_2$;

(SEQ ID NO: 226)
Ac-c(Cys-Glu-His-D-2-Nal-Arg-1-Nal-Ala-Cys)-$(Pro)_2$-Arg-Asp-β-Ala-Tyr-Gly-$(Arg)_5$-Gln-$(Arg)_3$-$NH_2$;

(SEQ ID NO: 227)
Ac-c(Cys-Glu-His-D-2-Nal-Arg-1-Nal-Ala-Cys)-$(Pro)_2$-Lys-Asp-β-Ala-Tyr-Gly-$(Arg)_5$-Gln-$(Arg)_4$-$NH_2$;

(SEQ ID NO: 228)
Ac-c(Cys-Glu-His-D-2-Nal-Arg-1-Nal-Ala-Cys)-$(Pro)_2$-Arg-Asp-β-Ala-Tyr-Gly-$(Arg)_5$-Gln-$(Arg)_4$-$NH_2$;

(SEQ ID NO: 229)
Ac-c(Cys-Glu-His-D-2-Nal-Arg-1-Nal-Ala-Cys)-$(Pro)_2$-Lys-Asp-β-Ala-Tyr-Gly-$(Arg)_6$-Gln-$(Arg)_3$-$NH_2$;

(SEQ ID NO: 230)
Ac-c(Cys-Glu-His-D-2-Nal-Arg-1-Nal-Ala-Cys)-$(Pro)_2$-Arg-Asp-β-Ala-Tyr-Gly-(Arg)6-Gln-$(Arg)_3$-$NH_2$;

(SEQ ID NO: 231)
Ac-c(Cys-Glu-His-D-2-Nal-Arg-2-Nal-Ala-Cys)-$(Pro)_2$-Arg-Asp-β-Ala-$(Arg)_6$-Gln-$(Arg)_3$-$NH_2$;

(SEQ ID NO: 232)
Ac-c(Cys-Glu-His-D-2-Nal-Arg-2-Nal-Ala-Cys)-$(Pro)_2$-Lys-Asp-β-Ala-$(Arg)_5$-Gln-$(Arg)_4$-$NH_2$;

(SEQ ID NO: 233)
Ac-c(Cys-Glu-His-D-2-Nal-Arg-2-Nal-Ala-Cys)-$(Pro)_2$-Arg-Asp-β-Ala-$(Arg)_5$-Gln-$(Arg)_4$-$NH_2$;

(SEQ ID NO: 234)
Ac-c(Cys-Glu-His-D-2-Nal-Arg-2-Nal-Ala-Cys)-$(Pro)_2$-Lys-Asp-β-Ala-Tyr-Gly-$(Arg)_5$-Gln-$(Arg)_3$-$NH_2$;

(SEQ ID NO: 235)
Ac-c(Cys-Glu-His-D-2-Nal-Arg-2-Nal-Ala-Cys)-$(Pro)_2$-Arg-Asp-β-Ala-Tyr-Gly-$(Arg)_5$-Gln-$(Arg)_3$-$NH_2$;

(SEQ ID NO: 236)
Ac-c(Cys-Glu-His-D-2-Nal-Arg-2-Nal-Ala-Cys)-$(Pro)_2$-Lys-Asp-β-Ala-Tyr-Gly-$(Arg)_6$-Gln-$(Arg)_3$-$NH_2$;

(SEQ ID NO: 237)
Ac-c(Cys-Glu-His-D-2-Nal-Arg-2-Nal-Ala-Cys)-$(Pro)_2$-Arg-Asp-β-Ala-Tyr-Gly-$(Arg)_6$-Gln-$(Arg)_3$-$NH_2$;

(SEQ ID NO: 238)
Ac-c(Cys-Glu-His-D-2-Nal-Arg-2-Nal-Ala-Cys)-$(Pro)_2$-Lys-Asp-β-Ala-Tyr-Gly-$(Arg)_5$-Gln-$(Arg)_4$-$NH_2$;

(SEQ ID NO: 239)
Ac-c(Cys-Glu-His-D-2-Nal-Arg-2-Nal-Ala-Cys)-$(Pro)_2$-Arg-Asp-β-Ala-Tyr-Gly-$(Arg)_5$-Gln-$(Arg)_4$-$NH_2$;

(SEQ ID NO: 240)
Ac-c(Cys-Glu-His-D-2-Nal-Arg-Bal-Ala-Cys)-$(Pro)_2$-Lys-Asp-β-Ala-$(Arg)_5$-Gln-$(Arg)_4$-$NH_2$;

(SEQ ID NO: 241)
Ac-c(Cys-Glu-His-D-2-Nal-Arg-Bal-Ala-Cys)-$(Pro)_2$-Arg-Asp-β-Ala-$(Arg)_5$-Gln-$(Arg)_4$-$NH_2$;

(SEQ ID NO: 242)
Ac-c(Cys-Glu-His-D-2-Nal-Arg-Bal-Ala-Cys)-$(Pro)_2$-Arg-Asp-β-Ala-Tyr-Gly-$(Arg)_5$-Gln-$(Arg)_3$-$NH_2$;

(SEQ ID NO: 243)
Ac-c(Cys-Glu-His-D-2-Nal-Arg-Bal-Ala-Cys)-$(Pro)_2$-Lys-Asp-β-Ala-Tyr-Gly-$(Arg)_5$-Gln-$(Arg)_4$-$NH_2$;

(SEQ ID NO: 244)
Ac-c(Cys-Glu-His-D-2-Nal-Arg-Bal-Ala-Cys)-$(Pro)_2$-Arg-Asp-β-Ala-Tyr-Gly-$(Arg)_5$-Gln-$(Arg)_4$-$NH_2$;

-continued (SEQ ID NO: 245)
Ac-c(Cys-Glu-His-D-2-Nal-Arg-Bal-Ala-Cys)-$(Pro)_2$-Lys-Asp-β-Ala-Tyr-Gly-$(Arg)_6$-Gln-$(Arg)_3$-$NH_2$;

(SEQ ID NO: 246)
Ac-c(Cys-Glu-His-D-2-Nal-Arg-Bal-Ala-Cys)-$(Pro)_2$-Arg-Asp-β-Ala-Tyr-Gly-$(Arg)_6$-Gln-$(Arg)_3$-$NH_2$;

(SEQ ID NO: 247)
Ac-Nle-c(Cys-D-Ala-His-D-Phe-Arg-Trp-Cys)-$(Doc)_2$-Tyr-Gly-Arg-$(Lys)_2$-$(Arg)_2$-Gln-$(Arg)_3$-$NH_2$;

(SEQ ID NO: 248)
Ac-Nle-c(Cys-D-Ala-His-D-Phe-Arg-Trp-Cys)-β-Ala-Tyr-Gly-Arg-$(Lys)_2$-Arg-Gln-$(Arg)_4$-$NH_2$;

(SEQ ID NO: 249)
Ac-Nle-c(Cys-D-Ala-His-D-Phe-Arg-Trp-Cys)-Doc-Tyr-Gly-Arg-$(Lys)_2$-$(Arg)_2$-Gln-$(Arg)_3$-$NH_2$;

(SEQ ID NO: 250)
Ac-Nle-c(Cys-D-Ala-His-D-Phe-Arg-Trp-Cys)-β-Ala-$(Arg)_5$-Gln-$(Arg)_3$-$NH_2$;

(SEQ ID NO: 251)
Ac-Nle-c(Cys-D-Ala-His-D-Phe-Arg-Trp-Cys)-β-Ala-Gly-$(Arg)_5$-Gln-$(Arg)_3$-$NH_2$;

(SEQ ID NO: 252)
Ac-Nle-c(Cys-D-Ala-His-D-Phe-Arg-Trp-Cys)-β-Ala-Tyr-Gly-$(Arg)_5$-Gln-$(Arg)_3$-$NH_2$;

(SEQ ID NO: 253)
Ac-Nle-c(Cys-D-Ala-His-D-Phe-Arg-Trp-Cys)-β-Ala-Gly-$(Arg)_5$-Gln-$(Arg)_4$-$NH_2$;

(SEQ ID NO: 254)
Ac-Nle-c(Cys-D-Ala-His-D-Phe-Arg-Trp-Cys)-β-Ala-Tyr-Gly-$(Arg)_2$-Lys-$(Arg)_2$-Gln-$(Arg)_3$-$NH_2$;

(SEQ ID NO: 255)
Ac-Nle-c(Cys-D-Ala-His-D-Phe-Arg-Trp-Cys)-β-Ala-Tyr-Gly-Arg-Lys-$(Arg)_3$-Gln-$(Arg)_3$-$NH_2$;

(SEQ ID NO: 256)
Ac-Nle-c(Cys-D-Ala-His-D-Phe-Arg-Trp-Cys)-β-Ala-Gly-$(Arg)_2$-Lys-$(Arg)_2$-Gln-$(Arg)_3$-$NH_2$;

(SEQ ID NO: 257)
Ac-Nle-c(Cys-D-Ala-His-D-Phe-Arg-Trp-Cys)-β-Ala-Gly-Arg-Lys-$(Arg)_3$-Gln-$(Arg)_3$-$NH_2$;

(SEQ ID NO: 258)
Ac-Nle-c(Cys-D-Ala-His-D-Phe-Arg-Trp-Cys)-β-Ala-$(Arg)_2$-Lys-$(Arg)_2$-Gln-$(Arg)_3$-$NH_2$;

(SEQ ID NO: 259)
Ac-Nle-c(Cys-D-Ala-His-D-Phe-Arg-Trp-Cys)-β-Ala-Arg-Lys-$(Arg)_3$-Gln-$(Arg)_3$-$NH_2$;

(SEQ ID NO: 260)
Ac-Nle-c(Cys-D-Ala-His-D-Phe-Arg-Trp-Cys)-$(β\text{-}Ala)_2$-$(Arg)_5$-Gln-$(Arg)_3$-$NH_2$;

(SEQ ID NO: 261)
Ac-Nle-c(Cys-D-Ala-His-D-Phe-Arg-Trp-Cys)-$(β\text{-}Ala)_2$-Gly-$(Arg)_5$-Gln-$(Arg)_3$-$NH_2$;

(SEQ ID NO: 262)
Ac-Nle-c(Cys-D-Ala-His-D-Phe-Arg-Trp-Cys)-$(β\text{-}Ala)_2$-Tyr-Gly-$(Arg)_5$-Gln-$(Arg)_3$-$NH_2$;

(SEQ ID NO: 263)
Ac-Nle-c(Cys-D-Ala-His-D-Phe-Arg-Trp-Cys)-Doc-$(Arg)_5$-Gln-$(Arg)_3$-$NH_2$;

(SEQ ID NO: 264)
Ac-Nle-c(Cys-D-Ala-His-D-Phe-Arg-Trp-Cys)-Doc-Gly-$(Arg)_5$-Gln-$(Arg)_3$-$NH_2$;

-continued (SEQ ID NO: 265)
Ac-Nle-c(Cys-D-Ala-His-D-Phe-Arg-Trp-Cys)-Doc-Tyr-Gly-$(Arg)_5$-Gln-$(Arg)_3$-$NH_2$;

(SEQ ID NO: 266)
Ac-Nle-c(Cys-D-Ala-His-D-Phe-Arg-Trp-Cys)-$(Doc)_2$-$(Arg)_5$-Gln-$(Arg)_3$-$NH_2$;

(SEQ ID NO: 267)
Ac-Nle-c(Cys-D-Ala-His-D-Phe-Arg-Trp-Cys)-$(Doc)_2$-Gly-(Arg)-Gln-$(Arg)_3$-$NH_2$;

(SEQ ID NO: 268)
Ac-Nle-c(Cys-D-Ala-His-D-Phe-Arg-Trp-Cys)-$(Doc)_2$-Tyr-Gly-$(Arg)_5$-Gln-$(Arg)_3$-$NH_2$;

(SEQ ID NO: 269)
Ac-Nle-c(Cys-D-Ala-His-D-Phe-Arg-Trp-Cys)-β-Ala-$(Arg)_5$-Gln-$(Arg)_4$-$NH_2$;

(SEQ ID NO: 270)
Ac-Nle-c(Cys-D-Ala-His-D-Phe-Arg-Trp-Cys)-β-Ala-Tyr-Gly-$(Arg)_5$-Gln-$(Arg)_4$-$NH_2$;

(SEQ ID NO: 271)
Ac-Nle-c(Cys-D-Ala-His-D-Phe-Arg-Trp-Cys)-$(\beta\text{-Ala})_2$-$(Arg)_5$-Gln-$(Arg)_4$-$NH_2$;

(SEQ ID NO: 272)
Ac-Nle-c(Cys-D-Ala-His-D-Phe-Arg-Trp-Cys)-$(\beta\text{-Ala})_2$-Gly-$(Arg)_5$-Gln-$(Arg)_4$-$NH_2$;

(SEQ ID NO: 273)
Ac-Nle-c(Cys-D-Ala-His-D-Phe-Arg-Trp-Cys)-$(\beta\text{-Ala})_2$-Tyr-Gly-$(Arg)_5$-Gln-$(Arg)_4$-$NH_2$;

(SEQ ID NO: 274)
Ac-Nle-c(Cys-D-Ala-His-D-Phe-Arg-Trp-Cys)-Doc-$(Arg)_5$-Gln-$(Arg)_4$-$NH_2$;

(SEQ ID NO: 275)
Ac-Nle-c(Cys-D-Ala-His-D-Phe-Arg-Trp-Cys)-Doc-Gly-$(Arg)_5$-Gln-$(Arg)_4$-$NH_2$;

(SEQ ID NO: 276)
Ac-Nle-c(Cys-D-Ala-His-D-Phe-Arg-Trp-Cys)-Doc-Tyr-Gly-$(Arg)_5$-Gln-$(Arg)_4$-$NH_2$;

(SEQ ID NO: 277)
Ac-Nle-c(Cys-D-Ala-His-D-Phe-Arg-Trp-Cys)-$(Doc)_2$-$(Arg)_5$-Gln-$(Arg)_4$-$NH_2$;

(SEQ ID NO: 278)
Ac-Nle-c(Cys-D-Ala-His-D-Phe-Arg-Trp-Cys)-$(Doc)_2$-Gly-$(Arg)_5$-Gln-$(Arg)_4$-$NH_2$;

(SEQ ID NO: 279)
Ac-Nle-c(Cys-D-Ala-His-D-Phe-Arg-Trp-Cys)-$(Doc)_2$-Tyr-Gly-$(Arg)_5$-Gln-$(Arg)_4$-$NH_2$;

(SEQ ID NO: 280)
Ac-Nle-c(Cys-His-D-Phe-Arg-Trp-Gaba-Cys)-β-Ala-Tyr-Gly-$(Arg)_5$-Gln-$(Arg)_3$-$NH_2$;

(SEQ ID NO: 281)
Ac-Nle-c(Cys-His-D-Phe-Arg-Trp-Gaba-Cys)-β-Ala-$(Arg)_5$-Gln-$(Arg)_3$-$NH_2$;

(SEQ ID NO: 282)
Ac-Nle-c(Asp-His-D-Phe-Arg-Trp-Ala-Lys)-β-Ala-Tyr-Gly-$(Arg)_5$-Gln-$(Arg)_3$-$NH_2$;

(SEQ ID NO: 283)
Ac-Nle-c(Asp-His-D-Phe-Arg-Trp-Ala-Lys)-β-Ala-$(Arg)_5$-Gln-$(Arg)_3$-$NH_2$;

(SEQ ID NO: 284)
Ac-Nle-c(Asp-His-D-Phe-Arg-Trp-Lys)-β-Ala-Tyr-Gly-$(Arg)_5$-Gln-$(Arg)_3$-$NH_2$;

(SEQ ID NO: 285)
Ac-Nle-c(Asp-His-D-Phe-Arg-Trp-Lys)-β-Ala-Gly-$(Arg)_5$-Gln-$(Arg)_3$-$NH_2$;

-continued (SEQ ID NO: 286)
Ac-Nle-c(Asp-His-D-Phe-Arg-Trp-Lys)-β-Ala-$(Arg)_5$-Gln-$(Arg)_3$-$NH_2$;

(SEQ ID NO: 287)
Ac-Nle-c(Asp-His-D-Phe-Arg-Trp-Lys)-$(\beta\text{-Ala})_2$-Tyr-Gly-$(Arg)_5$-Gln-$(Arg)_3$-$NH_2$;

(SEQ ID NO: 288)
Ac-Nle-c(Asp-His-D-Phe-Arg-Trp-Lys)-$(\beta\text{-Ala})_2$-Gly-$(Arg)_5$-Gln-$(Arg)_3$-$NH_2$;

(SEQ ID NO: 289)
Ac-Nle-c(Asp-His-D-Phe-Arg-Trp-Lys)-$(\beta\text{-Ala})_2$-$(Arg)_5$-Gln-$(Arg)_3$-$NH_2$;

(SEQ ID NO: 290)
Ac-Nle-c(Asp-His-D-Phe-Arg-Trp-Lys)-Doc-Tyr-Gly-$(Arg)_5$-Gln-$(Arg)_3$-$NH_2$;

(SEQ ID NO: 291)
Ac-Nle-c(Asp-His-D-Phe-Arg-Trp-Lys)-Doc-Gly-$(Arg)_5$-Gln-$(Arg)_3$-$NH_2$;

(SEQ ID NO: 292)
Ac-Nle-c(Asp-His-D-Phe-Arg-Trp-Lys)-Doc-$(Arg)_5$-Gln-$(Arg)_3$-$NH_2$;

(SEQ ID NO: 293)
Ac-Nle-c(Asp-His-D-Phe-Arg-Trp-Lys)-$(Doc)_2$-Tyr-Gly-$(Arg)_5$-Gln-$(Arg)_3$-$NH_2$;

(SEQ ID NO: 294)
Ac-Nle-c(Asp-His-D-Phe-Arg-Trp-Lys)-$(Doc)_2$-Gly-$(Arg)_5$-Gln-$(Arg)_3$-$NH_2$;

(SEQ ID NO: 295)
Ac-Nle-c(Asp-His-D-Phe-Arg-Trp-Lys)-$(Doc)_2$-$(Arg)_5$-Gln-$(Arg)_3$-$NH_2$;

(SEQ ID NO: 296)
Ac-Nle-c(Asp-His-D-Phe-Arg-Trp-Lys)-β-Ala-Tyr-Gly-$(Arg)_5$-Gln-$(Arg)_4$-$NH_2$;

(SEQ ID NO: 297)
Ac-Nle-c(Asp-His-D-Phe-Arg-Trp-Lys)-β-Ala-Gly-$(Arg)_5$-Gln-$(Arg)_4$-$NH_2$;

(SEQ ID NO: 298)
Ac-Nle-c(Asp-His-D-Phe-Arg-Trp-Lys)-β-Ala-$(Arg)_5$-Gln-$(Arg)_4$-$NH_2$;

(SEQ ID NO: 299)
Ac-Nle-c(Asp-His-D-Phe-Arg-Trp-Lys)-$(\beta\text{-Ala})_2$-Tyr-Gly-$(Arg)_5$-Gln-$(Arg)_4$-$NH_2$;

(SEQ ID NO: 300)
Ac-Nle-c(Asp-His-D-Phe-Arg-Trp-Lys)-$(\beta\text{-Ala})_2$-Gly-$(Arg)_5$-Gln-$(Arg)_4$-$NH_2$;

(SEQ ID NO: 301)
Ac-Nle-c(Asp-His-D-Phe-Arg-Trp-Lys)-$(\beta\text{-Ala})_2$-$(Arg)_5$-Gln-$(Arg)_4$-$NH_2$;

(SEQ ID NO: 302)
Ac-Nle-c(Asp-His-D-Phe-Arg-Trp-Lys)-Doc-Tyr-Gly-$(Arg)_5$-Gln-$(Arg)_4$-$NH_2$;

(SEQ ID NO: 303)
Ac-Nle-c(Asp-His-D-Phe-Arg-Trp-Lys)-Doc-Gly-$(Arg)_5$-Gln-$(Arg)_4$-$NH_2$;

(SEQ ID NO: 304)
Ac-Nle-c(Asp-His-D-Phe-Arg-Trp-Lys)-Doc-$(Arg)_5$-Gln-$(Arg)_4$-$NH_2$;

(SEQ ID NO: 305)
Ac-Nle-c(Asp-His-D-Phe-Arg-Trp-Lys)-$(Doc)_2$-Tyr-Gly-$(Arg)_5$-Gln-$(Arg)_4$-$NH_2$;

(SEQ ID NO: 306)
Ac-Nle-c(Asp-His-D-Phe-Arg-Trp-Lys)-$(Doc)_2$-Gly-$(Arg)_5$-Gln-$(Arg)_4$-$NH_2$;

(SEQ ID NO: 307)
Ac-Nle-c(Asp-His-D-Phe-Arg-Trp-Lys)-$(Doc)_2$-$(Arg)_5$-Gln-$(Arg)_4$-$NH_2$;

(SEQ ID NO: 308)
Ac-Nle-c(Asp-His-D-Phe-Arg-Trp-β-Ala-Lys)-β-Ala-Tyr-Gly-$(Arg)_5$-Gln-$(Arg)_3$-$NH_2$;

-continued (SEQ ID NO: 309)
Ac-Nle-c(Asp-His-D-Phe-Arg-Trp-β-Ala-Lys)-β-Ala-$(Arg)_5$-Gln-$(Arg)_3$-$NH_2$;

(SEQ ID NO: 310)
Ac-Nle-c(Cys-His-D-Phe-Arg-Trp-Ahx-Cys)-β-Ala-Tyr-Gly-$(Arg)_5$-Gln-$(Arg)_3$-$NH_2$;

(SEQ ID NO: 311)
Ac-Nle-c(Cys-His-D-Phe-Arg-Trp-Ahx-Cys)-β-Ala-$(Arg)_5$-Gln-$(Arg)_3$-$NH_2$;

(SEQ ID NO: 312)
D-Phe-c(Cys-His-D-Phe-Arg-Trp-β-Ala-D-Cys)-Thr-β-Ala-Tyr-Gly-$(Arg)_5$-Gln-$(Arg)_3$-$NH_2$;

(SEQ ID NO: 313)
D-Phe-c(Cys-His-D-Phe-Arg-Trp-β-Ala-D-Cys)-Thr-β-Ala-$(Arg)_5$-Gln-$(Arg)_3$-$NH_2$;

(SEQ ID NO: 314)
Ac-Nle-c(Cys-His-D-Phe-Arg-Trp-Apn-Cys)-β-Ala-Tyr-Gly-$(Arg)_5$-Gln-$(Arg)_3$-$NH_2$;

(SEQ ID NO: 315)
Ac-Nle-c(Cys-His-D-Phe-Arg-Trp-Apn-Cys)-β-Ala-$(Arg)_5$-Gln-$(Arg)_3$-$NH_2$;

(SEQ ID NO: 316)
Ac-Cha-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 317)
Ac-Cha-c(Asp-His-D-Phe-Arg-Trp-Gaba-Lys)-β-Ala-$(Arg)_5$-Gln-$(Arg)_3$-$NH_2$;

(SEQ ID NO: 318)
Ac-Nle-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 319)
Ac-Nle-c(Asp-His-D-Phe-Arg-Trp-Gaba-Lys)-β-Ala-$(Arg)_5$-Gln-$(Arg)_3$-$NH_2$;

(SEQ ID NO: 320)
Ac-Chg-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 321)
Ac-Chg-c(Asp-His-D-Phe-Arg-Trp-Gaba-Lys)-β-Ala-$(Arg)_5$-Gln-$(Arg)_3$-$NH_2$;

(SEQ ID NO: 322)
Ac-hCha-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 323)
Ac-hCha-c(Asp-His-D-Phe-Arg-Trp-Gaba-Lys)-β-Ala-$(Arg)_5$-Gln-$(Arg)_3$-$NH_2$;

(SEQ ID NO: 324)
Ac-hCha-c(Asp-His-D-Phe-Arg-Trp-Gaba-Lys)-$(β-Ala)_2$-Tyr-Gly-$(Arg)_5$-Gln-$(Arg)_3$-$NH_2$;

(SEQ ID NO: 325)
Ac-hCha-c(Asp-His-D-Phe-Arg-Trp-Gaba-Lys)-$(β-Ala)_2$-$(Arg)_5$-Gln-$(Arg)_3$-$NH_2$;

(SEQ ID NO: 326)
Ac-hCha-c(Asp-His-D-Phe-Arg-Trp-Gaba-Lys)-Doc-Tyr-Gly-(Arg)5-Gln-(Arg)3-$NH_2$;

(SEQ ID NO: 327)
Ac-hCha-c(Asp-His-D-Phe-Arg-Trp-Gaba-Lys)-Doc-$(Arg)_5$-Gln-$(Arg)_3$-$NH_2$;

(SEQ ID NO: 328)
Ac-hCha-c(Asp-His-D-Phe-Arg-Trp-Gaba-Lys)-$(Doc)_2$-Tyr-Gly-$(Arg)_5$-Gln-$(Arg)_3$-$NH_2$;

(SEQ ID NO: 329)
Ac-hCha-c(Asp-His-D-Phe-Arg-Trp-Gaba-Lys)-$(Doc)_2$-$(Arg)_5$-Gln-$(Arg)_3$-$NH_2$;

-continued (SEQ ID NO: 330)
Ac-hCha-c(Asp-His-D-Phe-Arg-Trp-Gaba-Lys)-β-Ala-Tyr-Gly-$(Arg)_5$-Gln-$(Arg)_4$-$NH_2$;

(SEQ ID NO: 331)
Ac-hCha-c(Asp-His-D-Phe-Arg-Trp-Gaba-Lys)-β-Ala-$(Arg)_5$-Gln-$(Arg)_4$-$NH_2$;

(SEQ ID NO: 332)
Ac-hCha-c(Asp-His-D-Phe-Arg-Trp-Gaba-Lys)-$(β\text{-}Ala)_2$-Tyr-Gly-$(Arg)_5$-Gln-$(Arg)_4$-$NH_2$;

(SEQ ID NO: 333)
Ac-hCha-c(Asp-His-D-Phe-Arg-Trp-Gaba-Lys)-$(β\text{-}Ala)_2$-$(Arg)_5$-Gln-$(Arg)_4$-$NH_2$;

(SEQ ID NO: 334)
Ac-hCha-c(Asp-His-D-Phe-Arg-Trp-Gaba-Lys)-Doc-Tyr-Gly-$(Arg)_5$-Gln-$(Arg)_4$-$NH_2$;

(SEQ ID NO: 335)
Ac-hCha-c(Asp-His-D-Phe-Arg-Trp-Gaba-Lys)-Doc-$(Arg)_5$-Gln-$(Arg)_4$-$NH_2$;

(SEQ ID NO: 336)
Ac-hCha-c(Asp-His-D-Phe-Arg-Trp-Gaba-Lys)-$(Doc)_2$-Tyr-Gly-$(Arg)_5$-Gln-$(Arg)_4$-$NH_2$;

(SEQ ID NO: 337)
Ac-hCha-c(Asp-His-D-Phe-Arg-Trp-Gaba-Lys)-$(Doc)_2$-(Arg)5-Gln-$(Arg)_4$-$NH_2$;

(SEQ ID NO: 338)
Ac-D-Chg-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 339)
Ac-D-Chg-c(Asp-His-D-Phe-Arg-Trp-Gaba-Lys)-β-Ala-$(Arg)_5$-Gln-$(Arg)_3$-$NH_2$;

(SEQ ID NO: 340)
Ac-hPhe-c(Asp-His-D-Phe-Arg-Trp-Gaba-Lys)-β-Ala-Tyr-Gly-$(Arg)_5$-Gln-$(Arg)_3$-$NH_2$;

(SEQ ID NO: 341)
Ac-hPhe-c(Asp-His-D-Phe-Arg-Trp-Gaba-Lys)-β-Ala-$(Arg)_5$-Gln-$(Arg)_3$-$NH_2$;

(SEQ ID NO: 342)
Ac-Nle-c(Cys-His-D-Phe-Arg-D-Trp-Apn-Cys)-β-Ala-Tyr-Gly-$(Arg)_5$-Gln-$(Arg)_3$-$NH_2$;

(SEQ ID NO: 343)
Ac-Nle-c(Cys-His-D-Phe-Arg-D-Trp-Apn-Cys)-β-Ala-$(Arg)_5$-Gln-$(Arg)_3$-$NH_2$;

(SEQ ID NO: 344)
Ac-Nle-c(Cys-His-D-Phe-Arg-D-Trp-Ahx-Cys)-β-Ala-Tyr-Gly-$(Arg)_5$-Gln-$(Arg)_3$-$NH_2$;

(SEQ ID NO: 345)
Ac-Nle-c(Cys-His-D-Phe-Arg-D-Trp-Ahx-Cys)-β-Ala-$(Arg)_5$-Gln-$(Arg)_3$-$NH_2$;

(SEQ ID NO: 346)
Ac-Nle-c(Cys-His-D-Phe-Arg-D-Trp-β-Ala-Cys)-β-Ala-Tyr-Gly-$(Arg)_5$-Gln-$(Arg)_3$-$NH_2$;

(SEQ ID NO: 347)
Ac-Nle-c(Cys-His-D-Phe-Arg-D-Trp-β-Ala-Cys)-β-Ala-$(Arg)_5$-Gln-$(Arg)_3$-$NH_2$;

(SEQ ID NO: 348)
Ac-Nle-c(Cys-D-Ala-His-D-Phe-Arg-Trp-Pen)-β-Ala-Tyr-Gly-$(Arg)_5$-Gln-$(Arg)_3$-$NH_2$;

(SEQ ID NO: 349)
Ac-Nle-c(Cys-D-Ala-His-D-Phe-Arg-Trp-Pen)-β-Ala-Gly-$(Arg)_5$-Gln-$(Arg)_3$-$NH_2$;

-continued (SEQ ID NO: 350)
Ac-Nle-c(Cys-D-Ala-His-D-Phe-Arg-Trp-Pen)-β-Ala-$(Arg)_5$-Gln-$(Arg)_3$-$NH_2$;

(SEQ ID NO: 351)
Ac-Nle-c(Cys-D-Ala-His-D-Phe-Arg-Trp-Pen)-$(\beta\text{-Ala})_2$-Tyr-Gly-$(Arg)_5$-Gln-$(Arg)_3$-$NH_2$;

(SEQ ID NO: 352)
Ac-Nle-c(Cys-D-Ala-His-D-Phe-Arg-Trp-Pen)-$(\beta\text{-Ala})_2$-Gly-$(Arg)_5$-Gln-$(Arg)_3$-$NH_2$;

(SEQ ID NO: 353)
Ac-Nle-c(Cys-D-Ala-His-D-Phe-Arg-Trp-Pen)-(β-Ala)2-$(Arg)_5$-Gln-$(Arg)_3$-$NH_2$;

(SEQ ID NO: 354)
Ac-Nle-c(Cys-D-Ala-His-D-Phe-Arg-Trp-Pen)-Doc-Tyr-Gly-$(Arg)_5$-Gln-$(Arg)_3$-$NH_2$;

(SEQ ID NO: 355)
Ac-Nle-c(Cys-D-Ala-His-D-Phe-Arg-Trp-Pen)-Doc-Gly-$(Arg)_5$-Gln-$(Arg)_3$-$NH_2$;

(SEQ ID NO: 356)
Ac-Nle-c(Cys-D-Ala-His-D-Phe-Arg-Trp-Pen)-Doc-$(Arg)_5$-Gln-$(Arg)_3$-$NH_2$;

(SEQ ID NO: 357)
Ac-Nle-c(Cys-D-Ala-His-D-Phe-Arg-Trp-Pen)-$(Doc)_2$-Tyr-Gly-$(Arg)_5$-Gln-$(Arg)_3$-$NH_2$;

(SEQ ID NO: 358)
Ac-Nle-c(Cys-D-Ala-His-D-Phe-Arg-Trp-Pen)-$(Doc)_2$-Gly-$(Arg)_5$-Gln-$(Arg)_3$-$NH_2$;

(SEQ ID NO: 359)
Ac-Nle-c(Cys-D-Ala-His-D-Phe-Arg-Trp-Pen)-$(Doc)_2$-$(Arg)_5$-Gln-$(Arg)_3$-$NH_2$;

(SEQ ID NO: 360)
D-Phe-c(Cys-His-D-(Et)Tyr-Arg-Trp-β-Ala-D-Cys)-β-Ala-Tyr-Gly-$(Arg)_5$-Gln-$(Arg)_3$-$NH_2$;

(SEQ ID NO: 361)
D-Phe-c(Cys-His-D-(Et)Tyr-Arg-Trp-β-Ala-D-Cys)-β-Ala-$(Arg)_5$-Gln-$(Arg)_3$-$NH_2$;

(SEQ ID NO: 362)
D-Phe-c(Cys-His-D-(Et)Tyr-Arg-Trp-β-Ala-D-Cys)-β-Ala-Gly-$(Arg)_5$-Gln-$(Arg)_3$-$NH_2$;

(SEQ ID NO: 363)
D-Phe-c(Cys-His-D-(Et)Tyr-Arg-Trp-β-Ala-D-Cys)-β-Ala-$(Arg)_5$-Gln-$(Arg)_4$-$NH_2$;

(SEQ ID NO: 364)
D-Phe-c(Cys-His-D-(Et)Tyr-Arg-Trp-β-Ala-D-Cys)-$(\beta\text{-Ala})_2$-Tyr-Gly-(Arg)5-Gln-$(Arg)_3$-$NH_2$;

(SEQ ID NO: 365)
D-Phe-c(Cys-His-D-(Et)Tyr-Arg-Trp-β-Ala-D-Cys)-$(\beta\text{-Ala})_2$-$(Arg)_5$-Gln-$(Arg)_3$-$NH_2$;

(SEQ ID NO: 366)
D-Phe-c(Cys-His-D-(Et)Tyr-Arg-Trp-β-Ala-D-Cys)-$(\beta\text{-Ala})_2$-Gly-$(Arg)_5$-Gln-$(Arg)_3$-$NH_2$;

(SEQ ID NO: 367)
D-Phe-c(Cys-His-D-(Et)Tyr-Arg-Trp-β-Ala-D-Cys)-$(\beta\text{-Ala})_2$-$(Arg)_5$-Gln-$(Arg)_4$-$NH_2$;

(SEQ ID NO: 368)
D-Phe-c(Cys-His-D-(Et)Tyr-Arg-Trp-β-Ala-D-Cys)-Doc-Tyr-Gly-$(Arg)_5$-Gln-$(Arg)_3$-$NH_2$;

(SEQ ID NO: 369)
D-Phe-c(Cys-His-D-(Et)Tyr-Arg-Trp-β-Ala-D-Cys)-Doc-$(Arg)_5$-Gln-$(Arg)_3$-$NH_2$;

-continued (SEQ ID NO: 370)
D-Phe-c(Cys-His-D-(Et)Tyr-Arg-Trp-β-Ala-D-Cys)-Doc-Gly-$(Arg)_5$-Gln-$(Arg)_3$-$NH_2$;

(SEQ ID NO: 371)
D-Phe-c(Cys-His-D-(Et)Tyr-Arg-Trp-β-Ala-D-Cys)-Doc-$(Arg)_5$-Gln-$(Arg)_4$-$NH_2$;

(SEQ ID NO: 372)
D-Phe-c(Cys-His-D-(Et)Tyr-Arg-Trp-β-Ala-D-Cys)-$(Doc)_2$-Tyr-Gly-$(Arg)_5$-Gln-$(Arg)_3$-$NH_2$;

(SEQ ID NO: 373)
D-Phe-c(Cys-His-D-(Et)Tyr-Arg-Trp-β-Ala-D-Cys)-$(Doc)_2$-$(Arg)_5$-Gln-$(Arg)_3$-$NH_2$;

(SEQ ID NO: 374)
D-Phe-c(Cys-His-D-(Et)Tyr-Arg-Trp-β-Ala-D-Cys)-$(Doc)_2$-Gly-$(Arg)_5$-Gln-$(Arg)_3$-$NH_2$;

(SEQ ID NO: 375)
D-Phe-c(Cys-His-D-(Et)Tyr-Arg-Trp-β-Ala-D-Cys)-$(Doc)_2$-$(Arg)_5$-Gln-$(Arg)_4$-$NH_2$;

(SEQ ID NO: 376)
D-Phe-c(Cys-His-D-(Et)Tyr-hArg-Trp-β-Ala-D-Cys)-Thr-β-Ala-Tyr-Gly-$(Arg)_5$-Gln-$(Arg)_3$-$NH_2$;

(SEQ ID NO: 377)
D-Phe-c(Cys-His-D-(Et)Tyr-hArg-Trp-β-Ala-D-Cys)-Thr-β-Ala-$(Arg)_5$-Gln-$(Arg)_3$-$NH_2$;

(SEQ ID NO: 378)
D-Phe-c(Cys-His-D-(Et)Tyr-hArg-Trp-β-Ala-D-Cys)-Thr-(β-$Ala)_2$-Tyr-Gly-$(Arg)_5$-Gln-$(Arg)_3$-$NH_2$;

(SEQ ID NO: 379)
D-Phe-c(Cys-His-D-(Et)Tyr-hArg-Trp-β-Ala-D-Cys)-Thr-(β-$Ala)_2$-$(Arg)_5$-Gln-$(Arg)_3$-$NH_2$;

(SEQ ID NO: 380)
D-Phe-c(Cys-His-D-(Et)Tyr-hArg-Trp-β-Ala-D-Cys)-Thr-Doc-Tyr-Gly-$(Arg)_5$-Gln-$(Arg)_3$-$NH_2$;

(SEQ ID NO: 381)
D-Phe-c(Cys-His-D-(Et)Tyr-hArg-Trp-β-Ala-D-Cys)-Thr-Doc-$(Arg)_5$-Gln-$(Arg)_3$-$NH_2$;

(SEQ ID NO: 382)
D-Phe-c(Cys-His-D-(Et)Tyr-hArg-Trp-β-Ala-D-Cys)-Thr-$(Doc)_2$-Tyr-Gly-$(Arg)_5$-Gln-$(Arg)_3$-$NH_2$;

(SEQ ID NO: 383)
D-Phe-c(Cys-His-D-(Et)Tyr-hArg-Trp-β-Ala-D-Cys)-Thr-β-Ala-Tyr-Gly-$(Arg)_5$-Gln-$(Arg)_4$-$NH_2$;

(SEQ ID NO: 384)
D-Phe-c(Cys-His-D-(Et)Tyr-hArg-Trp-β-Ala-D-Cys)-Thr-β-Ala-$(Arg)_5$-Gln-$(Arg)_4$-$NH_2$;

(SEQ ID NO: 385)
D-Phe-c(Cys-His-D-(Et)Tyr-hArg-Trp-β-Ala-D-Cys)-Thr-(β-$Ala)_2$-Tyr-Gly-$(Arg)_5$-Gln-$(Arg)_4$-$NH_2$;

(SEQ ID NO: 386)
D-Phe-c(Cys-His-D-(Et)Tyr-hArg-Trp-β-Ala-D-Cys)-Thr-(β-$Ala)_2$-$(Arg)_5$-Gln-$(Arg)_4$-$NH_2$;

(SEQ ID NO: 387)
D-Phe-c(Cys-His-D-(Et)Tyr-hArg-Trp-β-Ala-D-Cys)-Thr-Doc-Tyr-Gly-$(Arg)_5$-Gln-$(Arg)_4$-$NH_2$;

(SEQ ID NO: 388)
D-Phe-c(Cys-His-D-(Et)Tyr-hArg-Trp-β-Ala-D-Cys)-Thr-Doc-$(Arg)_5$-Gln-$(Arg)_4$-$NH_2$;

(SEQ ID NO: 389)
D-Phe-c(Cys-His-D-(Et)Tyr-hArg-Trp-β-Ala-D-Cys)-Thr-$(Doc)_2$-Tyr-Gly-$(Arg)_5$-Gln-$(Arg)_4$-$NH_2$;

-continued (SEQ ID NO: 390)
D-Phe-c(Cys-His-D-(Et)Tyr-hArg-Trp-β-Ala-D-Cys)-Thr-$(Doc)_2$-$(Arg)_5$-Gln-$(Arg)_4$-$NH_2$;

(SEQ ID NO: 391)
D-Phe-c(Cys-His-D-(Et)Tyr-hArg-Bip-β-Ala-D-Cys)-Thr-β-Ala-Tyr-Gly-$(Arg)_5$-Gln-$(Arg)_3$-$NH_2$;

(SEQ ID NO: 392)
D-Phe-c(Cys-His-D-(Et)Tyr-hArg-Bip-β-Ala-D-Cys)-Thr-β-Ala-Tyr-Gly-$(Arg)_5$-Gln-$(Arg)_4$-$NH_2$;

(SEQ ID NO: 393)
D-Phe-c(Cys-His-D-(Et)Tyr-hArg-Bip-β-Ala-D-Cys)-Thr-β-Ala-$(Arg)_5$-Gln-$(Arg)_3$-$NH_2$;

(SEQ ID NO: 394)
D-Phe-c(Cys-His-D-(Et)Tyr-hArg-Bip-β-Ala-D-Cys)-Thr-$(β\text{-}Ala)_2$-Tyr-Gly-$(Arg)_5$-Gln-$(Arg)_3$-$NH_2$;

(SEQ ID NO: 395)
D-Phe-c(Cys-His-D-(Et)Tyr-hArg-Bip-β-Ala-D-Cys)-Thr-$(β\text{-}Ala)_2$-$(Arg)_5$-Gln-$(Arg)_3$-$NH_2$;

(SEQ ID NO: 396)
D-Phe-c(Cys-His-D-(Et)Tyr-hArg-Bip-β-Ala-D-Cys)-Thr-Doc-Tyr-Gly-$(Arg)_5$-Gln-$(Arg)_3$-$NH_2$;

(SEQ ID NO: 397)
D-Phe-c(Cys-His-D-(Et)Tyr-hArg-Bip-β-Ala-D-Cys)-Thr-Doc-Tyr-Gly-$(Arg)_5$-Gln-$(Arg)_4$-$NH_2$;

(SEQ ID NO: 398)
D-Phe-c(Cys-His-D-(Et)Tyr-hArg-Bip-β-Ala-D-Cys)-Thr-Doc-$(Arg)_5$-Gln-$(Arg)_3$-$NH_2$;

(SEQ ID NO: 399)
D-Phe-c(Cys-His-D-(Et)Tyr-hArg-Bip-β-Ala-D-Cys)-Thr-$(Doc)_2$-Tyr-Gly-$(Arg)_5$-Gln-$(Arg)_3$-$NH_2$;

(SEQ ID NO: 400)
D-Phe-c(Cys-His-D-(Et)Tyr-hArg-Bip-β-Ala-D-Cys)-Thr-$(Doc)_2$-$(Arg)_5$-Gln-$(Arg)_3$-$NH_2$;

(SEQ ID NO: 401)
Ac-Nle-c(Cys-D-Ala-His-D-Phe-Arg-Trp-Gly-Cys)-(β-Ala-Tyr-Gly-$(Arg)_5$-Gln-$(Arg)_3$-$NH_2$;

(SEQ ID NO: 402)
Ac-Nle-c(Cys-D-Ala-His-D-Phe-Arg-Trp-Gly-Cys)-(β-Ala-$(Arg)_5$-Gln-$(Arg)_3$-$NH_2$;

(SEQ ID NO: 403)
Nle-c(Cys-His-D-Phe-Arg-Trp-Apn-Cys)-β-Ala-Tyr-Gly-$(Arg)_5$-Gln-$(Arg)_3$-$NH_2$;

(SEQ ID NO: 404)
Nle-c(Cys-His-D-Phe-Arg-Trp-Apn-Cys)-β-Ala-$(Arg)_5$-Gln-$(Arg)_3$-$NH_2$;

(SEQ ID NO: 405)
Nle-c(Cys-His-D-Phe-Arg-Trp-Apn-Cys)-$(β\text{-}Ala)_2$-Tyr-Gly-$(Arg)_5$-Gln-$(Arg)_3$-$NH_2$;

(SEQ ID NO: 406)
Nle-c(Cys-His-D-Phe-Arg-Trp-Apn-Cys)-$(β\text{-}Ala)_2$-$(Arg)_5$-Gln-$(Arg)_3$-$NH_2$;

(SEQ ID NO: 407)
Nle-c(Cys-His-D-Phe-Arg-Trp-Apn-Cys)-β-Ala-Tyr-Gly-$(Arg)_5$-Gln-$(Arg)_4$-$NH_2$;

(SEQ ID NO: 408)
Nle-c(Cys-His-D-Phe-Arg-Trp-Apn-Cys)-β-Ala-$(Arg)_5$-Gln-$(Arg)_4$-$NH_2$;

(SEQ ID NO: 409)
Nle-c(Cys-His-D-Phe-Arg-Trp-Apn-Cys)-$(β\text{-}Ala)_2$-Tyr-Gly-$(Arg)_5$-Gln-$(Arg)_4$-$NH_2$;

(SEQ ID NO: 410)
Nle-c(Cys-His-D-Phe-Arg-Trp-Apn-Cys)-$(β\text{-}Ala)_2$-$(Arg)_5$-Gln-$(Arg)_4$-$NH_2$;

-continued (SEQ ID NO: 411)
Nle-c(Cys-His-D-Phe-Arg-Trp-Apn-Cys)-Doc-Tyr-Gly-$(Arg)_5$-Gln-$(Arg)_3$-$NH_2$;

(SEQ ID NO: 412)
Nle-c(Cys-His-D-Phe-Arg-Trp-Apn-Cys)-Doc-$(Arg)_5$-Gln-$(Arg)_3$-$NH_2$;

(SEQ ID NO: 413)
Nle-c(Cys-His-D-Phe-Arg-Trp-Apn-Cys)-$(Doc)_2$-Tyr-Gly-$(Arg)_5$-Gln-$(Arg)_3$-$NH_2$;

(SEQ ID NO: 414)
Nle-c(Cys-His-D-Phe-Arg-Trp-Apn-Cys)-$(Doc)_2$-$(Arg)_5$-Gln-$(Arg)_3$-$NH_2$;

(SEQ ID NO: 415)
Nle-c(Cys-His-D-Phe-Arg-Trp-Apn-Cys)-Doc-Tyr-Gly-$(Arg)_5$-Gln-$(Arg)_4$-$NH_2$;

(SEQ ID NO: 416)
Nle-c(Cys-His-D-Phe-Arg-Trp-Apn-Cys)-Doc-$(Arg)_5$-Gln-$(Arg)_4$-$NH_2$;

(SEQ ID NO: 417)
Nle-c(Cys-His-D-Phe-Arg-Trp-Apn-Cys)-$(Doc)_2$-Tyr-Gly-$(Arg)_5$-Gln-$(Arg)_4$-$NH_2$;

(SEQ ID NO: 418)
Nle-c(Cys-His-D-Phe-Arg-Trp-Apn-Cys)-$(Doc)_2$-$(Arg)_5$-Gln-$(Arg)_4$-$NH_2$;

(SEQ ID NO: 419)
Ac-Nle-c(Cys-D-Leu-His-D-Phe-Arg-Trp-Cys)-β-Ala-Tyr-Gly-$(Arg)_5$-Gln-$(Arg)_3$-$NH_2$;

(SEQ ID NO: 420)
Ac-Nle-c(Cys-D-Leu-His-D-Phe-Arg-Trp-Cys)-β-Ala-$(Arg)_5$-Gln-$(Arg)_3$-$NH_2$;

(SEQ ID NO: 421)
Ac-Nle-c(Cys-D-Leu-His-D-Phe-Arg-Trp-Cys)-$(β\text{-Ala})_2$-Tyr-Gly-$(Arg)_5$-Gln-$(Arg)_3$-$NH_2$;

(SEQ ID NO: 422)
Ac-Nle-c(Cys-D-Leu-His-D-Phe-Arg-Trp-Cys)-$(β\text{-Ala})_2$-$(Arg)_5$-Gln-$(Arg)_3$-$NH_2$;

(SEQ ID NO: 423)
Ac-Nle-c(Cys-D-Leu-His-D-Phe-Arg-Trp-Cys)-Doc-Tyr-Gly-$(Arg)_5$-Gln-$(Arg)_3$-$NH_2$;

(SEQ ID NO: 424)
Ac-Nle-c(Cys-D-Leu-His-D-Phe-Arg-Trp-Cys)-Doc-$(Arg)_5$-Gln-$(Arg)_3$-$NH_2$;

(SEQ ID NO: 425)
Ac-Nle-c(Cys-D-Leu-His-D-Phe-Arg-Trp-Cys)-$(Doc)_2$-Tyr-Gly-$(Arg)_5$-Gln-$(Arg)_3$-$NH_2$;

(SEQ ID NO: 426)
Ac-Nle-c(Cys-D-Leu-His-D-Phe-Arg-Trp-Cys)-$(Doc)_2$-$(Arg)_5$-Gln-$(Arg)_3$-$NH_2$;

(SEQ ID NO: 427)
Ac-Nle-c(Cys-D-Leu-His-D-Phe-Arg-Trp-Cys)-β-Ala-Tyr-Gly-$(Arg)_5$-Gln-$(Arg)_4$-$NH_2$;

(SEQ ID NO: 428)
Ac-Nle-c(Cys-D-Leu-His-D-Phe-Arg-Trp-Cys)-β-Ala-$(Arg)_5$-Gln-$(Arg)_4$-$NH_2$;

(SEQ ID NO: 429)
Ac-Nle-c(Cys-D-Leu-His-D-Phe-Arg-Trp-Cys)-$(β\text{-Ala})_2$-Tyr-Gly-$(Arg)_5$-Gln-$(Arg)_4$-$NH_2$;

(SEQ ID NO: 430)
Ac-Nle-c(Cys-D-Leu-His-D-Phe-Arg-Trp-Cys)-$(β\text{-Ala})_2$-$(Arg)_5$-Gln-$(Arg)_4$-$NH_2$;

(SEQ ID NO: 431)
Ac-Nle-c(Cys-D-Leu-His-D-Phe-Arg-Trp-Cys)-Doc-Tyr-Gly-$(Arg)_5$-Gln-$(Arg)_4$-$NH_2$;

-continued (SEQ ID NO: 432)
Ac-Nle-c(Cys-D-Leu-His-D-Phe-Arg-Trp-Cys)-Doc-$(Arg)_5$-Gln-$(Arg)_4$-$NH_2$;

(SEQ ID NO: 433)
Ac-Nle-c(Cys-D-Leu-His-D-Phe-Arg-Trp-Cys)-$(Doc)_2$-Tyr-Gly-$(Arg)_5$-Gln-$(Arg)_4$-$NH_2$;

(SEQ ID NO: 434)
Ac-Nle-c(Cys-D-Leu-His-D-Phe-Arg-Trp-Cys)-$(Doc)_2$-$(Arg)_5$-Gln-$(Arg)_4$-$NH_2$;

(SEQ ID NO: 435)
Ac-Nle-c(Cys-D-Cha-His-D-Phe-Arg-Trp-Cys)-β-Ala-Tyr-Gly-$(Arg)_5$-Gln-$(Arg)_3$-$NH_2$;

(SEQ ID NO: 436)
Ac-Nle-c(Cys-D-Cha-His-D-Phe-Arg-Trp-Cys)-β-Ala-$(Arg)_5$-Gln-$(Arg)_3$-$NH_2$;

(SEQ ID NO: 437)
Ac-Nle-c(Cys-D-Cha-His-D-Phe-Arg-Trp-Cys)-$(\beta\text{-Ala})_2$-Tyr-Gly-$(Arg)_5$-Gln-$(Arg)_3$-$NH_2$;

(SEQ ID NO: 438)
Ac-Nle-c(Cys-D-Cha-His-D-Phe-Arg-Trp-Cys)-$(\beta\text{-Ala})_2$-$(Arg)_5$-Gln-$(Arg)_3$-$NH_2$;

(SEQ ID NO: 439)
Ac-Nle-c(Cys-D-Cha-His-D-Phe-Arg-Trp-Cys)-Doc-Tyr-Gly-$(Arg)_5$-Gln-$(Arg)_3$-$NH_2$;

(SEQ ID NO: 440)
Ac-Nle-c(Cys-D-Cha-His-D-Phe-Arg-Trp-Cys)-Doc-$(Arg)_5$-Gln-$(Arg)_3$-$NH_2$;

(SEQ ID NO: 441)
Ac-Nle-c(Cys-D-Cha-His-D-Phe-Arg-Trp-Cys)-$(Doc)_2$-Tyr-Gly-$(Arg)_5$-Gln-$(Arg)_3$-$NH_2$;

(SEQ ID NO: 442)
Ac-Nle-c(Cys-D-Cha-His-D-Phe-Arg-Trp-Cys)-$(Doc)_2$-$(Arg)_5$-Gln-$(Arg)_3$-$NH_2$;

(SEQ ID NO: 443)
Ac-Nle-c(Cys-D-Cha-His-D-Phe-Arg-Trp-Cys)-β-Ala-Tyr-Gly-$(Arg)_5$-Gln-$(Arg)_4$-$NH_2$;

(SEQ ID NO: 444)
Ac-Nle-c(Cys-D-Cha-His-D-Phe-Arg-Trp-Cys)-β-Ala-$(Arg)_5$-Gln-(Arg)-$NH_2$;

(SEQ ID NO: 445)
Ac-Nle-c(Cys-D-Cha-His-D-Phe-Arg-Trp-Cys)-$(\beta\text{-Ala})_2$-Tyr-Gly-$(Arg)_5$-Gln-$(Arg)_4$-$NH_2$;

(SEQ ID NO: 446)
Ac-Nle-c(Cys-D-Cha-His-D-Phe-Arg-Trp-Cys)-$(\beta\text{-Ala})_2$-$(Arg)_5$-Gln-$(Arg)_4$-$NH_2$;

(SEQ ID NO: 447)
Ac-Nle-c(Cys-D-Cha-His-D-Phe-Arg-Trp-Cys)-Doc-Tyr-Gly-$(Arg)_5$-Gln-$(Arg)_4$-$NH_2$;

(SEQ ID NO: 448)
Ac-Nle-c(Cys-D-Cha-His-D-Phe-Arg-Trp-Cys)-Doc-$(Arg)_5$-Gln-$(Arg)_4$-$NH_2$;

(SEQ ID NO: 449)
Ac-Nle-c(Cys-D-Cha-His-D-Phe-Arg-Trp-Cys)-$(Doc)_2$-Tyr-Gly-$(Arg)_5$-Gln-$(Arg)_4$-$NH_2$;

(SEQ ID NO: 450)
Ac-Nle-c(Cys-D-Cha-His-D-Phe-Arg-Trp-Cys)-$(Doc)_2$-$(Arg)_5$-Gln-$(Arg)_4$-$NH_2$;

(SEQ ID NO: 451)
Nle-c(Cys-His-D-Phe-Arg-Trp-Gaba-Cys)-β-Ala-Tyr-Gly-$(Arg)_5$-Gln-$(Arg)_3$-$NH_2$;

-continued (SEQ ID NO: 452)
Nle-c(Cys-His-D-Phe-Arg-Trp-Gaba-Cys)-β-Ala-$(Arg)_5$-Gln-$(Arg)_3$-$NH_2$;

(SEQ ID NO: 453)
Nle-c(Cys-His-D-Phe-Arg-Trp-Gaba-Cys)-$(β-Ala)_2$-Tyr-Gly-$(Arg)_5$-Gln-$(Arg)_3$-$NH_2$;

(SEQ ID NO: 454)
Nle-c(Cys-His-D-Phe-Arg-Trp-Gaba-Cys)-$(β-Ala)_2$-$(Arg)_5$-Gln-$(Arg)_3$-$NH_2$;

(SEQ ID NO: 455)
Nle-c(Cys-His-D-Phe-Arg-Trp-Gaba-Cys)-β-Ala-Tyr-Gly-$(Arg)_5$-Gln-$(Arg)_4$-$NH_2$;

(SEQ ID NO: 456)
Nle-c(Cys-His-D-Phe-Arg-Trp-Gaba-Cys)-β-Ala-$(Arg)_5$-Gln-$(Arg)_4$-$NH_2$;

(SEQ ID NO: 457)
Nle-c(Cys-His-D-Phe-Arg-Trp-Gaba-Cys)-$(β-Ala)_2$-Tyr-Gly-$(Arg)_5$-Gln-$(Arg)_4$-$NH_2$;

(SEQ ID NO: 458)
Nle-c(Cys-His-D-Phe-Arg-Trp-Gaba-Cys)-$(β-Ala)_2$-$(Arg)_5$-Gln-$(Arg)_4$-$NH_2$;

(SEQ ID NO: 459)
Nle-c(Cys-His-D-Phe-Arg-Trp-Gaba-Cys)-Doc-Tyr-Gly-$(Arg)_5$-Gln-$(Arg)_3$-$NH_2$;

(SEQ ID NO: 460)
Nle-c(Cys-His-D-Phe-Arg-Trp-Gaba-Cys)-Doc-$(Arg)_5$-Gln-$(Arg)_3$-$NH_2$;

(SEQ ID NO: 461)
Nle-c(Cys-His-D-Phe-Arg-Trp-Gaba-Cys)-$(Doc)_2$-Tyr-Gly-$(Arg)_5$-Gln-$(Arg)_3$-$NH_2$;

(SEQ ID NO: 462)
Nle-c(Cys-His-D-Phe-Arg-Trp-Gaba-Cys)-$(Doc)_2$-$(Arg)_5$-Gln-$(Arg)_3$-$NH_2$;

(SEQ ID NO: 463)
Nle-c(Cys-His-D-Phe-Arg-Trp-Gaba-Cys)-Doc-Tyr-Gly-$(Arg)_5$-Gln-$(Arg)_4$-$NH_2$;

(SEQ ID NO: 464)
Nle-c(Cys-His-D-Phe-Arg-Trp-Gaba-Cys)-Doc-$(Arg)_5$-Gln-$(Arg)_4$-$NH_2$;

(SEQ ID NO: 465)
Nle-c(Cys-His-D-Phe-Arg-Trp-Gaba-Cys)-$(Doc)_2$-Tyr-Gly-$(Arg)_5$-Gln-$(Arg)_4$-$NH_2$;

(SEQ ID NO: 466)
Nle-c(Cys-His-D-Phe-Arg-Trp-Gaba-Cys)-$(Doc)_2$-$(Arg)_5$-Gln-$(Arg)_4$-$NH_2$;

(SEQ ID NO: 467)
Ac-c(Cys-Glu-His-D-4-Br-Phe-Arg-Trp-Gly-Cys)-$(Pro)_2$-Lys-Asp-$NH_2$;

(SEQ ID NO: 468)
Ac-c(Cys-Glu-His-D-2-Nal-Arg-Trp-Ala-Cys)-$(Pro)_2$-Lys-Asp-$NH_2$;

(SEQ ID NO: 469)
Ac-c(Cys-Glu-His-D-2-Nal-Arg-2-Nal-Ala-Cys)-$(Pro)_2$-Lys-Asp-$NH_2$;

(SEQ ID NO: 470)
Ac-c(Cys-Glu-His-D-2-Nal-Arg-1-Nal-Ala-Cys)-$(Pro)_2$-Lys-Asp-$NH_2$;

(SEQ ID NO: 471)
Ac-c(Cys-Glu-His-D-2-Nal-Arg-Bal-Ala-Cys)-$(Pro)_2$-Lys-Asp-$NH_2$;

(SEQ ID NO: 472)
Ac-c(Cys-Glu-His-D-2-Nal-Arg-2-Nal-β-Ala-Cys)-$(Pro)_2$-Lys-Asp-$NH_2$;

(SEQ ID NO: 473)
Ac-c(Cys-Glu-His-D-2-Nal-Arg-2-Nal-Aib-Cys)-$(Pro)_2$-Lys-Asp-$NH_2$;

(SEQ ID NO: 474)
c[Hydantoin(C(O)-(Cys-D-Ala))-His-D-Phe-Arg-Trp-Cys]-$NH_2$;

(SEQ ID NO: 475)
c[Hydantoin(C(O)-(hCys-D-Ala))-His-D-Phe-Arg-Trp-Cys]-$NH_2$;

-continued (SEQ ID NO: 476)
c[Hydantoin(C(O)-(Cys-D-Ala))-His-D-2-Nal-Arg-Trp-Cys]-$NH_2$;

(SEQ ID NO: 477)
c[Hydantoin(C(O)-(hCys-D-Ala))-His-D-2-Nal-Arg-Trp-Cys]-$NH_2$;

(SEQ ID NO: 478)
c[Hydantoin(C(O)-(Asp-D-Ala))-His-D-Phe-Arg-Trp-Lys]-$NH_2$;

(SEQ ID NO: 479)
c[Hydantoin(C(O)-(Asp-D-Ala))-His-D-Phe-Arg-Trp-Orn]-$NH_2$;

(SEQ ID NO: 480)
c[Hydantoin(C(O)-(Asp-D-Ala))-His-D-Phe-Arg-Trp-DaN-$NH_2$;

(SEQ ID NO: 481)
c[Hydantoin(C(O)-(Asp-D-Ala))-His-D-Phe-Arg-Trp-Dap]-$NH_2$;

(SEQ ID NO: 482)
c[Hydantoin(C(O)-(Asp-His))-D-2-Nal-Arg-Trp-Lys]-$NH_2$;

(SEQ ID NO: 483)
c[Hydantoin(C(O)-(Asp-His))-D-Phe-Arg-Trp-Lys]-$NH_2$;

(SEQ ID NO: 484)
c[Hydantoin(C(O)-(Asp-A3c))-D-Phe-Arg-Trp-Lys]-$NH_2$;

(SEQ ID NO: 485)
c[Hydantoin(C(O)-(Asp-A5c))-D-Phe-Arg-Trp-Lys]-$NH_2$;

(SEQ ID NO: 486)
c[Hydantoin(C(O)-(Asp-A6c))-D-Phe-Arg-Trp-Lys]-$NH_2$;

(SEQ ID NO: 487)
c[Hydantoin(C(O)-(Asp-A3c))-D-2-Nal-Arg-Trp-Lys]-$NH_2$;

(SEQ ID NO: 488)
c[Hydantoin(C(O)-(Asp-A5c))-D-2-Nal-Arg-Trp-Lys]-$NH_2$;

(SEQ ID NO: 489)
c[Hydantoin(C(O)-(Asp-A6c))-D-2-Nal-Arg-Trp-Lys]-$NH_2$;

(SEQ ID NO: 490)
c[Hydantoin(C(O)-(Asp-Aic))-D-Phe-Arg-Trp-Lys]-$NH_2$;

(SEQ ID NO: 491)
c[Hydantoin(C(O)-(Asp-Apc))-D-Phe-Arg-Trp-Lys]-$NH_2$;

(SEQ ID NO: 492)
c[Hydantoin(C(O)-(Asp-Aic))-D-2-Nal-Arg-Trp-Lys]-$NH_2$;

(SEQ ID NO: 493)
c[Hydantoin(C(O)-(Asp-Apc))-D-2-Nal-Arg-Trp-Lys]-$NH_2$;

(SEQ ID NO: 494)
c[Hydantoin(C(O)-(Glu-D-Ala))-His-D-Phe-Arg-Trp-Orn]-$NH_2$;

(SEQ ID NO: 495)
c[Hydantoin(C(O)-(Glu-D-Ala))-His-D-Phe-Arg-Trp-DaN-$NH_2$;

(SEQ ID NO: 496)
c[Hydantoin(C(O)-(Glu-D-Ala))-His-D-Phe-Arg-Trp-Dap]-$NH_2$;

(SEQ ID NO: 497)
c[Hydantoin(C(O)-(Glu-D-Ala))-His-D-Phe-Arg-Trp-Lys]-$NH_2$;

(SEQ ID NO: 498)
c[Hydantoin(C(O)-(Glu-His))-D-Phe-Arg-Trp-Dap]-$NH_2$;

(SEQ ID NO: 499)
c[Hydantoin(C(O)-(Glu-His))-D-Phe-Arg-Trp-Lys]-$NH_2$;

(SEQ ID NO: 500)
Hydantoin(C(O)-(Arg-Gly))-c(Cys-Glu-His-D-Phe-Arg-Trp-Cys)-$NH_2$;

(SEQ ID NO: 501)
Hydantoin(C(O)-(Nle-Gly))-c(Cys-Glu-His-D-Phe-Arg-Trp-Cys)-$NH_2$;

(SEQ ID NO: 502)
Hydantoin(C(O)-(Gly-Gly))-c(Cys-Glu-His-D-Phe-Arg-Trp-Cys)-$NH_2$;

-continued (SEQ ID NO: 503)
Hydantoin(C(O)-(Nle-Gly))-c(Cys-D-Ala-His-D-Phe-Arg-Trp-Cys)-$NH_2$;

(SEQ ID NO: 504)
Hydantoin(C(O)-(Gly-Gly))-c(Cys-D-Ala-His-D-Phe-Arg-Trp-Cys)-$NH_2$;

(SEQ ID NO: 505)
Hydantoin(C(O)-(Nle-Gly))-c(Cys-D-Ala-His-D-Phe-Arg-Trp-Pen)-$NH_2$;

(SEQ ID NO: 506)
Hydantoin(C(O)-(Gly-Gly))-c(Cys-D-Ala-His-D-Phe-Arg-Trp-Pen)-$NH_2$;

(SEQ ID NO: 507)
Hydantoin(C(O)-(Ala-Gly))-c(Cys-D-Ala-His-D-Phe-Arg-Trp-Cys)-$NH_2$;

(SEQ ID NO: 508)
Hydantoin(C(O)-(D-Ala-Gly))-c(Cys-D-Ala-His-D-Phe-Arg-Trp-Cys)-$NH_2$;

(SEQ ID NO: 509)
Hydantoin(C(O)-(Aib-Gly))-c(Cys-D-Ala-His-D-Phe-Arg-Trp-Cys)-$NH_2$;

(SEQ ID NO: 510)
Hydantoin(C(O)-(Val-Gly))-c(Cys-D-Ala-His-D-Phe-Arg-Trp-Cys)-$NH_2$;

(SEQ ID NO: 511)
Hydantoin(C(O)-(Ile-Gly))-c(Cys-D-Ala-His-D-Phe-Arg-Trp-Cys)-$NH_2$;

(SEQ ID NO: 512)
Hydantoin(C(O)-(Leu-Gly))-c(Cys-D-Ala-His-D-Phe-Arg-Trp-Cys)-$NH_2$;

(SEQ ID NO: 513)
Hydantoin(C(O)-(Gly-Gly))-c(Cys-Glu-His-D-2-Nal-Arg-Trp-Cys)-$NH_2$;

(SEQ ID NO: 514)
Hydantoin(C(O)-(Nle-Gly))-c(Cys-Glu-His-D-2-Nal-Arg-Trp-Cys)-$NH_2$;

(SEQ ID NO: 515)
Hydantoin(C(O)-(D-Arg-Gly))-c(Cys-Glu-His-D-Phe-Arg-Trp-Cys)-$NH_2$;

(SEQ ID NO: 516)
Hydantoin(C(O)-(D-Arg-Gly))-c(Cys-D-Ala-His-D-Phe-Arg-Trp-Cys)-$NH_2$;

(SEQ ID NO: 517)
Hydantoin(C(O)-(Arg-Gly))-c(Cys-D-Ala-His-D-Phe-Arg-Trp-Cys)-$NH_2$;

(SEQ ID NO: 518)
Hydantoin(C(O)-(D-Arg-Gly))-c(Cys-D-Ala-His-D-2-Nal-Arg-Trp-Cys)-$NH_2$;

(SEQ ID NO: 519)
Hydantoin(C(O)-(Arg-Gly))-c(Cys-D-Ala-His-D-2-Nal-Arg-Trp-Cys)-$NH_2$;

(SEQ ID NO: 520)
Hydantoin(C(O)-(Ala-Nle))-c(Cys-Glu-His-D-Phe-Arg-Trp-Cys)-$NH_2$;

(SEQ ID NO: 521)
Hydantoin(C(O)-(Val-Nle))-c(Cys-Glu-His-D-Phe-Arg-Trp-Cys)-$NH_2$;

(SEQ ID NO: 522)
Hydantoin(C(O)-(Gly-Nle))-c(Cys-Glu-His-D-Phe-Arg-Trp-Cys)-$NH_2$;

(SEQ ID NO: 523)
Hydantoin(C(O)-(A6c-Nle))-c(Cys-D-Ala-His-D-Phe-Arg-Trp-Cys)-$NH_2$;

(SEQ ID NO: 524)
Hydantoin(C(O)-(Gly-Nle))-c(Cys-D-Ala-His-D-Phe-Arg-Trp-Cys)-$NH_2$;

(SEQ ID NO: 525)
Hydantoin(C(O)-(Ala-Nle))-c(Cys-D-Ala-His-D-Phe-Arg-Trp-Cys)-$NH_2$;

(SEQ ID NO: 526)
Hydantoin(C(O)-(D-Ala-Nle))-c(Cys-D-Ala-His-D-Phe-Arg-Trp-Cys)-$NH_2$;

(SEQ ID NO: 527)
Hydantoin(C(O)-(Val-Nle))-c(Cys-D-Ala-His-D-Phe-Arg-Trp-Cys)-$NH_2$;

(SEQ ID NO: 528)
Hydantoin(C(O)-(Leu-Nle))-c(Cys-D-Ala-His-D-Phe-Arg-Trp-Cys)-$NH_2$;

(SEQ ID NO: 529)
Hydantoin(C(O)-(Cha-Nle))-c(Cys-D-Ala-His-D-Phe-Arg-Trp-Cys)-$NH_2$;

-continued (SEQ ID NO: 530)
Hydantoin(C(O)-(Aib-Nle))-c(Cys-D-Ala-His-D-Phe-Arg-Trp-Cys)-$NH_2$;

(SEQ ID NO: 531)
Hydantoin(C(O)-(Gly-Arg))-c(Cys-Glu-His-D-Phe-Arg-Trp-Cys)-$NH_2$;

(SEQ ID NO: 532)
Hydantoin(C(O)-(Gly-Arg))-c(Cys-Glu-His-D-2-Nal-Arg-Trp-Cys)-$NH_2$;

(SEQ ID NO: 533)
Hydantoin(C(O)-(Gly-Arg))-c(Cys-D-Ala-His-D-Phe-Arg-Trp-Cys)-$NH_2$;

(SEQ ID NO: 534)
Hydantoin(C(O)-(Gly-Arg))-c(Cys-D-Ala-His-D-2-Nal-Arg-Trp-Cys)-$NH_2$;

(SEQ ID NO: 535)
Hydantoin(C(O)-(Gly-D-Arg))-c(Cys-Glu-His-D-Phe-Arg-Trp-Cys)-$NH_2$;

(SEQ ID NO: 536)
Hydantoin(C(O)-(Gly-D-Arg))-c(Cys-D-Ala-His-D-Phe-Arg-Trp-Cys)-$NH_2$;

(SEQ ID NO: 537)
Hydantoin(C(O)-(Gly-D-Arg))-c(Cys-D-Ala-His-D-2-Nal-Arg-Trp-Cys)-$NH_2$;

(SEQ ID NO: 538)
Hydantoin(C(O)-(Nle-Ala))-c(Cys-Glu-His-D-Phe-Arg-Trp-Cys)-$NH_2$;

(SEQ ID NO: 539)
c[Hydantoin(C(O)-(Nle-Cys))-D-Ala-His-D-Phe-Arg-Trp-Cys]-$NH_2$;

(SEQ ID NO: 540)
c[Hydantoin(C(O)-(Ala-Cys))-D-Ala-His-D-Phe-Arg-Trp-Cys]-$NH_2$;

(SEQ ID NO: 541)
c[Hydantoin(C(O)-(D-Ala-Cys))-D-Ala-His-D-Phe-Arg-Trp-Cys]-$NH_2$;

(SEQ ID NO: 542)
c[Hydantoin(C(O)-(Aib-Cys))-D-Ala-His-D-Phe-Arg-Trp-Cys]-$NH_2$;

(SEQ ID NO: 543)
c[Hydantoin(C(O)-(Val-Cys))-D-Ala-His-D-Phe-Arg-Trp-Cys]-$NH_2$;

(SEQ ID NO: 544)
c[Hydantoin(C(O)-(Abu-Cys))-D-Ala-His-D-Phe-Arg-Trp-Cys]-$NH_2$;

(SEQ ID NO: 545)
c[Hydantoin(C(O)-(Leu-Cys))-D-Ala-His-D-Phe-Arg-Trp-Cys]-$NH_2$;

(SEQ ID NO: 546)
c[Hydantoin(C(O)-(Ile-Cys))-D-Ala-His-D-Phe-Arg-Trp-Cys]-$NH_2$;

(SEQ ID NO: 547)
c[Hydantoin(C(O)-(Cha-Cys))-D-Ala-His-D-Phe-Arg-Trp-Cys]-$NH_2$;

(SEQ ID NO: 548)
c[Hydantoin(C(O)-(A6c-Cys))-D-Ala-His-D-Phe-Arg-Trp-Cys]-$NH_2$;

(SEQ ID NO: 549)
c[Hydantoin(C(O)-(Phe-Cys))-D-Ala-His-D-Phe-Arg-Trp-Cys]-$NH_2$;

(SEQ ID NO: 550)
c[Hydantoin(C(O)-(Gly-Cys))-D-Ala-His-D-Phe-Arg-Trp-Cys]-$NH_2$;

(SEQ ID NO: 551)
c[Hydantoin(C(O)-(Gly-Cys))-Glu-His-D-Phe-Arg-Trp-Cys]-$NH_2$;

(SEQ ID NO: 552)
Ac-Tyr-Arg-c(Cys-D-Ala-His-D-Phe-Arg-Trp-Cys)-$NH_2$;

(SEQ ID NO: 553)
Ac-2-Nal-Arg-c(Cys-D-Ala-His-D-Phe-Arg-Trp-Cys)-$NH_2$;

(SEQ ID NO: 554)
Ac-1-Nal-Arg-c(Cys-D-Ala-His-DPhe-Arg-Trp-Cys)-$NH_2$;

(SEQ ID NO: 555)
Ac-Phe-Arg-c(Cys-D-Ala-His-D-Phe-Arg-Trp-Cys)-$NH_2$;

(SEQ ID NO: 556)
Ac-Trp-Arg-c(Cys-D-Ala-His-D-Phe-Arg-Trp-Cys)-$NH_2$;

-continued (SEQ ID NO: 557);
Ac-Pff-Arg-c(Cys-D-Ala-His-D-Phe-Arg-Trp-Cys)-$NH_2$;

(SEQ ID NO: 558)
H-His-Arg-c(Cys-D-Ala-His-D-Phe-Arg-Trp-Cys)-$NH_2$;
and (SEQ ID NO: 559)
Ac-His-Arg-c(Cys-D-Ala-His-D-Phe-Arg-Trp-Cys)-$NH_2$;

or a pharmaceutically acceptable salt thereof.

* * * * *